(12) United States Patent
Imai et al.

(10) Patent No.: US 11,918,589 B2
(45) Date of Patent: Mar. 5, 2024

(54) MEDICAMENT FOR TREATMENT OF MULTIPLE SCLEROSIS

(71) Applicants: NIPPON CHEMIPHAR CO., LTD., Tokyo (JP); KYUSHU UNIVERSITY, NATIONAL UNIVERSITY CORPORATION, Fukuoka (JP)

(72) Inventors: Toshiyasu Imai, Misato (JP); Toru Kawasaki, Misato (JP); Toru Ogawa, Misato (JP); Kazuhide Inoue, Fukuoka (JP)

(73) Assignees: NIPPON CHEMIPHAR CO., LTD., Tokyo (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 406 days.

(21) Appl. No.: 16/350,297

(22) PCT Filed: Apr. 27, 2017

(86) PCT No.: PCT/JP2017/016690
§ 371 (c)(1),
(2) Date: Oct. 26, 2018

(87) PCT Pub. No.: WO2017/188365
PCT Pub. Date: Nov. 2, 2017

(65) Prior Publication Data
US 2021/0121478 A1 Apr. 29, 2021

(30) Foreign Application Priority Data
Apr. 28, 2016 (JP) .............................. JP2016-090715

(51) Int. Cl.
*A61K 31/5513* (2006.01)
*A61P 25/04* (2006.01)

(52) U.S. Cl.
CPC .......... *A61K 31/5513* (2013.01); *A61P 25/04* (2018.01)

(58) Field of Classification Search
CPC ............................ A61K 31/5513; A61P 25/04
See application file for complete search history.

(56) References Cited

U.S. PATENT DOCUMENTS

| 2005/0074819 | A1 | 4/2005 | Inoue et al. | |
|---|---|---|---|---|
| 2013/0172550 | A1* | 7/2013 | Sakuma | C07D 487/04 540/495 |

FOREIGN PATENT DOCUMENTS

| CA | 2861024 | * | 7/2013 |
| EP | 2397480 | | 12/2011 |
| EP | 2803662 | | 11/2014 |
| JP | 2006-521308 | | 9/2006 |
| WO | WO-2004-085440 | | 10/2004 |
| WO | WO-2007-049825 | | 5/2007 |
| WO | WO-2008-023847 | | 2/2008 |
| WO | WO-2008-020651 | | 1/2010 |
| WO | WO-2010-090300 | | 8/2010 |
| WO | WO-2012-011549 | | 1/2012 |
| WO | WO-2010-093061 | | 8/2012 |
| WO | WO-2012-008478 | | 9/2013 |
| WO | WO-2012-014910 | | 9/2013 |
| WO | WO-2012-017876 | | 10/2013 |
| WO | WO-2013-105608 | | 5/2015 |
| WO | WO-2015-088564 | | 6/2015 |
| WO | WO-2015-088565 | | 6/2015 |
| WO | WO-2015-005467 | | 3/2017 |
| WO | WO-2015-005468 | | 3/2017 |

OTHER PUBLICATIONS

Scadding. ACNR, 2003, 3(2), pp. 8, 10, 12, and 14 (Year: 2003).*
Matsumura. Scientific Reports, 2016, 6:32461, 1-11 (Year: 2016).*
Koles. Current Pharmaceutical Design, 2007, 13(23), 2368-2384 (Year: 2007).*
Chinese Office Action for Application No. 201780026148.4, dated Sep. 30, 2020.
Bibolini ct al., "Inhibitory Role of Diazepam on Autoimmune Inflammation in Rats With Experimental Autoimmune Encephalomyelitis", Neuroscience, vol. 199, 2011, pp. 421-428.
Matute et al., Neuroscience, 2003 Abstract, No. 213.3.
Österberg et al., "Central Pain in Multiple Sclerosis—Prevalence and Clinical Characteristics", European Journal of Pain No. 9, 2005, pp. 531-542.
Hadjimichael et al., "Persistent Pain and Uncomfortable sensations in Persons with Multiple Sclerosis", Pain, No. 127, 2007, pp. 35-41.
Kanner et al., "Multiple Sclerosis as a Painful Disease", International Review of Neurobiology, vol. 79, 2007, pp. 303-321.
Practice of Pain Management vol. 5, No. 2, Jun. 2014, pp. 88-90.
Aicher et al., "Hyperalgesia in an Animal Model of Multiple Sclerosis", Pain, 110, 2004, pp. 560-570.
Olechowski et al., "Neuropathic Pain Behaviours in a Chronic-Relapsing model of Experimental Autoimmune Encephalomyelitis (EAE)", Pain. 141, 2009. pp. 156-164.
Petzold et al., "Markers for Different Glial Cell Responses in Multiple Sclerosis: Clinical and Pathological Correlations", Guarantors of Brain, 2002, No. 125, pp. 1462-1473.
Grav et al., "Elevated Activity and Microglial Expression of Myeloperoxidase in Demyelinated Cerebral Cortex in Multiple Sclerosis", Research Article, Brain Pathology, No. 18, 2008, pp. 86-95.

(Continued)

*Primary Examiner* — Noble E Jarrell
(74) *Attorney, Agent, or Firm* — NIXON PEABODY LLP; Jeffrey L. Costellia

(57) ABSTRACT

A medicament for preventive and/or therapeutic treatment of multiple sclerosis, especially a pain accompanying multiple sclerosis such as neuropathic pain, which contains a compound having a P2X4 receptor antagonist activity such as a compound represented by the general formula (IH), or a salt thereof or a hydrate or solvate thereof as an active ingredient.

22 Claims, 4 Drawing Sheets
(1 of 4 Drawing Sheet(s) Filed in Color)
Specification includes a Sequence Listing.

(56) References Cited

OTHER PUBLICATIONS

Buell et al.. "An Antagonist-Insensitive $P_{2x}$ Receptor Expressed in Epithelia and Brain", The EMBO, Journal, vol. 15. No. 1, 1996, pp. 55-62.
Séguéla et al., "A Novel Neuronal $P_{2x}$ ATP Receptor Ion Channel with Widespread Distribution in the Brain", The Journal of Neuroscience, Jan. 15, 1996, vol. 16, No. 2, pp. 448-455.
Bo, et al., "A P2X Purinoceptor cDNA Conferring a Novel Pharmacological Profile", FEBS Letter, 375, 1995, pp. 129-133.
Soto et al., "$P2X_4$: An ATP—Activated Ionotropic Receptor Cloned from Rat Brain", Proc. Natl. Acad. Sci. USA, vol. 93, Apr. 1996, Neurobiology, pp. 3684-3688.
Wang, et al., "Cloning and Pharmacological Characterization of a Fourth P2X Receptor Subtype Widely Expressed in Brain and Peripheral Tissues Including Various Endocrine Tissues", Biochemical and Biophysical Research Communications, 220, 1996, Article No. 0380, pp. 196-202.
Coull et al., "BDNF from Microglia Causes the Shift in Neuronal Anion gradient Underlying Neuropathic Pain", vol. 438, Dec. 15, 2005, Nature, pp. 1017-1021.
Vázquez-Villoldo, et al., "P2X4 Receptors Control the Fate and Survival of Activated Microglia", Research Article, vol. 62, No. 2, pp. 171-184.
International Search Report and Written Opinion for PCT/JP2017/016690, dated Jun. 7, 2017.
International Preliminary Report on Patentability for PCT/JP2017/016690, dated Oct. 30, 2018.
MTsuda et al., "P2X4 Receptors Induced in Spinal Microglia Gate Tactile Allodynia After Nerve Injury", 424, 2003, pp. 778-783.
European Search Report for 17789647.9, dated Nov. 6, 2019.
Japanese Office Action for JP App No. 2018-514692, dated May 25, 2021.
Chinese Office Action in Chinese Application No. 201780026148.4, dated Jul. 26, 2021, 35 pages.
European Office Action for Application No. 17789647.9, dated Jul. 28, 2020.
Korean Office Action (App. No. 10-2018-7034415) dated Oct. 28, 2021 (11 pages).
Chinese Office Action (App. No. 201780026148.4) dated Dec. 29, 2021 (21 pages).
Keio Hospital Information & Patient Assistance Service (15 pages). http://kompas.hosp.keio.ac.jp/contents/000331.html.
Guo, et al., "Lesional Accumulation of $P2X_4$ Receptor[+] Macrophages in Rat CNS During Experimental Autoimmune Encephalomyelitis", Neuroscience 134, (2005), pp. 199-205.
Ajami et al., "Infiltrating monocytes trigger EAE progression, but do not contribute to the resident microglia pool", Articles, Nature Neuroscience, vol. 14, No. 9, Sep. 2011, pp. 1142-1150.
Terai et al., "Japanese translation of neuropathic pain—Report by the Committee on Terminology of the Japan Society of Pain Clinicians", Journal of Japan Society of Pain Clinicians, vol. 16, No. 4, 2009, pp. 509-515,.
Australian Office Action (Application No. 2017255086) dated May 13, 2022 (3 pages).
Chinese Office Action (App. No. 201780026148.4) dated Jun. 23, 2022 (21 pages).
Japanese Office Action (App. No. 2018-514692) dated Feb. 1, 2022 (8 pages).
Eriko Nakata, "A Study on the Analgesic Effect of NCP-308, a P2X4 Receptor Antagonist, on Neuropathic Pain", Mar. 2013, Department of Molecular and System Pharmacology, Clinical Pharmaceutical Sciences Major, Graduate School of Pharmaceutical Sciences, Kyushu University (117 pages).
Canadian Office Action (Application No. 3,022,358) dated Jun. 7, 2023, (4pgs).
Australian Office Action (Application No. 2017255086) dated Feb. 20, 2023. (3pgs).

* cited by examiner

[Fig. 1]
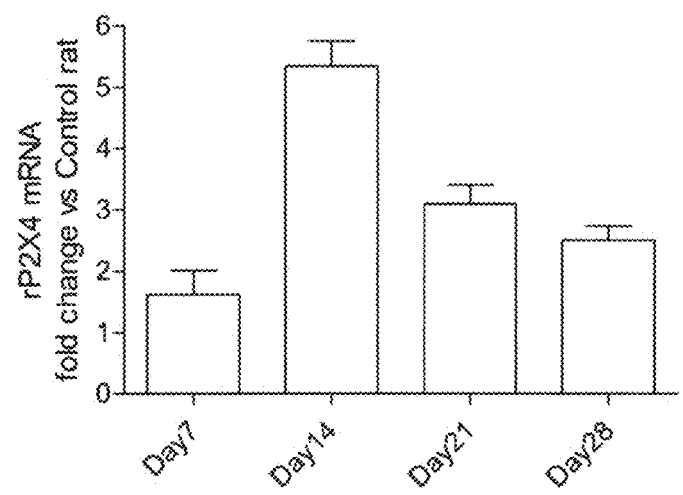

[Fig. 2]
A
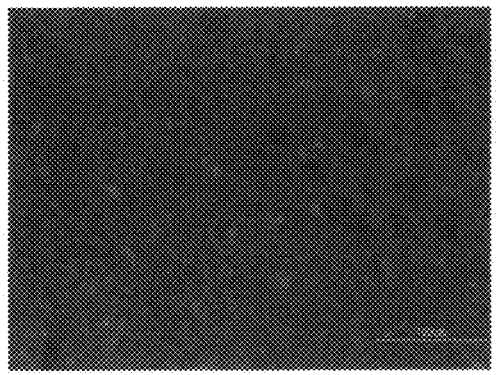
B
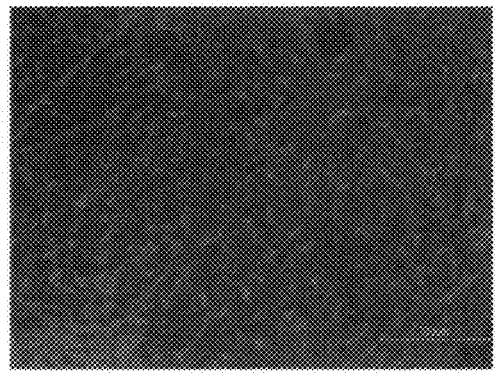
C
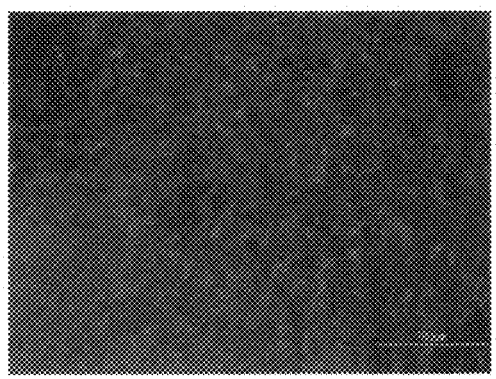
D
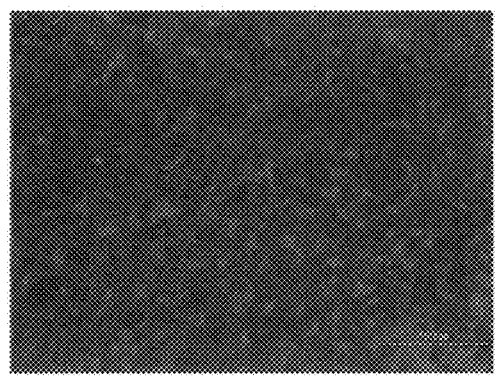
E
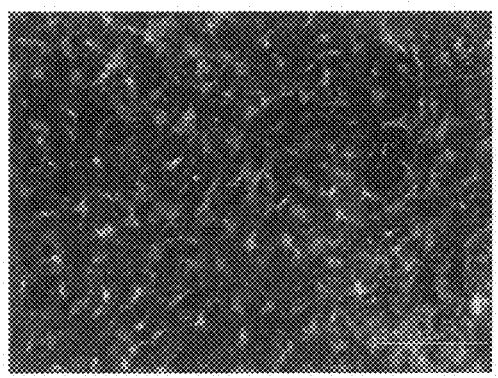
F
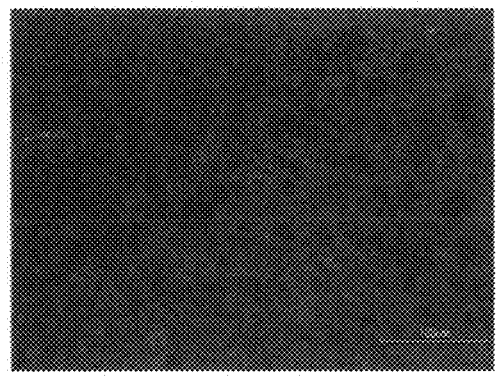
(Scale bar=100μm)

[Fig. 3]
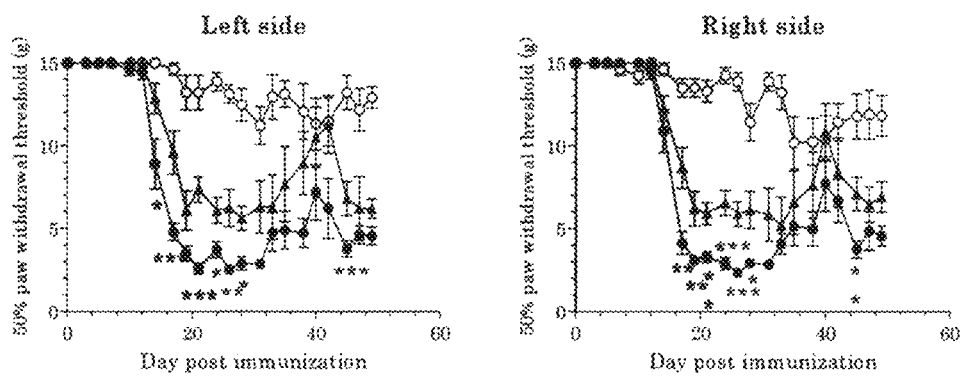
[Fig. 4]
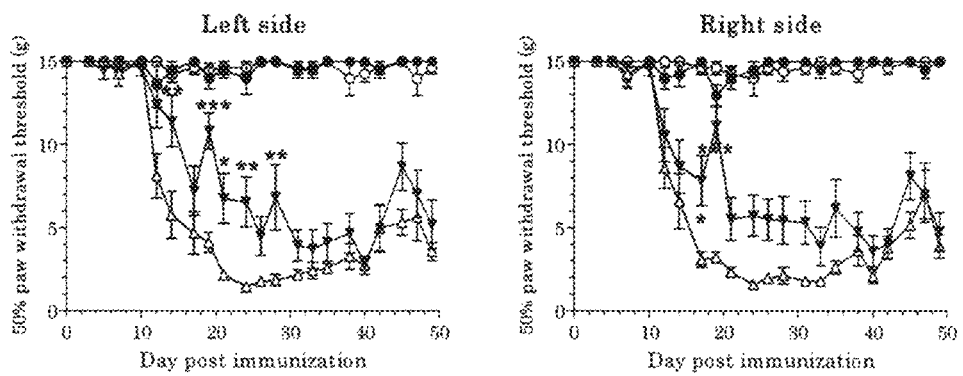

[Fig. 5]
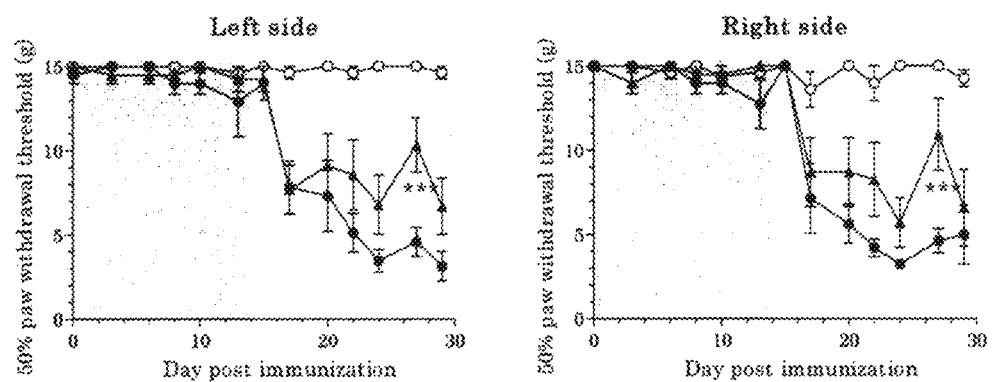

MEDICAMENT FOR TREATMENT OF MULTIPLE SCLEROSIS

The instant application contains a Sequence Listing which has been filed electronically in ASCII format and is hereby incorporated by reference in its entirety. Said ASCII copy, created on May 28, 2020, is named 084319-000002_SL.txt and is 1,508 bytes in size.

TECHNICAL FIELD

The present invention relates to a medicament for preventive and/or therapeutic treatment of multiple sclerosis.

BACKGROUND ART

Multiple sclerosis (MS) is an inflammatory demyelinating disease of the central nerves, and is characterized by central nerve lesions frequently occurring spatially and temporally. It is the most frequently occurring disease among neurological disorders that affect young adults in Europe and America, where the prevalence rate per population of 100,000 is around 50, and the number of persons with this disease in Japan is estimated to be about 13,000 as a whole (about 8 or 9 persons per population of 100,000). It cannot be said that causes of the onset of this disease have fully been elucidated, although genetic factors, environmental factors, virus infection, and the like have been suggested, and it is a designated intractable disease authorized as a specified disease in Japan. It is characterized by long affection period with repeating recurrence and remission, inflammation and disruption of myelin due to autoimmunity, and dyscrasia of the optic nerve or spine due to damages to nerve fibers, and as the symptoms, although they vary depending on parts and times of demyelination, there are caused sensation abnormalities (numbness, abnormalities of thermal sensation, migraine, trigeminal neuralgia, itching, etc. (European Journal of Pain, 9, pp. 531-542, 2005; Pain, 127, pp. 35-41, 2007; International Review of Neurobiology, 79, pp. 303-321, 2007)), and motor dysfunctions.

Although pregabalin, tricyclic antidepressants, antiepileptics, and narcotic analgesics are used for central pain of multiple sclerosis patients, the effect of such symptomatic therapies for pains is considered restrictive at present (Practice of Pain Management, 5, pp. 88-90, 2014). It has been reported that, in experimental autoimmune encephalomyelitis (EAE) model animals, which is an animal model of multiple sclerosis, pain symptoms such as hyperalgesia and allodynia accompany, like clinical cases (Pain, 110, pp. 560-570, 2004; Pain, 141, pp. 156-164, 2009). It has been reported that the analgesic action of morphine markedly decreases in allodynia observed in the EAE model. It has also been pointed out that glia cells are activated in the brain and spine of EAE model rats, and this may be involved in advance of the pathological conditions and demyelination (Brain: A Journal of Neurology, 125, pp. 1462-1473, 2002; Brain Pathology (Zurich, Switzerland), 18, pp. 86-95, 2008). IDCAl Sub,AMD By the way, the ATP receptors are broadly classified into the P2X family of the ion channel type receptors, and the P2Y family of the G protein coupling type receptors, and the P2X4 receptor (Genebank No. X87763), a subtype of the P2X family, has been reported to be widely expressed in the central nervous system, and the like (EMBO J., 15, pp. 55-62, 1996; J. Neurosci., 16, pp. 448-455, 1996; FEBS Lett., 375, pp. 129-133, 1995; Proc. Natl. Acad. Sci. USA. 93, pp. 3684-3788, 1996; Biochem. Res., Commun., 220. pp. 196-202, 1996). Recently, Inoue et al. verified the involvement of the P2X receptor in neuropathic pain by using a spinal nerve-damaged animal model in which allodynia can be detected, and they reported that nerve-damaged type unusual pain (especially allodynia) is induced through the P2X4 receptor expressed in the microglia cells of the spinal cord (Nature, 424, pp. 778-783, 2003; Nature, 438, pp. 1017-1021, 2005; U.S. Patent Published Application No. 2005/74819).

Guo et al. (Neuroscience, 134, pp. 199-205, 2005) elucidated that the P2X4 receptors existing in the circumference of blood vessels of the spine or brain markedly increase with advance of the pathological symptoms in the EAE model, marked increase of the expression is also observed not only in the circumference of blood vessels, but also in tissue parenchyma, and P2X4 receptor-positive cells expressed in the parenchyma exist mainly on infiltrating macrophages by double staining, and reported the relation of the P2X4 receptors and the pathology. Nuria et al. reported that expression of the P2X4 receptors is accelerated and P2X4 receptor-positive cells increase in the spine of EAE rat and optic nerve of multiple sclerosis patients (Glia, 62, pp. 171-184, 2014). Although Nakata reported an analgesic action of NCP-308, a P2X4 receptor antagonist, for a neuropathic pain by using an EAE model animal, the chemical structure of that substance has not been clarified (Kyushu University, Graduate School of Pharmaceutical Sciences, Department of Molecular and System Pharmacology, doctoral thesis, March, 2013).

As compounds having a P2X4 receptor antagonist activity, there are known benzofuro-1,4-diazepin-2-one derivatives (WO2004/085440), and naphthodiazepinedione derivatives (WO2010/093061, WO2012/008478, WO2012/14910, WO2012/17876, WO2013/105608, WO2015/005468, WO2015/005467, etc.). WO2008/020651, WO2007/049825, WO2015/088664, and WO2015/088565 also disclose compounds having a P2X4 receptor antagonist activity, and although they suggest effectiveness of the compounds on pain of multiple sclerosis as general descriptions, they do not disclose any verification data obtained by using EAE model animals.

PRIOR ART REFERENCES

Patent Documents

Patent document 1: U.S. Patent Published Application No. 2005/074819
Patent document 2: WO2004/085440
Patent document 3: WO2010/093061
Patent document 4: WO2012/008478
Patent document 5: WO2012/014910
Patent document 6: WO2012/017876
Patent document 7: WO2013/105608
Patent document 8: WO2015/005468
Patent document 9: WO2015/005467
Patent document 10: WO2008/020651
Patent document 11: WO2007/049825
Patent document 12: WO2015/088564
Patent document 13: WO2015/088565

Non-Patent Documents

Non-patent document 1: European Journal of Pain (London, England), 9, pp. 531-542, 2005
Non-patent document 2: Pain, 127, pp. 35-41, 2007
Non-patent document 3: International Review of Neurobiology, 79, pp. 303-321, 2007
Non-patent document 4: Practice of Pain Management, 5, pp. 88-90, 2014
Non-patent document 5: Pain, 110, pp. 560-570, 2004
Non-patent document 6: Pain, 141, pp. 156-164, 2009
Non-patent document 7: Brain: A Journal of Neurology, 125, pp. 1462-1473, 2002
Non-patent document 8: Brain Pathology (Zurich, Switzerland), 18, pp. 86-95, 2008
Non-patent document 9: ENBO J., 15, pp. 55-62, 1996
Non-patent document 10: J. Neurosci., 16, pp. 448-455, 1996 Non-patent document 11 FEBS Lett., 375, pp. 129-133, 1995
Non-patent document 12: Proc. Natl. Acad. Sci, USA, 93, pp. 3684-3788, 1996
Non-patent document 13: Biochem. Res. Commun., 220, pp. 196-202, 1996
Non-patent document 14: Nature, 424, pp. 778-783, 2003
Non-patent document 15: Nature, 438, pp. 1017-1021, 2005
Non-patent document 16: Neuroscience, 134, pp. 199-205, 2005
Non-patent document 17: Glia, 62, pp. 171-184, 2014
Non-patent document 18: Kyushu University, Graduate School of Pharmaceutical Sciences, Department of Molecular and System Pharmacology, doctoral thesis of Eriko Nakata, March, 2013

SUMMARY OF THE INVENTION

Object to be Achieved by the Invention

An object of the present invention is to provide a medicament for preventive and/or therapeutic treatment of multiple sclerosis.

A more preferred object of the present invention is to provide a medicament for preventive and/or therapeutic treatment of a pain such as neuropathic pain accompanying multiple sclerosis, especially a medicament for preventive and/or therapeutic treatment of a convalescent pain accompanying multiple sclerosis.

Means for Achieving the Object

The inventors of the present invention conducted various researches in order to achieve the aforementioned object, as a result, found that naphthodiazepinedione derivatives having a P2X4 receptor antagonist activity are highly effective for preventive and/or therapeutic treatment of neuropathic pain accompanying multiple sclerosis, and accomplished the present invention.

The present invention thus provides a medicament for preventive and/or therapeutic treatment of multiple sclerosis, which contains a compound having a P2X4 receptor antagonist activity, or a salt thereof, or a hydrate or solvate thereof as an active ingredient.

As the compound having a P2X4 receptor antagonist activity, for example, the compounds represented by the following general formulas (IA) to (IG) can be used.

More preferably, as the compound having a P2X4 receptor antagonist activity, the compounds represented by the following general formula OIH) can be used. IDC-A2 Su, The medicament of the present invention can be used for, for example, preventive and/or therapeutic treatment of a pain, preferably a neuropathic pain, accompanying multiple sclerosis, and can be more preferably used for preventive and/or therapeutic treatment of a convalescent neuropathic pain accompanying multiple sclerosis.

As other aspects of the present invention, there are provided use of a compound having a P2X4 receptor antagonist activity or a salt thereof, or a hydrate or solvate thereof for manufacture of the aforementioned medicament; and a method for preventive and/or therapeutic treatment of multiple sclerosis, preferably a pain accompanying multiple sclerosis, more preferably a neuropathic pain accompanying multiple sclerosis, particularly preferably a convalescent neuropathic pain accompanying multiple sclerosis, which comprises the step of administering a preventively and/or therapeutically effective amount of a compound having a P2X4 receptor antagonist activity or a salt thereof, or a hydrate or solvate thereof to a mammal including human.

Effect of the Invention

The medicament of the present invention is useful as a medicament for preventive and/or therapeutic treatment of multiple sclerosis, and can exhibit high effectiveness in preventive and/or therapeutic treatment of a neuropathic pain accompanying multiple sclerosis, especially a convalescent pain accompanying multiple sclerosis.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 is a graph showing the results of observation of daily basis change of P2X4 expression performed in Example 2 by calculating P2X4/GAPDH ratios, and ratio of the ratios (EAE model group/control group).

FIG. 2 shows results of the immunohistological staining performed in Example 3. A: P2X4 receptor staining image of the posterior horn of spinal cord in an EAE model rat on Day 7, B: P2X4 receptor staining image of the posterior horn of spinal cord in the EAE model rat on Day 14, C: P2X4 receptor staining image of the posterior horn of spinal cord in the EAE model rat on Day 21, D: P2X4 receptor staining image of the posterior horn of spinal cord in the EAE model rat on Day 28, E: Iba1 (red) and P2X4 receptor (green) staining image of the posterior horn of spinal cord in the EAE model rat on Day 28, and F: P2X4 receptor staining image of the posterior horn of spinal cord in a control rat on Day 28.

FIG. 3 shows influences of preventive administration of the compound A to an EAE model rat on the pain threshold observed in Example 4. The gray backgrounds indicate the administration periods. ○: Adjuvant+medium (n=8), ●: gpMBP(68-84)-adjuvant+medium (n=7 or 8), ▲: gpMBP(68-84)-adjuvant+compound A (n=5 to 8).

FIG. 4 shows influences of preventive administration of the compound A to an EAE model rat on the pain threshold observed in Example 5. The gray backgrounds indicate the administration periods. ○: Adjuvant+medium (n=8), ●: Adjuvant+medium (n=6), ∆: gpMBP(68-84)-adjuvant+medium (n=7 to 11), ▲: gpMBP(68-84)-adjuvant+compound A (n=7 to 11).

FIG. 5 shows influences of preventive continuous administration of the compound B to an EAE model rat on the pain threshold observed in Example 6. The gray backgrounds indicate the administration periods. ○: Adjuvant+medium (n=7 or 8), ●: gpMBP(68-84)-adjuvant+medium (n=2 to 6), ▲: gpMBP(68-84)-adjuvant+compound B (n=3 to 6).

MODES FOR CARRYING OUT THE INVENTION

As the active ingredient of the medicament of the present invention, the compounds represented by the general formulas (1A) to 0IH) shown below can be used. The abbreviations used in the tables mentioned below, and the like are as follows. Me: methyl group, Et: ethyl group, Pr: n-propyl group, iPr: isopropyl group, tBu: tert-butyl group, Ac: acetyl group, Ph: phenyl group.

(A-1) A compound represented by the following general formula (IA):

[Formula 1]

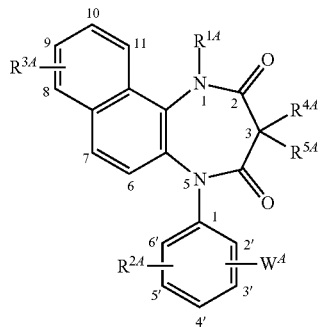

(IA)

wherein, in the formula, $R^{1A}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, or an alkyl group having 1 to 3 carbon atoms and substituted with phenyl group, $R^{2A}$ and $R^{3A}$ may be the same or different, and represent hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, or sulfamoyl group, $R^{4A}$ and $R^{5A}$ may be the same or different, and represent hydrogen atom, an alkyl group having 1 to 8 carbon atoms, an alkyl group having 1 to 8 carbon atoms and substituted with 1 to 3 halogen atoms, or an alkyl group having 1 to 3 carbon atoms and substituted with phenyl group, and $W^{A}$ represents a 5- or 6-membered heterocyclic ring which contains 1 to 4 nitrogen atoms as ring-constituting elements, and may have a substituent.

As for the general formula (IA), examples of the alkyl group having 1 to 8 carbon atoms as $R^{1A}$, $R^{2A}$, $R^{3A}$, $R^{4A}$, and $R^{5A}$ include methyl group, ethyl group, propyl group, isopropyl group, butyl group, i-butyl group, t-butyl group, pentyl group, hexyl group, and the like.

Examples of the alkenyl group having 2 to 8 carbon atoms as $R^{1A}$ include allyl group, and the like.

Examples of the alkyl group having 1 to 8 carbon atoms and substituted with 1 to 3 halogen atoms as $R^{1A}$, $R^{2A}$, $R^{3A}$, $R^{4A}$, and $R^{5A}$ include methyl group, ethyl group, propyl group, isopropyl group, butyl group, or t-butyl group, and the like substituted with 1 to 3 halogen atoms such as fluorine atom, chlorine atom, and bromine atom, and preferred examples of the same include trifluoromethyl group, chloromethyl group, 2-chloroethyl group, 2-bromoethyl group, 2-fluoroethyl group, and the like.

Examples of the alkyl group having 1 to 3 carbon atoms and substituted with phenyl group as $R^{1A}$, $R^{4A}$, and $R^{5A}$ include benzyl group, and the like.

Examples of the alkoxy group having 1 to 8 carbon atoms as $R^{2A}$ and $R^{3A}$ include methoxy group, ethoxy group, propoxy group, isopropoxy group, butoxy group, i-butoxy group, t-butoxy group, pentyloxy group, hexyloxy group, and the like.

Examples of the alkoxy group having 1 to 8 carbon atoms and substituted with 1 to 3 halogen atoms as $R^{2A}$ and $R^{3A}$ include methyl group ethyl group, propyl group, isopropyl group, butyl group, or t-butyl group, and the like substituted with 1 to 3 halogen atoms such as fluorine atom, chlorine atom, and bromine atom, and preferred examples of the same include trifluoromethoxy group, 2-chloroethoxy group, 2-bromoethoxy group, 2-fluoroethoxy group, and the like.

Examples of the halogen atom as $R^{2A}$ and $R^{3A}$ include fluorine atom, chlorine atom, bromine atom, and the like.

Examples of the alkylamino group having 1 to 8 carbon atoms as $R^{2A}$ and $R^{3A}$ include methylamino group, ethylamino group, and the like.

Examples of the dialkylamino group having 1 to 8 carbon atoms as $R^{2A}$ and $R^{3A}$ include dimethylamino group, diethylamino group, and the like.

Examples of the acylamino group having 2 to 8 carbon atoms as $R^{2A}$ and $R^{3A}$ include acetylamino group.

Examples of the acylamino group having 2 to 8 carbon atoms and substituted with 1 to 3 halogen atoms as $R^{2A}$ and $R^{3A}$ include trifluoromethylcarbonylamino group.

Examples of the alkylsulfonylamino group having 1 to 8 carbon atoms as $R^{2A}$ and $R^{3A}$ include methylsulfonylamino group.

Examples of the acyl group having 2 to 8 carbon atoms as $R^{2A}$ and $R^{3A}$ include acetyl group.

Examples of the alkoxycarbonyl group (the alkoxy moiety thereof has 1 to 8 carbon atoms) as $R^{2A}$ and $R^{3A}$ include methoxycarbonyl group, ethoxycarbonyl group, and the like.

Examples of the alkylthio group having 1 to 8 carbon atoms as $R^{2A}$ and $R^{3A}$ include methylthio group.

Examples of the alkylsulfinyl group having 1 to 8 carbon atoms as $R^{2A}$ and $R^{3A}$ include methylsulfinyl group.

Examples of the alkylsulfonyl group having 1 to 8 carbon atoms as $R^{2A}$ and $R^{3A}$ include methylsulfonyl group.

Examples of the 5- or 6-membered heterocyclic ring which contains 1 to 4 nitrogen atoms as ring-constituting elements, and may have a substituent, as $W^{A}$ include tetrazole, 1,2,4-triazole, 1,2,3-triazole, 1,2,4-oxadiazole, pyrazole, imidazole, oxazole, isoxazole, pyrrole, thiazole, pyridine, and pyrrolidine.

Examples of the substituent which the 5- or 6-membered heterocyclic ring which contains 1 to 4 nitrogen atoms as ring-constituting elements, and may have a substituent, as $W^A$ may have include an alkyl group having 1 to 8 carbon atoms such as methyl group and ethyl group, an alkyl group having 1 to 8 carbon atoms and substituted with 1 to 3 halogen atoms such as trifluoromethyl group, a halogen atom such as fluorine atom, cyano group, oxo group, thioxo group, and the like.

In the general formula (A), 1 to 3 of the same or different $R^{2A}$ and $R^{3A}$ may exist on the benzene rings on which $R^{2A}$ and $R^{3A}$ substitute.

As the compounds of the general formula (A), the following compounds are preferred.

(A-2) The compound according to (A-1), wherein $W^A$ is tetrazole, 1,2,4-triazole, 1,2,3-triazole, 1,2,4-oxadiazole, pyrazole, or imidazole which may have a substituent selected from an alkyl group having 1 to 8 carbon atoms, an alkyl group having 1 to 8 carbon atoms and substituted with 1 to 3 halogen atoms, a halogen atom, cyano group, oxo group, and thioxo group.

(A-3) The compound according to (A-1) or (A-2), wherein $W^A$ is tetrazole, 1,2,4-triazole, or 1,2,3-triazole which may have a substituent selected from an alkyl group having 1 to 8 carbon atoms, an alkyl group having 1 to 8 carbon atoms and substituted with 1 to 3 halogen atoms, a halogen atom, and cyano group.

(A-4) The compound according to any one of (A-1) to (A-3), wherein $W^A$ is 5-oxo-1,2,4-oxadiazole, or 5-thioxo-1,2,4-oxadiazole.

(A-5) The compound according to any one of (A-1) to (A-3), wherein $W^A$ is tetrazole.

A diazepinedione derivative of the aforementioned general formula (IA), or a pharmacologically acceptable salt thereof.

(A-6) The compound according to any one of (A-1) to (A-5), wherein $R^{1A}$ is hydrogen atom, or an alkyl group having 1 to 8 carbon atoms.

(A-7) The compound according to any one of (A-1) to (A-6), wherein $R^{1A}$ is hydrogen atom.

(A-8) The compound according to any one of (A-1) to (A-7), wherein $R^{4A}$ is hydrogen atom, and $R^{5A}$ is hydrogen atom, or an alkyl group having 1 to 8 carbon atoms.

(A-9) The compound according to any one of (A-1) to (A-8), wherein both $R^{4A}$ and $R^{5A}$ are hydrogen atoms.

(A-10) The compound according to any one of (A-1) to (A-9), wherein $R^{2A}$ is hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, carboxyl group, an acyl group having 2 to 8 carbon atoms, or an alkoxycarbonyl group (the alkoxy moiety thereof has 1 to 8 carbon atoms).

(A-11) The compound according to any one of (A-1) to (A-10), wherein $R^{2A}$ is hydrogen atom.

(A-12) The compound according to any one of (A-1) to (A-11), wherein $R^{3A}$ is hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, carboxyl group, an acyl group having 2 to 8 carbon atoms, or an alkoxycarbonyl group (the alkoxy moiety thereof has 1 to 8 carbon atoms).

(A-13) The compound according to any one of (A-1) to (A-12), wherein $R^{3A}$ is hydrogen atom.

Typical compounds falling within the scope of the general formula (IA) are mentioned below.

<Typical Compound IA-1>

[Formula 2]

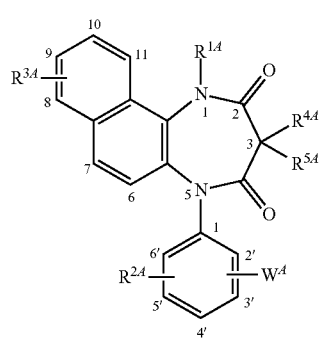

(IA)

(In the formula, $R^{2A}$ and $R^{3A}$ represent hydrogen atom, and $R^{1A}$, $R^{4A}$, $R^{5A}$, and $W^A$ as well as the substitution position of $W^A$ are as shown in Tables 1 to 3)

TABLE 1

| $R^{1A}$ | Substitution position of $W^A$ | $W^A$ | $R^{4A}/R^{5A}$ |
|---|---|---|---|
| H | 2- | 1H-Tetrazol-5-yl | H/H |
| H | 3- | 1H-Tetrazol-5-yl | H/H |
| H | 3- | (1-Methyl-1H-tetrazol)-5-yl | H/H |
| H | 4- | 1H-Tetrazol-5-yl | H/H |
| Me | 3- | 1H-Tetrazol-5-yl | H/H |
| Me | 3- | 1H-Tetrazol-5-yl | Me/H |
| Bn | 3- | 1H-Tetrazol-5-yl | H/H |
| H | 3- | 1H-Tetrazol-1-yl | H/H |
| H | 3- | 1H-Tetrazol-1-yl | Me/Me |
| H | 3- | (1,2,3-Triazol)-5-yl | H/H |
| H | 3- | (1,2,4-Triazol)-3-yl | H/H |
| H | 4- | (1,2,4-Triazol)-3-yl | H/H |

TABLE 2

| $R^{1A}$ | Substitution position of $W^A$ | $W^A$ | $R^{4A}/R^{5A}$ |
|---|---|---|---|
| H | 2- | (1,2,4-Triazol)-1-yl | H/H |
| H | 3- | (1,2,4-Triazol)-1-yl | H/H |
| H | 3- | [5-(Trifluoromethyl)-1,2,4-triazol]-3-yl | H/H |
| H | 3- | [5-(Trifluoromethyl)-1,2,4-triazol]-3-yl | Et/H |
| H | 3- | [5-Fluoro-1,2,3-triazol]-4-yl | H/H |
| H | 3- | [5-Fluoro-1,2,3-triazol]-4-yl | Me/Me |
| H | 3- | [5-Cyano-1,2,3-triazol]-4-yl | H/H |
| H | 4- | 1H-Imidazol-1-yl | H/H |
| H | 4- | 1H-Imidazol-1-yl | Pr/H |
| H | 3- | 1H-Imidazol-2-yl | H/H |
| H | 3- | 1H-Imidazol-4-yl | H/H |
| H | 3- | Imidazolin-2-yl | H/H |

TABLE 3

| $R^{1A}$ | Substitution position of $W^A$ | $W^A$ | $R^{4A}/R^{5A}$ |
|---|---|---|---|
| H | 2- | Pyrazol-3-yl | H/H |
| H | 3- | Pyrazol-4-yl | H/H |
| H | 3- | Pyrazol-5-yl | Me/H |
| H | 3- | (1,2,4-Oxadiazol)-3-yl | H/H |
| H | 3- | (1,3,4-Oxadiazol)-2-yl | H/H |
| H | 3- | (5-Oxo-1,2,4-oxadiazol)-3-yl | H/H |
| H | 3- | Pyrrol-1-yl | H/H |
| H | 4- | Pyrrolidin-2-yl | H/H |
| Me | 4- | Pyrrolidin-2-yl | Me/H |
| H | 4- | (1,3-Oxazol)-5-yl | H/H |
| H | 3- | (1,3-Oxazol)-5-yl | H/H |
| H | 2- | (1,3-Thiazol)-5-yl | H/H |

<Typical Compound IA-2>

[Formula 3]

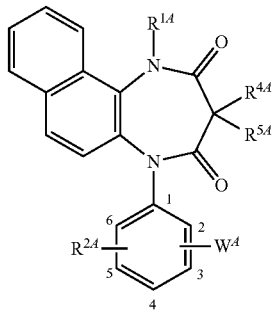

(In the formula, $R^{1A}$, $R^{2A}$, $R^{4A}$, $R^{5A}$, and $W^A$ as well as the substitution position of $W^A$ are as shown in Table 4.)

TABLE 4

| $R^{1A}$ | $R^{2A}$ | Substitution position of $W^A$ | $W^A$ | $R^{4A}/R^{5A}$ |
|---|---|---|---|---|
| H | 4-OH | 3- | 1H-Tetrazol-5-yl | H/H |
| H | 4-OMe | 3- | 1H-Tetrazol-5-yl | H/H |
| Me | 2-Cl | 3- | 1H-Tetrazol-5-yl | H/H |
| H | 2,6-Cl | 3- | 1H-Tetrazol-5-yl | H/H |
| H | 4-F | 3- | 1H-Tetrazol-5-yl | H/H |
| H | 4-Br | 3- | 1H-Tetrazol-5-yl | Et/H |
| H | 3-OMe | 4- | (1-Methyl-1H-tetrazol)-5-yl | H/H |
| H | 4-Me | 3- | 1H-Tetrazol-5-yl | H/H |
| H | 4-Cl | 3- | (1,2,3-Triazol)-5-yl | Me/H |
| H | 4-CF$_3$ | 3- | (1,2,3-Triazol)-5-yl | H/H |
| H | 3-SMe | 4- | (1,2,4-Triazol)-1-yl | H/H |
| H | 3-SO$_2$Me | 4- | 1H-Imidazol-1-yl | H/H |
| H | 3-NHSO$_2$Me | 4- | 1H-Imidazol-1-yl | H/H |
| H | 4-OMe | 3- | 1H-Imidazol-4-yl | H/H |
| H | 4-F | 2- | Pyrazol-3-yl | H/H |

<Typical Compound IA-3>

[Formula 4]

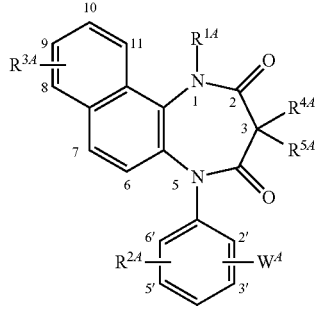

(In the formula, $R^{1A}$, $R^{2A}$, $R^{3A}$, $R^{4A}$, $R^{5A}$, and $W^A$ as well as the substitution position of $W^A$ are as shown in Tables 5 and 6.)

TABLE 5

| $R^{1A}$ | $R^{2A}$ | Substitution position of $W^A$ | $W^A$ | $R^{3A}$ | $R^{4A}/R^{5A}$ |
|---|---|---|---|---|---|
| H | H | 3- | 1H-Tetrazol-5-yl | 9-Br | H/H |
| H | 4-OMe | 3- | 1H-Tetrazol-5-yl | 9-Cl | H/H |
| H | 4-OH | 3- | 1H-Tetrazol-5-yl | 10-OMe | H/H |
| H | 2-Cl | 3- | 1H-Tetrazol-5-yl | 9-Br | H/H |
| H | 2,6-Cl | 3- | 1H-Tetrazol-5-yl | 9-Me | H/H |
| H | H | 3- | 1H-Tetrazol-5-yl | 10-Cl | Me/H |
| H | 3-OMe | 4- | (1-Methyl-1H-tetrazol)-5-yl | 9-CF$_3$ | H/H |

TABLE 6

| $R^{1A}$ | $R^{2A}$ | Substitution position of $W^A$ | $W^A$ | $R^{3A}$ | $R^{4A}/R^{5A}$ |
|---|---|---|---|---|---|
| H | 4-Me | 3- | 1H-Tetrazol-1-yl | 9-CN | Pr/H |
| Me | H | 3- | (1,2,3-Triazol)-5-yl | 9-OH | H/H |
| Et | H | 3- | (1,2,3-Triazol)-5-yl | 10-F | H/H |
| H | 3-Br | 4- | (1,2,4-Triazol)-1-yl | 9-SMe | H/H |
| Allyl | H | 4- | 1H-Imidazol-1-yl | 8-OMe | H/H |
| H | H | 3- | 1H-Imidazol-1-yl | 10-OMe | Me/Me |

(B-1) A compound represented by the following general formula (IB):

[Formula 5]

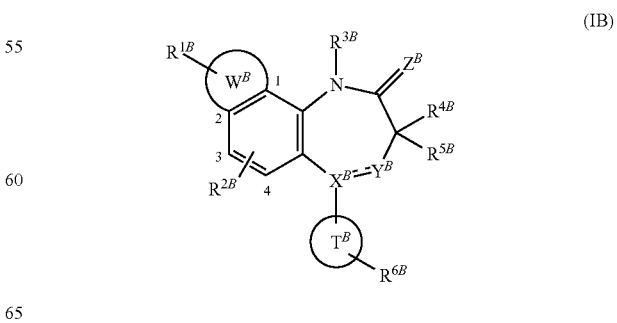

wherein, in the formula, $R^{1B}$ and $R^{2B}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, or sulfamoyl group, $R^{3B}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, or an alkyl group having 1 to 3 carbon atoms and substituted with phenyl group, $R^{4B}$ and $R^{5B}$ may be the same or different, and represent hydrogen atom, an alkyl group having 1 to 8 carbon atoms, an alkyl group having 1 to 8 carbon atoms and substituted with 1 to 3 halogen atoms, a halogen atom, hydroxyl group, nitro group, cyano group, amino group, or an alkyl group having 1 to 3 carbon atoms and substituted with phenyl group, $R^{6B}$ represents hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, sulfamoyl group, a phenyl group which may have a substituent, or a heterocyclic group which may have a substituent,

[Formula 6]

represents a 5- to 8-membered non-aromatic ring, which may contain 1 or 2 heteroatoms selected from N, S, and O as ring-constituting elements, and condenses at the 1- and 2-positions of the benzene ring,

[Formula 7]

represents an aromatic ring selected from benzene ring, naphthalene ring, thiophene ring, pyridine ring, pyrimidine ring, indole ring, indazole ring, benzotriazole ring, benzisoxazole ring, benzimidazole ring, and quinoline ring, $Z^B$ represents O or S, when $X^B$ is N, $Y^B$ represents C=O or C=S, and the double line consisting of the solid line and the broken line represents a single bond, and when $X^B$ is C, $Y^B$ represents N, and the double line consisting of the solid line and the wavy line represents a double bond.

(B-2) A compound represented by the following general formula (IIB):

[Formula 8]

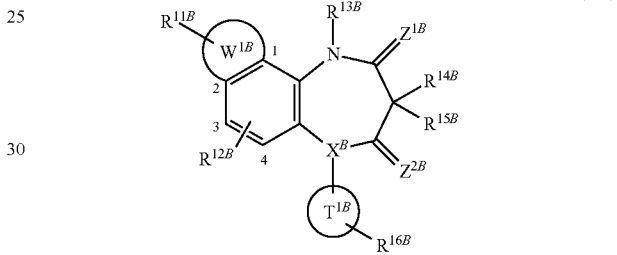

(IIB)

wherein, in the formula, $R^{11B}$ and $R^{12B}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, or sulfamoyl group, $R^{13B}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, or an alkyl group having 1 to 3 carbon atoms and substituted with phenyl group, $R^{14B}$ and $R^{15B}$ may be the same or different, and represent hydrogen atom, an alkyl group having 1 to 8 carbon atoms, an alkyl group having 1 to 8 carbon atoms and substituted with 1 to 3 halogen atoms, a halogen atom, hydroxyl group, nitro group, cyano group, amino group, or an alkyl group having 1 to 3 carbon atoms and substituted with phenyl group, $R^{16B}$ represents hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, sulfamoyl group, a phenyl group which may have a substituent, or a heterocyclic group which may have a substituent,

[Formula 9]

represents a 5- to 8-membered non-aromatic ring which may contain 1 or 2 heteroatoms selected from N, S, and O as ring-constituting elements, and condenses at the 1- and 2-positions of the benzene ring,

[Formula 10]

represents an aromatic ring selected from benzene ring, naphthalene ring, thiophene ring, pyridine ring, pyrimidine ring, indole ring, indazole ring, benzotriazole ring, benzisoxazole ring, benzimidazole ring, and quinoline ring, and $Z^{1B}$ and $Z^{2B}$ may be the same or different, and represent O or S.

(B-3) A compound represented by the following general formula (IIIB),

[Formula 11]

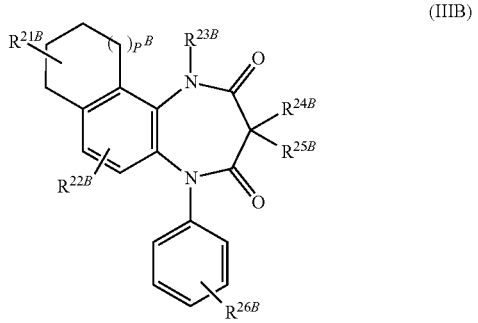

(IIIB)

wherein, in the formula, $R^{21B}$ and $R^{22B}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, or sulfamoyl group, $R^{23B}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, or an alkyl group having 1 to 3 carbon atoms and substituted with phenyl group, $R^{24B}$ and $R^{25B}$ may be the same or different, and represent hydrogen atom, an alkyl group having 1 to 8 carbon atoms, an alkyl group having 1 to 8 carbon atoms and substituted with 1 to 3 halogen atoms, a halogen atom, hydroxyl group, nitro group, cyano group, amino group, or an alkyl group having 1 to 3 carbon atoms and substituted with phenyl group, $R^{26B}$ represents hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, sulfamoyl group, a phenyl group which may have a substituent, or a heterocyclic group which may have a substituent, and $p^B$ represents 0 or 1.

As for the aforementioned general formulas (IB), (IIB), and (IIIB), examples of the alkyl group having 1 to 8 carbon atoms as $R^{1B}$, $R^{2B}$, $R^{3B}$, $R^{4B}$, $R^{5B}$, and $R^{6B}$ include methyl group, ethyl group, propyl group, isopropyl group, butyl group, i-butyl group, t-butyl group, pentyl group, hexyl group, and the like.

Examples of the alkenyl group having 2 to 8 carbon atoms as $R^{1B}$, $R^{2B}$, $R^{3B}$, and $R^{6B}$ include allyl group, and the like.

Examples of the alkyl group having 1 to 8 carbon atoms and substituted with 1 to 3 halogen atoms as $R^{1B}$, $R^{2B}$, $R^{3B}$, $R^{4B}$, $R^{5B}$, and $R^{6B}$ include methyl group, ethyl group, propyl group, isopropyl group, butyl group, and t-butyl group substituted with 1 to 3 halogen atoms such as fluorine atom, chlorine atom, and bromine atom, and the like, and preferred examples of the same include trifluoromethyl group, chloromethyl group, 2-chloroethyl group, 2-bromoethyl group, 2-fluoroethyl group, and the like.

Examples of the alkyl group having 1 to 3 carbon atoms and substituted with phenyl group as $R^{3B}$, $R^{4B}$, and $R^{5B}$ include benzyl group, and the like.

Examples of the alkoxy group having 1 to 8 carbon atoms as $R^{1B}$, $R^{2B}$, and $R^{6B}$ include methoxy group, ethoxy group, propoxy group, isopropoxy group, butoxy group, i-butoxy group, t-butoxy group, pentyloxy group, hexyloxy group, and the like.

Examples of the alkoxy group having 1 to 8 carbon atoms and substituted with 1 to 3 halogen atoms as $R^{1B}$, $R^{2B}$, and $R^{6B}$ include methoxy group, ethoxy group, propoxy group, isopropoxy group, butoxy group, t-butoxy group substituted with 1 to 3 halogen atoms such as fluorine atom, chlorine atom, and bromine atom, and the like, and preferred examples of the same include trifluoromethoxy group, chloromethoxy group, 2-chloroethoxy group, 2-bromoethoxy group, 2-fluoroethoxy group, and the like.

Examples of the halogen atom as as $R^{1B}$, $R^{2B}$, $R^{4B}$, $R^{5B}$, and $R^{6B}$ include fluorine atom, chlorine atom, bromine atom, and the like.

Examples of the alkylamino group having 1 to 8 carbon atoms as $R^{1B}$, $R^{2B}$, and $R^{6B}$ include methylamino group, ethylamino group, and the like.

Examples of the dialkylamino group having 2 to 8 carbon atoms as $R^{1B}$, $R^{2B}$, and $R^{6B}$ include dimethylamino group, diethylamino group, and the like.

Examples of the acylamino group having 2 to 8 carbon atoms as $R^{1B}$, $R^{2B}$, and $R^{6B}$ include acetylamino group.

Examples of the acylamino group having 2 to 8 carbon atoms and substituted with 1 to 3 halogen atoms as $R^{1B}$, $R^{2B}$, and $R^{6B}$ include trifluoromethylcarbonylamino group.

Examples of the alkylsulfonylamino group having 1 to 8 carbon atoms as $R^{1B}$, $R^{2B}$, and $R^{6B}$ include methylsulfonylamino group.

Examples of the acyl group having 2 to 8 carbon atoms as $R^{1B}$, $R^{2B}$, and $R^{6B}$ include acetyl group.

Examples of the alkoxycarbonyl group (the alkoxy moiety thereof has 1 to 8 carbon atoms) as $R^{1B}$, $R^{2B}$, and $R^{6B}$ include methoxycarbonyl group, ethoxycarbonyl group, and the like.

Examples of the alkylthio group having 1 to 8 carbon atoms as $R^{1B}$, $R^{2B}$, and $R^{6B}$ include methylthio group.

Examples of the alkylsulfinyl group having 1 to 8 carbon atoms as $R^{1B}$, $R^{2B}$, and $R^{6B}$ include methylsulfinyl group.

Examples of the alkylsulfonyl group having 1 to 8 carbon atoms as $R^{1B}$, $R^{2B}$, and $R^{6B}$ include methylsulfonyl group.

Preferred examples of the substituent of the phenyl group which may have a substituent as $R^{6B}$ include an alkyl group having 1 to 8 carbon atoms such as methyl group and ethyl group, an alkyl group having 1 to 8 carbon atoms and substituted with 1 to 3 halogen atoms such as trifluoromethyl group, a halogen atom such as fluorine atom, cyano group, and the like.

Preferred examples of the heterocyclic group of the heterocyclic group which may have a substituent as $R^{6B}$ include tetrazolyl group, triazolyl group, pyridyl group, imidazolyl group, oxazolyl group, thiazolyl group, and the like, and it may also be oxadiazole group.

Preferred examples of the substituent of the heterocyclic ring which may have a substituent as $R^{6B}$ include an alkyl group having 1 to 8 carbon atoms such as methyl group and ethyl group, an alkyl group having 1 to 8 carbon atoms and substituted with 1 to 3 halogen atoms such as trifluoromethyl group, a halogen atom such as fluorine atom, cyano group, oxo, and the like, and it may also be phenyl group.

Examples of

[Formula 12]

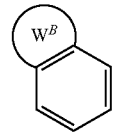

include tetrahydronaphthalene, indane, indoline, tetrahydroquinoline, tetrahydroisoquinoline, and the like.

In the aforementioned general formula (IB), a plurality of the same or different $R^{1B}$, $R^{2B}$, and $R^{6B}$ may exist on the rings on which $R^{1B}$, $R^{2B}$, and $R^{6B}$ substitute.

As for $R^{11B}$ to $R^{16B}$ in the aforementioned general formula (IIB), and $R^{21B}$ to $R^{26B}$ in the aforementioned general formula (IIIB), examples of the alkyl group having 1 to 8 carbon atoms, alkenyl group having 2 to 8 carbon atoms, alkyl group having 1 to 8 carbon atoms and substituted with 1 to 3 halogen atoms, alkyl group having 1 to 3 carbon atoms and substituted with phenyl group, alkoxy group having 1 to 8 carbon atoms, alkoxy group having 1 to 8 carbon atoms and substituted with 1 to 3 halogen atoms, halogen atom, alkylamino group having 1 to 8 carbon atoms, dialkylamino group having 1 to 8 carbon atoms, acylamino group having 2 to 8 carbon atoms, acylamino group having 2 to 8 carbon atoms and substituted with 1 to 3 halogen atoms, alkylsulfonylamino group having 1 to 8 carbon atoms, acyl group having 2 to 8 carbon atoms, alkoxycarbonyl group (the alkoxy moiety thereof has 1 to 8 carbon atoms), alkylthio group having 1 to 8 carbon atoms, alkylsulfinyl group having 1 to 8 carbon atoms, alkylsulfonyl group having 1 to 8 carbon atoms, phenyl group which may have a substituent, heterocyclic group which may have a substituent, and the like include those similar to the examples mentioned above for $R^{1B}$ to $R^{6B}$ in the general formula (IB).

Similarly, as for the heterocyclic group which may have a substituent as $R^{16B}$ in the general formula (IIB), and $R^{26B}$ in the general formula (IIIB), examples of the alkyl group having 1 to 8 carbon atoms, alkoxy group having 1 to 8 carbon atoms, alkyl group having 1 to 8 carbon atoms and substituted with 1 to 3 halogen atoms, alkoxy group having 1 to 8 carbon atoms and substituted with 1 to 3 halogen atoms, halogen atom, alkylamino group having 1 to 8 carbon atoms, and dialkylamino group having 2 to 8 carbon atoms as the substituent include those mentioned above for $R^{1B}$ to $R^{6B}$ in the general formula (IB).

Examples of

[Formula 13]

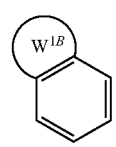

include tetrahydronaphthalene, indane, indoline, tetrahydroquinoline, tetrahydroisoquinoline, and the like.

In the aforementioned general formula (IIB), a plurality of the same or different $R^{11B}$, $R^{12B}$, and $R^{16B}$ may exist on the rings on which $R^{11B}$, $R^{12B}$, and $R^{16B}$ substitute.

In the aforementioned general formula (IIIB), a plurality of the same or different $R^{21B}$, $R^{22B}$, and $R^{26B}$ may exist on the rings on which $R^{21B}$, $R^{22B}$, and $R^{26B}$ substitute.

As compounds falling within the scope of the aforementioned general formula (IIB), the following compounds are preferred.

(B-2-1) The compound according to (B-2), wherein $R^{11B}$ is hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, a halogen atom, hydroxyl group, amino group, an alkylamino group having 1 to 8 carbon atoms, a dialkylamino group having 2 to 8 carbon atoms, or an acylamino group having 2 to 8 carbon atoms.

(B-2-2) The compound according to (B-2) or (B-2-1), wherein $R^{12B}$ is hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, or an acylamino group having 2 to 8 carbon atoms and substituted with 1 to 3 halogen atoms.

(B-2-3) The compound according to (B-2), or any one of (B-2-1) and (B-2-2), wherein $R^{13B}$ is hydrogen atom, an alkyl group having 1 to 8 carbon atoms, or an alkyl group having 1 to 8 carbon atoms and substituted with 1 to 3 halogen atoms.

(B-2-4) The compound according to (B-2), or any one of (B-2-1) to (B-2-3), wherein $R^{14B}$ and $R^{15B}$ may be the same or different, and are hydrogen atom, an alkyl group having 1 to 8 carbon atoms, or an alkyl group having 1 to 8 carbon atoms and substituted with 1 to 3 halogen atoms.

(B-2-5) The compound according to (B-2), or any one of (B-2-1) to (B-2-4), wherein $R^{16B}$ is hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, or a heterocyclic group which may have a substituent.

(B-2-6) The compound according to (B-2), or any one of (B-2-1) to (B-2-5), wherein $R^{16B}$ is a tetrazolyl group, triazolyl group, pyridyl group, pyrazolyl group, oxadiazolyl group, isoxazolyl group, pyrrolyl group, pyrrolidinyl group, imidazolyl group, oxazolyl group, or thiazolyl group which may have a substituent selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(B-2-7) The compound according to (B-2), or any one of (B-2-1) to (B-2-6), wherein $R^{16B}$ is a tetrazolyl group, triazolyl group, pyridyl group, imidazolyl group, oxazolyl group, or thiazolyl group which may have a substituent selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, cyano group, and amino group.

(B-2-8) The compound according to (B-2), or any one of (B-2-1) to (B-2-7), wherein

[Formula 14]

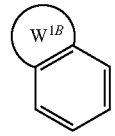

is tetrahydronaphthalene, indane, indoline, tetrahydroquinoline, or tetrahydroisoquinoline.

(B-2-9) The compound according to (B-2), or any one of (B-2-1) to (B-2-8), wherein

[Formula 15]

is a benzene ring.

(B-2-10) The compound according to (B-2), or any one of (B-2-1) to (B-2-9), wherein both $Z^{1B}$ and $Z^{2B}$ are O.

As the compounds of the general formula (IIIB), the compounds mentioned below are preferred.

(B-3-1) The compound according to (B-3), wherein $R^{21B}$ is hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, a halogen atom, hydroxyl group, amino group, an alkylamino group having 1 to 8 carbon atoms, a dialkylamino group having 2 to 8 carbon atoms, or an acylamino group having 2 to 8 carbon atoms.

(B-3-2) The compound according to (B-3) or (B-3-1), wherein $R^{22B}$ is hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, or an acylamino group having 2 to 8 carbon atoms and substituted with 1 to 3 halogen atoms.

(B-3-3) The compound according to (B-3), (B-3-1), or (B-3-2), wherein $R^{23B}$ is hydrogen atom, an alkyl group having 1 to 8 carbon atoms, or an alkyl group having 1 to 8 carbon atoms and substituted with 1 to 3 halogen atoms.

(B-3-4) The compound according to (B-3), or any one of (B-3-1) to (B-3-3), wherein $R^{24B}$, and $R^{25B}$ may be the same or different, and are hydrogen atom, an alkyl group having 1 to 8 carbon atoms, or an alkyl group having 1 to 8 carbon atoms and substituted with 1 to 3 halogen atoms.

(B-3-5) The compound according to (B-3), or any one of (B-3-1) to (B-3-4), wherein $R^{26B}$ is hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, or a heterocyclic group which may have a substituent.

(B-3-6) The compound according to (B-3), or any one of (B-3-1) to (B-3-5), wherein $R^{26B}$ is a tetrazolyl group, triazolyl group, pyridyl group, pyrazolyl group, oxadiazolyl group, isoxazolyl group, pyrrolyl group, pyrrolidinyl group, imidazolyl group, oxazolyl group, or thiazolyl group which may have a substituent selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(B-3-7) The compound according to (B-3), or any one of (B-3-1) to (B-3-6), wherein $R^{16B}$ is a tetrazolyl group, triazolyl group, pyridyl group, imidazolyl group, oxazolyl group, or thiazolyl group which may have a substituent selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, cyano group, and amino group.

$R^{3B}$ in the general formula (IB), $R^{13B}$ in the general formula (IB), and $R^{23B}$ in the general formula (IIIB) may be an acyl group having 2 to 8 carbon atoms such as acetyl.

$R^{6B}$ in the general formula (IB), $R^{16B}$ in the general formula (IIB), and $R^{26B}$ in the general formula (IIIB) may be an alkoxycarbonylamino group having 3 to 8 carbon atoms such as tert-butoxycarbonylamino group.

Further,

[Formula 16]

in the general formula (IB), and

[Formula 17]

in the general formula (IIB) may be 2,3-dihydrobenzo[1,4]dioxine.

Typical compounds falling within the scope of the general formula (IB) are mentioned below.

<Typical Compound IB-1>

[Formula 18]

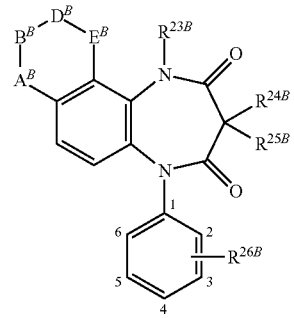

(In the formula, $A^B$-$B^B$-$D^B$-$E^B$, $R^{23B}$, $R^{24B}/R^{25B}$, and $R^{26B}$ are as shown in Tables 7 to 9.)

TABLE 7

| $A^B$-$B^B$-$D^B$-$E^B$ | $R^{23B}$ | $R^{24B}/R^{25B}$ | $R^{26B}$ |
|---|---|---|---|
| $CH_2CH_2CH_2CH_2$ | H | H/H | 3-CN |
| $CH_2CH_2CH_2CH_2$ | H | H/H | 3-OH |
| $CH_2CH_2CH_2CH_2$ | H | H/H | 3-$CO_2$H |
| $CH_2CH_2CH_2CH_2$ | H | H/H | 3-$CONH_2$ |
| $C(CH_3)_2CH_2CH_2CH_2$ | H | H/H | 3,4-OMe |
| $CH_2C(CH_3)_2CH_2CH_2$ | Me | H/H | 3,4-OMe |
| $CH_2CH_2C(CH_3)_2CH_2$ | Et | H/H | 3-OH, 4-F |
| $CH_2CH_2CH_2CH_2$ | H | H/H | 3-$NH_2$ |
| $NHCH_2CH_2CH_2$ | H | H/H | 3-NHMe |
| $NMeCH_2CH_2CH_2$ | H | H/H | 3-$CF_3$ |
| $OCH_2CH_2O$ | H | H/H | 3-$NHCH_2CF_3$ |
| $OCH_2CH_2O$ | Me | H/H | 2-OH, 3-OH |
| $C(CH_3)_2CH_2CH_2C(CH_3)_2$ | Et | H/H | 3,4,5-Me |

TABLE 8

| $A^B$-$B^B$-$D^B$-$E^B$ | $R^{23B}$ | $R^{24B}/R^{25B}$ | $R^{26B}$ |
|---|---|---|---|
| $CH_2CH_2CH_2CH_2$ | H | Me/H | 4-OH |
| $CH_2CH_2CH_2CH_2$ | H | Me/Me | 4-$NH_2$ |
| $CH_2CH_2CH_2CH_2$ | H | Pr/H | 4-$NO_2$ |
| $C(CH_3)_2CH_2CH_2CH_2$ | H | H/H | 4-CN |
| $CH_2C(CH_3)_2CH_2CH_2$ | Me | $CF_3$/H | 4-Ph |
| $CH_2CH_2C(CH_3)_2CH_2$ | Et | H/H | 4-$CH_2OH$ |
| $CH_2CH_2CH_2CH_2$ | H | H/H | 3-$CH_2OH$ |
| $NHCH_2CH_2CH_2$ | H | H/H | 3-Ac |
| $NMeCH_2CH_2CH_2$ | H | H/H | 3,5-OMe |
| $OCH_2CH_2O$ | H | H/H | 3-OH, 4-$NH_2$ |
| $OCH_2CH_2O$ | Me | H/H | 3-$CH_2NH_2$ |
| $C(CH_3)_2CH_2CH_2C(CH_3)_2$ | Et | H/H | 3-$SO_2CH_3$ |
| $CH_2CH_2CH_2CH_2$ | H | Me/H | 3-iPr |
| $CH_2CH_2CH_2CH_2$ | H | Me/H | 3-$NMe_2$ |

TABLE 9

| $A^B$-$B^B$-$D^B$-$E^B$ | $R^{23B}$ | $R^{24B}/R^{25B}$ | $R^{26B}$ |
|---|---|---|---|
| CH$_2$CH$_2$CH$_2$CH$_2$ | H | Me/H | 3-Ac |
| C(CH$_3$)$_2$CH$_2$CH$_2$CH$_2$ | H | Pr/H | 3,4-NH$_2$ |
| CH$_2$C(CH$_3$)$_2$CH$_2$CH$_2$ | H | H/H | NHMe |
| CH$_2$CH$_2$C(CH$_3$)$_2$CH$_2$ | Et | H/H | 3-NHCH$_2$CF$_3$ |
| CH$_2$CH$_2$CH$_2$CH$_2$ | H | H/H | 3-NHAc |
| NHCH$_2$CH$_2$CH$_2$ | H | H/H | 3-SO$_2$Me |
| NMeCH$_2$CH$_2$CH$_2$ | H | H/H | 4-Me |
| OCH$_2$CH$_2$O | H | H/H | 4-iPr |
| OCH$_2$CH$_2$O | Me | H/H | 3-Ph |
| C(CH$_3$)$_2$CH$_2$CH$_2$C(CH$_3$)$_2$ | Et | H/H | 3-F, 4-OH |
| CH$_2$CH$_2$CH$_2$CH$_2$ | Ac | H/H | 3-F, 4-OMe |
| CH$_2$CH$_2$CH$_2$CH$_2$ | H | Me/H | 4-NHEt |

<Typical Compound IB-2>

[Formula 19]

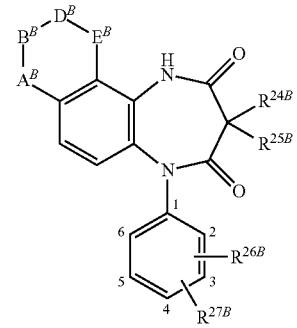

(In the formula, $A^B$-$B^B$-$D^B$-$E^B$, $R^{24B}/R^{25B}$, $R^{26B}$, and $R^{27B}$ are as shown in Tables 10 to 12, and "Position" in the tables means the substitution position of $R^{26B}$.)

TABLE 10

| $A^B$-$B^B$-$D^B$-$E^B$ | $R^{24B}/R^{25B}$ | Position | $R^{26B}$ | $R^{27B}$ |
|---|---|---|---|---|
| CH$_2$CH$_2$CH$_2$CH$_2$ | H/H | 3 | 1H-Tetrazol-5-yl | H |
| C(CH$_3$)$_2$CH$_2$CH$_2$CH$_2$ | H/H | 3 | 1H-Tetrazol-5-yl | H |
| C(CH$_3$)$_2$CH$_2$CH$_2$CH$_2$ | H/H | 3 | 1H-Tetrazol-1-yl | 4-F |
| C(CH$_3$)$_2$CH$_2$CH$_2$C(CH$_3$)$_2$ | H/H | 3 | 2-Methyl-2H-tetrazol-5-yl | 3-F |
| CH$_2$CH$_2$C(CH$_3$)$_2$CH$_2$ | H/H | 3 | 1,2,3-Triazol-5-yl | 2-F |
| CH$_2$CH$_2$CH$_2$CH$_2$ | H/H | 3 | 1,2,4-Triazol-3-yl | H |
| NHCH$_2$CH$_2$CH$_2$ | H/H | 3 | 5-(Trifluoromethyl)-1,2,4-triazol-3-yl | H |
| NMeCH$_2$CH$_2$CH$_2$ | H/H | 4 | 1H-Imidazol-1-yl | H |
| OCH$_2$CH$_2$O | H/H | 4 | 1H-Imidazol-2-yl | H |
| OCH$_2$CH$_2$O | H/H | 3 | 5-Cyano-1H-1,2,3-triazol-4-yl | H |
| C(CH$_3$)$_2$CH$_2$CH$_2$C(CH$_3$)$_2$ | H/H | 3 | 1-Methyl-1H-tetrazol-5-yl | H |
| CH$_2$CH$_2$CH$_2$CH$_2$ | Me/H | 3 | Pyrazol-3-yl | 4-OH |
| CH$_2$CH$_2$CH$_2$CH$_2$ | Me/Me | 3 | Pyrazol-4-yl | H |

TABLE 11

| $A^B$-$B^B$-$D^B$-$E^B$ | $R^{24B}/R^{25B}$ | Position | $R^{26B}$ | $R^{27B}$ |
|---|---|---|---|---|
| C(CH$_3$)$_2$CH$_2$CH$_2$CH$_2$ | H/H | 3 | 5-Oxo-1,2,4-oxadiazol-3-yl | 4-NH$_2$ |
| CH$_2$C(CH$_3$)$_2$CH$_2$CH$_2$ | CF$_3$/H | 3 | 1,2,4-Oxadiazol-3-yl | H |
| CH$_2$CH$_2$C(CH$_3$)$_2$CH$_2$ | H/H | 3 | 1,3,4-Oxadiazol-2-yl | 4-F |
| CH$_2$CH$_2$CH$_2$CH$_2$ | H/H | 4 | Pyrrol-1-yl | 3-F |
| NHCH$_2$CH$_2$CH$_2$ | H/H | 4 | Pyrrolidin-2-yl | H |
| NMeCH$_2$CH$_2$CH$_2$ | H/H | 2 | 1,3-Oxazol-5-yl | H |
| OCH$_2$CH$_2$O | H/H | 3 | 1,3-Thiazol-5-yl | H |
| OCH$_2$CH$_2$O | H/H | 3 | 5-(Trifluoromethyl)-1H-imidazol-2-yl | H |
| C(CH$_3$)$_2$CH$_2$CH$_2$C(CH$_3$)$_2$ | H/H | 3 | 5-Chloro-1H-imidazol-2-yl | 4-OH |

TABLE 12

| $A^B$-$B^B$-$D^B$-$E^B$ | $R^{24B}/R^{25B}$ | Position | $R^{26B}$ | $R^{27B}$ |
|---|---|---|---|---|
| CH$_2$CH$_2$CH$_2$CH$_2$ | Me/H | 4 | 5-Methyl-1H-imidazol-2-y | 4-NH$_2$ |
| CH$_2$CH$_2$CH$_2$CH$_2$ | Me/H | 4 | 5-Amino-1H-imidazol-2-y | 3-F |
| CH$_2$CH$_2$CH$_2$CH$_2$ | Me/H | 3 | 2-Ethyl-2H-tetrazol-5-yl | H |

TABLE 12-continued

| $A^B$-$B^B$-$D^B$-$E^B$ | $R^{24B}/R^{25B}$ | Position | $R^{26B}$ | $R^{27B}$ |
|---|---|---|---|---|
| C(CH$_3$)$_2$CH$_2$CH$_2$CH$_2$ | Pr/H | 3 | 2-(2,2,2-Trifluoroethyl)-2H-tetrazol-5-yl | 2,6-F |
| CH$_2$C(CH$_3$)$_2$CH$_2$CH$_2$ | H/H | 3 | 1,3-Oxazol-2-yl | H |
| CH$_2$CH$_2$C(CH$_3$)$_2$CH$_2$ | H/H | 3 | 1,3-Thiazol-2-yl | H |
| CH$_2$CH$_2$CH$_2$CH$_2$ | H/H | 4 | 3,5-Dimethylisoxazol-4-yl | H |
| NH$_2$CH$_2$CH$_2$NH | H/H | 3 | 3-Methyl-1,2,4-oxadiazol-5-yl | H |

<Typical Compound IB-3>

[Formula 20]

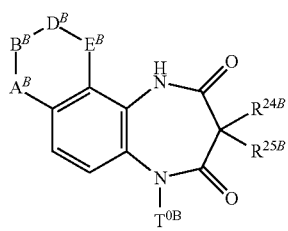

(In the formula, $A^B$-$B^B$-$D^B$-$E^B$, $R^{24B}/R^{25B}$, and $T^{0B}$ are as shown in Tables 13 to 15.)

TABLE 13

| $A^B$-$B^B$-$D^B$-$E^B$ | $R^{24B}/R^{25B}$ | $T^{0B}$ |
|---|---|---|
| CH$_2$CH$_2$CH$_2$CH$_2$ | H/H | Pyrimidin-2-yl |
| C(CH$_3$)$_2$CH$_2$CH$_2$CH$_2$ | H/H | Pyrimidin-5-yl |
| CH$_2$C(CH$_3$)$_2$CH$_2$CH$_2$ | H/H | Pyridin-2-yl |
| CH$_2$CH$_2$C(CH$_3$)$_2$CH$_2$ | H/H | Pyridin-3-yl |
| CH$_2$CH$_2$CH$_2$CH$_2$ | H/H | Pyridin-4-yl |
| NHCH$_2$CH$_2$CH$_2$ | Me/H | Thiophen-2-yl |
| NMeCH$_2$CH$_2$CH$_2$ | H/H | Thiophen-3-yl |
| OCH$_2$CH$_2$O | H/H | Thiophen-3-yl |
| OCH$_2$CH$_2$O | H/H | 5-Hydroxypyridin-3-yl |
| C(CH$_3$)$_2$CH$_2$CH$_2$C(CH$_3$)$_2$ | H/H | 5-Methoxypyridin-3-yl |
| CH$_2$CH$_2$CH$_2$CH$_2$ | F/H | 5-Aminopyridin-3-yl |
| CH$_2$CH$_2$CH$_2$CH$_2$ | Me/Me | 5-Chloropyridin-3-yl |
| CH$_2$CH$_2$CH$_2$CH$_2$ | Pr/H | 6-Chloropyridin-3-yl |

TABLE 14

| $A^B$-$B^B$-$D^B$-$E^B$ | $R^{24B}/R^{25B}$ | $T^{0B}$ |
|---|---|---|
| CH$_2$CH$_2$CH$_2$CH$_2$ | Pr/H | 6-Chloropyridin-3-yl |
| CH$_2$CH$_2$CH$_2$CH$_2$ | H/H | 1H-Indazol-6-yl |
| C(CH$_3$)$_2$CH$_2$CH$_2$CH$_2$ | H/H | 1H-Indazol-5-yl |
| CH$_2$C(CH$_3$)$_2$CH$_2$CH$_2$ | H/H | 1H-Indazol-4-yl |
| CH$_2$CH$_2$C(CH$_3$)$_2$CH$_2$ | H/H | 1H-Benzotriazol-6-yl |
| C(CH$_3$)$_2$CH$_2$CH$_2$CH$_2$ | H/H | 1H-Benzotriazol-4-yl |
| CH$_2$CH$_2$CH$_2$CH$_2$ | H/H | 1H-Benzimidazol-6-yl |
| CH$_2$C(CH$_3$)$_2$CH$_2$CH$_2$ | H/H | 1H-Indazol-4-yl |
| CH$_2$C(CH$_3$)$_2$CH$_2$CH$_2$ | H/H | 1H-Indol-6-yl |
| C(CH$_3$)$_2$CH$_2$CH$_2$CH$_2$ | H/H | 1H-Indol-5-yl |
| C(CH$_3$)$_2$CH$_2$CH$_2$CH$_2$ | H/H | 1H-Indol-4-yl |
| CH$_2$C(CH$_3$)$_2$CH$_2$CH$_2$ | H/H | Benzisoxazol-6-yl |
| C(CH$_3$)$_2$CH$_2$CH$_2$CH$_2$ | H/H | 1H-Benzimidazol-5-yl |

TABLE 15

| $A^B$-$B^B$-$D^B$-$E^B$ | $R^{24B}/R^{25B}$ | $T^{0B}$ |
|---|---|---|
| C(CH$_3$)$_2$CH$_2$CH$_2$CH$_2$ | H/H | 1H-Benzimidazol-6-yl |
| CH$_2$C(CH$_3$)$_2$CH$_2$CH$_2$ | H/H | 2-(Trifluoromethyl)-1H-benzimidazol-5-yl |
| CH$_2$CH$_2$CH$_2$CH$_2$ | H/H | Quinolin-5-yl |
| C(CH$_3$)$_2$CH$_2$CH$_2$CH$_2$ | H/H | Quinolin-8-yl |

<Typical Compound IB-4>

[Formula 21]

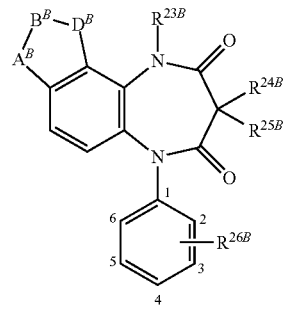

(In the formula, $A^B$-$B^B$-$D^B$, $R^{23B}$, $R^{24B}/R^{25B}$, and $R^{26B}$ are as shown in Tables 16 to 18.)

TABLE 16

| $A^B$-$B^B$-$D^B$ | $R^{23B}$ | $R^{24B}/R^{25B}$ | $R^{26B}$ |
|---|---|---|---|
| CH$_2$CH$_2$CH$_2$ | H | H/H | 3-CN |
| CH$_2$CH$_2$CH$_2$ | H | H/H | 3-OH |
| CH$_2$CH$_2$CH$_2$ | H | H/H | 3-CO$_2$H |
| CH$_2$CH$_2$CH$_2$ | H | H/H | 3-CONH$_2$ |
| OCH$_2$O | H | H/H | 3,4-OMe |
| OCH$_2$O | Me | H/H | 3,4-OMe |
| OCH$_2$O | Et | H/H | 3-OH, 4-F |
| OCH$_2$O | H | H/H | 3-NH$_2$ |
| CH$_2$CH$_2$CH$_2$ | H | H/H | 3-NHMe |
| CH$_2$CH$_2$CH$_2$ | H | H/H | 3-CF$_3$ |
| CH$_2$CH$_2$CH$_2$ | H | H/H | 3-NHCH$_2$CF$_3$ |
| CH$_2$CH$_2$CH$_2$ | Me | H/H | 2-OH, 3-OH |
| OCH$_2$O | Et | H/H | 3,4,5-Me |

TABLE 17

| $A^B$-$B^B$-$D^B$ | $R^{23B}$ | $R^{24B}/R^{25B}$ | $R^{26B}$ |
|---|---|---|---|
| OCH$_2$O | H | Me/H | 4-OH |
| OCH$_2$O | H | Me/Me | 4-NH$_2$ |
| OCH$_2$O | H | Pr/H | 4-NO$_2$ |
| CH$_2$CH$_2$CH$_2$ | H | H/H | 4-CN |

TABLE 17-continued

| $A^B$-$B^B$-$D^B$ | $R^{23B}$ | $R^{24B}/R^{25B}$ | $R^{26B}$ |
|---|---|---|---|
| CH$_2$CH$_2$CH$_2$ | Me | CF$_3$/H | 4-Ph |
| CH$_2$CH$_2$CH$_2$ | Et | H/H | 4-CH$_2$OH |
| OCH$_2$O | H | H/H | 3-CH$_2$OH |
| CH$_2$CH$_2$CH$_2$ | H | H/H | 3-Ac |
| CH$_2$CH$_2$CH$_2$ | H | H/H | 3,5-OMe |
| CH$_2$CH$_2$CH$_2$ | H | H/H | 3-OH, 4-NH$_2$ |
| OCH$_2$O | Me | H/H | 3-CH$_2$NH$_2$ |
| CH$_2$CH$_2$CH$_2$ | Et | H/H | 3-SO$_2$CH$_3$ |
| CH$_2$CH$_2$CH$_2$ | H | Me/H | 3-iPr |
| CH$_2$CH$_2$CH$_2$ | H | Me/H | 3-NMe$_2$ |
| OCH$_2$O | H | Me/H | 3-Ac |
| CH$_2$CH$_2$CH$_2$ | H | Pr/H | 3,4-NH$_2$ |

TABLE 18

| $A^B$-$B^B$-$D^B$ | $R^{23B}$ | $R^{24B}/R^{25B}$ | $R^{26B}$ |
|---|---|---|---|
| CH$_2$CH$_2$CH$_2$ | H | H/H | NHMe |
| CH$_2$CH$_2$CH$_2$ | Et | H/H | 3-NHCH$_2$CF$_3$ |
| OCH$_2$O | H | H/H | 3-NHAc |
| CH$_2$CH$_2$CH$_2$ | H | H/H | 3-SO$_2$Me |
| CH$_2$CH$_2$CH$_2$ | H | H/H | 4-Me |
| CH$_2$CH$_2$CH$_2$ | H | H/H | 4-iPr |
| OCH$_2$O | Me | H/H | 3-Ph |
| CH$_2$CH$_2$CH$_2$ | Et | H/H | 3-F, 4-OH |
| CH$_2$CH$_2$CH$_2$ | Ac | H/H | 3-F, 4-OMe |

<Typical Compound IB-5>

[Formula 22]

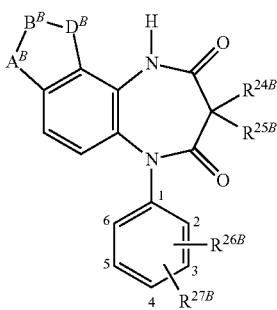

(In the formula, $A^B$-$B^B$-$D^B$, $R^{2B}/R^{25B}$, $R^{26B}$, and $R^{27B}$ are as shown in Tables 19 to 21, and "Position" in the tables means the substitution positions of $R^{26B}$.)

TABLE 19

| $A^B$-$B^B$-$D^B$ | $R^{24B}/R^{25B}$ | Position | $R^{26B}$ | $R^{27B}$ |
|---|---|---|---|---|
| CH$_2$CH$_2$CH$_2$ | H/H | 3 | 1H-Tetrazol-5-yl | H |
| CH$_2$CH$_2$CH$_2$ | H/H | 4 | 1H-Tetrazol-5-yl | H |
| CH$_2$CH$_2$CH$_2$ | H/H | 3 | 1H-Tetrazol-1-yl | H |
| CH$_2$CH$_2$CH$_2$ | H/H | 3 | 2-Methyl-2H-tetrazol-5-yl | H |
| OCH$_2$O | H/H | 3 | 1,2,3-Triazol-5-yl | 2-F |
| OCH$_2$O | H/H | 3 | 1,2,4-Triazol-3-yl | H |
| OCH$_2$O | H/H | 3 | 5-(Trifluoromethyl)-1,2,4-triazol-3-yl | H |
| OCH$_2$O | H/H | 4 | 1H-Imidazol-1-yl | H |
| CH$_2$CH$_2$CH$_2$ | H/H | 4 | 1H-Imidazol-2-y | H |

TABLE 19-continued

| $A^B$-$B^B$-$D^B$ | $R^{24B}/R^{25B}$ | Position | $R^{26B}$ | $R^{27B}$ |
|---|---|---|---|---|
| CH$_2$CH$_2$CH$_2$ | H/H | 3 | 5-Cyano-1H-1,2,3-triazol-4-yl | H |
| CH$_2$CH$_2$CH$_2$ | H/H | 3 | 1-Methyl-1H-tetrazol-5-yl | H |
| CH$_2$CH$_2$CH$_2$ | Me/H | 3 | Pyrazol-3-yl | 4-OH |

TABLE 20

| $A^B$-$B^B$-$D^B$ | $R^{24B}/R^{25B}$ | Position | $R^{26B}$ | $R^{27B}$ |
|---|---|---|---|---|
| OCH$_2$O | Me/Me | 3 | Pyrazol-4-yl | H |
| OCH$_2$O | H/H | 3 | 5-Oxo-1,2,4-oxadiazol-3-yl | 4-NH$_2$ |
| OCH$_2$O | CF$_3$/H | 3 | 1,2,4-Oxadiazol-3-yl | H |
| CH$_2$CH$_2$CH$_2$ | H/H | 3 | 1,3,4-Oxadiazol-2-yl | 4-F |
| CH$_2$CH$_2$CH$_2$ | H/H | 4 | Pyrrol-1-yl | 3-F |
| CH$_2$CH$_2$CH$_2$ | H/H | 4 | Pyrrolidin-2-yl | H |
| OCH$_2$O | H/H | 2 | 1,3-Oxazol-5-yl | H |
| CH$_2$CH$_2$CH$_2$ | H/H | 3 | 1,3-Thiazol-5-yl | H |
| CH$_2$CH$_2$CH$_2$ | H/H | 3 | 5-(Trifluoromethyl)-1H-imidazol-2-y | H |
| CH$_2$CH$_2$CH$_2$ | H/H | 3 | 5-Chloro-1H-imidazol-2-y | 4-OH |
| OCH$_2$O | Me/H | 4 | 5-Methyl-1H-imidazol-2-yl | 4-NH$_2$ |
| CH$_2$CH$_2$CH$_2$ | Me/H | 4 | 5-Amino-1H-imidazol-2-y | 3-F |

TABLE 21

| $A^B$-$B^B$-$D^B$ | $R^{24B}/R^{25B}$ | Position | $R^{26B}$ | $R^{27B}$ |
|---|---|---|---|---|
| CH$_2$CH$_2$CH$_2$ | Me/H | 3 | 2-Ethyl-2H-tetrazol-5-yl | H |
| CH$_2$CH$_2$CH$_2$ | Pr/H | 3 | 2-(2,2,2-Trifluoroethyl)-2H-tetrazol-5-yl | 2,6-F |
| OCH$_2$O | H/H | 3 | 1,3-Oxazol-2-yl | H |
| CH$_2$CH$_2$CH$_2$ | H/H | 3 | 1,3-Thiazol-2-yl | H |
| CH$_2$CH$_2$CH$_2$ | H/H | 4 | 3,5-Dimethylisoxazol-4-yl | H |
| CH$_2$CH$_2$CH$_2$ | H/H | 3 | 3-Methyl-1,2,4-oxadiazol-5-yl | H |

<Typical Compound IB-6>

[Formula 23]

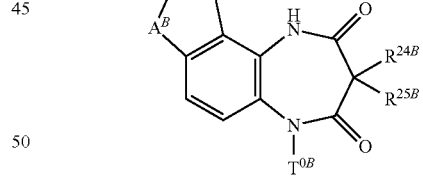

(In the formula, $A^B$-$B^B$-$D^B$, $R^{24B}/R^{25B}$, and $T^{0B}$ are as shown in Tables 22 to 24.)

TABLE 22

| $A^B$-$B^B$-$D^B$ | $R^{24B}/R^{25B}$ | $T^{0B}$ |
|---|---|---|
| CH$_2$CH$_2$CH$_2$ | H/H | Pyrimidin-2-yl |
| CH$_2$CH$_2$CH$_2$ | H/H | Pyrimidin-5-yl |
| CH$_2$CH$_2$CH$_2$ | H/H | Pyridin-2-yl |
| CH$_2$CH$_2$CH$_2$ | H/H | Quinolin-2-yl |
| CH$_2$CH$_2$CH$_2$ | H/H | Quinolin-3-yl |
| CH$_2$CH$_2$CH$_2$ | H/H | Pyridin-3-yl |
| OCH$_2$O | H/H | Pyridin-4-yl |
| OCH$_2$O | Me/H | Thiophen-2-yl |
| OCH$_2$O | H/H | Thiophen-3-yl |

TABLE 22-continued

| $A^B$-$B^B$-$D^B$ | $R^{24B}/R^{25B}$ | $T^{OB}$ |
|---|---|---|
| OCH$_2$O | H/H | Thiophen-3-yl |
| CH$_2$CH$_2$CH$_2$ | H/H | 5-Hydroxypyridin-3-yl |
| CH$_2$CH$_2$CH$_2$ | H/H | 5-Methoxypyridin-3-yl |
| NHCH$_2$CH$_2$ | F/H | 5-Aminopyridin-3-yl |

TABLE 23

| $A^B$-$B^B$-$D^B$ | $R^{24B}/R^{25B}$ | $T^{OB}$ |
|---|---|---|
| CH$_2$CH$_2$CH$_2$ | Me/Me | 5-Chloropyridin-3-yl |
| OCH$_2$O | Pr/H | 6-Chloropyridin-3-yl |
| OCH$_2$O | Pr/H | 6-Chloropyridin-3-yl |
| OCH$_2$O | H/H | 1H-Indazol-6-yl |
| OCH$_2$O | H/H | 1H-Indazol-5-yl |
| CH$_2$CH$_2$CH$_2$ | H/H | 1H-Indazol-4-yl |
| CH$_2$CH$_2$CH$_2$ | H/H | 1H-Benzotriazol-6-yl |
| CH$_2$CH$_2$CH$_2$ | H/H | 1H-Benzotriazol-4-yl |
| OCH$_2$O | H/H | 1H-Benzimidazol-6-yl |
| CH$_2$CH$_2$CH$_2$ | H/H | 1H-Indazol-4-yl |
| CH$_2$CH$_2$CH$_2$ | H/H | 1H-Indol-6-yl |

TABLE 24

| $A^B$-$B^B$-$D^B$ | $R^{24B}/R^{25B}$ | $T^{OB}$ |
|---|---|---|
| NHCH$_2$CH$_2$ | H/H | 1H-Indol-5-yl |
| OCH$_2$O | H/H | 1H-Indol-4-yl |
| CH$_2$CH$_2$CH$_2$ | H/H | Benzisoxazol-6-yl |
| CH$_2$CH$_2$CH$_2$ | H/H | 1H-Benzimidazol-5-yl |
| CH$_2$CH$_2$CH$_2$ | H/H | 1H-Benzimidazol-6-yl |
| OCH$_2$O | H/H | 2-Trifluoromethyl-1H-benzimidazol-5-yl |
| CH$_2$CH$_2$CH$_2$ | H/H | Quinolin-5-yl |
| CH$_2$CH$_2$CH$_2$ | H/H | Quinolin-8-yl |

(C-1) A compound represented by the following general formula (IC):

[Formula 24]

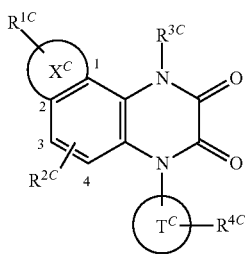

(IC)

wherein, in the formula, $R^{1C}$ and $R^{2C}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, an aralkyl group (the aryl moiety thereof has 6 to 10 carbon atoms, and the alkylene moiety thereof has 1 to 3 carbon atoms), a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, or sulfamoyl group, $R^{3C}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, or an aralkyl group (the aryl moiety thereof has 6 to 10 carbon atoms, and the alkylene moiety thereof has 1 to 3 carbon atoms), $R^{4C}$ represents hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, an aralkyl group (the aryl moiety thereof has 6 to 10 carbon atoms, and the alkylene moiety thereof has 1 to 3 carbon atoms), an alkyl group having 1 to 8 carbon atoms and substituted with hydroxyl group, a halogen atom, hydroxyl group, nitro group, cyano group, amino group, an alkylamino group having 1 to 8 carbon atoms, an alkylamino group having 1 to 5 carbon atoms and substituted with 1 to 5 halogen atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, a benzenesulfonylamino group which may have a substituent, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, sulfamoyl group, a phenyl group which may have a substituent, or a heterocyclic group which may have a substituent,

[Formula 25]

represents a 5- to 8-membered ring which condenses at the 1- and 2-positions of the benzene ring, and may contain a heteroatom selected from N, S, and O as a ring-constituting element, and

[Formula 26]

represents an aromatic ring selected from benzene ring, naphthalene ring, pyridine ring, pyrimidine ring, quinoline ring, indole ring, indoline ring, benzimidazole ring, indazole ring, benzisoxazole ring, and benztriazole ring.

(C-2) A compound represented by the following general formula (IIC):

[Formula 27]

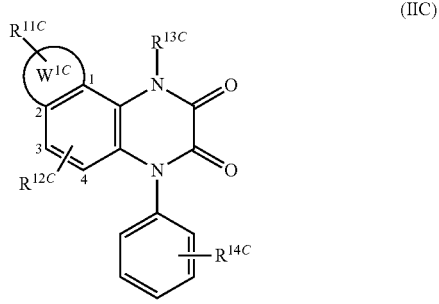

(IIC)

wherein, in the formula, $R^{11C}$ and $R^{12C}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, an aralkyl group (the aryl moiety thereof has 6 to 10 carbon atoms, and the alkylene moiety thereof has 1 to 3 carbon atoms), a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, or sulfamoyl group, $R^{13C}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, or an aralkyl group (the aryl moiety thereof has 6 to 10 carbon atoms, and the alkylene moiety thereof has 1 to 3 carbon atoms), $R^{14C}$ represents hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, an aralkyl group (the aryl moiety thereof has 6 to 10 carbon atoms, and the alkylene moiety thereof has 1 to 3 carbon atoms), an alkyl group having 1 to 8 carbon atoms and substituted with hydroxyl group, a halogen atom, hydroxyl group, nitro group, cyano group, amino group, an alkylamino group having 1 to 8 carbon atoms, an alkylamino group having 1 to 5 carbon atoms and substituted with 1 to 5 halogen atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, a benzenesulfonylamino group which may have a substituent, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, sulfamoyl group, a phenyl group which may have a substituent, or a heterocyclic group which may have a substituent, and

[Formula 28]

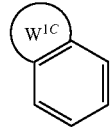

represents naphthalene ring, tetrahydronaphthalene ring, or indane ring.

As for the general formulas (IC) and (IIC), examples of the alkyl group having 1 to 8 carbon atoms as $R^{1C}$, $R^{2C}$, $R^{3C}$, and $R^{4C}$ include methyl group, ethyl group, propyl group, isopropyl group, butyl group, i-butyl group, t-butyl group, pentyl group, hexyl group, and the like.

Examples of the alkenyl group having 2 to 8 carbon atoms as $R^{1C}$, $R^{2C}$, $R^{3C}$, and $R^{4C}$ include allyl group, and the like.

Examples of the alkyl group having 1 to 8 carbon atoms and substituted with 1 to 3 halogen atoms as $R^{1C}$, $R^{2C}$, $R^{3C}$, and $R^{4C}$ include methyl group, ethyl group, propyl group, isopropyl group, butyl group, t-butyl group substituted with 1 to 3 halogen atoms such as fluorine atom, chlorine atom, and bromine atom, and the like, and preferred examples of the same include trifluoromethyl group, chloromethyl group, 2-chloroethyl group, 2-bromoethyl group, 2-fluoroethyl group, and the like.

Examples of the aralkyl group (the aryl moiety thereof has 6 to 10 carbon atoms, and the alkylene moiety thereof has 1 to 3 carbon atoms) as $R^{1C}$, $R^{2C}$, $R^{3C}$, and $R^{4C}$ include benzyl group, and the like.

Examples of the alkoxy group having 1 to 8 carbon atoms as $R^{1C}$, $R^{2C}$, and $R^{4C}$ include methoxy group, ethoxy group, propoxy group, isopropoxy group, butoxy group, i-butoxy group, t-butoxy group, pentyloxy group, hexyloxy group, and the like.

Examples of the alkoxy group having 1 to 8 carbon atoms and substituted with 1 to 3 halogen atoms as $R^{1C}$, $R^{2C}$, and $R^{4C}$ include methoxy group, ethoxy group, propoxy group, isopropoxy group, butoxy group, t-butoxy group substituted with 1 to 3 halogen atoms such as fluorine atom, chlorine atom, and bromine atom, and the like, and preferred examples of the same include trifluoromethoxy group, chloromethoxy group, 2-chloroethoxy group, 2-bromoethoxy group, 2-fluoroethoxy group, and the like.

Examples of the halogen atom as $R^{1C}$, $R^{2C}$, and $R^{4C}$ include fluorine atom, chlorine atom, bromine atom, and the like.

Examples of the alkylamino group having 1 to 8 carbon atoms as $R^{1C}$, $R^{2C}$, and $R^{4C}$ include methylamino group, ethylamino group, and the like.

Examples of the alkylamino group having 1 to 5 carbon atoms and substituted with 1 to 5 halogen atoms as $R^{4C}$ include 2,2,2-trifluoroethylamino group, and the like.

Examples of the dialkylamino group having 2 to 8 carbon atoms as $R^{1C}$, $R^{2C}$, and $R^{4C}$ include dimethylamino group, diethylamino group, and the like.

Examples of the acylamino group having 2 to 8 carbon atoms as $R^{1C}$, $R^{2C}$, and $R^{4C}$ include acetylamino group. Examples further include a benzoylamino group which may have a substituent (an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, halogen, and the like).

Examples of the acylamino group having 2 to 8 carbon atoms and substituted with 1 to 3 halogen atoms as $R^{1C}$, $R^{2C}$, and $R^{4C}$ include trifluoromethylcarbonylamino group.

Examples of the alkylsulfonylamino group having 1 to 8 carbon atoms as $R^{1C}$, $R^{2C}$, and $R^{4C}$ include methylsulfonylamino group.

Examples of the acyl group having 2 to 8 carbon atoms as $R^{1C}$, $R^{2C}$, and $R^{4C}$ include acetyl group.

Examples of the alkoxycarbonyl group (the alkoxy moiety thereof has 1 to 8 carbon atoms) as $R^{1C}$, $R^{2C}$, and $R^{4C}$ include methoxycarbonyl group, ethoxycarbonyl group, and the like.

Examples of the alkylthio group having 1 to 8 carbon atoms as $R^{1C}$, $R^{2C}$, and $R^{4C}$ include methylthio group.

Examples of the alkylsulfinyl group having 1 to 8 carbon atoms as $R^{1C}$, $R^{2C}$, and $R^{4C}$ include methylsulfinyl group.

Examples of the alkylsulfonyl group having 1 to 8 carbon atoms as $R^{1C}$, $R^{2C}$, and $R^{4C}$ include methylsulfonyl group.

Examples of the alkyl group having 1 to 8 carbon atoms and substituted with hydroxyl group as $R^{4C}$ include hydroxymethyl group, and the like.

Examples of the benzenesulfonylamino group which may have a substituent as $R^{4C}$ include a benzenesulfonylamino group which may have a substituent selected from an alkyl group having 1 to 8 carbon atoms (for example, methyl group, ethyl group, and the like), an alkoxy group having 1 to 8 carbon atoms (for example, methoxy group, ethoxy group, and the like), a halogen atom (for example, fluorine atom, chlorine atom, and the like), nitro group, and the like, and preferred examples of the same include o-nitrobenzenesulfonylamino group, and the like.

Preferred examples of the substituent of the phenyl group which may have a substituent as $R^{4C}$ include an alkyl group having 1 to 8 carbon atoms such as methyl group and ethyl group, an alkyl group having 1 to 8 carbon atoms and substituted with 1 to 3 halogen atoms such as trifluoromethyl group, a halogen atom such as fluorine atom, cyano group, and the like.

Preferred examples of the heterocyclic group of the heterocyclic group which may have a substituent as $R^{4C}$ include tetrazolyl group, triazolyl group, pyridyl group, imidazolyl group, oxazolyl group, thiazolyl group, and the like. Examples further include oxadiazole group.

Preferred examples of the substituent of the heterocyclic ring which may have a substituent as $R^{4C}$ include an alkyl group having 1 to 8 carbon atoms such as methyl group and ethyl group, an alkyl group having 1 to 8 carbon atoms and substituted with 1 to 3 halogen atoms such as trifluoromethyl group, a halogen atom such as fluorine atom, cyano group, oxo, and the like.

In the aforementioned general formula (IC), a plurality of the same or different $R^{1C}$, $R^{2C}$, and $R^{4C}$ may exist on the rings on which $R^{1C}$, $R^{2C}$, and $R^{4C}$ substitute.

Examples of the alkyl group having 1 to 8 carbon atoms, alkenyl group having 2 to 8 carbon atoms, alkoxy group having 1 to 8 carbon atoms, alkyl group having 1 to 8 carbon atoms and substituted with 1 to 3 halogen atoms, alkoxy group having 1 to 8 carbon atoms and substituted with 1 to 3 halogen atoms, aralkyl group (the aryl moiety thereof has 6 to 10 carbon atoms, and the alkylene moiety thereof has 1 to 3 carbon atoms), alkyl group having 1 to 8 carbon atoms and substituted with hydroxyl group, halogen atom, alkylamino group having 1 to 8 carbon atoms, alkylamino group having 1 to 5 carbon atoms and substituted with 1 to 5 halogen atoms, dialkylamino group having 2 to 8 carbon atoms, acylamino group having 2 to 8 carbon atoms, acylamino group having 2 to 8 carbon atoms and substituted with 1 to 3 halogen atoms, alkylsulfonylamino group having 1 to 8 carbon atoms, benzenesulfonylamino group which may have a substituent, acyl group having 2 to 8 carbon atoms, alkoxycarbonyl group (the alkoxy moiety thereof has 1 to 8 carbon atoms), alkylthio group having 1 to 8 carbon atoms, alkylsulfinyl group having 1 to 8 carbon atoms, alkylsulfonyl group having 1 to 8 carbon atoms, phenyl group which may have a substituent, heterocyclic group which may have a substituent, and the like as $R^{11C}$, $R^{12C}$, $R^{13C}$, and $R^{14C}$ in the aforementioned general formula (IIC) include those similar to those mentioned above for $R^{1C}$, $R^{2C}$, $R^{3C}$, and $R^{4C}$ in the general formula IC).

Examples of the alkyl group having 1 to 8 carbon atoms, alkoxy group having 1 to 8 carbon atoms, alkyl group having 1 to 8 carbon atoms and substituted with 1 to 3 halogen atoms, alkoxy group having 1 to 8 carbon atoms and substituted with 1 to 3 halogen atoms, halogen atom, alkylamino group having 1 to 8 carbon atoms, and dialkylamino group having 2 to 8 carbon atoms as the substituent of the heterocyclic group which may have a substituent as $R^{14C}$ in the general formula (IIC) include those exemplified for $R^{1C}$ to $R^{4C}$ in the general formula (IC) mentioned above.

In the aforementioned general formula (IIC), a plurality of the same or different $R^{11C}$, $R^{12C}$, and $R^{14C}$ may exist on the rings on which $R^{11C}$, $R^{12C}$, and $R^{14C}$ substitute.

As compounds falling within the scope of the general formula (IC), the following compounds are preferred.

(C-1-1) The compound according to (C-1), wherein $R^{1C}$ and $R^{2C}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, or amino group.

(C-1-2) The compound according to (C-1) or (C-1-1), wherein $R^{3C}$ is hydrogen atom, or an alkyl group having 1 to 8 carbon atoms.

(C-1-3) The compound according to (C-1), (C-1-1), or (C-1-2), wherein $R^{4C}$ is hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, an alkyl group having 1 to 8 carbon atoms and substituted with hydroxyl group, a halogen atom, hydroxyl group, cyano group, amino group, an alkylamino group having 1 to 8 carbon atoms, a dialkylamino group having 2 to 8 carbon atoms, an alkylsulfonylamino group having 1 to 8 carbon atoms, a benzenesulfonylamino group which may have a substituent, a phenyl group which may have a substituent, or a heterocyclic group which may have a substituent.

(C-1-4) The compound according to (C-1), or any one of (C-1-1) to (C-1-3), wherein $R^{4C}$ is a tetrazolyl group, triazolyl group, pyridyl group, imidazolyl group, oxazolyl group, or thiazolyl group which may have a substituent selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(C-1-5) The compound according to (C-1), or any one of (C-1-1) to (C-1-4), wherein $R^{4C}$ is hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, cyano group, amino group, an alkylamino group having 1 to 8 carbon atoms, a dialkylamino group having 2 to 8 carbon atoms, or a benzenesulfonylamino group which may have a substituent selected from an alkyl group having 1 to 8 carbon atoms, an alkoxy group having 1 to 8 carbon atoms, a halogen atom, and nitro group.

(C-1-6) The compound according to (C-1), or any one of (C-1-1) to (C-1-5), wherein

[Formula 29]

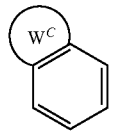

is a naphthalene ring, tetrahydronaphthalene ring, or indane ring.

(C-1-7) The compound according to (C-1), or any one of (C-1-1) to (C-1-6), wherein

[Formula 30]

is a benzene ring, or indole ring.

(C-2-1) The compound according to (C-2), wherein $R^{11C}$ and $R^{12C}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, or amino group.

(C-2-2) The compound according to (C-2) or (C-2-1), wherein $R^{13C}$ is hydrogen atom, or an alkyl group having 1 to 8 carbon atoms.

(C-2-3) The compound according to (C-2), (C-2-1), or (C-2-2), wherein $R^{14C}$ is hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, an alkyl group having 1 to 8 carbon atoms and substituted with hydroxyl group, a halogen atom, hydroxyl group, cyano group, amino group, an alkylamino group having 1 to 8 carbon atoms, a dialkylamino group having 2 to 8 carbon atoms, an alkylsulfonylamino group having 1 to 8 carbon atoms, a benzenesulfonylamino which may have a substituent, a phenyl group which may have a substituent, or a heterocyclic group which may have a substituent.

(C-2-4) The compound according to (C-2), or any one of (C-2-1) to (C-2-3), wherein $R^{14C}$ is a tetrazolyl group, triazolyl group, pyridyl group, imidazolyl group, oxazolyl group, or thiazolyl group which may have a substituent selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(C-2-5) The compound according to (C-2), or any one of (C-2-1) to (C-2-4), wherein $R^{14C}$ is hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, cyano group, amino group, an alkylamino group having 1 to 8 carbon atoms, a dialkylamino group having 2 to 8 carbon atoms, or a benzenesulfonylamino group which may have a substituent selected from an alkyl group having 1 to 8 carbon atoms, an alkoxy group having 1 to 8 carbon atoms, a halogen atom, and nitro group.

(C-2-6) The compound according to (C-2), or any one of (C-2-1) to (C-2-5), wherein

[Formula 31]

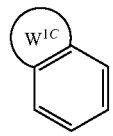

is a naphthalene ring.

Examples further include the following compounds.

(C-2-7) The compound according to (C-2), wherein $R^{11C}$, $R^{12C}$, $R^{13C}$, and

[Formula 32]

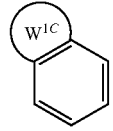

are the same as those of the general formula (IIC), and $R^{14C}$ is $NHSO_2R^C$ ($R^C$ represents an aryl group which may have a substituent, or a heterocyclic group).

(C-2-8) The compound according to (C-2-7), wherein $R^C$ is phenyl, naphthyl, quinolyl, pyridyl, or thienyl which may have a substituent selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, hydroxyl group, amino group, nitro, and halogen.

<Typical Compound IC-1>

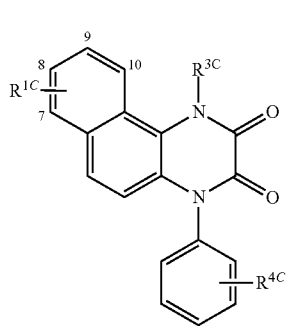

[Formula 33]

(In the formula, $R^{1C}$, $R^{3C}$, and $R^{4C}$ are as shown in Tables 25 to 27.)

TABLE 25

| $R^{1C}$ | $R^{3C}$ | $R^{4C}$ |
|---|---|---|
| H | H | 3-OH |
| H | H | 3-Ome |
| H | H | 4-OH |
| H | H | 4-Ome |
| H | H | 2-OH |
| H | H | 2-Ome |
| H | H | 2,3-OH |
| H | H | 3-OH, 4-F |
| H | H | 3,4-OH |
| H | H | 3,4-OMe |
| H | H | 3,4,5-OMe |
| H | H | 3-CN |

TABLE 26

| $R^{1C}$ | $R^{3C}$ | $R^{4C}$ |
|---|---|---|
| H | H | 4-CN |
| H | H | 3-CO$_2$H |
| H | H | 3-CO$_2$Me |
| H | H | 3-Br |
| H | H | 3-F |
| H | H | 4-Me |
| H | H | 3-NH$_2$ |
| H | H | 3-NHSO$_2$Ph |
| H | H | 3-NHSO$_2$(2-NO$_2$)Ph |
| H | H | 4-NHSO$_2$Ph |
| H | Me | 4-NHSO$_2$(2-NO$_2$)Ph |
| H | Et | 3-NHEt |
| H | H | 3-CH$_2$OH |
| H | H | 4-CH$_2$OH |

TABLE 27

| $R^{1C}$ | $R^{3C}$ | $R^{4C}$ |
|---|---|---|
| H | H | 3-CF$_3$ |
| H | H | 3-Ph |
| H | H | 3-N(Me)$_2$ |
| H | H | 3,5-OH |
| H | H | 4-OAc |
| H | H | 2-Me |
| 9-Me | H | 3-NH$_2$ |
| 9-Cl | H | 3-NH$_2$ |
| 8-Me | H | 3-NH$_2$ |
| 8-Cl | H | 3-NH$_2$ |

<Typical Compound IC-2>

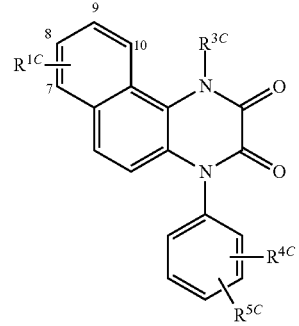

[Formula 34]

(In the formula, $R^{1C}$, $R^{3C}$, $R^{4C}$, and $R^{5C}$ are as shown in Tables 28 to 30.)

TABLE 28

| $R^{1C}$ | $R^{3C}$ | Position of $R^{4C}$ | $R^{4C}$ | $R^{5C}$ |
|---|---|---|---|---|
| H | H | 3 | 1H-Tetrazol-5-yl | H |
| H | H | 4 | 1H-Tetrazol-5-yl | H |
| 8-Me | H | 3 | 1H-Tetrazol-5-yl | H |
| 8-Cl | H | 3 | 1H-Tetrazol-5-yl | H |
| H | H | 3 | 1H-Tetrazol-5-yl | 4-F |
| H | H | 3 | 1H-Tetrazol-5-yl | 4-Me |
| H | H | 3 | 1H-Tetrazol-5-yl | 5-Br |
| H | H | 3 | 1H-Tetrazol-5-yl | 6-Me |
| H | H | 3 | 1H-Tetrazol-5-yl | 6-Cl |
| H | H | 3 | (5-Thioxo-1,2,4-oxadiazol)-3-yl | H |
| H | H | 3 | (5-Oxo-1,2,4-oxadiazol)-3-yl | H |
| H | H | 3 | (5-Cyano-1H-1,2,3-triazol)-4-yl | H |

TABLE 29

| $R^{1C}$ | $R^{3C}$ | Position of $R^{4C}$ | $R^{4C}$ | $R^{5C}$ |
|---|---|---|---|---|
| H | H | 3 | 1H-Tetrazol-5-yl | 6-OH |
| H | H | 3 | (2-Methyl-2H-tetrazol)-5-yl | H |
| H | Me | 3 | (2-Methyl-2H-tetrazol)-5-yl | H |
| H | Et | 3 | (2-Ethyl-2H-tetrazol)-5-yl | H |
| H | H | 3 | (1-Methyl-1H-tetrazol)-5-yl | H |
| H | H | 3 | 4-Methyl-(5-thioxo-1,2,4-oxadiazol)-3-yl | H |
| H | H | 3 | 1-Methyl-1H-imidazol-2-yl | H |
| H | H | 3 | 1-Methyl-1H-imidazol-4-yl | H |
| H | H | 3 | 1,3-Oxazol-2-yl | H |
| H | H | 3 | 1,3-Thiazol-2-yl | H |
| H | H | 3 | Pyrrol-2-yl | H |
| H | H | 3 | Thiophen-2-yl | H |
| H | H | 3 | 1-H-Imidazol-2-yl | H |
| H | H | 3 | 1-H-Imidazol-4-yl | H |

TABLE 30

| $R^{1C}$ | $R^{3C}$ | Position of $R^{4C}$ | $R^{4C}$ | $R^{5C}$ |
|---|---|---|---|---|
| H | H | 3 | Pyrazol-4-yl | H |
| H | H | 3 | 5-(Chloro)-1H-imidazol-2-yl | H |
| H | H | 3 | 5-(Trifluoromethyl)-1H-imidazol-2-yl | H |
| H | H | 3 | (1,2,3-Triazol)-4-yl | H |
| H | H | 3 | (1,2,4-Triazol)-3-yl | H |
| H | H | 3 | 3-Methyl-(1,2,4-oxadiazol)-5-yl | H |
| H | H | 3 | 3,5-Dimethylisoxazol-4-yl | H |
| H | H | 3 | 1-Tetrazol-1-yl | H |

TABLE 30-continued

| $R^{1C}$ | $R^{3C}$ | Position of $R^{4C}$ | $R^{4C}$ | $R^{5C}$ |
|---|---|---|---|---|
| H | H | 3 | Phenyl | H |
| H | H | 3 | Pyridin-3-yl | H |
| H | H | 3 | Pyrimidin-5-yl | H |
| H | H | 3 | 2-Aminopyridin-5-yl | H |

<Typical Compound IC-3>

[Formula 35]

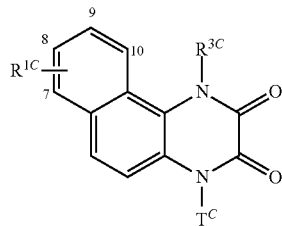

(In the formula, $R^{1C}$, $R^{3C}$, and $T^C$ are as shown in Tables 31 and 32.)

TABLE 31

| $R^{1C}$ | $R^{3C}$ | $T^C$ |
|---|---|---|
| H | H | 1H-Indol-6-yl |
| H | H | 1H-Indolin-6-yl |
| H | H | 1H-Indol-4-yl |
| H | H | 1H-Indazol-6-yl |
| H | Me | 1H-Indazol-6-yl |
| H | Et | 1H-Indazol-6-yl |
| 8-Me | H | 1H-Indazol-6-yl |
| 8-Cl | H | 1H-Indazol-6-yl |
| H | H | 1H-Indazol-4-yl |
| H | H | 1H-Benzimidazol-6-yl |
| H | H | 2-(Trifluoromethyl)-1h-benzimidazol-6-yl |
| H | H | 1H-Benzotriazol-6-yl |

TABLE 32

| $R^{1C}$ | $R^{3C}$ | $T^C$ |
|---|---|---|
| H | H | 3-Methylbenzoisoxazol-6-yl |
| H | H | Pyridin-4-yl |
| H | H | 3-Methoxypyridin-5-yl |
| H | H | 3-Hydroxypyridin-5-yl |
| H | H | Pyridin-3-yl |
| H | H | 7-Hydroxyquinolin-3-yl |
| H | H | Pyrimidin-2-yl |
| H | H | Thiophen-2-yl |
| H | H | Pyridin-2-yl |
| H | H | 4-Methylpyridin-2-yl |
| H | H | 2-Bromopyridin-5-yl |

<Typical Compound IC-4>

[Formula 36]

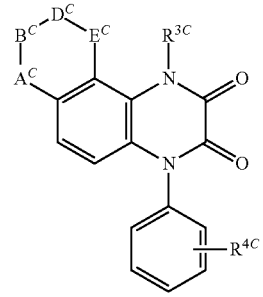

(In the formula, $A^C$-$B^C$-$D^C$-$E^C$, $R^{3C}$, and $R^{4C}$ are as shown in Tables 33 to 35.)

TABLE 33

| $A^C$-$B^C$-$D^C$-$E^C$ | $R^{3C}$ | $R^{4C}$ |
|---|---|---|
| CH$_2$CH$_2$CH$_2$CH$_2$ | H | 3-OH |
| CH$_2$CH$_2$CH$_2$CH$_2$ | H | 3-OMe |
| CH$_2$CH$_2$CH$_2$CH$_2$ | H | 4-OH |
| CH$_2$CH$_2$CH$_2$CH$_2$ | H | 4-OMe |
| CH$_2$CH$_2$CH$_2$CH$_2$ | H | 2-OH |
| CH$_2$CH$_2$CH$_2$CH$_2$ | H | 2-OMe |
| CH$_2$CH$_2$CH$_2$CH$_2$ | H | 2,3-OH |
| CH$_2$CH$_2$CH$_2$CH$_2$ | H | 3-OH, 4-F |
| CH$_2$CH$_2$CH$_2$CH$_2$ | H | 3,4-OH |
| CH$_2$CH$_2$CH$_2$CH$_2$ | H | 3,4-OMe |
| CH$_2$CH$_2$CH$_2$CH$_2$ | H | 3,4,5-OMe |
| CH$_2$CH$_2$CH$_2$CH$_2$ | H | 3-CN |

TABLE 34

| $A^C$-$B^C$-$D^C$-$E^C$ | $R^{3C}$ | $R^{4C}$ |
|---|---|---|
| CH$_2$NHCH$_2$CH$_2$ | H | 4-CN |
| CH$_2$CH$_2$CH$_2$CH$_2$ | H | 3-CO$_2$H |
| CH$_2$NHCH$_2$CH$_2$ | H | 3-CO$_2$Me |
| CH$_2$CH$_2$CH$_2$CH$_2$ | H | 3-Br |
| CH$_2$CH$_2$NHCH$_2$ | H | 3-F |
| CH$_2$CH$_2$OCH$_2$ | H | 4-Me |
| CH$_2$CH$_2$CH$_2$CH$_2$ | H | 3-NH$_2$ |
| CH$_2$CH$_2$CH$_2$CH$_2$ | H | 3-NHSO$_2$Ph |
| CH$_2$CH$_2$CH$_2$CH$_2$ | H | 3-NHSO$_2$(2-NO$_2$)Ph |
| CH$_2$CH$_2$CH$_2$CH$_2$ | H | 4-NHSO$_2$Ph |
| CH$_2$CH$_2$CH$_2$CH$_2$ | Me | 4-NHSO$_2$(2-NO$_2$)Ph |
| CH$_2$CH$_2$CH$_2$CH$_2$ | Et | 3-NHEt |

TABLE 35

| $A^C$-$B^C$-$D^C$-$E^C$ | $R^{3C}$ | $R^{4C}$ |
|---|---|---|
| CH$_2$CH$_2$CH$_2$CH$_2$ | H | 3-CH$_2$OH |
| CH$_2$CH$_2$CH$_2$CH$_2$ | H | 3-NHSO$_2$CH$_3$ |
| CH$_2$CH$_2$CH$_2$CH$_2$ | H | 3-CF3 |
| CH$_2$CH$_2$CH$_2$CH$_2$ | H | 3-Ph |
| CH$_2$CH$_2$CH$_2$CH$_2$ | H | 3-N(Me)$_2$ |
| CH$_2$CH$_2$CH$_2$CH$_2$ | H | 3,5-OH |
| CH$_2$CH$_2$CH$_2$CH$_2$ | H | 4-OAc |
| CH$_2$CH$_2$CH$_2$CH$_2$ | H | 2-Me |
| CH$_2$CH(Me)CH$_2$CH$_2$ | H | 3-NH$_2$ |

<Typical Compound IC-5>

[Formula 37]

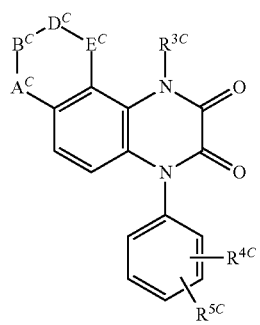

(In the formula, $A^C$-$B^C$-$D^C$-$E^C$, $R^{3C}$, $R^{4C}$, and $R^{5C}$ are as shown in Tables 36 to 38.)

TABLE 36

| $A^C$-$B^C$-$D^C$-$E^C$ | $R^{3C}$ | Position of $R^{4C}$ | $R^{4C}$ | $R^{5C}$ |
|---|---|---|---|---|
| CH$_2$CH$_2$CH$_2$CH$_2$ | H | 3 | 1H-Tetrazol-5-yl | H |
| CH$_2$CH$_2$CH$_2$CH$_2$ | H | 4 | 1H-Tetrazol-5-yl | H |
| CH$_2$NHCH$_2$CH$_2$ | H | 3 | 1H-Tetrazol-5-yl | H |
| CH$_2$CH$_2$OCH$_2$ | H | 3 | 1H-Tetrazol-5-yl | 4-F |
| CH$_2$CH$_2$CH$_2$CH$_2$ | H | 3 | 1H-Tetrazol-5-yl | 4-Me |
| CH$_2$CH$_2$CH$_2$CH$_2$ | H | 3 | 1H-Tetrazol-5-yl | 5-Br |
| CH$_2$CH$_2$CH$_2$CH$_2$ | H | 3 | 1H-Tetrazol-5-yl | 6-Me |
| CH$_2$CH$_2$CH$_2$CH$_2$ | H | 3 | 1H-Tetrazol-5-yl | 6-Cl |
| CH$_2$CH$_2$CH$_2$CH$_2$ | H | 3 | (5-Thioxo-1,2,4-oxadiazol)-3-yl | H |
| CH$_2$CH$_2$CH$_2$CH$_2$ | H | 4 | (5-Oxo-1,2,4-oxadiazol)-3-yl | H |

TABLE 37

| $A^C$-$B^C$-$D^C$-$E^C$ | $R^{3C}$ | Position of $R^{4C}$ | $R^{4C}$ | $R^{5C}$ |
|---|---|---|---|---|
| CH$_2$CH$_2$CH$_2$CH$_2$ | H | 3 | (5-Cyano-1H-1,2,3-triazol)-4-yl | H |
| CH$_2$CH$_2$CH$_2$CH$_2$ | H | 3 | 1-H-Tetrazol-5-yl | 6-OH |
| CH$_2$CH$_2$CH$_2$CH$_2$ | H | 3 | (2-Methyl-2H-tetrazol)-5-yl | H |
| CH$_2$CH$_2$CH$_2$CH$_2$ | Me | 3 | (2-Methyl-2H-tetrazol)-5-yl | H |
| CH$_2$CH$_2$CH$_2$CH$_2$ | Et | 3 | (2-Ethyl-2H-tetrazol)-5-yl | H |
| CH$_2$NHCH$_2$CH$_2$ | H | 3 | (1-Methyl-1H-tetrazol)-5-yl | H |
| CH$_2$CH$_2$CH$_2$CH$_2$ | H | 3 | 4-Methyl-(5-thioxo-1,2,4-oxadiazol)-3-yl | H |
| CH$_2$CH$_2$CH$_2$CH$_2$ | H | 3 | 1-Methyl-1H-imidazol-2-yl | H |
| CH$_2$CH$_2$CH$_2$CH$_2$ | H | 3 | 1-Methyl-1H-imidazol-4-yl | H |
| CH$_2$CH$_2$CH$_2$CH$_2$ | H | 3 | 1,3-Oxazol-2-yl | H |
| CH$_2$CH$_2$CH$_2$CH$_2$ | H | 3 | 1,3-Thiazol-2-yl | H |
| CH$_2$CH$_2$CH$_2$CH$_2$ | H | 3 | Pyrrol-2-yl | H |
| CH$_2$CH$_2$CH$_2$CH$_2$ | H | 3 | Thiophen-2-yl | H |

TABLE 38

| $A^C$-$B^C$-$D^C$-$E^C$ | $R^{3C}$ | Position of $R^{4C}$ | $R^{4C}$ | $R^{5C}$ |
|---|---|---|---|---|
| CH$_2$CH$_2$CH$_2$CH$_2$ | H | 3 | 1-H-Imidazol-2-yl | H |
| CH$_2$CH$_2$CH$_2$CH$_2$ | H | 3 | 1-H-Imidazol-4-yl | H |
| CH$_2$CH$_2$CH$_2$CH$_2$ | H | 4 | Pyrazol-4-yl | H |
| CH$_2$CH$_2$CH$_2$CH$_2$ | H | 3 | 5-(Chloro)-1H-imidazol-2-yl | H |
| CH$_2$CH$_2$CH$_2$CH$_2$ | H | 3 | 5-(Trifluoromethyl)-1H-imidazol-2-yl | H |
| CH$_2$CH$_2$CH$_2$CH$_2$ | H | 3 | (1,2,3-Triazol)-4-yl | H |
| CH$_2$CH$_2$CH$_2$CH$_2$ | H | 3 | (1,2,4-Triazol)-3-yl | H |

TABLE 38-continued

| $A^C$-$B^C$-$D^C$-$E^C$ | $R^{3C}$ | Position of $R^{4C}$ | $R^{4C}$ | $R^{5C}$ |
|---|---|---|---|---|
| CH$_2$CH$_2$CH$_2$CH$_2$ | H | 3 | 3-Methyl-(1,2,4-oxadiazol)-5-yl | H |
| CH$_2$CH$_2$CH$_2$CH$_2$ | H | 4 | 3,5-Dimethylisoxazol-4-yl | H |
| CH$_2$CH$_2$CH$_2$CH$_2$ | H | 3 | 1-Tetrazol-1-yl | H |
| CH$_2$CH(Me)CH$_2$CH$_2$ | H | 3 | Phenyl | H |
| CH$_2$CH$_2$CH(Me)CH$_2$ | H | 3 | Pyrimidin-5-yl | H |

<Typical Compound IC-6>

[Formula 38]

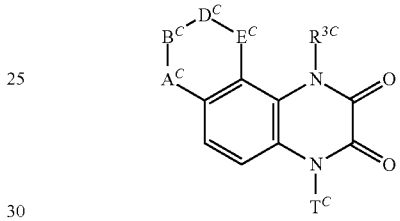

(In the formula, $A^C$-$B^C$-$D^C$-$E^C$, $R^{3C}$, and $T^C$ are as shown in Tables 39 and 40.)

TABLE 39

| $A^C$-$B^C$-$D^C$-$E^C$ | $R^{3C}$ | $T^C$ |
|---|---|---|
| CH$_2$CH$_2$CH$_2$CH$_2$ | H | 1H-Indol-6-yl |
| CH$_2$CH$_2$CH$_2$CH$_2$ | H | 1H-Iindolin-6-yl |
| CH$_2$CH$_2$CH$_2$CH$_2$ | H | 1H-Indol-4-yl |
| CH$_2$CH$_2$CH$_2$CH$_2$ | H | 1H-Indazol-6-yl |
| CH$_2$CH$_2$CH$_2$CH$_2$ | Me | 1H-Indazol-6-yl |
| CH$_2$CH$_2$CH$_2$CH$_2$ | Et | 1H-Indazol-6-yl |
| CH$_2$CH$_2$CH$_2$CH$_2$ | H | 1H-Indazol-4-yl |
| CH$_2$CH$_2$CH$_2$CH$_2$ | H | 1H-Benzimidazol-6-yl |
| CH$_2$CH$_2$CH$_2$CH$_2$ | H | 2-(Trifluoromethyl)-1H-benzimidazol-6-yl |
| CH$_2$CH$_2$CH$_2$CH$_2$ | H | 1H-Benzotriazol-6-yl |
| CH$_2$CH$_2$CH$_2$CH$_2$ | H | 3-Methylbenzoisoxazol-6-yl |

TABLE 40

| $A^C$-$B^C$-$D^C$-$E^C$ | $R^{3C}$ | $T^C$ |
|---|---|---|
| CH$_2$CH$_2$CH$_2$CH$_2$ | H | Pyridin-4-yl |
| CH$_2$CH$_2$CH$_2$CH$_2$ | H | 3-Methoxypyridin-5-yl |
| CH$_2$CH$_2$CH$_2$CH$_2$ | H | 3-Hydroxypyridin-5-yl |
| CH$_2$CH$_2$CH$_2$CH$_2$ | H | Pyridin-3-yl |
| CH$_2$CH$_2$CH$_2$CH$_2$ | H | 7-hydroxyquinolin-3-yl |
| CH$_2$CH$_2$CH$_2$CH$_2$ | H | Pyrimidin-2-yl |
| CH$_2$CH$_2$CH$_2$CH$_2$ | H | Thiophen-2-yl |
| CH$_2$CH$_2$CH$_2$CH$_2$ | H | Pyridin-2-yl |
| CH$_2$CH$_2$CH$_2$CH$_2$ | H | 4-Methylpyridin-2-yl |
| CH$_2$CH$_2$CH$_2$CH$_2$ | H | 2-Bromopyridin-5-yl |
| CH$_2$CH(Me)CH$_2$CH$_2$ | H | 1H-Indol-6-yl |
| CH$_2$CH(Me)CH$_2$CH$_2$ | H | 1H-Indol-5-yl |
| CH$_2$CH(Me)CH$_2$CH$_2$ | H | 1H-Indol-4-yl |

<Typical Compound IC-7>

[Formula 39]

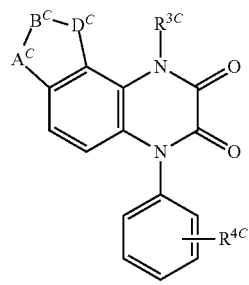

(In the formula, $A^C$-$B^C$-$D^C$, $R^{3C}$, and $R^{4C}$ are as shown in Tables 41 to 43.)

TABLE 41

| $A^C$-$B^C$-$D^C$ | $R^{3C}$ | $R^{4C}$ |
|---|---|---|
| CH₂CH₂CH₂ | H | 3-OH |
| CH₂CH₂CH₂ | H | 3-OMe |
| CH₂CH₂CH₂ | H | 4-OH |
| CH₂CH₂CH₂ | H | 4-OMe |
| OCH₂O | H | 2,3-OH |
| CH₂CH₂CH₂ | H | 3,4-OH |
| NHCH₂CH₂ | H | 3,4,5-OMe |
| CH₂CH₂CH₂ | H | 3-CN |

TABLE 42

| $A^C$-$B^C$-$D^C$ | $R^{3C}$ | $R^{4C}$ |
|---|---|---|
| CH₂CH₂CH₂ | H | 3-CO₂H |
| OCH₂O | H | 3-Br |
| CH₂CH₂CH₂ | H | 4-Me |
| CH₂NHCH₂ | H | 3-NHSO₂Ph |
| CH₂CH₂CH₂ | H | 3-NHSO₂(2-NO₂)Ph |
| CH₂CH₂CH₂ | H | 4-NHSO₂Ph |
| CH₂CH₂CH₂ | Me | 4-NHSO₂(2-NO₂)Ph |
| CH₂CH₂CH₂ | Et | 3-NHEt |

TABLE 43

| $A^C$-$B^C$-$D^C$ | $R^{3C}$ | $R^{4C}$ |
|---|---|---|
| CH₂CH₂CH₂ | H | 3-NHSO₂CH₃ |
| CH₂CH₂CH₂ | H | 3-Ph |
| CH₂CH₂CH₂ | H | 3-N(Me)₂ |
| CH₂CH₂NH | H | 2-Me |
| CH₂CH(Me)CH₂ | H | 3-NH₂ |
| CH₂CH(Me)CH₂ | H | 4-NH₂ |

<Typical Compound IC-8>

[Formula 40]

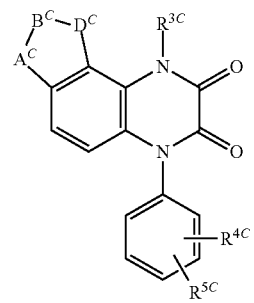

(In the formula, $A^C$-$B^C$-$D^C$, $R^{3C}$, $R^{4C}$, and $R^{5C}$ are as shown in Tables 44 to 46.)

TABLE 44

| $A^C$-$B^C$-$D^C$ | $R^{3C}$ | Position of $R^{4C}$ | $R^{4C}$ | $R^{5C}$ |
|---|---|---|---|---|
| CH₂CH₂CH₂ | H | 3 | 1H-Tetrazol-5-yl | H |
| OCH₂O | H | 4 | 1H-Tetrazol-5-yl | H |
| CH₂CH(Me)CH₂ | H | 3 | 1H-Tetrazol-5-yl | H |
| CH₂CH(Me)CH₂ | H | 4 | 1H-Tetrazol-5-yl | H |
| CH₂CH₂CH₂ | H | 3 | 1H-Tetrazol-5-yl | 4-F |
| CH₂CH₂CH₂ | H | 3 | 1H-Tetrazol-5-yl | 4-Me |
| CH₂CH₂CH₂ | H | 3 | 1H-Tetrazol-5-yl | 5-Br |
| CH₂NHCH₂ | H | 3 | 1H-Tetrazol-5-yl | 6-Me |
| CH₂CH₂CH₂ | H | 3 | (5-Thioxo-1,2,4-oxadiazol)-3-yl | H |

TABLE 45

| $A^C$-$B^C$-$D^C$ | $R^{3C}$ | Position of $R^{4C}$ | $R^{4C}$ | $R^{5C}$ |
|---|---|---|---|---|
| CH₂CH₂CH₂ | H | 3 | 1H-Tetrazol-5-yl | 6-OH |
| CH₂CH₂CH₂ | H | 3 | (2-Methyl-2H-tetrazol)-5-yl | H |
| CH₂CH₂CH₂ | Me | 3 | (2-Methyl-2H-tetrazol)-5-yl | H |
| CH₂CH₂CH₂ | Et | 3 | (2-Ethyl-2H-tetrazol)-5-yl | H |
| CH₂CH₂CH₂ | H | 3 | 4-Methyl-(5-thioxo-1,2,4-oxadiazol)-3-yl | H |
| CH₂CH₂CH₂ | H | 3 | 1-Methyl-1H-imidazol-2-yl | H |
| CH₂CH₂CH₂ | H | 3 | 1,3-Oxazol-2-yl | H |
| CH₂CH₂CH₂ | H | 3 | 1,3-Thiazol-2-yl | H |
| CH₂CH₂CH₂ | H | 3 | Thiophen-2-yl | H |

TABLE 46

| $A^C$-$B^C$-$D^C$ | $R^{3C}$ | Position of $R^{4C}$ | $R^{4C}$ | $R^{5C}$ |
|---|---|---|---|---|
| CH₂CH₂CH₂ | H | 3 | 1H-Imidazol-4-yl | H |
| CH₂CH₂CH₂ | H | 3 | Pyrazol-4-yl | H |
| CH₂CH₂CH₂ | H | 3 | 5-(Chloro)-1H-imidazol-2-yl | H |
| CH₂CH₂CH₂ | H | 3 | (1,2,4-Triazol)-3-yl | H |
| CH₂CH₂CH₂ | H | 3 | 1-Tetrazol-1-yl | H |
| OCH₂O | H | 3 | Phenyl | H |
| CH₂CH₂CH₂ | H | 3 | Pyridin-3-yl | H |
| NHCH₂CH₂ | H | 3 | Pyrimidin-5-yl | H |

<Typical Compound IC-9>

[Formula 41]

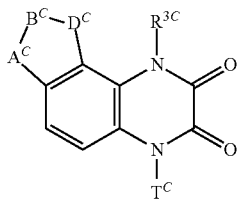

(In the formula, $A^C$-$B^C$-$D^C$, $R^{3C}$, and $T^C$ are as shown in Tables 47 and 48.)

TABLE 47

| $A^C$-$B^C$-$D^C$ | $R^{3C}$ | $T^C$ |
|---|---|---|
| CH$_2$CH$_2$CH$_2$ | H | 1H-Indol-6-yl |
| OCH$_2$O | H | 1H-Indolin-6-yl |
| CH$_2$CH$_2$CH$_2$ | Me | 1H-Indazol-6-yl |
| CH$_2$CH$_2$CH$_2$ | Et | 1H-Indazol-6-yl |
| CH$_2$CH$_2$CH$_2$ | H | 1H-Indazol-4-yl |
| CH$_2$NHCH$_2$ | H | 1H-Benzotriazol-6-yl |
| CH$_2$CH$_2$CH$_2$ | H | 3-Methylbenzisoxazol-6-yl |

TABLE 48

| $A^C$-$B^C$-$D^C$ | $R^{3C}$ | $T^C$ |
|---|---|---|
| CH$_2$CH$_2$CH$_2$ | H | Pyridin-4-yl |
| CH$_2$CH$_2$CH$_2$ | H | Thiophen-2-yl |
| CH$_2$NHCH$_2$ | H | 4-Methylpyridin-2-yl |
| CH$_2$CH(Me)CH$_2$ | H | 1H-Indol-6-yl |

(D-1) A compound represented by the following general formula (ID):

[Formula 42]

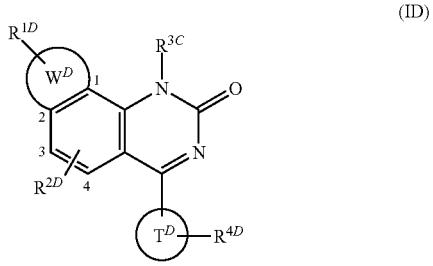

wherein, in the formula, $R^{1D}$ and $R^{2D}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, an aralkyl group (the aryl moiety thereof has 6 to 10 carbon atoms, and the alkylene moiety thereof has 1 to 3 carbon atoms), a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, or sulfamoyl group, $R^{3D}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, or an aralkyl group (the aryl moiety thereof has 6 to 10 carbon atoms, and the alkylene moiety thereof has 1 to 3 carbon atoms), $R^{4D}$ represents hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, an aralkyl group (the aryl moiety thereof has 6 to 10 carbon atoms, and the alkylene moiety thereof has 1 to 3 carbon atoms), an alkyl group having 1 to 8 carbon atoms and substituted with hydroxyl group, a halogen atom, hydroxyl group, nitro group, cyano group, amino group, an alkylamino group having 1 to 8 carbon atoms, an alkylamino group having 1 to 5 carbon atoms and substituted with 1 to 5 halogen atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, a benzenesulfonylamino group which may have a substituent, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, sulfamoyl group, a phenyl group which may have a substituent, or a heterocyclic group which may have a substituent,

[Formula 43]

represents a 5- to 8-membered ring which condenses at the 1- and 2-positions of the benzene ring, and may contain 1 or 2 nitrogen atoms as ring-constituting elements, and

[Formula 44]

represents an aromatic ring selected from benzene ring, naphthalene ring, pyridine ring, pyrimidine ring, quinoline ring, indole ring, indoline ring, benzimidazole ring, pyrazole ring, indazole ring, benzisoxazole ring, and benzotriazole ring.

(D-2) A compound represented by the following general formula (IID):

[Formula 45]

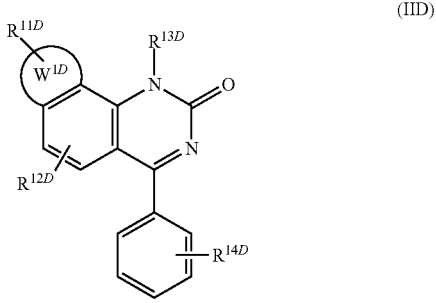

(IID)

wherein, in the formula, $R^{11D}$ and $R^{12D}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, an aralkyl group (the aryl moiety thereof has 6 to 10 carbon atoms, and the alkylene moiety thereof has 1 to 3 carbon atoms), a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, or sulfamoyl group, $R^{13D}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, or an aralkyl group (the aryl moiety thereof has 6 to 10 carbon atoms, and the alkylene moiety thereof has 1 to 3 carbon atoms), $R^{14D}$ represents an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, an aralkyl group (the aryl moiety thereof has 6 to 10 carbon atoms, and the alkylene moiety thereof has 1 to 3 carbon atoms), an alkyl group having 1 to 8 carbon atoms and substituted with hydroxyl group, hydroxyl group, nitro group, cyano group, amino group, an alkylamino group having 1 to 8 carbon atoms, an alkylamino group having 1 to 5 carbon atoms and substituted with 1 to 5 halogen atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, a benzenesulfonylamino group which may have a substituent, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, sulfamoyl group, a phenyl group which may have a substituent, or a heterocyclic group which may have a substituent, and,

[Formula 46]

represents naphthalene ring, tetrahydronaphthalene ring, or indane ring.

As for the general formula (ID), examples of the alkyl group having 1 to 8 carbon atoms as $R^{1D}$, $R^{2D}$, $R^{3D}$, and $R^{4D}$ include methyl group, ethyl group, propyl group, isopropyl group, butyl group, i-butyl group, t-butyl group, pentyl group, hexyl group, and the like.

Examples of the alkenyl group having 2 to 8 carbon atoms as $R^{1D}$, $R^{2D}$, $R^{3D}$, and $R^{4D}$ include allyl group, and the like.

Examples of the alkyl group having 1 to 8 carbon atoms and substituted with 1 to 3 halogen atoms as $R^{1D}$, $R^{2D}$, $R^{3D}$, and $R^{4D}$ include methyl group, ethyl group, propyl group, isopropyl group, butyl group, t-butyl group substituted with 1 to 3 halogen atoms such as fluorine atom, chlorine atom, and bromine atom, and the like, and preferred examples of the same include trifluoromethyl group, chloromethyl group, 2-chloroethyl group, 2-bromoethyl group, 2-fluoroethyl group, and the like.

Examples of the aralkyl group (the aryl moiety thereof has 6 to 10 carbon atoms, and the alkylene moiety thereof has 1 to 3 carbon atoms) as $R^{1D}$, $R^{2D}$, $R^{3D}$, and $R^{4D}$ include benzyl group, and the like.

Examples of the alkoxy group having 1 to 8 carbon atoms as $R^{1D}$, $R^{2D}$, and $R^{4D}$ include methoxy group, ethoxy group, propoxy group, isopropoxy group, butoxy group, i-butoxy group, t-butoxy group, pentyloxy group, hexyloxy group, and the like.

Examples of the alkoxy group having 1 to 8 carbon atoms and substituted with 1 to 3 halogen atoms as $R^{1D}$, $R^{2D}$, and $R^{4D}$ include methoxy group, ethoxy group, propoxy group, isopropoxy group, butoxy group, t-butoxy group substituted with 1 to 3 halogen atoms such as fluorine atom, chlorine atom, and bromine atom, and the like, and preferred examples of the same include trifluoromethoxy group, chloromethoxy group, 2-chloroethoxy group, 2-bromoethoxy group, 2-fluoroethoxy group, and the like.

Examples of the halogen atom as $R^{1D}$, $R^{2D}$, and $R^{4D}$ include fluorine atom, chlorine atom, bromine atom, and the like.

Examples of the alkylamino group having 1 to 8 carbon atoms as $R^{1D}$, $R^{2D}$, and $R^{4D}$ include methylamino group, ethylamino group, and the like.

Examples of the alkylamino group having 1 to 5 carbon atoms and substituted with 1 to 5 halogen atoms as $R^{4D}$ include 2,2,2-trifluoroethylamino group, and the like.

Examples of the dialkylamino group having 2 to 8 carbon atoms as $R^{1D}$, $R^{2D}$, and $R^{4D}$ include dimethylamino group, diethylamino group, and the like.

Examples of the acylamino group having 2 to 8 carbon atoms as $R^{1D}$, $R^{2D}$, and $R^{4D}$ include acetylamino group.

Examples of the acylamino group having 2 to 8 carbon atoms and substituted with 1 to 3 halogen atoms as $R^{1D}$, $R^{2D}$, and $R^{4D}$ include trifluoromethylcarbonylamino group.

Examples of the alkylsulfonylamino group having 1 to 8 carbon atoms as $R^{1D}$, $R^{2D}$, and $R^{4D}$ include methylsulfonylamino group.

Examples of the acyl group having 2 to 8 carbon atoms as $R^{1D}$, $R^{2D}$, and $R^{4D}$ include acetyl group.

Examples of the alkoxycarbonyl group (the alkoxy moiety thereof has 1 to 8 carbon atoms) as $R^{1D}$, $R^{2D}$, and $R^{4D}$ include methoxycarbonyl group, ethoxycarbonyl group, and the like.

Examples of the alkylthio group having 1 to 8 carbon atoms as $R^{1D}$, $R^{2D}$, and $R^{4D}$ include methylthio group.

Examples of the alkylsulfinyl group having 1 to 8 carbon atoms as $R^{1D}$, $R^{2D}$, and $R^{4D}$ include methylsulfinyl group.

Examples of the alkylsulfonyl group having 1 to 8 carbon atoms as $R^{1D}$, $R^{2D}$, and $R^{4D}$ include methylsulfonyl group.

Examples of the alkyl group having 1 to 8 carbon atoms and substituted with hydroxyl group as $R^{4D}$ include hydroxymethyl group, and the like.

Examples of the benzenesulfonylamino group which may have a substituent as $R^{4D}$ include a benzenesulfonylamino group which may have a substituent selected from an alkyl group having 1 to 8 carbon atoms (for example, methyl group, ethyl group, and the like), an alkoxy group having 1 to 8 carbon atoms (for example, methoxy group, ethoxy group, and the like), a halogen atom (for example, fluorine atom, chlorine atom, and the like), nitro group, and the like, and preferred examples of the same include o-nitrobenzenesulfonylamino group, and the like.

Preferred examples of the substituent of the phenyl group which may have a substituent as $R^{4D}$ include an alkyl group having 1 to 8 carbon atoms such as methyl group and ethyl group, an alkyl group having 1 to 8 carbon atoms and substituted with 1 to 3 halogen atoms such as trifluoromethyl group, a halogen atom such as fluorine atom, cyano group, and the like.

Preferred examples of the heterocyclic group of the heterocyclic group which may have a substituent as $R^{4D}$ include a tetrazolyl group, triazolyl group, pyridyl group, imidazolyl group, oxazolyl group, thiazolyl group, and the like.

Preferred examples of the substituent of the heterocyclic ring which may have a substituent as $R^{4D}$ include an alkyl group having 1 to 8 carbon atoms such as methyl group and ethyl group, an alkyl group having 1 to 8 carbon atoms and substituted with 1 to 3 halogen atoms such as trifluoromethyl group, a halogen atom such as fluorine atom, cyano group, oxo, and the like.

In the general formula (ID), a plurality of the same or different $R^{1D}$, $R^{2D}$, and $R^{4D}$ may exist on the rings on which $R^{1D}$, $R^{2D}$, and $R^{4D}$ substitute.

Examples of the alkyl group having 1 to 8 carbon atoms, alkenyl group having 2 to 8 carbon atoms, alkoxy group having 1 to 8 carbon atoms, alkyl group having 1 to 8 carbon atoms and substituted with 1 to 3 halogen atoms, alkoxy group having 1 to 8 carbon atoms and substituted with 1 to 3 halogen atoms, aralkyl group (the aryl moiety thereof has 6 to 10 carbon atoms, and the alkylene moiety thereof has 1 to 3 carbon atoms), alkyl group having 1 to 8 carbon atoms and substituted with hydroxyl group, halogen atom, alkylamino group having 1 to 8 carbon atoms, alkylamino group having 1 to 5 carbon atoms and substituted with 1 to 5 halogen atoms, dialkylamino group having 2 to 8 carbon atoms, acylamino group having 2 to 8 carbon atoms, acylamino group having 2 to 8 carbon atoms and substituted with 1 to 3 halogen atoms, alkylsulfonylamino group having 1 to 8 carbon atoms, benzenesulfonylamino group which may have a substituent, acyl group having 2 to 8 carbon atoms, alkoxycarbonyl group (the alkoxy moiety thereof has 1 to 8 carbon atoms), alkylthio group having 1 to 8 carbon atoms, alkylsulfinyl group having 1 to 8 carbon atoms, alkylsulfonyl group having 1 to 8 carbon atoms, phenyl group which may have a substituent, heterocyclic group which may have a substituent, and the like as $R^{11D}$, $R^{12D}$, $R^{13D}$, and $R^{14D}$ in the aforementioned general formula (IID) include those similar to the examples of the same as $R^{1D}$, $R^{2D}$, $R^{3D}$, and $R^{4D}$ in the general formula (ID) mentioned above.

Examples of the alkyl group having 1 to 8 carbon atoms, alkoxy group having 1 to 8 carbon atoms, alkyl group having 1 to 8 carbon atoms and substituted with 1 to 3 halogen atoms, alkoxy group having 1 to 8 carbon atoms and substituted with 1 to 3 halogen atoms, halogen atom, alkylamino group having 1 to 8 carbon atoms, and dialkylamino group having 2 to 8 carbon atoms as the substituent of the heterocyclic group which may have a substituent as $R^{14D}$ in the general formula (IID) include the examples of the same mentioned for $R^{1D}$ to $R^{4D}$ of the general formula (ID) mentioned above.

In the aforementioned general formula (IID), a plurality of the same or different $R^{11D}$, $R^{12D}$, and $R^{14D}$ may exist on the rings on which $R^{11D}$, $R^{12D}$, and $R^{14D}$ substitute.

As the compounds of the general formula (ID), the following compounds are preferred.

(D-1-1) The compound according to (D-1), wherein $R^{1D}$ and $R^{2D}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, or amino group.

(D-1-2) The compound according to (D-1) or (D-1-1), wherein $R^{3D}$ is hydrogen atom, or an alkyl group having 1 to 8 carbon atoms.

(D-1-3) The compound according to any one of (D-1), (D-1-1), and (D-1-2), wherein $R^{4D}$ is hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, an alkyl group having 1 to 8 carbon atoms and substituted with hydroxyl group, a halogen atom, hydroxyl group, cyano group, amino group, an alkylamino group having 1 to 8 carbon atoms, a dialkylamino group having 2 to 8 carbon atoms, an alkylsulfonylamino group having 1 to 8 carbon atoms, a benzenesulfonylamino group which may have a substituent, a phenyl group which may have a substituent, or a heterocyclic group which may have a substituent.

(D-1-4) The compound according to (D-1), or any one of (D-1-1) to (D-1-3), wherein $R^{4D}$ is a tetrazolyl group, triazolyl group, pyridyl group, imidazolyl group, oxazolyl group, or thiazolyl group which may have a substituent selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(D-1-5) The compound according to (D-1), or any one of (D-1-1) to (D-1-4), wherein $R^{4D}$ is an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, hydroxyl group, cyano group, amino group, an alkylamino group having 1 to 8 carbon atoms, a dialkylamino group having 2 to 8 carbon atoms, or a benzenesulfonylamino group which may have a substituent selected from an alkyl group having 1 to 8 carbon atoms, an alkoxy group having 1 to 8 carbon atoms, a halogen atom, and nitro group.

(D-1-6) The compound according to (D-1), or any one of (D-1-1) to (D-1-5), wherein

[Formula 47]

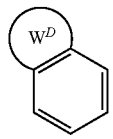

is a naphthalene ring, tetrahydronaphthalene ring, or indane ring.

(D-1-7) The compound according to (D-1), or any one of (D-1-1) to (D-1-6), wherein

[Formula 48]

is a benzene ring, or indole ring.

As the compounds represented by the general formula (IID), the following compounds are preferred.

(D-2-1) The compound according to (D-2), wherein $R^{11D}$ and $R^{12D}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, or amino group.

(D-2-2) The compound according to (D-2) or (D-2-1), wherein $R^{13D}$ is hydrogen atom.

(D-2-3) The compound according to any one of (D-2), (D-2-1), and (D-2-2), wherein $R^{14D}$ is an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, an alkyl group having 1 to 8 carbon atoms and substituted with hydroxyl group, hydroxyl group, cyano group, amino group, an alkylamino group having 1 to 8 carbon atoms, a dialkylamino group having 2 to 8 carbon atoms, an alkylsulfonylamino group having 1 to 8 carbon atoms, a benzenesulfonylamino group which may have a substituent, a phenyl group which may have a substituent, or a heterocyclic group which may have a substituent.

(D-2-4) The compound according to (D-2), or any one of (D-2-1) to (D-2-3), wherein $R^{14D}$ is a tetrazolyl group, triazolyl group, pyridyl group, imidazolyl group, oxazolyl group, or thiazolyl group which may have a substituent selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(D-2-5) The compound according to (D-2), or any one of (D-2-1) to (D-2-4), wherein $R^{14D}$ is an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, hydroxyl group, cyano group, amino group, an alkylamino group having 1 to 8 carbon atoms, a dialkylamino group having 2 to 8 carbon atoms, or a benzenesulfonylamino group which may have a substituent selected from an alkyl group having 1 to 8 carbon atoms, an alkoxy group having 1 to 8 carbon atoms, a halogen atom, and nitro group.

(D-2-6) The compound according to (D-2), or any one of (D-2-1) to (D-2-5), wherein

[Formula 49]

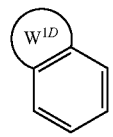

is a naphthalene ring.

<Typical Compound ID-1>

[Formula 50]

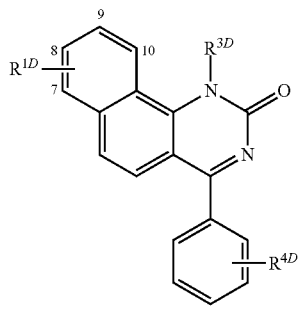

(In the formula, $R^{1D}$, $R^{3D}$, and $R^{4D}$ are as shown in Table 49.)

TABLE 49

| $R^{1D}$ | $R^{3D}$ | $R^{4D}$ |
|---|---|---|
| H | H | 3-OH |
| 8-Me | H | 3-OMe |
| 8-Cl | H | 4-OH |
| 9-Me | H | 3,4-OH |
| 9-Cl | H | 3-CN |
| H | H | 4-CN |
| H | H | 3-CO$_2$H |
| H | H | 3-NH$_2$ |
| H | H | 3-NHMe |
| H | Me | 3-NHMe |
| H | Et | 3-NHEt |
| H | H | 3-NHCH$_2$CF$_3$ |

TABLE 49-continued

| $R^{1D}$ | $R^{3D}$ | $R^{4D}$ |
|---|---|---|
| H | H | 3-NHSO$_2$Ph |
| H | H | 3-NHSO$_2$(2-NO$_2$)Ph |
| H | H | 1H-Tetrazol-5-yl |
| H | H | 1H-Tetrazol-1-yl |
| H | H | (2-Methyl-2H-tetrazol)-5-yl |
| H | H | 1,3-Oxazol-2-yl |
| H | H | 1-H-Imidazol-2-yl |
| H | H | (1,2,4-Triazol)-3-yl |

<Typical Compound ID-2>

[Formula 51]

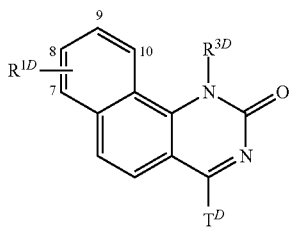

(In the formula, $R^{1D}$, $R^{3D}$, and $T^D$ are as shown in Table 50.)

TABLE 50

| $R^{1D}$ | $R^{3D}$ | $T^D$ |
|---|---|---|
| H | H | 1H-Indol-6-yl |
| 8-Me | H | 1H-Indol-4-yl |
| 8-Cl | H | 1H-Indazol-6-yl |
| 9-Me | H | 1H-Indazol-4-yl |
| 9-Cl | H | 1H-Indolin-6-yl |
| H | Me | 1H-Benzimidazol-6-yl |
| H | Et | 1H-Benzotriazol-6-yl |
| H | H | 3-Methylbenzisoxazol-6-yl |
| H | H | Pyridin-3-yl |
| H | H | 1H-Pyrazol-4-yl |
| H | H | Pyridin-2-yl |
| H | H | 4-Methylpyridin-2-yl |
| H | H | 2-Bromopyridin-5-yl |

<Typical Compound ID-3>

[Formula 52]

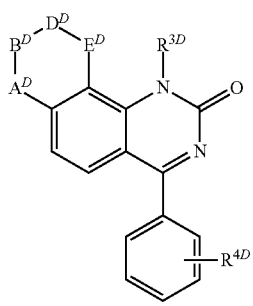

(In the formula, $A^D$-$B^D$-$D^D$-$E^D$, $R^{3D}$, and $R^{4D}$ are as shown in Table 51.)

TABLE 51

| $A^D$-$B^D$-$D^D$-$E^D$ | $R^{3D}$ | $R^{4D}$ |
|---|---|---|
| CH$_2$CH$_2$CH$_2$CH$_2$ | H | 3-OH |
| CH$_2$CH$_2$CH$_2$ | H | 3-OMe |
| CH$_2$CH$_2$(CH$_2$)$_2$CH$_2$ | H | 4-OH |
| CH$_2$CH$_2$(CH$_2$)$_3$CH$_2$ | H | 3,4-OH |
| CH$_2$CH$_2$CH$_2$CH$_2$ | H | 3-CN |
| CH$_2$CH$_2$NHCH$_2$ | H | 4-CN |
| CH$_2$CH$_2$CH$_2$CH$_2$ | H | 3-CO$_2$H |
| CH$_2$CH$_2$NHCH$_2$ | H | 3-NH$_2$ |
| CH$_2$CH$_2$CH$_2$CH$_2$ | H | 3-NHMe |
| CH$_2$CH$_2$CH$_2$CH$_2$ | Me | 3-NHMe |
| CH$_2$CH$_2$CH$_2$CH$_2$ | Et | 3-NHEt |
| CH$_2$CH$_2$CH$_2$CH$_2$ | H | 3-NHCH$_2$CF$_3$ |
| CH$_2$CH$_2$CH$_2$CH$_2$ | H | 3-NHSO$_2$Ph |
| CH$_2$CH$_2$CH$_2$CH$_2$ | H | 3-NHSO$_2$(2-NO$_2$)Ph |
| CH$_2$CH$_2$CH$_2$CH$_2$ | H | 1H-Tetrazol-5-yl |
| CH$_2$NHCH$_2$CH$_2$ | H | 1H-Tetrazol-1-yl |
| CH$_2$CH(Me)CH$_2$CH$_2$ | H | (2-Methyl-2H-tetrazol)-5-yl |
| CH$_2$CH(Me)CH$_2$CH$_2$ | H | 1,3-Oxazol-2-yl |
| CH$_2$CH$_2$CH(Me)CH$_2$ | H | 1H-Imidazol-2-yl |
| CH$_2$CH$_2$CH(Me)CH$_2$ | H | (1,2,4-Triazol)-3-yl |

<Typical Compound ID-4>

[Formula 53]

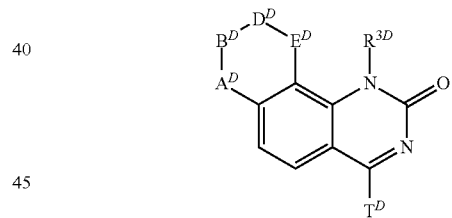

(In the formula, $A^D$-$B^D$-$D^D$-$E^D$, $R^{3D}$, and $T^D$ are as shown in Table 52.)

TABLE 52

| $A^D$-$B^D$-$D^D$-$E^D$ | $R^{3D}$ | $T^D$ |
|---|---|---|
| CH$_2$CH$_2$CH$_2$CH$_2$ | H | 1H-Indol-6-yl |
| CH$_2$CH$_2$CH$_2$ | H | 1H-Indol-4-yl |
| CH$_2$CH$_2$(CH$_2$)$_2$CH$_2$ | H | 1H-Indazol-6-yl |
| CH$_2$CH$_2$(CH$_2$)$_3$CH$_2$ | H | 1H-Indazol-4-yl |
| CH$_2$CH$_2$CH$_2$CH$_2$ | Me | 1H-Indolin-6-yl |
| CH$_2$NHCH$_2$CH$_2$ | Et | 1H-Benzimidazol-6-yl |
| CH$_2$CH$_2$CH$_2$CH$_2$ | H | 1H-Benzotriazol-6-yl |
| CH$_2$CH$_2$CH$_2$CH$_2$ | H | 3-Methylbenzisoxazol-6-yl |
| CH$_2$CH$_2$CH$_2$CH$_2$ | H | Pyridin-3-yl |
| CH$_2$N(Me)CH$_2$CH$_2$ | H | 1H-Pyrazol-4-yl |
| CH$_2$CH(Me)CH$_2$CH$_2$ | H | Pyridin-2-yl |
| CH$_2$CH$_2$CH(Me)CH$_2$ | H | 4-Methylpyridin-2-yl |
| CH$_2$CH$_2$CH(Me)CH$_2$ | H | 2-Bromopyridin-5-yl |

(E-1) A compound represented by the following general formula (IE):

[Formula 54]

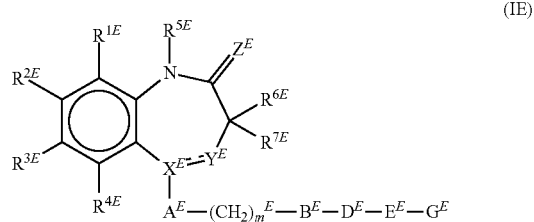

(IE)

wherein, in the formula, $R^{1E}$ and $R^{2E}$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), a phenyl group which may have a substituent, a pyridyl group which may have a substituent, or an aralkyl group (the aryl moiety thereof has 6 to 10 carbon atoms, and the alkylene moiety thereof has 1 to 8 carbon atoms), or $R^{1E}$ and $R^{2E}$ may bind together to form a condensed ring selected from naphthalene ring, quinoline ring, isoquinoline ring, tetrahydronaphthalene ring, indane ring, tetrahydroquinoline ring, and tetrahydroisoquinoline ring together with the benzene ring to which they bind, and the ring formed by $R^{1E}$, $R^{2E}$ binding together, and the carbon atoms to which $R^{1E}$ and $R^{2E}$ bind may be substituted with 1 to 4 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), and an aralkyl group (the aryl moiety thereof has 6 to 10 carbon atoms, and the alkylene moiety thereof has 1 to 8 carbon atoms), $R^{3E}$ and $R^{4E}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), or an aralkyl group (the aryl moiety thereof has 6 to 10 carbon atoms, and the alkylene moiety thereof has 1 to 8 carbon atoms), $R^{5E}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety thereof has 6 to 10 carbon atoms, and the alkylene moiety thereof has 1 to 8 carbon atoms), $R^{6E}$ and $R^{7E}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, or amino group, $X^E$ represents C, CH, or N, $Y^E$ represents N, NH, or C(=O), provided that when $X^E$ is N, $Y^E$ is not N or NH, and when $X^E$ is C or CH, $Y^E$ is not C(=O), the double line consisting of the solid line and the broken line represents a single bond or a double bond, $Z^E$ represents oxygen atom or sulfur atom, $A^E$ represents benzene ring, pyridine ring, thiophene ring, pyrimidine ring, naphthalene ring, quinoline ring, or indole ring which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group (the aryl moiety thereof has 6 to 10 carbon atoms, and the alkylene moiety thereof has 1 to 8 carbon atoms), phenyl group, and pyridyl group, or an atomic bond, $B^E$ represents $N(R^{8E})C(=O)$, NHCONH, $CON(R^{9E})$, $NHC(=S)NH$, $N(R^{10E})SO_2$, $SO_2N(R^{11E})$, or $OSO_2$, wherein $R^{8E}$, $R^{9E}$, $R^{10E}$, and $R^{11E}$ represent hydrogen atom, an alkyl group having 1 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety thereof has 6 to 10 carbon atoms, and the alkylene moiety thereof has 1 to 8 carbon atoms), $D^E$ represents an alkylene chain having 1 to 6 carbon atoms which may have 1 to 4 of the same or different substituents selected from an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety thereof has 6 to 10 carbon atoms, and the alkylene moiety thereof has 1 to 8 carbon atoms), and may further contain a double bond, or an atomic bond, $E^E$ represents O, S, $NR^{12E}$, or an atomic bond, wherein $R^{12E}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety thereof has 6 to 10 carbon atoms, and the alkylene moiety thereof has 1 to 8 carbon atoms), $G^E$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, an alkylsulfonyl group having 1 to 6 carbon atoms, an aralkyl group (the aryl moiety thereof has 6 to 10 carbon atoms, and the alkylene moiety thereof has 1 to 8 carbon atoms), a phenyl group which may have a substituent, a pyridyl group which may have a substituent, an imidazolyl group which may have a substituent, an oxazolyl group may have a substituent, and a thiazolyl group which may have a substituent, and $m^E$ represents an integer of 0 to 5, provided that compounds where $R^{1E}$ and $R^{2E}$ do not bind together to form a ring, $X^E$ is C, $Y^E$ is N, the double line consisting of the solid line and the broken line is a double bond, $Z^E$ is oxygen atom, $A^E$ is a benzene ring, $m^E$ is 0, $B^E$ is C(=O)NH, $E^E$ is an atomic bond, and $G^E$ is phenyl group are excluded.

(E-2) A compound represented by the following general formula (IIE):

[Formula 55]

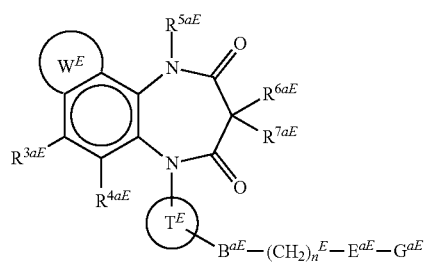

(IIE)

wherein, in the formula,

[Formula 56]

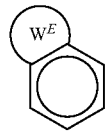

represents naphthalene ring, quinoline ring, isoquinoline ring, tetrahydronaphthalene ring, indane ring, tetrahydroquinoline ring, or tetrahydroisoquinoline ring, and these rings may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), and an aralkyl group (the aryl moiety thereof has 6 to 10 carbon atoms, and the alkylene moiety thereof has 1 to 8 carbon atoms), $R^{3aE}$ and $R^{4aE}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), or an aralkyl group (the aryl moiety thereof has 6 to 10 carbon atoms, and the alkylene moiety thereof has 1 to 8 carbon atoms), $R^{5aE}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety thereof has 6 to 10 carbon atoms, and the alkylene moiety thereof has 1 to 8 carbon atoms), $R^{6aE}$ and $R^{7aE}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, or amino group,

[Formula 57]

represents benzene ring, pyridine ring, thiophene ring, pyrimidine ring, naphthalene ring, quinoline ring, or indole ring which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group (the aryl moiety thereof has 6 to 10 carbon atoms, and the alkylene moiety thereof has 1 to 8 carbon atoms), phenyl group, and pyridyl group, $B^{aE}$ represents $N(R^{8aE})C(=O)$, NHCONH, $CON(R^{9aE})$, NHC(=S)NH, $N(R^{10aE})SO_2$, $SO_2N(R^{11aE})$, or $OSO_2$, wherein $R^{8aE}$, $R^{9aE}$, $R^{10aE}$, and $R^{11aE}$ represent hydrogen atom, an alkyl group having 1 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety thereof has 6 to 10 carbon atoms, and the alkylene moiety thereof has 1 to 8 carbon atoms), $E^{aE}$ represents O, S, $NR^{12aE}$, or an atomic bond, wherein $R^{12aE}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety thereof has 6 to 10 carbon atoms, and the alkylene moiety thereof has 1 to 8 carbon atoms), $G^{aE}$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, an alkylsulfonyl group having 1 to 6 carbon atoms, an aralkyl group (the aryl moiety thereof has 6 to 10 carbon atoms, and the alkylene moiety thereof has 1 to 8 carbon atoms), a phenyl group which may have a substituent, a pyridyl group which may have a substituent, an imidazolyl group which may have a substituent, an oxazolyl group which may have a substituent, and a thiazolyl group which may have a substituent, and $n^E$ represents an integer of 0 to 5.

As for the general formulas (IE) and (IIE), examples of the alkyl group having 1 to 8 carbon atoms include methyl group, ethyl group, propyl group, isopropyl group, butyl group, i-butyl group, t-butyl group, pentyl group, hexyl group, and the like.

Examples of the cycloalkyl group having 3 to 8 carbon atoms include cyclopropyl group, cyclohexyl group, and the like.

Examples of the alkenyl group having 2 to 8 carbon atoms include allyl group, and the like.

Examples of the alkoxy group having 1 to 8 carbon atoms include methoxy group, ethoxy group, propoxy group, isopropoxy group, butoxy group, i-butoxy group, t-butoxy group, pentyloxy group, hexyloxy group, and the like.

Examples of the alkyl group having 1 to 8 carbon atoms and substituted with 1 to 3 halogen atoms include methyl group, ethyl group, propyl group, isopropyl group, butyl group, t-butyl group substituted with 1 to 3 halogen atoms such as fluorine atom, chlorine atom, and bromine atom, and the like, and preferred examples of the same include trifluoromethyl group, chloromethyl group, 2-chloroethyl group, 2-bromoethyl group, 2-fluoroethyl group, and the like.

Examples of the alkoxy group having 1 to 8 carbon atoms and substituted with 1 to 3 halogen atoms include methoxy group, ethoxy group, propoxy group, isopropoxy group, butoxy group, t-butoxy group substituted with 1 to 3 halogen atoms such as fluorine atom, chlorine atom, and bromine atom, and the like, and preferred examples of the same include trifluoromethoxy group, chloromethoxy group, 2-chloroethoxy group, 2-bromoethoxy group, 2-fluoroethoxy group, and the like.

Examples of the halogen atom include fluorine atom, chlorine atom, bromine atom, and the like.

Examples of the alkylamino group having 1 to 8 carbon atoms include methylamino group, ethylamino group, and the like.

Examples of the dialkylamino group having 2 to 8 carbon atoms include dimethylamino group, diethylamino group, and the like.

Examples of the acylamino group having 2 to 8 carbon atoms include acetylamino group.

Examples of the acyl group having 2 to 8 carbon atoms include acetyl group, and the like.

Examples of the alkoxycarbonyl group (the alkoxy moiety thereof has 1 to 8 carbon atoms) include methoxycarbonyl group, and the like.

Examples of the aralkyl group (the aryl moiety thereof has 6 to 10 carbon atoms, and the alkylene moiety thereof has 1 to 8 carbon atoms) include benzyl group, and the like.

Examples of the alkyl group having 1 to 8 carbon atoms and substituted with hydroxyl group include 2-hydroxyethyl group, and the like.

Examples of the alkylsulfinyl group having 1 to 6 carbon atoms include methanesulfinyl group, and the like.

Examples of the alkylthio group having 1 to 6 carbon atoms include methylthio group, and the like.

Examples of the alkylsulfonyl group having 1 to 6 carbon atoms include methanesulfonyl group, and the like.

Examples of the substituent of the phenyl group which may have a substituent, pyridyl group which may have a substituent, imidazolyl group which may have a substituent, oxazolyl group which may have a substituent, and thiazolyl group which may have a substituent include a halogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, and the like.

As the compounds of the general formula (IE) of the present invention, the following compounds are preferred.

(E-1-1) The compound according to (E-1), wherein $R^{1E}$, and $R^{2E}$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, a phenyl group which may have a substituent, a pyridyl group which may have a substituent, or an aralkyl group (the aryl moiety thereof has 6 to 10 carbon atoms, and the alkylene moiety thereof has 1 to 8 carbon atoms).

(E-1-2) The compound according to (E-1), wherein $R^{1E}$ and $R^{2E}$ bind together to form naphthalene ring, or tetrahydronaphthalene ring together with the benzene ring to which they bind, and the benzene ring, or cyclohexene ring formed by $R^{1E}$, $R^{2E}$ binding together, and the carbon atoms to which $R^{1E}$ and $R^{2E}$ bind may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), and an aralkyl group (the aryl moiety thereof has 6 to 10 carbon atoms, and the alkylene moiety thereof has 1 to 8 carbon atoms).

(E-1-3) The compound according to (E-1), wherein $R^{1E}$ and $R^{2E}$ bind together to form naphthalene ring together with the benzene ring to which they bind, and the benzene ring formed by $R^{1E}$, $R^{2E}$ binding together, and the carbon atoms to which $R^{1E}$ and $R^{2E}$ bind may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, and amino group.

(E-1-4) The compound according to (E-1), or any one of (E-1-1) to (E-1-3), wherein $R^{3E}$ and $R^{4E}$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, or an aralkyl group (the aryl moiety thereof has 6 to 10 carbon atoms, and the alkylene moiety thereof has 1 to 8 carbon atoms).

(E-1-5) The compound according to (E-1), or any one of (E-1-1) to (E-1-4), wherein $R^{5E}$ is hydrogen atom, an alkyl group having 1 to 8 carbon atoms, or an aralkyl group (the aryl moiety thereof has 6 to 10 carbon atoms, and the alkylene moiety thereof has 1 to 8 carbon atoms).

(E-1-6) The compound according to (E-1), or any one of (E-1-1) to (E-1-5), wherein $R^{5E}$ is hydrogen atom.

(E-1-7) The compound according to (E-1), or any one of (E-1-1) to (E-1-6), wherein $R^{6E}$ and $R^{7E}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, or an alkoxy group having 1 to 8 carbon atoms and substituted with 1 to 3 halogen atoms.

(E-1-8) The compound according to (E-1), or any one of (E-1-1) to (E-1-7), wherein both $R^{6E}$ and $R^{7E}$ are hydrogen atoms.

(E-1-9) The compound according to (E-1), or any one of (E-1-1) to (E-1-8), wherein $X^E$ is N, $Y^E$ is C(=O), and the double line consisting of the solid line and the broken line is a single bond.

(E-1-10) The compound according to (E-1), or any one of (E-1-1) to (E-1-9), wherein $X^E$ is C, $Y^E$ is N, and the double line consisting of the solid line and the broken line is a double bond.

(E-1-11) The compound according to (E-1), or any one of (E-1-1) to (E-1-10), wherein $Z^E$ is oxygen atom.

(E-1-12) The compound according to (E-1), or any one of (E-1-1) to (E-1-11), wherein $A^E$ is a phenyl group or pyridyl group which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group (the aryl moiety thereof has 6 to 10 carbon atoms, and the alkylene moiety thereof has 1 to 8 carbon atoms), phenyl group, and pyridyl group.

(E-1-13) The compound according to (E-1), or any one of (E-1-1) to (E-1-12), wherein $A^E$ is a phenyl group which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, and amino group.

(E-1-14) The compound according to (E-1), or any one of (E-1-1) to (E-1-13), wherein $A^E$ is an atomic bond.

(E-1-15) The compound according to (E-1), or any one of (E-1-1) to (E-1-14), wherein $B^E$ is NHC(=O), NHCONH, CONH, NHC(=S)NH, NHSO$_2$, SO$_2$NH, or OSO$_2$.

(E-1-16) The compound according to (E-1), or any one of (E-1-1) to (E-1-15), wherein $B^E$ is NHC(=O), NHCONH, or NHSO$_2$.

(E-1-17) The compound according to (E-1), or any one of (E-1-1) to (E-1-16), wherein $D^E$ is an alkylene chain having 1 to 6 carbon atoms which may have 1 to 4 of the same or different substituents selected from an alkyl group having 1 to 8 carbon atoms, and an alkyl group having 1 to 8 carbon atoms and substituted with 1 to 3 halogen atoms, and may further contain a double bond.

(E-1-18) The compound according to (E-1), or any one of (E-1-1) to (E-1-16), wherein $D^E$ is an atomic bond.

(E-1-19) The compound according to (E-1), or any one of (E-1-1) to (E-1-18), wherein $E^E$ is an atomic bond.

(E-1-20) The compound according to (E-1), or any one of (E-1-1) to (E-1-19), wherein $G^E$ is piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, and an alkylsulfonyl group having 1 to 6 carbon atoms.

(E-1-21) The compound according to (E-1), or any one of (E-1-1) to (E-1-20), wherein $G^E$ is benzene which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, and an alkylsulfonyl group having 1 to 6 carbon atoms.

(E-1-22) The compound according to (E-1), or any one of (E-1-1) to (E-1-21), wherein $m^E$ is 0.

As the compounds represented by the general formula (IIE), the following compounds are preferred.

(E-2-1) The compound according to (E-2), wherein

[Formula 58]

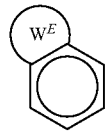

is a naphthalene ring or tetrahydronaphthalene ring which may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), and an aralkyl group (the aryl moiety thereof has 6 to 10 carbon atoms, and the alkylene moiety thereof has 1 to 8 carbon atoms).

(E-2-2) The compound according to (E-2), wherein

[Formula 59]

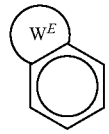

is a naphthalene ring which may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, and amino group.

(E-2-3) The compound according to (E-2), (E-2-1), or (E-2-2), wherein $R^{3aE}$ and $R^{4aE}$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, or an aralkyl group (the aryl moiety thereof has 6 to 10 carbon atoms, and the alkylene moiety thereof has 1 to 8 carbon atoms).

(E-2-4) The compound according to (E-2), or any one of (E-2-1) to (E-2-3), wherein $R^{5aE}$ is hydrogen atom, an alkyl group having 1 to 8 carbon atoms, or an aralkyl group (the aryl moiety thereof has 6 to 10 carbon atoms, and the alkylene moiety has 1 to 8 carbon atoms).

(E-2-5) The compound according to (E-2), or any one of (E-2-1) to (E-2-4), wherein $R^{5aE}$ is hydrogen atom.

(E-2-6) The compound according to (E-2), or any one of (E-2-1) to (E-2-5), wherein $R^{6aE}$ and $R^{7aE}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, or an alkoxy group having 1 to 8 carbon atoms and substituted with 1 to 3 halogen atoms.

(E-2-7) The compound according to (E-2), or any one of (E-2-1) to (E-2-6), wherein both $R^{6aE}$ and $R^{7aE}$ are hydrogen atoms.

(E-2-8) The compound according to (E-2), or any one of (E-2-1) to (E-2-7), wherein

[Formula 60]

is a phenyl group or pyridyl group which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group (the aryl moiety thereof has 6 to 10 carbon atoms, and the alkylene moiety thereof has 1 to 8 carbon atoms), phenyl group, and pyridyl group.

(E-2-9) The compound according to (E-2), or any one of (E-2-1) to (E-2-8), wherein

[Formula 61]

is a phenyl group which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, and amino group.

(E-2-10) The compound according to (E-2), or any one of (E-2-1) to (E-2-7), wherein

[Formula 62]

is an atomic bond.

(E-2-11) The compound according to (E-2), or any one of (E-2-1) to (E-2-10), wherein $B^{aE}$ is NHC(=O), NHCONH, CONH, NHC(=S)NH, NHSO$_2$, SO$_2$NH, or OSO$_2$.

(E-2-12) The compound according to (E-2), or any one of (E-2-1) to (E-2-11), wherein $B^{aE}$ is NHC(=O), NHCONH, or NHSO$_2$.

(E-2-13) The compound according to (E-2), or any one of (E-2-1) to (E-2-10), wherein $E^{aE}$ is an atomic bond.

(E-2-14) The compound according to (E-2), or any one of (E-2-1) to (E-2-13), wherein $G^{aE}$ is piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, and an alkylsulfonyl group having 1 to 6 carbon atoms.

(E-2-15) The compound according to (E-2), or any one of (E-2-1) to (E-2-14), wherein $G^{aE}$ is benzene which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, and an alkylsulfonyl group having 1 to 6 carbon atoms.

(E-2-16) The compound according to (E-2), or any one of (E-2-1) to (E-2-15), wherein $n^E$ is 0.

<Typical Compound IE-1>

[Formula 63]

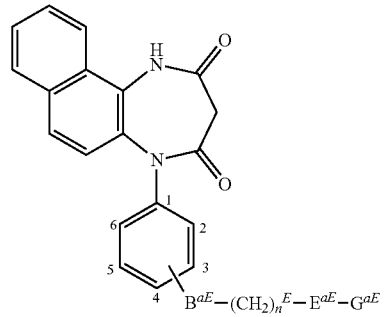

(In the formula, $B^{aE}$ (substitution position), $n^E$, $E^{aE}$, and $G^{aE}$ are as shown in Tables 53 to 61.)

TABLE 53

| $B^{aE}$ (substitution position) | $n^E$ | $E^{aE}$ | $G^{aE}$ |
|---|---|---|---|
| NHCO(4) | 0 | Atomic bond | Phenyl |
| NHCO(4) | 0 | Atomic bond | (2-CF$_3$)Phenyl |
| NHCO(4) | 0 | Atomic bond | (3-Br)Phenyl |
| NHCO(4) | 0 | Atomic bond | (4-CF$_3$)Phenyl |
| NHCO(4) | 0 | Atomic bond | (2-Me)Phenyl |
| NHCO(4) | 0 | Atomic bond | (2,6-Me)Phenyl |
| NHCO(4) | 0 | Atomic bond | (2,6-Cl)Phenyl |
| NHCO(4) | 0 | Atomic bond | (3-Cl)Phenyl |
| NHCO(4) | 1 | Atomic bond | Phenyl |
| NHC(=S)NH(4) | 0 | Atomic bond | Phenyl |
| NHCO(4) | 0 | Atomic bond | (2,3-OMe)Phenyl |
| NHCO(4) | 0 | Atomic bond | (2-OMe)Phenyl |
| NHCO(4) | 1 | Atomic bond | (2-Cl)Phenyl |
| NHCO(4) | 0 | Atomic bond | (2,3-Me)Phenyl |
| NHCO(4) | 0 | Atomic bond | (2,5-Me)Phenyl |
| NHCO(4) | 0 | Atomic bond | (2-Cl, 5-Br)Phenyl |

TABLE 54

| $B^{aE}$ (substitution position) | $n^E$ | $E^{aE}$ | $G^{aE}$ |
|---|---|---|---|
| NHCO(4) | 0 | Atomic bond | (2,4-Cl)Phenyl |
| NHCO(4) | 0 | Atomic bond | (2-OH)Phenyl |
| NHCO(4) | 0 | Atomic bond | (2,3-OH)Phenyl |
| NHC(=O)NH(4) | 0 | Atomic bond | Phenyl |
| NHCO(4) | 1 | Atomic bond | (2,6-Cl)Phenyl |
| NHCO(4) | 1 | Atomic bond | (2-OMe)Phenyl |
| NHCO(4) | 1 | Atomic bond | (2-OH)Phenyl |
| NHC(=S)NH(4) | 0 | Atomic bond | (2-Cl)Phenyl |
| NHCO(4) | 0 | Atomic bond | (3-CF$_3$)Phenyl |
| NHCO(4) | 1 | Atomic bond | (2-CF$_3$)Phenyl |
| NHC(=O)NH(4) | 0 | Atomic bond | (2-Cl)Phenyl |
| NHCO(4) | 0 | Atomic bond | (2-Cl, 3-OMe)Phenyl |
| NHCO(4) | 2 | Atomic bond | Phenyl |
| NHCO(4) | 0 | Atomic bond | 3-Indolyl |
| NHCO(4) | 0 | Atomic bond | (2-Cl, 3-OH)Phenyl |
| NHCO(4) | 1 | O | Phenyl |

TABLE 55

| $B^{aE}$ (substitution position) | $n^E$ | $E^{aE}$ | $G^{aE}$ |
|---|---|---|---|
| NHCO(4) | 1 | Atomic bond | (2-Cl, 4-OMe)Phenyl |
| NHCO(4) | 0 | Atomic bond | (1-Me)Imidazol-2-yl |

TABLE 55-continued

| $B^{aE}$ (substitution position) | $n^E$ | $E^{aE}$ | $G^{aE}$ |
|---|---|---|---|
| NHCO(4) | 1 | Atomic bond | (2,4-Cl)Phenyl |
| NHCO(4) | 1 | Atomic bond | (2-Cl, 4-OH)Phenyl |
| NHCO(4) | 1 | Atomic bond | Pyridin-3-yl |
| NHCO(4) | 0 | Atomic bond | Benzimidazol-2-yl |
| NHCO(4) | 0 | Atomic bond | (2-Cl)Phenyl |
| NHCO(4) | 0 | Atomic bond | (2-Br)Phenyl |
| NHCO(4) | 0 | Atomic bond | (2-I)Phenyl |
| NHCO(4) | 1 | Atomic bond | (2-Me)Phenyl |
| NHCO(4) | 0 | Atomic bond | Quinoxalin-2-yl |
| NHCO(4) | 0 | Atomic bond | (5-Me)Thiophen-2-yl |
| NHCO(3) | 1 | Atomic bond | (2-Cl)Phenyl |
| NHCO(4) | 0 | Atomic bond | (2,4,6-Me)Phenyl |
| NHCO(4) | 0 | Atomic bond | (2-Et)Phenyl |
| NHC(=S)NH(4) | 0 | Atomic bond | (2-Me)Phenyl |

TABLE 56

| $B^{aE}$ (substitution position) | $n^E$ | $E^{aE}$ | $G^{aE}$ |
|---|---|---|---|
| NHCO(4) | 0 | Atomic bond | (4-NMe$_2$)Phenyl |
| NHCO(4) | 1 | O | (2,4-Cl)Phenyl |
| NHCO(4) | 1 | O | (2-Me)Phenyl |
| NHCO(4) | 0 | Atomic bond | (2-Ac)Phenyl |
| NHCO(4) | 0 | Atomic bond | (2-tBu)Phenyl |
| NHCO(3) | 0 | Atomic bond | (2-I)Phenyl |
| NHCO(4) | 0 | Atomic bond | (1-Me)Piperidin-4-yl |
| NHCO(4) | 0 | Atomic bond | Benzofuran-2-yl |
| NHCO(4) | 0 | Atomic bond | (1-Me)Indol-3-yl |
| NHCO(4) | 0 | Atomic bond | (2-Allyl)phenyl |
| NHCO(4) | 0 | Atomic bond | (2-nPr)Phenyl |
| NHCO(4) | 0 | Atomic bond | (2-iPrO)Phenyl |
| NHCO(4) | 0 | Atomic bond | (3-Me)Thiophen-2-yl |
| NHCO(4) | 1 | O | (2-Me, 3-Cl)Phenyl |
| NHCO(4) | 0 | Atomic bond | (2-CF$_3$, 4-F)Phenyl |
| NHCO(4) | 0 | Atomic bond | (2-OMe, 4-F)Phenyl |

TABLE 57

| $B^{aE}$ (substitution position) | $n^E$ | $E^{aE}$ | $G^{aE}$ |
|---|---|---|---|
| NHCO(4) | 0 | Atomic bond | (2-OH, 4-F)Phenyl |
| NHCO(3) | 1 | Atomic bond | (2-I)Phenyl |
| NHCO(4) | 0 | Atomic bond | (3-NMe$_2$)Phenyl |
| NHCO(4) | 0 | Atomic bond | (2-OMe, 4-I)Phenyl |
| NHCO(4) | 0 | Atomic bond | (2-OMe, 6-F)Phenyl |
| NHCO(4) | 0 | Atomic bond | (2-OH, 4-I)Phenyl |
| NHCO(4) | 0 | Atomic bond | (2-OH, 6-F)Phenyl |
| NHCO(4) | 0 | Atomic bond | (2-F)Phenyl |
| NHCO(4) | 0 | Atomic bond | (2-NMe$_2$)Phenyl |
| NHCO(4) | 0 | Atomic bond | (2-OMe, 6-Me)Phenyl |
| NHCO(4) | 0 | Atomic bond | (2-OH, 6-Me)Phenyl |
| NHCO(4) | 2 | Atomic bond | (2-Me)Phenyl |
| CONH(4) | 0 | Atomic bond | Phenyl |
| CONH(4) | 1 | Atomic bond | Phenyl |
| NHCO(4) | 2 | Atomic bond | (2-Cl)Phenyl |
| CONH(4) | 1 | Atomic bond | (2-Cl)Phenyl |

TABLE 58

| $B^{aE}$ (substitution position) | $n^E$ | $E^{aE}$ | $G^{aE}$ |
|---|---|---|---|
| CONH(4) | 0 | Atomic bond | (2-Cl)Phenyl |
| NHCO(4) | 0 | Atomic bond | (5-Br, 2,3-Methylenedioxy)phenyl |
| NHCO(4) | 0 | Atomic bond | (2-OMe, 6-Br)Phenyl |
| NHCO(4) | 0 | Atomic bond | (2-OH, 6-Br)Phenyl |
| NHCO(4) | 0 | Atomic bond | (2-OMe, 6-Cl)Phenyl |
| NHCO(4) | 0 | Atomic bond | (2-OH, 6-Cl)Phenyl |

TABLE 58-continued

| $B^{aE}$ (substitution position) | $n^E$ | $E^{aE}$ | $G^{aE}$ |
|---|---|---|---|
| NHCO(4) | 0 | Atomic bond | (2-OH, 6-OMe)Phenyl |
| NHCO(4) | 0 | Atomic bond | (2-OMe, 6-CF$_3$)Phenyl |
| NHCO(4) | 0 | Atomic bond | (2-OH, 6-CF$_3$)Phenyl |
| NHCO(4) | 0 | Atomic bond | (2-Cl, 5-SMe)Phenyl |
| NHCO(4) | 0 | Atomic bond | (2-SMe)Phenyl |
| NHCO(4) | 0 | Atomic bond | (3-SMe)Phenyl |
| NHCO(4) | 0 | Atomic bond | (2-OMe, 6-Et)Phenyl |
| NHCO(4) | 0 | Atomic bond | (3-SO$_2$Me)Phenyl |
| NHCO(4) | 0 | Atomic bond | (2-OH, 6-Et)Phenyl |
| NHCO(4) | 0 | Atomic bond | (3-S(=O)Me)Phenyl |

TABLE 59

| $B^{aE}$ (substitution position) | $n^E$ | $E^{aE}$ | $G^{aE}$ |
|---|---|---|---|
| NHCO(4) | 0 | Atomic bond | (2-Cl, 5-S(=O)Me)Phenyl |
| NHCO(4) | 0 | Atomic bond | (2-S(=O)Me)Phenyl |
| NHCO(4) | 0 | Atomic bond | (3-Cl)Pyridin-2-yl |
| NHCO(4) | 0 | Atomic bond | (2-OMe, 3-Cl)Phenyl |
| NHCO(4) | 0 | Atomic bond | (3-Me)Pyridin-2-yl |
| NHCO(4) | 0 | Atomic bond | (2-OH, 3-Cl)Phenyl |
| NHCO(4) | 0 | Atomic bond | (3-OH)Pyridin-2-yl |
| NHCO(4) | 0 | Atomic bond | (3-Vinyl)pyridin-2-yl |
| NHCO(4) | 0 | Atomic bond | (2-Et)Pyridin-2-yl |
| NHSO$_2$(4) | 0 | Atomic bond | (2-NO$_2$)Phenyl |
| NHSO$_2$(4) | 0 | Atomic bond | Phenyl |
| NHSO$_2$(4) | 0 | Atomic bond | (3-Br)Phenyl |
| NHSO$_2$(4) | 0 | Atomic bond | (3-OMe)Phenyl |
| NHSO$_2$(3) | 0 | Atomic bond | (2-NO$_2$)Phenyl |
| NMeSO$_2$(3) | 0 | Atomic bond | (2-NO$_2$)Phenyl |
| NHSO$_2$(3) | 0 | Atomic bond | Naphthalen-2-yl |

TABLE 60

| $B^{aE}$ (substitution position) | $n^E$ | $E^{aE}$ | $G^{aE}$ |
|---|---|---|---|
| NHSO$_2$(3) | 0 | Atomic bond | Naphthalen-1-yl |
| NHSO$_2$(4) | 0 | Atomic bond | Cyclohexyl |
| NHSO$_2$(4) | 0 | Atomic bond | Pyridin-3-yl |
| NHSO$_2$(4) | 0 | Atomic bond | (4-iPr)Phenyl |
| NHSO$_2$(4) | 1 | Atomic bond | Phenyl |
| NHSO$_2$(4) | 0 | Atomic bond | Thiophen-2-yl |
| NHSO$_2$(4) | 0 | Atomic bond | Naphthalen-2-yl |
| NBnSO$_2$(4) | 0 | Atomic bond | (2-NO$_2$)Phenyl |
| NMeSO$_2$(4) | 0 | Atomic bond | (3-Br)Phenyl |
| NMeSO$_2$(4) | 0 | Atomic bond | (2-NO$_2$)Phenyl |
| N(CH$_2$CH$_2$OH)SO$_2$(4) | 0 | Atomic bond | (2-NO$_2$)Phenyl |
| NHSO$_2$(4) | 1 | Atomic bond | (2-Cl)Phenyl |
| NHSO$_2$(4) | 1 | Atomic bond | (3-Br)Phenyl |
| NHSO$_2$(4) | 0 | Atomic bond | (2-CF$_3$)Phenyl |
| NHSO$_2$(4) | 1 | Atomic bond | (2-Br)Phenyl |
| NHSO$_2$(4) | 1 | Atomic bond | (2-Me)Phenyl |

TABLE 61

| $B^{aE}$ (substitution position) | $n^E$ | $E^{aE}$ | $G^{aE}$ |
|---|---|---|---|
| NHSO$_2$(4) | 1 | Atomic bond | (2-NO$_2$)Phenyl |
| NHSO$_2$(4) | 2 | Atomic bond | Phenyl |
| NHSO$_2$(4) | 1 | Atomic bond | (4-Cl)Phenyl |
| NMeSO$_2$(4) | 1 | Atomic bond | (2-CF$_3$)Phenyl |
| NMeSO$_2$(4) | 1 | Atomic bond | (2-Et)Phenyl |
| NMeSO$_2$(4) | 1 | Atomic bond | (2,3-Me)Phenyl |
| NMeSO$_2$(4) | 2 | Atomic bond | (2-Cl)Phenyl |

TABLE 61-continued

| $B^{aE}$ (substitution position) | $n^E$ | $E^{aE}$ | $G^{aE}$ |
|---|---|---|---|
| NMeSO$_2$(4) | 1 | Atomic bond | (2-NO$_2$)Phenyl |
| NMeSO$_2$(4) | 1 | Atomic bond | (2-NH$_2$)Phenyl |
| NMeSO$_2$(4) | 1 | Atomic bond | (2-NMe$_2$)Phenyl |

TABLE 62

| $B^{aE}$ (substitution position) | $n^E$ | $E^{aE}$ | $G^{aE}$ |
|---|---|---|---|
| NHCO(4) | 0 | Atomic bond | Pyridin-4-yl |
| NHCO(4) | 1 | O | Pyridin-3-yl |
| NHCO(4) | 0 | Atomic bond | Pyridin-3-yl |
| NHCO(4) | 0 | Atomic bond | (2-Me)Pyridin-3-yl |
| NHCO(4) | 0 | Atomic bond | (2-Cl)Pyridin-3-yl |
| NHCO(4) | 1 | O | Pyridin-2-yl |
| NHCO(4) | 0 | Atomic bond | (4-CF$_3$)Pyridin-3-yl |
| NHCO(4) | 0 | Atomic bond | (2-iPr)Phenyl |

<Typical Compound IE-2>

[Formula 64]

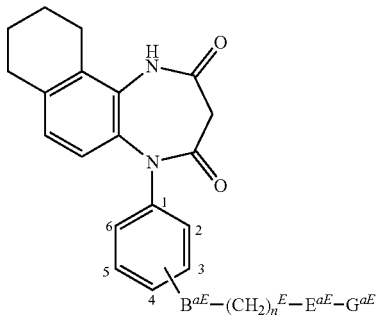

(In the formula, $B^{aE}$ (substitution position), $n^E$, $E^{aE}$, and $G^{aE}$ are as shown in Tables 63 and 64.)

TABLE 63

| $B^{aE}$ (substitution position) | $n^E$ | $E^{aE}$ | $G^{aE}$ |
|---|---|---|---|
| NHCO(4) | 0 | Atomic bond | Cyclohexyl |
| NHCO(4) | 0 | Atomic bond | (6-Me)Pyridin-2-yl |
| NHCO(4) | 0 | Atomic bond | (2-Me)Pyridin-3-yl |
| NHCO(4) | 0 | Atomic bond | (2-OMe, 3-Me)Phenyl |
| NHCO(4) | 0 | Atomic bond | (2,3-Cl)Phenyl |
| NHCO(4) | 0 | Atomic bond | (2-OH, 3-Me)Phenyl |
| NHCO(4) | 0 | Atomic bond | (2-I)Phenyl |
| NHCO(4) | 1 | Atomic bond | (1-Me)Pyrrol-2-yl |
| NHCO(4) | 1 | Atomic bond | (2-tBu)Phenyl |
| NHCO(4) | 0 | Atomic bond | (2-Isopropenyl)phenyl |
| NHCO(4) | 0 | Atomic bond | (2-iPr)Phenyl |
| NHCO(4) | 1 | Atomic bond | Morpholin-2-yl |
| NHCO(4) | 0 | Atomic bond | (2-Cl)Pyridin-2-yl |

TABLE 64

| $B^{aE}$ (substitution position) | $n^E$ | $E^{aE}$ | $G^{aE}$ |
|---|---|---|---|
| NHSO$_2$(4) | 0 | Atomic bond | (2-NO$_2$)Phenyl |
| NMeSO$_2$(4) | 0 | Atomic bond | (2-NO$_2$)Phenyl |
| SO$_2$NH(4) | 0 | Atomic bond | Phenyl |

TABLE 64-continued

| $B^{aE}$ (substitution position) | $n^E$ | $E^{aE}$ | $G^{aE}$ |
|---|---|---|---|
| OSO$_2$(4) | 0 | Atomic bond | (3-Br)Phenyl |
| NHSO$_2$(4) | 1 | Atomic bond | (2-Cl)Phenyl |
| NHSO$_2$(4) | 0 | Atomic bond | (3-Br)Phenyl |
| NHSO$_2$(4) | 0 | Atomic bond | (3-OMe)Phenyl |
| NHSO$_2$(4) | 1 | Atomic bond | (2,3-Cl)Phenyl |
| NHSO$_2$(4) | 1 | Atomic bond | (2,6-Cl)Phenyl |
| NHSO$_2$(4) | 1 | Atomic bond | (2-I)Phenyl |
| NMeSO$_2$(4) | 1 | Atomic bond | (2-Cl)Phenyl |

<Typical Compound IE-3>

[Formula 65]

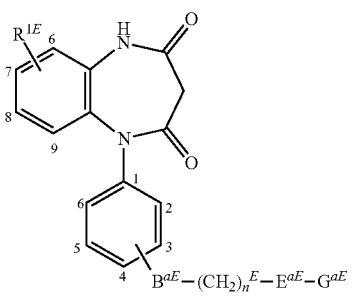

(In the formula, $R^{1E}$, $B^{aE}$ (substitution position), $n^E$, $E^{aE}$, and $G^{aE}$ are as shown in Table 65.)

TABLE 65

| $R^{1E}$ | $B^{aE}$ (substitution position) | $n^E$ | $E^{aE}$ | $G^{aE}$ |
|---|---|---|---|---|
| 7-OMe | NHCO(4) | 0 | Atomic bond | (2,3-Me)Phenyl |
| 7-OH | NHCO(4) | 0 | Atomic bond | (2,3-Me)Phenyl |
| 6-Me | NHCO(4) | 0 | Atomic bond | (2,3-Me)Phenyl |
| 6,7-Me | NHCO(4) | 0 | Atomic bond | (2-I)Phenyl |
| 6-Et | NHCO(4) | 0 | Atomic bond | (2-I)Phenyl |
| 7-Ph | NHCO(4) | 0 | Atomic bond | (2-Isopropyl)phenyl |
| 7-(Pyridin-3-yl) | NHCO(4) | 0 | Atomic bond | (2-Isopropyl)phenyl |
| 7-(Pyridin-2-yl) | NHCO(4) | 0 | Atomic bond | (2-Isopropyl)phenyl |
| 7-Cl | NHSO$_2$(4) | 0 | Atomic bond | (2-Isopropyl)phenyl |
| 7-Br | NHSO$_2$(4) | 0 | Atomic bond | (2-Isopropyl)phenyl |
| 7-CF$_3$ | NHSO$_2$(4) | 0 | Atomic bond | (2-Isopropyl)phenyl |
| H | NHSO$_2$(4) | 0 | Atomic bond | (2-Isopropyl)phenyl |
| 6-Me, 7-Br | NHSO$_2$(4) | 0 | Atomic bond | (2-Isopropyl)phenyl |
| 7-OMe | NHSO$_2$(4) | 1 | Atomic bond | (2-Cl)Phenyl |
| 7-OH | NHSO$_2$(4) | 1 | Atomic bond | (2-Cl)Phenyl |
| 6-Me | NHSO$_2$(4) | 1 | Atomic bond | (2-Cl)Phenyl |

<Typical Compound IE-4>

[Formula 66]

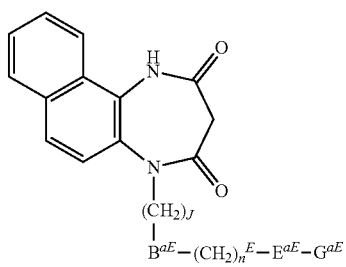

(In the formula, B$^{aE}$ (substitution position), n$^E$, E$^{aE}$, and G$^{aE}$ are as shown in Table 66.)

TABLE 66

| B$^{aE}$ (substitution position) | n$^E$ | E$^{aE}$ | G$^{aE}$ |
|---|---|---|---|
| NHCO | 0 | Atomic bond | (2-Cl, 3-OMe)Phenyl |
| NHCO | 0 | Atomic bond | (2-I)Phenyl |
| NHSO$_2$ | 1 | Atomic bond | (2-Cl)Phenyl |
| NHSO$_2$ | 1 | Atomic bond | (2-Cl)Phenyl |

<Typical Compound IE-5>

[Formula 67]

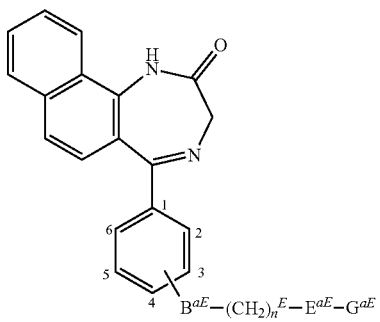

(In the formula, B$^{aE}$ (substitution position), n$^E$, E$^{aE}$, and G$^{aE}$ are as shown in Table 67.)

TABLE 67

| B$^{aE}$ (substitution position) | n$^E$ | E$^{aE}$ | G$^{aE}$ |
|---|---|---|---|
| NHCO(4) | 0 | Atomic bond | (2-Cl, 3-Ome)Phenyl |
| NHCO(4) | 0 | Atomic bond | (2-Cl, 3-OH)Phenyl |
| NHCO(4) | 0 | Atomic bond | (2-tBu)Phenyl |
| NHCO(4) | 0 | Atomic bond | (2-Cl, 6-Ome)Phenyl |
| NHCO(4) | 0 | Atomic bond | (2-Cl, 6-OH)Phenyl |
| NHSO$_2$(3) | 0 | Atomic bond | Phenyl |
| NHSO$_2$(4) | 1 | Atomic bond | (2-Cl)Phenyl |

<Typical Compound IE-6>

[Formula 68]

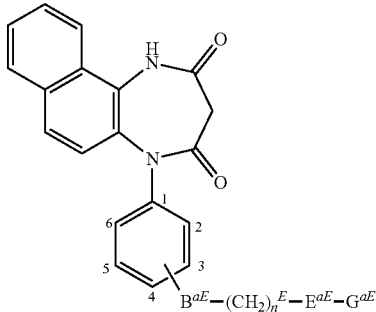

(In the formula, B$^E$ (substitution position), D$^E$, E$^E$, and G$^E$ are as shown in Table 68.)

TABLE 68

| B$^E$ (substitution position) | D$^E$ | E$^E$ | G$^E$ |
|---|---|---|---|
| NHCO(4) | C(Me)H | Atomic bond | Phenyl |
| NHCO(4) | C(Me)$_2$ | Atomic bond | Phenyl |
| NHCO(4) | CH=CH | Atomic bond | Phenyl |
| NHCO(4) | C(Me)H | O | Phenyl |
| NHCO(4) | C(Me)$_2$ | O | Phenyl |
| NHCO(4) | CH=CH | Atomic bond | (2-Me)Phenyl |
| NHCO(4) | CH=CH | Atomic bond | (2-Cl)Phenyl |

<Typical Compound IE-7>

[Formula 69]

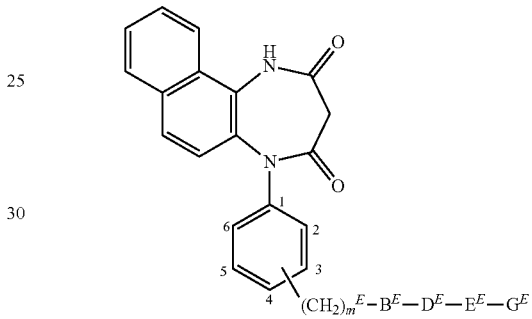

(In the formula, m$^E$ (substitution position), B$^E$, D$^E$, E$^E$, and G$^E$ are as shown in Table 69.)

TABLE 69

| m$^E$ (substitution position) | B$^E$ | D$^E$ | E$^E$ | G$^E$ |
|---|---|---|---|---|
| 1(4) | NHCO | Atomic bond | Atomic bond | Phenyl |
| 1(4) | NHCO | Atomic bond | Atomic bond | (2-Cl)Phenyl |
| 1(4) | NHSO$_2$ | CH$_2$ | Atomic bond | (2-Cl)Phenyl |

<Typical Compound IE-8>

[Formula 70]

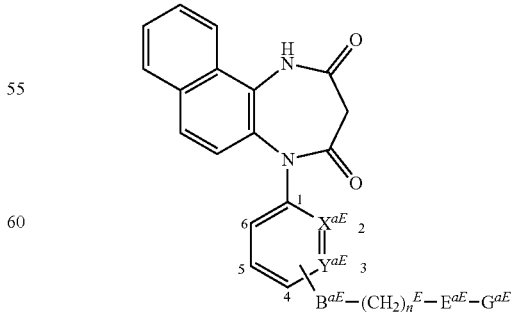

(In the formula, X$^{aE}$, Y$^{aE}$, B$^{aE}$ (substitution position), n$^E$, E$^{aE}$, and G$^{aE}$ are as shown in Table 70.)

TABLE 70

| $X^{aE}$ | $Y^{aE}$ | $B^{aE}$ (substitution position) | $n^E$ | $E^{aE}$ | $G^{aE}$ |
|---|---|---|---|---|---|
| CH | C—F | NHCO(4) | 0 | Atomic bond | (2,3-Me)Phenyl |
| CH | C—OH | NHCO(4) | 0 | Atomic bond | (2,3-Me)Phenyl |
| CH | C—F | NHCO(4) | 0 | Atomic bond | (2-I)Phenyl |
| CH | N | NHCO(4) | 0 | Atomic bond | (2-I)Phenyl |
| CH | N | NHCO(4) | 0 | Atomic bond | Phenyl |
| N | CH | NHCO(4) | 0 | Atomic bond | (2-I)Phenyl |
| CH | N | NHCO(4) | 0 | Atomic bond | (2-Cl)Phenyl |
| CH | N | NHCO(4) | 0 | Atomic bond | (2-OH)Phenyl |
| CH | N | NHC(=O)NH(4) | 0 | Atomic bond | (2-OH)Phenyl |
| CH | N | NHCO(4) | 0 | Atomic bond | (2-OH, 6-Me)Phenyl |
| CH | N | NHCO(4) | 0 | Atomic bond | (2-OH, 6-Cl)Phenyl |
| CH | N | NHCO(3) | 0 | Atomic bond | (2-OH, 6-Cl)Phenyl |
| CH | N | NHCO(4) | 0 | Atomic bond | (2-Cl)Pyridin-2-yl |
| CH | N | NHCO(4) | 1 | Atomic bond | (2-Cl)Pyridin-2-yl |
| CH | N | NHCO(4) | 0 | Atomic bond | (2-Me)Pyridin-2-yl |
| CH | C—OMe | NHSO$_2$(4) | 1 | Atomic bond | (2-Cl)Phenyl |
| CH | C—OH | NHSO$_2$(4) | 1 | Atomic bond | (2-Cl)Phenyl |

<Typical Compound IE-9>

[Formula 71]

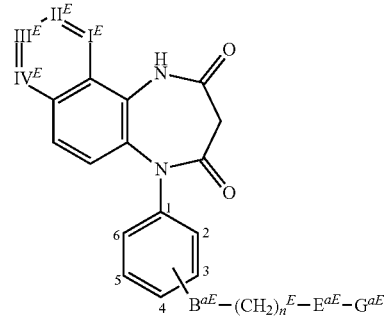

(In the formula, $I^E=II^E\text{-}III^E=IV^E$, $B^{aE}$ (substitution position), $n^E$, $E^{aE}$, and $G^{aE}$ are as shown in Table 71.)

TABLE 71

| $I^E=II^E\text{-}III^E=IV^E$ | $B^{aE}$ (substitution position) | $n^E$ | $E^{aE}$ | $G^{aE}$ |
|---|---|---|---|---|
| N=CH—CH=CH | NHCO(4) | 0 | Atomic bond | (2-I)Phenyl |
| CH=N—CH=CH | NHCO(4) | 0 | Atomic bond | (2-I)Phenyl |
| CH=CH—N=CH | NHCO(4) | 0 | Atomic bond | (2-I)Phenyl |
| CH=CH—CH=N | NHCO(4) | 0 | Atomic bond | (2-I)Phenyl |
| N=CH—CH=CH | NHCO(4) | 1 | O | Phenyl |
| N=CH—CH=CH | NHCO(3) | 0 | Atomic bond | (2-I)Phenyl |
| N=CH—CH=CH | NHCO(4) | 0 | Atomic bond | (2-Cl)Phenyl |
| N=CH—CH=CH | NHCO(4) | 0 | Atomic bond | (2-OH)Phenyl |
| N=CH—CH=CH | NHC(=O)NH(4) | 0 | Atomic bond | (2-OH)Phenyl |
| N=CH—CH=CH | NHCO(4) | 1 | O | (2-OH, 6-Me)Phenyl |
| N=CH—CH=CH | NHCO(4) | 0 | Atomic bond | (2-OH, 6-Cl)Phenyl |
| N=CH—CH=CH | NHCO(3) | 0 | Atomic bond | (2-OH, 6-Cl)Phenyl |
| N=CH—CH=CH | NHCO(4) | 0 | Atomic bond | (2-Cl)Pyridin-2-yl |
| N=CH—CH=CH | NHCO(4) | 1 | Atomic bond | (2-Cl)Pyridin-2-yl |
| N=CH—CH=CH | NHCO(4) | 0 | Atomic bond | (2-Me)Pyridin-2-yl |
| CH=CH—N=CH | NHCO(4) | 0 | Atomic bond | (2-Cl)Pyridin-3-yl |

<Typical Compound IE-10>

[Formula 72]

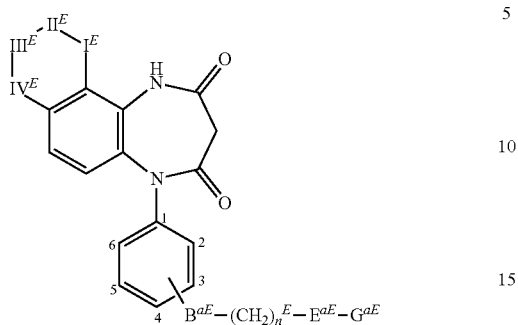

(In the formula, $I^E$-$II^E$-$III^E$-$IV^E$, $B^{aE}$ (substitution position), $n^E$, $E^{aE}$, and $G^{aE}$ are as shown in Table 72.)

TABLE 72

| $I^E$-$II^E$-$III^E$-$IV^E$ | $B^{aE}$ (substitution position) | $n^E$ | $E^{aE}$ | $G^{aE}$ |
|---|---|---|---|---|
| NH—CH$_2$—CH$_2$—CH$_2$ | NHCO(4) | 0 | Atomic bond | (2-I)Phenyl |
| CH$_2$—NH—CH$_2$—CH$_2$ | NHCO(4) | 0 | Atomic bond | (2-I)Phenyl |
| CH$_2$—CH$_2$—NH—CH$_2$ | NHCO(4) | 0 | Atomic bond | (2-I)Phenyl |
| CH$_2$—CH$_2$—CH$_2$—NH | NHCO(4) | 0 | Atomic bond | (2-I)Phenyl |
| CH$_2$—CH$_2$—NH—CH$_2$ | NHCO(4) | 1 | O | Phenyl |
| CH$_2$—CH$_2$—NH—CH$_2$ | NHCO(3) | 0 | Atomic bond | (2-I)Phenyl |
| CH$_2$—CH$_2$—NH—CH$_2$ | NHCO(4) | 0 | Atomic bond | (2-Cl)Phenyl |
| CH$_2$—CH$_2$—NH—CH$_2$ | NHCO(4) | 0 | Atomic bond | (2-Cl)Pyridin-3-yl |
| CH$_2$—CH$_2$—NH—CH$_2$ | NHCO(4) | 0 | Atomic bond | (2-OH)Phenyl |
| CH$_2$—CH$_2$—NH—CH$_2$ | NHC(=O)NH(4) | 0 | Atomic bond | (2-OH)Phenyl |
| CH$_2$—CH$_2$—NH—CH$_2$ | NHCO(4) | 1 | O | (2-OH, 6-Me)Phenyl |
| CH$_2$—CH$_2$—NH—CH$_2$ | NHCO(4) | 0 | Atomic bond | (2-OH, 6-Cl)Phenyl |
| CH$_2$—CH$_2$—NH—CH$_2$ | NHCO(3) | 0 | Atomic bond | (2-OH, 6-Cl)Phenyl |
| CH$_2$—CH$_2$—NH—CH$_2$ | NHCO(4) | 0 | Atomic bond | (2-Cl)Pyridin-2-yl |
| CH$_2$—CH$_2$—NH—CH$_2$ | NHCO(4) | 1 | Atomic bond | (2-Cl)Pyridin-2-yl |
| CH$_2$—CH$_2$—NH—CH$_2$ | NHCO(4) | 0 | Atomic bond | (2-Me)Pyridin-2-yl |
| CH$_2$—CH$_2$—NH—CH$_2$ | NHCO(4) | 0 | Atomic bond | (2-Cl)Pyridin-3-yl |

<Typical Compound IE-11>

[Formula 73]

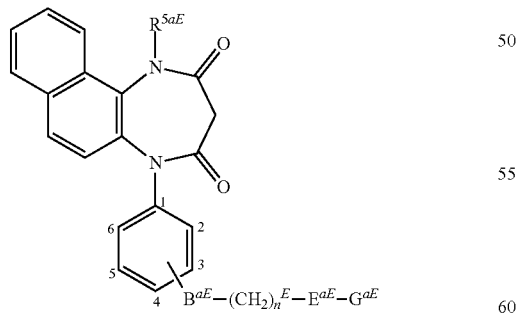

(In the formula, $R^{5aE}$, $B^{aE}$ (substitution position), $n^E$, $E^{aE}$, and $G^{aE}$ are as shown in Table 73.)

TABLE 73

| $R^{5aE}$ | $B^{aE}$ (substitution position) | $n^E$ | $E^{aE}$ | $G^{aE}$ |
| --- | --- | --- | --- | --- |
| Bn | NBnSO$_2$(4) | 0 | Atomic bond | (2-NO$_2$)Phenyl |
| Me | NBnSO$_2$(4) | 0 | Atomic bond | (2-NO$_2$)Phenyl |
| Et | NBnSO$_2$(4) | 0 | Atomic bond | (2-NO$_2$)Phenyl |

(F-1) A compound represented by the following general formula (IF):

[Formula 74]

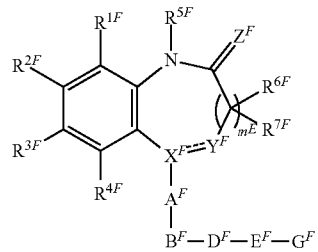

(IF)

wherein, in the formula, $R^{1F}$ and $R^{2F}$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), a phenyl group which may have a substituent, a pyridyl group which may have a substituent, or an aralkyl group (the aryl moiety thereof has 6 to 10 carbon atoms, and the alkylene moiety thereof has 1 to 8 carbon atoms),
or $R^{1F}$ and $R^{2F}$ may bind together to form a condensed ring selected from naphthalene ring, quinoline ring, isoquinoline ring, tetrahydronaphthalene ring, indane ring, tetrahydroquinoline ring, and tetrahydroisoquinoline ring together with the benzene ring to which they bind, and the ring consisting of $R^{1F}$, $R^{2F}$ binding together, and the carbon atoms to which $R^{1F}$ and $R^{2F}$ bind may be substituted with 1 to 4 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), and an aralkyl group (the aryl moiety thereof has 6 to 10 carbon atoms, and the alkylene moiety thereof has 1 to 8 carbon atoms), $R^{3F}$ and $R^{4F}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), or an aralkyl group (the aryl moiety thereof has 6 to 10 carbon atoms, and the alkylene moiety thereof has 1 to 8 carbon atoms), $R^{5F}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety thereof has 6 to 10 carbon atoms, and the alkylene moiety thereof has 1 to 8 carbon atoms), $R^{6F}$ and $R^{7F}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, or amino group, $X^F$ represents C or N, $Y^F$ represents N or C(=O), provided that when $X^F$ is C, $Y^F$ represents N, and when $X^F$ is N, $Y^F$ represents C(=O), the double line consisting of the solid line and the broken line represents a single bond or a double bond, $Z^F$ represents O, S, or NH, $A^F$ represents benzene ring, pyridine ring, pyrimidine ring, pyridazine ring, thiophene ring, furan ring, pyrazole ring, imidazole ring, quinoline ring, benzimidazole ring, or indane ring which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, $B^F$ represents O, S, NR$^{8F}$, or an atomic bond, $R^{8F}$ represents hydrogen atom, or an alkyl group having 1 to 8 carbon atoms, $D^F$ represents benzene ring, pyridine ring, pyrimidine ring, pyridazine ring, thiophene ring, furan ring, tetrazole ring, imidazole ring, imidazoline ring, triazole ring, thiazole ring, oxazole ring, isoxazole ring, pyrazole ring, pyrrole ring, pyrrolidine ring, piperazine ring, piperidine ring, or 5- to 8-membered cycloalkyl ring which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, $E^F$ represents $—(CR^{9F}R^{10F})_n{}^F-T^F-$, wherein $R^{9F}$ and $R^{10F}$ may be the same or different, and represent hydrogen atom, hydroxyl group, or an alkyl group having 1 to 8 carbon atoms, or $R^{9F}$ and $R^{10F}$ may bind together to form an ethylene chain, $n^F$ represents an integer of 0 to 8, and $T^F$ represents O, S, $NR^{11F}$, or an atomic bond, wherein $R^{11F}$ represents hydrogen atom, or an alkyl group having 1 to 8 carbon atoms, $G^F$ represents benzene ring, pyridine ring, imidazole ring, pyrrole ring, pyrazole ring, thiophene ring, furan ring, thiazole ring, oxazole ring, pyrimidine ring, pyridazine ring, pyrazine ring, naphthalene ring, quinoline ring, quinazoline ring, indole ring, indoline ring, piperazine ring, piperidine ring, morpholine ring, or 5- to 8-membered cycloalkyl ring which may have 1 to 5 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, carbamoyl group, and methanesulfonyl group, and $m^F$ represents an integer of 0 to 2.

(F-2) A compound represented by the following general formula (IIF):

[Formula 75

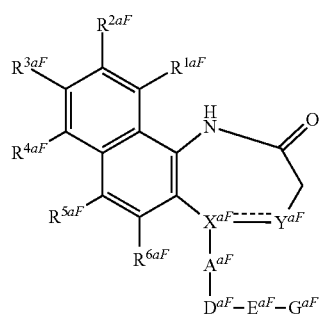

(IIF)

wherein, in the formula, $R^{1aF}$, $R^{2aF}$, $R^{3aF}$, $R^{4aF}$, $R^{5aF}$, and $R^{6aF}$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), a phenyl group which may have a substituent, a pyridyl group which may have a substituent, or an aralkyl group (the aryl moiety thereof has 6 to 10 carbon atoms, and the alkylene moiety thereof has 1 to 8 carbon atoms), $X^{aF}$ represents C or N, $Y^{aF}$ represents N or C(=O), provided that when $X^{aF}$ is C, $Y^{aF}$ represents N, and when $X^{aF}$ is N, $Y^{aF}$ represents C(=O), the double line consisting of the solid line and the broken line represents a single bond or a double bond, $A^{aF}$ represents benzene ring, pyridine ring, pyrimidine ring, pyridazine ring, thiophene ring, furan ring, pyrazole ring, imidazole ring, quinoline ring, benzimidazole ring, or indane ring which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, $D^{aF}$ represents benzene ring, pyridine ring, pyrimidine ring, pyridazine ring, thiophene ring, furan ring, tetrazole ring, imidazole ring, imidazoline ring, triazole ring, thiazole ring, oxazole ring, isoxazole ring, pyrazole ring, pyrrole ring, pyrrolidine ring, piperazine ring, piperidine ring, or 5- to 8-membered cycloalkyl ring which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, $E^{aF}$ represents $—(CR^{9aF}R^{10aF})_p{}^F-T^{aF}-$, wherein $R^{9aF}$ and $R^{10aF}$ are the same or different, and represent hydrogen atom, hydroxyl group, or an alkyl group having 1 to 8 carbon atoms, or $R^{9aF}$ and $R^{10aF}$ may bind together to form an ethylene chain, $p^F$ represents an integer of 0 to 8, and $T^{aF}$ represents O, S, $NR^{11aF}$, or an atomic bond, wherein $R^{11aF}$ represents hydrogen atom, or an alkyl group having 1 to 8 carbon atoms, and $G^{aF}$ represents benzene ring, pyridine ring, imidazole ring, pyrrole ring, pyrazole ring, thiophene ring, furan ring, thiazole ring, oxazole ring, pyrimidine ring, pyridazine ring, pyrazine ring, naphthalene ring, quinoline ring, quinazoline ring, indole ring, indoline ring, piperazine ring, piperidine ring, morpholine ring, or 5- to 8-membered cycloalkyl ring which may have 1 to 5 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, carbamoyl group, and methanesulfonyl group.

As for the general formulas (IF) and GIF), examples of the alkyl group having 1 to 8 carbon atoms include methyl group, ethyl group, propyl group, isopropyl group, butyl group, i-butyl group, t-butyl group, pentyl group, hexyl group, and the like.

Examples of the 5- to 8-membered cycloalkyl ring include cyclopentyl ring, cyclohexyl ring, and the like.

Examples of the cycloalkyl group having 3 to 8 carbon atoms include cyclopropyl group, cyclohexyl group, and the like.

Examples of the alkenyl group having 2 to 8 carbon atoms include allyl group, and the like.

Examples of the alkoxy group having 1 to 8 carbon atoms include methoxy group, ethoxy group, propoxy group, isopropoxy group, butoxy group, i-butoxy group, t-butoxy group, pentyloxy group, hexyloxy group, and the like.

Examples of the alkyl group having 1 to 8 carbon atoms and substituted with 1 to 3 halogen atoms include methyl group, ethyl group, propyl group, isopropyl group, butyl group, t-butyl group substituted with 1 to 3 halogen atoms such as fluorine atom, chlorine atom, and bromine atom, and the like, and preferred examples of the same include trifluoromethyl group, chloromethyl group, 2-chloroethyl group, 2-bromoethyl group, 2-fluoroethyl group, and the like.

Examples of the alkoxy group having 1 to 8 carbon atoms and substituted with 1 to 3 halogen atoms include methoxy group, ethoxy group, propoxy group, isopropoxy group, butoxy group, t-butoxy group substituted with 1 to 3 halogen atoms such as fluorine atom, chlorine atom, and bromine atom, and the like, and preferred examples of the same include trifluoromethoxy group, chloromethoxy group, 2-chloroethoxy group, 2-bromoethoxy group, 2-fluoroethoxy group, and the like.

Examples of the halogen atom include fluorine atom, chlorine atom, bromine atom, and the like.

Examples of the alkylamino group having 1 to 8 carbon atoms include methylamino group, ethylamino group, and the like.

Examples of the dialkylamino group having 2 to 8 carbon atoms include dimethylamino group, diethylamino group, and the like.

Examples of the acylamino group having 2 to 8 carbon atoms include acetylamino group.

Examples of the acyl group having 2 to 8 carbon atoms include acetyl group, and the like.

Examples of the alkoxycarbonyl group (the alkoxy moiety thereof has 1 to 8 carbon atoms) include methoxycarbonyl group, and the like.

Examples of the aralkyl group (the aryl moiety thereof has 6 to 10 carbon atoms, and the alkylene moiety thereof has 1 to 8 carbon atoms) include benzyl group, and the like.

Examples of the alkyl group having 1 to 8 carbon atoms and substituted with hydroxyl group include 2-hydroxyethyl group, and the like.

Examples of the substituent of the phenyl group which may have a substituent, and pyridyl group which may have a substituent include a halogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, and the like.

For $E^F$ and $E^{aF}$ in the aforementioned general formulas (IF) and (IIF), the expression that "$R^{9aF}$ and $R^{10aF}$ may bind together to form an ethylene chain" means that $E^F$ and $E^{aF}$ may contain a double bond.

As the compounds represented by the general formula (IF), the following compounds are preferred.

(F-1-1) The compound according to (F-1), a tautomer or stereoisomer of the compound, or a pharmaceutically acceptable salt thereof, or a solvate thereof, wherein $m^F$ is 1.

(F-1-2) The compound according to (F-1) or (F-1-1) mentioned above, a tautomer or stereoisomer of the compound, or a pharmaceutically acceptable salt thereof, or a solvate thereof, wherein $R^{1F}$ and $R^{2F}$ bind together to form naphthalene ring together with the benzene ring to which they bind, and the naphthalene ring may be substituted with 1 to 4 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(F-1-3) The compound according to (F-1), or any one of (F-1-1) and (F-1-2) mentioned above, a tautomer or stereoisomer of the compound, or a pharmaceutically acceptable salt thereof, or a solvate thereof, wherein $R^{3F}$ and $R^{4F}$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, or a dialkylamino group having 2 to 8 carbon atoms.

(F-1-4) The compound according to (F-1), or any one of (F-1-1) to (F-1-3) mentioned above, a tautomer or stereoisomer of the compound, or a pharmaceutically acceptable salt thereof, or a solvate thereof, wherein $R^{5F}$ is hydrogen atom.

(F-1-5) The compound according to (F-1), or any one of (F-1-1) to (F-1-4) mentioned above, a tautomer or stereoisomer of the compound, or a pharmaceutically acceptable salt thereof, or a solvate thereof, wherein $R^{6F}$ and $R^{7F}$ are hydrogen atoms.

(F-1-6) The compound according to (F-1), or any one of (F-1-1) to (F-1-5) mentioned above, a tautomer or stereoisomer of the compound, or a pharmaceutically acceptable salt thereof, or a solvate thereof, wherein $X^F$ is N, and $Y^F$ is C(=O).

(F-1-7) The compound according to (F-1), or any one of (F-1-1) to (F-1-6) mentioned above, a tautomer or stereoisomer of the compound, or a pharmaceutically acceptable salt thereof, or a solvate thereof, wherein $Z^F$ is O.

(F-1-8) The compound according to (F-1), or any one of (F-1-1) to (F-1-7) mentioned above, a tautomer or stereoisomer of the compound, or a pharmaceutically acceptable salt thereof, or a solvate thereof, wherein $A^F$ is a benzene ring or pyridine ring which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(F-1-9) The compound according to (F-1), or any one of (F-1-1) to (F-1-8) mentioned above, a tautomer or stereoisomer of the compound, or a pharmaceutically acceptable salt thereof, or a solvate thereof, wherein $D^F$ is a tetrazole ring, imidazole ring, imidazoline ring, triazole ring, pyrrole ring, pyrrolidine ring, piperazine ring, or piperidine ring which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(F-1-10) The compound according to (F-1), or any one of (F-1-1) to (F-1-9) mentioned above, a tautomer or stereoisomer of the compound, or a pharmaceutically acceptable salt thereof, or a solvate thereof, wherein $B^F$ is an atomic bond.

(F-1-11) The compound according to (F-1-10) mentioned above, a tautomer or stereoisomer of the compound, or a pharmaceutically acceptable salt thereof, or a solvate thereof, wherein $D^F$ binds to $A^F$ via a nitrogen atom.

(F-1-12) The compound according to (F-1), or any one of (F-1-1) to (F-1-11) mentioned above, a tautomer or stereoisomer of the compound, or a pharmaceutically acceptable salt thereof, or a solvate thereof, wherein $E^F$ is an alkylene chain having 1 to 5 carbon atoms.

(F-1-13) The compound according to (F-1), or any one of (F-1-1) to (F-1-12) mentioned above, a tautomer or stereoisomer of the compound, or a pharmaceutically acceptable salt thereof, or a solvate thereof, wherein $G^F$ is a benzene ring, pyridine ring, imidazole ring, pyrrole ring, pyrazole ring, pyrimidine ring, pyridazine ring, pyrazine ring, or 5- to 7-membered cycloalkyl ring which may have 1 to 5 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, carbamoyl group, and methanesulfonyl group.

(F-1-14) The compound according to (F-1), a tautomer or stereoisomer of the compound, or a pharmaceutically acceptable salt thereof, or a solvate thereof, wherein $R^{1F}$ and $R^{2F}$ bind together to form naphthalene ring or indane ring together with the benzene ring to which they bind, the naphthalene ring or indane ring may be substituted with 1 to 4 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), and an aralkyl group (the aryl moiety thereof has 6 to 10 carbon atoms, and the alkylene moiety thereof has 1 to 8 carbon atoms), $R^{3F}$ and $R^{4F}$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), or an aralkyl group (the aryl moiety thereof has 6 to 10 carbon atoms, and the alkylene moiety thereof has 1 to 8 carbon atoms), $R^{5F}$ is hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety thereof has 6 to 10 carbon atoms, and the alkylene moiety thereof has 1 to 8 carbon atoms), $R^{6F}$ and $R^{7F}$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, or amino group, $X^F$ is N, $Y^F$ is C(=O), the double line consisting of the solid line and the broken line is a single bond, $Z^F$ is O, $A^F$ is a benzene ring or pyridine ring which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, $B^F$ is an atomic bond, $D^F$ is a tetrazole ring or imidazole ring which may have 1 or 2 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, $D^F$ binds to $A^F$ via a nitrogen atom of $D^F$, and binds to $E^F$ via a carbon atom of $D^F$, $E^F$ is —$(CR^{9F}R^{10F})_{n^F}$—, wherein $R^{9F}$ and $R^{10F}$ may be the same or different, and are hydrogen atom, hydroxyl group, or an alkyl group having 1 to 8 carbon atoms, and $n^F$ is an integer of 1 to 8, $G^F$ is a benzene ring which may have 1 to 5 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, carbamoyl group, and methanesulfonyl group, and m is 1.

(F-1-15) The compound according to (F-1), a tautomer or stereoisomer of the compound, or a pharmaceutically acceptable salt thereof, or a solvate thereof, wherein $R^{1F}$ and $R^{2F}$ bind together to form naphthalene ring or indane ring together with the benzene ring to which they bind, $R^{3F}$ and $R^{4F}$ are hydrogen atoms, $R^{5F}$ is hydrogen atom, $R^{6F}$ and $R^{7F}$ are hydrogen atoms, $X^F$ is N, $Y^F$ is C(=O), the double line consisting of the solid line and the broken line is single bond, $Z^F$ is O, $A^F$ is a benzene ring which may have 1 to 4 of the same or different substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, $B^F$ is an atomic bond, $D^F$ is a tetrazole ring or imidazole ring which may have 1 or 2 ofan alkyl group having 1 to 8 carbon atoms, or an alkyl group having 1 to 8 carbon atoms and substituted with 1 to 3 halogen atoms, as a substituent, $D^F$ binds to $A^F$ via a nitrogen atom of $D^F$, and binds to $E^F$ via a carbon atom of $D^F$, $E^F$ is —$(CR^{9F}R^{10F})_{n^F}$—, wherein $R^{9F}$ and $R^{10F}$ are the same or different, and are hydrogen atom, or an alkyl group having 1 to 8 carbon atoms, and $n^F$ is an integer of 1 to 4, $G^F$ is a benzene ring which may have 1 to 5 of the same or different substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, and carbamoyl group, and $m^F$ is 1.

(F-1-16) The compound according to (F-1), a tautomer or stereoisomer of the compound, or a pharmaceutically acceptable salt thereof, or a solvate thereof, wherein $R^{1F}$ and $R^{2F}$ bind together to form naphthalene ring or indane ring together with the benzene ring to which they bind, $R^{3F}$ and $R^{4F}$ are hydrogen atoms, $R^{5F}$ is hydrogen atom, $R^{6F}$ and $R^{7F}$ are hydrogen atoms, $X^F$ is N, $Y^F$ is C(=O), the double line consisting of the solid line and the broken line is a single bond, $Z^F$ is O, $A^F$ is a benzene ring which may have 1 to 4 of the same or different substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, $B^F$ is an atomic bond, $D^F$ is an imidazole ring which may have 1 or 2 ofan alkyl group having 1 to 8 carbon atoms, or an alkyl group having 1 to 8 carbon atoms and substituted with 1 to 3 halogen atoms, as a substituent, $D^F$ binds to $A^F$ at the 2-position of the imidazole ring, and binds to $E^F$ via a nitrogen atom of imidazole, $E^F$ is —$(CR^{9F}R^{10F})_{n^F}$—, wherein $R^{9F}$ and $R^{10F}$ are the same or different, and are hydrogen atom, or an alkyl group having 1 to 8 carbon atoms, and $n^F$ is an integer of 1 to 4, $G^F$ is a benzene ring which may have 1 to 5 of the same or different substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, and carbamoyl group, and $m^F$ is 1.

As the compounds represented by the general formula (IIF), the following compounds are preferred.

(F-2-1) The compound according to (F-2), a tautomer or stereoisomer of the compound, or a pharmaceutically acceptable salt thereof, or a solvate thereof, wherein $R^{1aF}$, $R^{2aF}$, $R^{3aF}$, $R^{4aF}$, $R^{5aF}$, and $R^{6aF}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, or hydroxyl group.

(F-2-2) The compound according to any one of (F-2) and (F-2-1) mentioned above, a tautomer or stereoisomer of the compound, or a pharmaceutically acceptable salt thereof, or a solvate thereof, wherein $X^{aF}$ is N, and $Y^{aF}$ is C(=O).

(F-2-3) The compound according to (F-2), or any one of (F-2-1) and (F-2-2) mentioned above, a tautomer or stereoisomer of the compound, or a pharmaceutically acceptable salt thereof, or a solvate thereof, wherein $A^{aF}$ is a benzene ring or pyridine ring which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(F-2-4) The compound according to (F-2), or any one of (F-2-1) and (F-2-2) mentioned above, a tautomer or stereoisomer of the compound, or a pharmaceutically acceptable salt thereof, or a solvate thereof, wherein $A^{aF}$ is a benzene ring which may have 1 to 4 of the same or different substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, and amino group.

(F-2-5) The compound according to (F-2), or any one of (F-2-1) to (F-1-4) mentioned above, a tautomer or stereoisomer of the compound, or a pharmaceutically acceptable salt thereof, or a solvate thereof, wherein $D^{aF}$ is a tetrazole ring, imidazole ring, imidazoline ring, triazole ring, pyrrole ring, pyrrolidine ring, piperazine ring, or piperidine ring which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(F-2-6) The compound according to (F-2), or any one of (F-2-1) to (F-1-4) mentioned above, a tautomer or stereoisomer of the compound, or a pharmaceutically acceptable salt thereof, or a solvate thereof, wherein $D^{aF}$ is a tetrazole ring.

(F-2-7) The compound according to any one of (F-1-5) and (F-1-6) mentioned above, a tautomer or stereoisomer of the compound, or a pharmaceutically acceptable salt thereof, or a solvate thereof, wherein $D^{aF}$ binds to $A^{aF}$ via a nitrogen atom.

(F-2-8) The compound according to (F-2), or any one of (F-2-1) to (F-1-7) mentioned above, a tautomer or stereoisomer of the compound, or a pharmaceutically acceptable salt thereof, or a solvate thereof, wherein $E^{aF}$ is an alkylene chain having 1 to 5 carbon atoms.

(F-2-9) The compound according to (F-2), or any one of (F-2-1) to (F-2-8) mentioned above, a tautomer or stereoisomer of the compound, or a pharmaceutically acceptable salt thereof, or a solvate thereof, wherein $G^{aF}$ is a benzene ring, pyridine ring, imidazole ring, pyrrole ring, pyrazole ring, pyrimidine ring, pyridazine ring, pyrazine ring, or 5- to 7-membered cycloalkyl ring which may have 1 to 5 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, carbamoyl group, and methanesulfonyl group.

In the compound of (F-1), when $A^F$ is a benzene ring which may have a substituent, and $B^F$ is an atomic bond, it is preferred that $X^F$ and $D^F$ are at the para-positions on the benzene ring.

In the compound of (F-1), when $A^F$ is a pyridine ring which may have a substituent, and $B^F$ is an atomic bond, it is preferred that the pyridine ring binds to $X^F$ at the 3-position, and binds to $D^F$ at the 6-positon.

In the compound of (F-2), when $A^{aF}$ is a benzene ring which may have a substituent, it is preferred that $X^{aF}$ and $D^{aF}$ are at the para-positions on the benzene ring.

In the compound of (F-2), when $A^{aF}$ is a pyridine ring which may have a substituent, it is preferred that the pyridine ring binds to $X^{aF}$ at the 3-position, and binds to $D^{aF}$ at the 6-position.

Examples of the pharmacologically acceptable salts of the compounds (F-1) and (F-2) include hydrochlorides, and alkali metal salts such as those of sodium, potassium, and lithium.

Further, there may be stereoisomers of the compounds of the present invention such as cis- and trans-isomers, optically active substances, and racemates.

<Typical Compound IF-1>

[Formula 76]

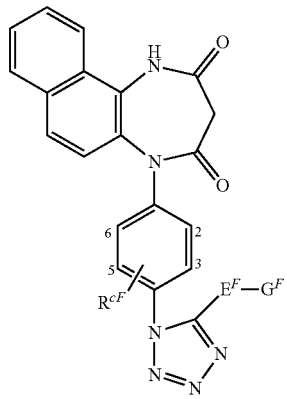

(In the formula, $R^{cF}$, $E^F$, and $G^F$ are as shown in Tables 74 to 76.)

TABLE 74

| $R^{cF}$ | $E^F$ | $G^F$ |
|---|---|---|
| H | $CH_2$ | (2-OMe)Phenyl |
| H | $CH_2$ | (2-OH)Phenyl |
| H | $CH_2—CH_2$ | Pyridin-3-yl |
| H | $CH_2—CH_2$ | Phenyl |
| H | $CH_2$ | Pyridin-4-yl |
| H | $CH_2$ | Phenyl |
| H | $CH_2$ | Pyridin-3-yl |
| H | $CH_2—CH_2$ | Cyclohexyl |
| H | $CH_2—CH_2$ | Pyridin-4-yl |
| H | $CH_2$ | Pyridin-2-yl |
| H | $CH_2—CH_2$ | Pyridin -2-yl |
| H | $CH_2$ | Imidazol-1-yl |

TABLE 75

| $R^{cF}$ | $E^F$ | $G^F$ |
|---|---|---|
| H | $CH_2—CH_2$ | Imidazol-1-yl |
| H | $CH_2—CH_2$ | (2-OMe)Phenyl |
| H | $CH_2—CH_2—CH_2$ | Phenyl |
| H | $NH—CH_2$ | Pyridin-2-yl |
| H | $CH_2—NH$ | Phenyl |
| H | $CH_2—O$ | Phenyl |
| H | $CH_2$ | (6-F)Pyridin-2-yl |
| H | $CH_2—CH_2$ | (6-F)Pyridin-2-yl |
| H | $C(Me)_2$ | (2-OMe)Phenyl |
| H | $C(Me)—CH_2$ | Pyridin-2-yl |
| H | $CH_2—C(Me)_2$ | Pyridin-2-yl |
| H | $CH_2—CH_2$ | Pyrimidin-2-yl |

TABLE 76

| $R^{cF}$ | $E^F$ | $G^F$ |
| --- | --- | --- |
| H | $CH_2$—$CH_2$ | Pyrazin-2-yl |
| H | $CH_2$—$CH_2$ | Pyridazin-3-yl |
| H | $CH_2$—$C(Me)_2$ | Pyridin-3-yl |
| 3-F | CH(Me) | (2-OMe)Phenyl |
| 3-Me | $CH_2$—$CH_2$ | Pyridin-3-yl |
| 3-OMe | $CH_2$—$CH_2$ | Phenyl |
| 3,5-F | $CH_2$ | Pyridin-4-yl |
| 3-$NH_2$ | $CH_2$ | Phenyl |
| 3,6-F | $CH_2$ | Pyridin-3-yl |
| 3-OMe | $CH_2$—$CH_2$ | Pyridin-2-yl |
| 3-CN | $CH_2$—$CH_2$ | Pyridin-2-yl |
| 3-$CF_3$ | $CH_2$—$CH_2$ | Pyridin-2-yl |

<Typical Compound IF-2>

[Formula 77]

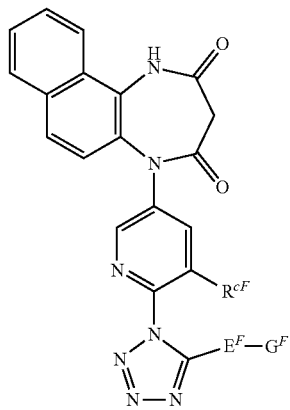

(In the formula, $R^{cF}$, $E^F$, and $G^F$ are as shown in Tables 77 to 79.)

TABLE 77

| $R^{cF}$ | $E^F$ | $G^F$ |
| --- | --- | --- |
| H | $CH_2$ | (2-OMe)Phenyl |
| H | $CH_2$ | (2-OH)Phenyl |
| H | $CH_2$—$CH_2$ | Pyridin-3-yl |
| H | $CH_2$—$CH_2$ | Phenyl |
| H | $CH_2$ | Pyridin-4-yl |
| H | $CH_2$ | Phenyl |
| H | $CH_2$ | Pyridin-3yl |
| H | $CH_2$—$CH_2$ | Cyclohexyl |
| H | $CH_2$—$CH_2$ | Pyridin-4-yl |
| H | $CH_2$ | Pyridin-2-yl |
| H | $CH_2$ | Pyridin-2-yl |

TABLE 78

| $R^{cF}$ | $E^F$ | $G^F$ |
| --- | --- | --- |
| H | $CH_2$ | Imidazol-1-yl |
| H | $CH_2$—$CH_2$ | Imidazol-1-yl |
| H | $CH_2$—$CH_2$ | (2-OMe)Phenyl |
| H | $CH_2$ | (2-OMe)Phenyl |
| H | $CH_2$—$CH_2$—$CH_2$ | Phenyl |
| H | $CH_2$ | (6-F)Pyridin-2-yl |
| H | $CH_2$—$CH_2$ | (6-F)Pyridin-2-yl |
| H | $C(Me)_2$ | (2-OMe)Phenyl |
| H | $C(Me)$—$CH_2$ | Pyridin-2-yl |
| H | $CH_2$—$C(Me)_2$ | Pyridin-2-yl |
| H | $CH_2$—$CH_2$ | Pyrimidin-2-yl |

TABLE 79

| $R^{cF}$ | $E^F$ | $G^F$ |
| --- | --- | --- |
| H | $CH_2$—$CH_2$ | Pyrazin-2-yl |
| H | $CH_2$—$CH_2$ | Pyridazin-3-yl |
| H | $CH_2$—$C(Me)_2$ | Pyridin-3-yl |
| F | CH(Me) | (2-OMe)Phenyl |
| Me | $CH_2$—$CH_2$ | Pyridin-3-yl |
| OMe | $CH_2$—$CH_2$ | Phenyl |
| F | $CH_2$ | Pyridine-4-yl |
| Me | $CH_2$ | Phenyl |
| OMe | $CH_2$ | Pyridin-3-yl |
| F | $CH_2$—$CH_2$ | Pyridin-2-yl |
| CN | $CH_2$—$CH_2$ | Pyridin-2-yl |
| F | $CH_2$—$CH_2$ | Pyridin-2-yl |

<Typical Compound IF-3>

[Formula 78]

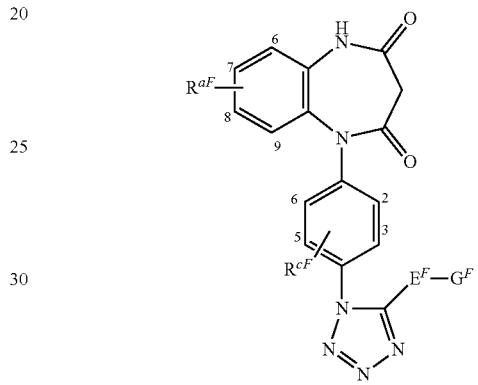

(In the formula, $R^{aF}$, $R^{cF}$, $E^F$, and $G^F$ are as shown in Tables 80 to 82.)

TABLE 80

| $R^{aF}$ | $R^{cF}$ | $E^F$ | $G^F$ |
| --- | --- | --- | --- |
| 7-OMe | H | $CH_2$ | (2-OMe)Phenyl |
| 6-OMe | H | $CH_2$ | (2-OH)Phenyl |
| 6,7-OMe | H | $CH_2$—$CH_2$ | Pyridin-3-yl |
| 7-Me | H | $CH_2$—$CH_2$ | Phenyl |
| 7-Et | H | $CH_2$ | Pyridin-4-yl |
| 7-Pr | H | $CH_2$ | Phenyl |
| 7-iPr | H | $CH_2$ | Pyridin-3-yl |
| 7-tBu | H | $CH_2$—$CH_2$ | Cyclohexyl |
| 7-CN | H | $CH_2$—$CH_2$ | Pyridin-4-yl |
| 7-$CF_3$ | H | $CH_2$ | Pyridin-2-yl |
| 7-$OCF_3$ | H | $CH_2$—$CH_2$ | Pyridin-2-yl |

TABLE 81

| $R^{aF}$ | $R^{cF}$ | $E^F$ | $G^F$ |
| --- | --- | --- | --- |
| 7,8-OMe | H | $CH_2$ | Imidazol-1-yl |
| 6,7-Me | H | $CH_2$—$CH_2$ | Imidazol-1-yl |
| 6,7-Cl | H | $CH_2$—$CH_2$ | (2-OMe)Phenyl |
| 7,8-Me | H | $CH_2$ | (2-OMe)Phenyl |
| 7,8-Et | H | $CH_2$—$CH_2$—$CH_2$ | Phenyl |
| 7-Cl | H | $CH_2$ | (6-F)Pyridin-2-yl |
| 6-OMe | H | $CH_2$—$CH_2$ | (6-F)Pyridin-2-yl |
| 6,7-OMe | H | $C(Me)_2$ | (2-OMe)Phenyl |
| 7-Me | H | $C(Me)$—$CH_2$ | Pyridin-2-yl |
| 7-Et | H | $CH_2$—$C(Me)_2$ | Pyridin-2-yl |
| 7-Pr | H | $CH_2$—$C(Me)_2$ | Pyridin-3-yl |

TABLE 82

| $R^{aF}$ | $R^{cF}$ | $E^F$ | $G^F$ |
|---|---|---|---|
| 7-iPr | 3-F | CH(Me) | (2-OMe)Phenyl |
| 7-tBu | 3-Me | CH$_2$—CH$_2$ | Pyridin-3-yl |
| 7-CN | 3-Ome | CH$_2$—CH$_2$ | Phenyl |
| 7-CF$_3$ | 3,5-F | CH$_2$ | Pyridin-4-yl |
| 7-OCF$_3$ | 3-NH$_2$ | CH$_2$ | Phenyl |
| 7,8-OMe | 3,6-F | CH$_2$ | Pyridin-3-yl |
| 6,7-Me | 3-OMe | CH$_2$—CH$_2$ | Pyridin-2-yl |
| 6,7-Et | 3-CN | CH$_2$—CH$_2$ | Pyridin-2-yl |
| 7,8-Me | 3-CF$_3$ | CH$_2$—CH$_2$ | Pyridin-2-yl |

<Typical Compound IF-4>

[Formula 79]

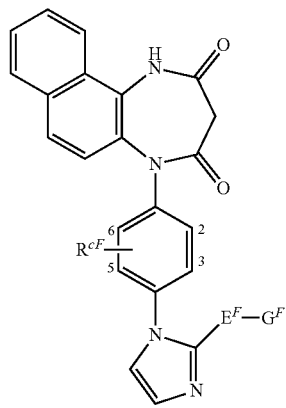

(In the formula, $R^{cF}$, $E^F$, and $G^F$ are as shown in Tables 83 to 85.)

TABLE 83

| $R^{cF}$ | $E^F$ | $G^F$ |
|---|---|---|
| H | CH$_2$—CH$_2$ | Phenyl |
| H | CH$_2$ | (2-OMe)Phenyl |
| H | CH$_2$ | (2-OH)Phenyl |
| H | CH$_2$—CH$_2$ | Pyridin-2-yl |
| H | CH$_2$—CH$_2$ | Pyridin-3-yl |
| H | CH$_2$—CH$_2$ | (2-CF$_3$)Phenyl |
| H | CH$_2$—CH$_2$ | (2-F)Phenyl |
| H | CH$_2$—CH$_2$ | (2-OMe)Phenyl |
| H | CH$_2$ | Pyridin-4-yl |
| H | CH$_2$ | Phenyl |
| H | CH$_2$ | Pyridin-3-yl |
| H | CH$_2$ | Cyclohexyl |
| H | CH$_2$ | Pyridin-4-yl |

TABLE 84

| $R^{cF}$ | $E^F$ | $G^F$ |
|---|---|---|
| H | CH$_2$ | Pyridin-2-yl |
| H | CH$_2$—CH$_2$ | Pyridin-2-yl |
| H | CH$_2$—CH$_2$ | (4-SO$_2$Me)Phenyl |
| H | CH$_2$—CH$_2$ | (4-F)Phenyl |
| H | CH$_2$—CH$_2$ | (4-CF$_3$)Phenyl |
| H | CH$_2$—CH$_2$ | (4-CONH$_2$)Phenyl |
| H | CH$_2$—CH$_2$—CH$_2$ | Phenyl |
| H | CH$_2$ | (6-F)Pyridin-2-yl |
| H | CH$_2$—CH$_2$ | (6-F)Pyridin-2-yl |

TABLE 84-continued

| $R^{cF}$ | $E^F$ | $G^F$ |
|---|---|---|
| H | C(Me)$_2$ | (2-OMe)Phenyl |
| H | C(Me)—CH$_2$ | Pyridm-2-yl |
| H | CH$_2$—C(Me)$_2$ | Pyridin-2-yl |
| H | CH$_2$—CH$_2$ | Pyrimidin2-yl |

TABLE 85

| $R^{cF}$ | $E^F$ | $G^F$ |
|---|---|---|
| H | CH$_2$—CH$_2$ | Pyrazin-2-yl |
| H | CH$_2$—CH$_2$ | Pyridazin-3-yl |
| H | CH$_2$—C(Me)$_2$ | Pyridin-3-yl |
| 3-F | CH(Me) | (2-OMe)Phenyl |
| 3-Me | CH$_2$—CH$_2$ | Pyridin-3-yl |
| 3-OMe | CH$_2$—CH$_2$ | Phenyl |
| 3,5-F | CH$_2$ | Pyridin-4-yl |
| 3-NH$_2$ | CH$_2$ | Phenyl |
| 3,6-F | CH$_2$ | Pyridin-3-yl |
| 3-OMe | CH$_2$—CH$_2$ | Pyridin-2-yl |
| 3-CN | CH$_2$—CH$_2$ | Pyridin-2-yl |
| 3-CF$_3$ | CH$_2$—CH$_2$ | Pyridin-2-yl |

<Typical Compound IF-5>

[Formula 80]

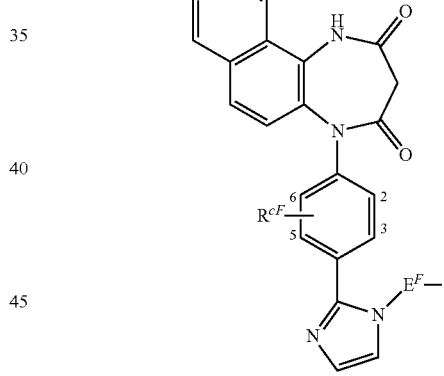

(In the formula, $R^{cF}$, $E^F$, and $G^F$ are as shown in Tables 86 to 88.)

TABLE 86

| $R^{cF}$ | $E^F$ | $G^F$ |
|---|---|---|
| H | CH$_2$—CH$_2$ | Phenyl |
| H | CH$_2$ | (2-OMe)Phenyl |
| H | CH$_2$ | (2-OH)Phenyl |
| H | CH$_2$—CH$_2$ | Pyridin-3-yl |
| H | CH$_2$—CH$_2$ | Phenyl |
| H | CH$_2$ | Pyridin-4-yl |
| H | CH$_2$ | Phenyl |
| H | CH$_2$ | Pyridin-3-yl |
| H | CH$_2$—CH$_2$ | Cyclohexyl |
| H | CH$_2$—CH$_2$ | Pyridin-4-yl |
| H | CH$_2$ | Pyridin-2-yl |
| H | CH$_2$—CH$_2$ | Pyridin-2-yl |

TABLE 87

| R<sup>cF</sup> | E<sup>F</sup> | G<sup>F</sup> |
|---|---|---|
| H | CH$_2$ | Imidazol-1-yl |
| H | CH$_2$—CH$_2$ | Imidazol-1-yl |
| H | CH$_2$—CH$_2$ | (2-OMe)Phenyl |
| H | CH$_2$ | (2-OMe)Phenyl |
| H | CH$_2$—CH$_2$—CH$_2$ | Phenyl |
| H | CH$_2$ | (6-F)Pyridin-2-yl |
| H | CH$_2$—CH$_2$ | (6-F)Pyridin-2-yl |
| H | C(Me)$_2$ | (2-OMe)Phenyl |
| H | C(Me)—CH$_2$ | Pyridin-2-yl |
| H | CH$_2$—C(Me)$_2$ | Pyridin-2-yl |
| H | CH$_2$—CH$_2$ | Pyrimidin-2-yl |
| H | CH$_2$—CH$_2$ | Pyrazin-2-yl |

TABLE 88

| R<sup>cF</sup> | E<sup>F</sup> | G<sup>F</sup> |
|---|---|---|
| H | CH$_2$—CH$_2$ | Pyridazin-3-yl |
| H | CH$_2$—C(Me)$_2$ | Pyridin-3-yl |
| 3-F | CH(Me) | (2-OMe)Phenyl |
| 3-Me | CH$_2$—CH$_2$ | Pyridin-3-yl |
| 3-OMe | CH$_2$—CH$_2$ | Phenyl |
| 3,5-F | CH$_2$ | Pyridin-4-yl |
| 3-NH$_2$ | CH$_2$ | Phenyl |
| 3,6-F | CH$_2$ | Pyridin-3-yl |
| 3-OMe | CH$_2$—CH$_2$ | Pyridin-2-yl |
| 3-CN | CH$_2$—CH$_2$ | Pyridin-2-yl |
| 3-CF$_3$ | CH$_2$—CH$_2$ | Pyridin-2-yl |

<Typical Compound IF-6>

[Formula 81]

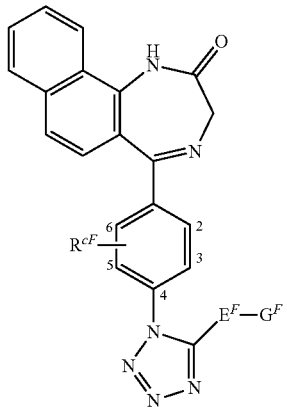

(In the formula, R<sup>cF</sup>, E<sup>F</sup>, and G<sup>F</sup> are as shown in Tables 89 to 91.)

TABLE 89

| R<sup>cF</sup> | E<sup>F</sup> | G<sup>F</sup> |
|---|---|---|
| H | CH$_2$—CH$_2$ | Pyridin-2-yl |
| H | CH$_2$ | (2-OMe)Phenyl |
| H | CH$_2$ | (2-OH)Phenyl |
| H | CH$_2$—CH$_2$ | Pyridin-3-yl |
| H | CH$_2$—CH$_2$ | Phenyl |
| H | CH$_2$ | Pyridin-4-yl |
| H | CH$_2$ | Phenyl |
| H | CH$_2$ | Pyridin-3-yl |

TABLE 89-continued

| R<sup>cF</sup> | E<sup>F</sup> | G<sup>F</sup> |
|---|---|---|
| H | CH$_2$—CH$_2$ | Cyclohexyl |
| H | CH$_2$—CH$_2$ | Pyridin-4-yl |
| H | CH$_2$ | Pyridin-2-yl |
| H | CH$_2$ | Imidazol-1-yl |

TABLE 90

| R<sup>cF</sup> | E<sup>F</sup> | G<sup>F</sup> |
|---|---|---|
| H | CH$_2$—CH$_2$ | Imidazol-1-yl |
| H | CH$_2$—CH$_2$ | (2-OMe)Phenyl |
| H | CH$_2$ | (2-OMe)Phenyl |
| H | CH$_2$—CH$_2$—CH$_2$ | Phenyl |
| H | CH$_2$ | (6-F)Pyridin-2-yl |
| H | CH$_2$—CH$_2$ | (6-F)Pyridin-2-yl |
| H | C(Me)$_2$ | (2-OMe)Phenyl |
| H | C(Me)—CH$_2$ | Pyridin-2-yl |
| H | CH$_2$—C(Me)$_2$ | Pyridin-2-yl |
| H | CH$_2$—C(Me)$_2$ | Pyridin-3-yl |
| 3-F | CH(Me) | (2-OMe)Phenyl |
| 3-Me | CH$_2$—CH$_2$ | Pyridin-3-yl |

TABLE 91

| R<sup>cF</sup> | E<sup>F</sup> | G<sup>F</sup> |
|---|---|---|
| 3-OMe | CH$_2$—CH$_2$ | Phenyl |
| 3,5-F | CH$_2$ | Pyridin-4-yl |
| 3-NH$_2$ | CH$_2$ | Phenyl |
| 3,6-F | CH$_2$ | Pyridin-3-yl |
| 3-OMe | CH$_2$—CH$_2$ | Pyridin-2-yl |
| 3-CN | CH$_2$—CH$_2$ | Pyridin-2-yl |
| 3-CF$_3$ | CH$_2$—CH$_2$ | Pyridin-2-yl |

<Typical Compound IF-7>

[Formula 82]

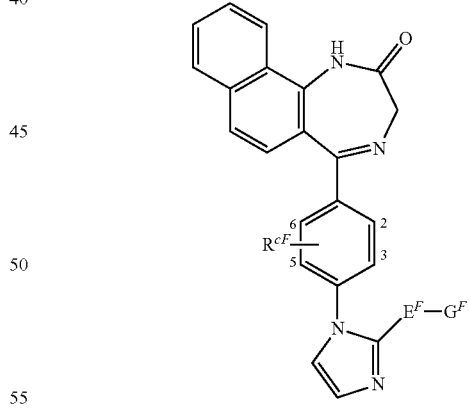

(In the formula, R<sup>cF</sup>, E<sup>F</sup>, and G<sup>F</sup> are as shown in Tables 92 to 94.)

TABLE 92

| R<sup>cF</sup> | E<sup>F</sup> | G<sup>F</sup> |
|---|---|---|
| H | CH$_2$—CH$_2$ | Phenyl |
| H | CH$_2$ | (2-OMe)Phenyl |
| H | CH$_2$ | (2-OH)Phenyl |
| H | CH$_2$—CH$_2$ | Pyridin-3-yl |

TABLE 92-continued

| R$^{cF}$ | E$^F$ | G$^F$ |
|---|---|---|
| H | CH$_2$—CH$_2$ | Phenyl |
| H | CH$_2$ | Pyridin-4-yl |
| H | CH$_2$ | Phenyl |
| H | CH$_2$ | Pyridin-3-yl |
| H | CH$_2$ | Cyclohexyl |
| H | CH$_2$—CH$_2$ | Pyridin-4-yl |
| H | CH$_2$ | Pyridin-2-yl |
| H | CH$_2$—CH$_2$ | Pyridin-2-yl |

TABLE 93

| R$^{cF}$ | E$^F$ | G$^F$ |
|---|---|---|
| H | CH$_2$ | Imidazol-1-yl |
| H | CH$_2$—CH$_2$ | Imidazol-1-yl |
| H | CH$_2$—CH$_2$ | (2-OMe)Phenyl |
| H | CH$_2$ | (2-OMe)Phenyl |
| H | CH$_2$—CH$_2$—CH$_2$ | Phenyl |
| H | CH$_2$ | (6-F)Pyridin-2-yl |
| H | CH$_2$—CH$_2$ | (6-F)Pyridin-2-yl |
| H | C(Me)$_2$ | (2-OMe)Phenyl |
| H | C(Me)—CH$_2$ | Pyridin-2-yl |
| H | CH$_2$—C(Me)$_2$ | Pyridin-2-yl |
| H | CH$_2$—CH$_2$ | Pyrimidin-2-yl |
| H | CH$_2$—CH$_2$ | Pyrazin-2-yl |

TABLE 94

| R$^{cF}$ | E$^F$ | G$^F$ |
|---|---|---|
| H | CH$_2$—CH$_2$ | Pyridazin-3-yl |
| H | CH$_2$—C(Me)$_2$ | Pyridin-3-yl |
| 3-F | CH(Me) | (2-OMe)Phenyl |
| 3-Me | CH$_2$—CH$_2$ | Pyridin-3-yl |
| 3-OMe | CH$_2$—CH$_2$ | Phenyl |
| 3,5-F | CH$_2$ | Pyridin-4-yl |
| 3-NH$_2$ | CH$_2$ | Phenyl |
| 3,6-F | CH$_2$ | Pyridin-3-yl |
| 3-OMe | CH$_2$—CH$_2$ | Pyridin-2-yl |
| 3-CN | CH$_2$—CH$_2$ | Pyridin-2-yl |
| 3-CF$_3$ | CH$_2$—CH$_2$ | Pyridin-2-yl |

<Typical Compound IF-8>

[Formula 83]

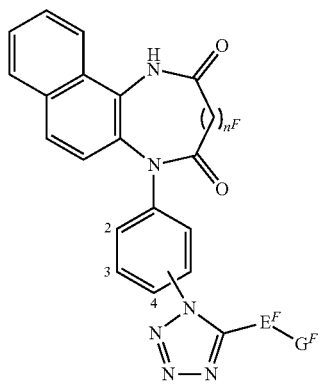

(In the formula, substitution position of the tetrazole ring, E$^F$-G$^F$, n$^F$, and type of salt are as shown in Table 95.)

TABLE 95

| Substitution position of tetrazole ring | E$^F$-G$^F$ | n$^F$ | Salt |
|---|---|---|---|
| 3 | CH$_2$CH$_2$(2-Py) | 0 | |
| 4 | CH$_2$CH$_2$(6-Methylpyridin-2-yl) | 1 | |
| 4 | CH$_2$CH$_2$(3-CN)Ph | 1 | |
| 4 | CH$_2$CH$_2$(3-CONH$_2$)Ph | 1 | |
| 4 | CH$_2$CH$_2$(2-Methoxypyridin-3-yl) | 1 | |
| 4 | CH$_2$(2-NMe$_2$)Ph | 1 | MsOH |
| 4 | CH$_2$C(Me)$_2$(2-Py) | 1 | HCl |
| 4 | CH$_2$CH$_2$(3-Methoxypyridin-2-yl) | 1 | HCl |
| 3 | CH$_2$CH$_2$CH$_2$(6-Methylpyridin-2-yl) | 1 | |
| 3 | CH$_2$CH$_2$CH$_2$(3-CN)Ph | 1 | |
| 3 | CH$_2$CH$_2$CH$_2$(3-CONH$_2$)Ph | 1 | |
| 3 | CH$_2$CH$_2$CH$_2$(2-Methoxypyridin-3-yl) | 1 | |
| 3 | CH$_2$CH$_2$(2-NMe$_2$)Ph | 1 | |
| 3 | CH$_2$CH$_2$C(Me)$_2$(2-Py) | 0 | |
| 3 | CH$_2$CH$_2$CH$_2$(3-Methoxypyridin-2-yl) | 0 | |

<Typical Compound IF-9>

Naphthalene Type

[Formula 84]

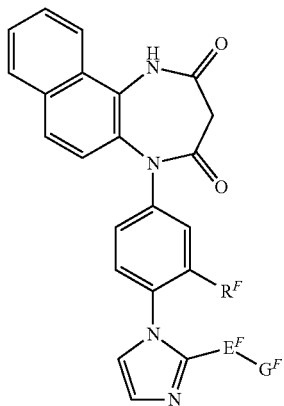

Indane Type

[Formula 85]

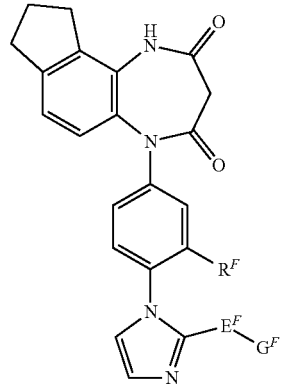

(In the formulas, E$^F$-G$^F$, R$^F$, and type of salt are as shown in Tables 96 and 97.)

TABLE 96

| Naphthalene type or indane type | $E^F$-$G^F$ | $R^F$ | Salt |
|---|---|---|---|
| Naphthalene type | CH$_2$CH$_2$(3-F)Ph | H | HCl |
| Naphthalene type | CH$_2$CH$_2$(2-OMe)Ph | H | HCl |
| Naphthalene type | CH$_2$CH$_2$(4-F)Ph | H | HCl |
| Naphthalene type | CH$_2$CH$_2$(2-F)Ph | H | HCl |
| Naphthalene type | CH$_2$CH$_2$(4-CF$_3$)Ph | H | HCl |
| Naphthalene type | CH$_2$CH$_2$(2,6-Me)Ph | H | HCl |
| Naphthalene type | CH$_2$CH$_2$(3-CF$_3$)Ph | H | HCl |
| Naphthalene type | CH$_2$CH$_2$(3-OMe)Ph | H | HCl |
| Naphthalene type | CH$_2$CH$_2$(3-OH)Ph | H | HCl |
| Naphthalene type | CH$_2$CH$_2$(4-CN)Ph | H | |
| Naphthalene type | CH$_2$CH$_2$(4-CONH$_2$)Ph | H | |
| Naphthalene type | CH$_2$CH$_2$(2-CN)Ph | H | |
| Naphthalene type | CH$_2$CH$_2$(2-CONH$_2$)Ph | H | |
| Naphthalene type | CH$_2$CH$_2$(3-CN)Ph | H | |
| Naphthalene type | CH$_2$CH$_2$(3-CONH$_2$)Ph | H | |
| Naphthalene type | CH$_2$CH$_2$(3-CONH$_2$)Ph | H | HCl |
| Naphthalene type | CH$_2$CH$_2$(4-SO$_2$Me)Ph | H | HCl |
| Naphthalene type | CH$_2$CH$_2$(3-OMe, 2-F)Ph | H | HCl |

TABLE 97

| Naphthalene type or indane type | $E^F$-$G^F$ | $R^F$ | Salt |
|---|---|---|---|
| Indane type | CH$_2$CH$_2$(3-OMe, 2-F)Ph | H | HCl |
| Naphthalene type | CH$_2$CH$_2$(3-Thienyl) | H | HCl |
| Naphthalene type | CH$_2$CH$_2$(2-Furanyl) | H | HCl |
| Indane type | CH$_2$CH$_2$(2-F)Ph | H | |
| Naphthalene type | CH$_2$CH$_2$(2-Pyridyl) | H | 2HCl |
| Indane type | CH$_2$CH$_2$(3-F)Ph | H | HCl |
| Naphthalene type | CH$_2$CH$_2$(2-OMe, 3-F)Ph | H | HCl |
| Naphthalene type | CH$_2$CH$_2$(3-F)Ph | F | |
| Naphthalene type | CH$_2$CH$_2$(2-OMe)Ph | OH | |
| Naphthalene type | CH$_2$CH$_2$(4-F)Ph | H | |
| Naphthalene type | CH$_2$CH$_2$(2-F)Ph | F | |
| Naphthalene type | CH$_2$CH$_2$(4-CF$_3$)Ph | OH | |
| Naphthalene type | CH$_2$CH$_2$(2,6-Me)Ph | H | |
| Naphthalene type | CH$_2$CH$_2$(3-CF$_3$)Ph | F | |
| Naphthalene type | CH$_2$CH$_2$(3-OMe)Ph | OH | |
| Naphthalene type | CH$_2$CH$_2$(3-OH)Ph | H | |
| Naphthalene type | CH$_2$CH$_2$(4-CN)Ph | F | |
| Indane type | CH$_2$CH$_2$(2,6-Me)Ph | H | |
| Indane type | CH$_2$CH$_2$(3-CF$_3$)Ph | F | |
| Indane type | CH$_2$CH$_2$(3-OMe)Ph | OH | |
| Indane type | CH$_2$CH$_2$(3-OH)Ph | H | |
| Indane type | CH$_2$CH$_2$(4-CN)Ph | F | |

<Typical Compound IF-10>

[Formula 86]

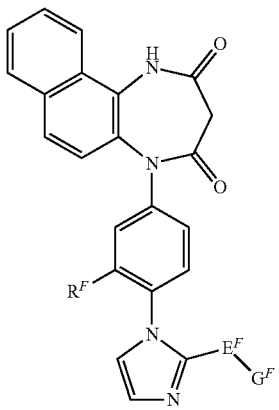

(In the formula, $E^F$-$G^F$, $R^F$, and type of salt are as shown in Tables 98.)

TABLE 98

| $E^F$-$G^F$ | $R^F$ |
|---|---|
| Bond-Ph | H |
| Bond-(2-OMe)Ph | H |
| CH$_2$OPh | H |
| NH-(2-OMe)Ph | H |
| NH—Ph | H |
| CH$_2$SPh | F |
| CH$_2$NHPh | OH |
| Bond-(2-F)Ph | F |
| Bond-(2CF$_3$)Ph | OH |
| Bond-(2Cl)Ph | F |
| Bond-(2-Me)Ph | OH |
| Bond-(2,6-Me)Ph | F |
| Bond-(2,6-F)Ph | OH |
| Bond-(2-OH)Ph | F |
| CH$_2$O(2-F)Ph | OH |
| NH-(2,6-Me)Ph | F |
| NH—(2CF$_3$)Ph | OH |
| Bond-(3-F)Ph | F |

<Typical Compound IF-11>

[Formula 87]

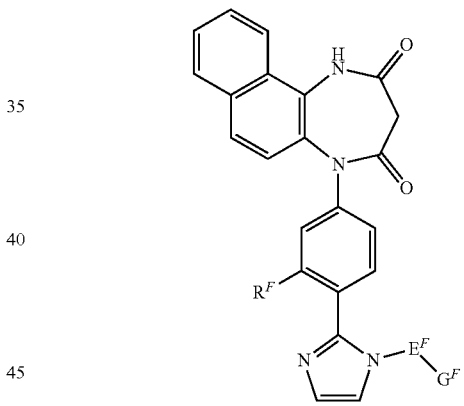

(In the formula, $E^F$-$G^F$, $R^F$, and type of salt are as shown in Table 99.)

TABLE 99

| $E^F$-$G^F$ | $R^F$ | Salt |
|---|---|---|
| CH$_2$CH$_2$Ph | H | HCl |
| CH$_2$(4-Cl)Ph | H | HCl |
| CH$_2$(2-OMe)Ph | H | |
| CH$_2$CH$_2$(3-OMe)Ph | H | |
| CH$_2$CH$_2$(3-OMe)Ph | H | HCl |
| CH$_2$CH$_2$(3-OH)Ph | H | |
| CH$_2$(2,4,6-Me)Ph | H | HCl |
| CH$_2$(2-CF$_3$)Ph | H | HCl |
| CH$_2$(2-CN)Ph | H | |
| CH$_2$(2-CONH$_2$)Ph | H | |
| CH$_2$(2-NH$_2$)Ph | H | |
| CH$_2$CH$_2$Ph | OMe | |
| CH$_2$CH$_2$Ph | OH | |
| CH$_2$(3-CN)Ph | H | |
| CH$_2$(3-CONH$_2$)Ph | H | |

TABLE 99-continued

| $E^F\text{-}G^F$ | $R^F$ | Salt |
| --- | --- | --- |
| CH$_2$CH$_2$(3-OMe)Ph | F | |
| CH$_2$CH$_2$(3-OH)Ph | F | |
| CH$_2$CH$_2$(3-F)Ph | H | |
| CH$_2$CH$_2$(2-F)Ph | F | |
| CH$_2$CH$_2$(2-F)Ph | H | |

<Typical Compound IF-12>

[Formula 88]

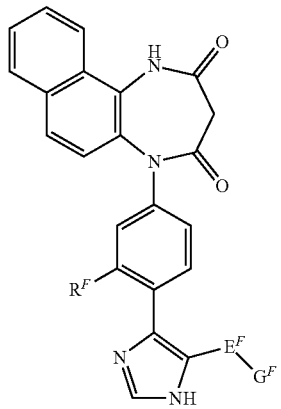

(In the formula, $E^F\text{-}G^F$, $R^F$, and type of salt are as shown in Table 100.)

TABLE 100

| $E^F\text{-}G^F$ | $R^F$ | Salt |
| --- | --- | --- |
| Bond-Ph | H | HCl |
| CH$_2$CH$_2$Ph | H | HCl |
| CH$_2$CH$_2$(2-F)Ph | H | |
| CH$_2$CH$_2$(3-F)Ph | F | |
| CH$_2$CH$_2$(2-OMe)Ph | F | |
| CH$_2$CH$_2$(3-OMe)Ph | F | |
| CH$_2$CH$_2$(2-OH)Ph | F | |
| CH$_2$CH$_2$(3-OH)Ph | F | |

<Typical Compound IF-13>

[Formula 89]

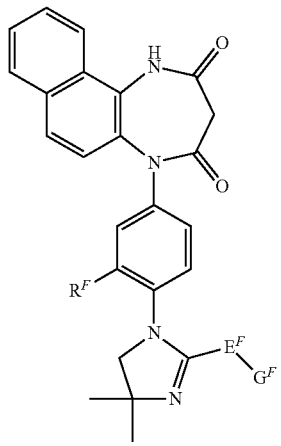

(In the formula, $E^F\text{-}G^F$, $R^F$, and type of salt are as shown in Table 101.)

TABLE 101

| $E^F\text{-}G^F$ | $R^F$ | Salt |
| --- | --- | --- |
| CH$_2$CH$_2$Ph | H | HCl |
| CH$_2$CH$_2$(2-F)Ph | H | |
| CH$_2$CH$_2$(3-F)Ph | F | |
| CH$_2$CH$_2$(2-OMe)Ph | F | |
| CH$_2$CH$_2$(3-OMe)Ph | F | |
| CH$_2$CH$_2$(2-OH)Ph | F | |
| CH$_2$CH$_2$(3-OH)Ph | F | |

(G-1) A compound represented by the following general formula (IG):

[Formula 90]

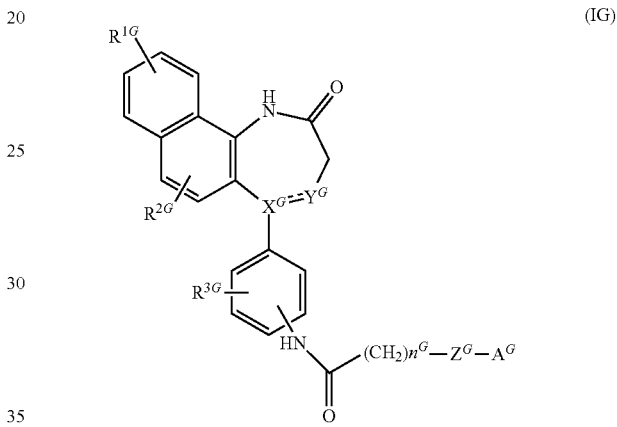

(IG)

wherein, in the formula, $R^{1G}$, $R^{2G}$, and $R^{3G}$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, or a dialkylamino group having 2 to 8 carbon atoms, $X^G$ represents C or N, $Y^G$ represents N or C(=O), provided that when $X^G$ is C, $Y^G$ represents N, and when $X^G$ is N, $Y^G$ represents C(=O), the double line consisting of the solid line and the broken line represents a single bond or a double bond, $n^G$ represents an integer of 0 to 6, $Z^G$ represents O, S, or an atomic bond, and $A^G$ represents benzene ring, pyridine ring, piperazine ring, piperidine ring, or morpholine ring which may have 1 to 5 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and N($R^{4G}$)($R^{5G}$), wherein $R^{4G}$ and $R^{5G}$ represent the same or different alkyl groups having 1 to 8 carbon atoms, or $R^{4G}$, $R^{5G}$ and the nitrogen atom to which $R^{4G}$ and $R^{5G}$ bind together to represent a 5- to 7-membered ring which may further contain oxygen atom or sulfur atom as a ring-forming heteroatom.

As for the general formula (IG), examples of the alkyl group having 1 to 8 carbon atoms include methyl group, ethyl group, propyl group, isopropyl group, butyl group, i-butyl group, t-butyl group, pentyl group, hexyl group, and the like.

Examples of the cycloalkyl group having 3 to 8 carbon atoms include cyclopropyl group, cyclohexyl group, and the like.

Examples of the alkenyl group having 2 to 8 carbon atoms include allyl group, and the like.

Examples of the alkoxy group having 1 to 8 carbon atoms include methoxy group, ethoxy group, propoxy group, isopropoxy group, butoxy group, i-butoxy group, t-butoxy group, pentyloxy group, hexyloxy group, and the like.

Examples of the alkyl group having 1 to 8 carbon atoms and substituted with 1 to 3 halogen atoms include methyl group, ethyl group, propyl group, isopropyl group, butyl group, t-butyl group substituted with 1 to 3 halogen atoms such as fluorine atom, chlorine atom, and bromine atom, and the like, and preferred examples of the same include trifluoromethyl group, chloromethyl group, 2-chloroethyl group, 2-bromoethyl group, 2-fluoroethyl group, and the like.

Examples of the alkoxy group having 1 to 8 carbon atoms and substituted with 1 to 3 halogen atoms include methoxy group, ethoxy group, propoxy group, isopropoxy group, butoxy group, t-butoxy group substituted with 1 to 3 halogen atoms such as fluorine atom, chlorine atom, and bromine atom, and the like, and preferred examples of the same include trifluoromethoxy group, chloromethoxy group, 2-chloroethoxy group, 2-bromoethoxy group, 2-fluoroethoxy group, and the like.

Examples of the halogen atom include iodine atom, fluorine atom, chlorine atom, bromine atom, and the like.

Examples of the alkylamino group having 1 to 8 carbon atoms include methylamino group, ethylamino group, and the like.

Examples of the dialkylamino group having 2 to 8 carbon atoms include dimethylamino group, diethylamino group, and the like.

Examples of the 5- to 7-membered ring which is formed by $R^{4G}$, $R^{5G}$, and the nitrogen atom to which $R^{4G}$ and $R^{5G}$ binding together, and may further contain oxygen atom, or sulfur atom as a ring-forming heteroatom include morpholin-4-yl, 1H-pyrrol-1-yl, pyrrolidin-1-yl, and the like.

$R^{1G}$ mentioned above may have 1 to 4 of the same or different substituents.

$R^{2G}$ mentioned above may have 1 or 2 of the same or different substituents.

$R^{3G}$ mentioned above may have 1 to 4 of the same or different substituents.

Aa the compounds represented by the general formula (IG), the following compounds are preferred.

(G-1-1) The compound according to (G-1), a tautomer or stereoisomer of the compound, or a pharmaceutically acceptable salt thereof, or a solvate thereof, wherein $A^G$ is a benzene ring, pyridine ring, piperazine ring, piperidine ring, or morpholine ring which may have 1 to 5 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(G-1-2) The compound according to (G-1), a tautomer or stereoisomer of the compound, or a pharmaceutically acceptable salt thereof, or a solvate thereof, wherein $A^G$ is a benzene ring or pyridine ring which may have 1 to 5 of the same or different substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, amino group, an alkylamino group having 1 to 8 carbon atoms, and a dialkylamino group having 2 to 8 carbon atoms.

(G-1-3) The compound according to (G-1), a tautomer or stereoisomer of the compound, or a pharmaceutically acceptable salt thereof, or a solvate thereof, wherein $A^G$ is a benzene ring which may have 1 to 5 of the same or different substituents selected from an alkyl group having 1 to 8 carbon atoms, an alkoxy group having 1 to 8 carbon atoms, a halogen atom, hydroxyl group, amino group, an alkylamino group having 1 to 8 carbon atoms, and a dialkylamino group having 2 to 8 carbon atoms.

(G-1-4) The compound according to (G-1), a tautomer or stereoisomer of the compound, or a pharmaceutically acceptable salt thereof, or a solvate thereof, wherein $A^G$ is a pyridine ring which has N($R^{4G}$)($R^{5G}$) wherein $R^{4G}$ and $R^{5G}$ represent a 5- to 7-membered ring which is formed by $R^{4G}$, $R^{5G}$ binding together and the nitrogen atom to which $R^{4G}$ and $R^{5G}$ bind, and may further contain oxygen atom or sulfur atom as a ring-forming heteroatom, as a substituent.

(G-1-5) The compound according to (G-1), a tautomer or stereoisomer of the compound, or a pharmaceutically acceptable salt thereof, or a solvate thereof, wherein $A^G$ is a pyridine ring which has a substituent selected from morpholin-4-yl, 1H-pyrrol-1-yl, and pyrrolidin-1-yl.

(G-1-6) The compound according to (G-1) or the compound according to any one of (G-1-1) to (G-1-5) mentioned above, a tautomer or stereoisomer of the compound, or a pharmaceutically acceptable salt thereof, or a solvate thereof, wherein $R^{1G}$, $R^{2G}$, and $R^{3G}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, or a halogen atom.

(G-1-7) The compound according to (G-1), or the compound according to any one of (G-1-1) to (G-1-5) mentioned above, a tautomer or stereoisomer of the compound, or a pharmaceutically acceptable salt thereof, or a solvate thereof, wherein $R^{1G}$, $R^{2G}$, and $R^{3G}$ may be the same or different, and are hydrogen atom, or a halogen atom.

(G-1-8) The compound according to (G-1), or the compound according to any one of (G-1-1) to (G-1-7) mentioned above, a tautomer or stereoisomer of the compound, or a pharmaceutically acceptable salt thereof, or a solvate thereof, wherein $n^G$ is 0.

(G-1-9) The compound according to (G-1), or the compound according to any one of (G-1-1) to (G-1-7) mentioned above, a tautomer or stereoisomer of the compound, or a pharmaceutically acceptable salt thereof, or a solvate thereof, wherein $n^G$ is 1 or 2.

(G-1-10) The compound according to (G-1), or the compound according to any one of (G-1-1) to (G-1-9) mentioned above, a tautomer or stereoisomer of the compound, or a pharmaceutically acceptable salt thereof, or a solvate thereof according to, wherein $Z^G$ is an atomic bond.

(G-1-11) The compound according to (G-1), a tautomer or stereoisomer of the compound, or a pharmaceutically acceptable salt thereof, or a solvate thereof, wherein $R^{1G}$, $R^{2G}$, and $R^{3G}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, or hydroxyl group, $X^G$ is N,
$Y^G$ is C(=O),
the double line consisting of the solid line and the broken line is a single bond,
$n^G$ is 0,
$Z^G$ is an atomic bond, and
$A^G$ is a benzene ring or pyridine ring which may have 1 to 3 of the same or different substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, amino group, an alkylamino group having 1 to 8 carbon atoms, and $N(R^{4G})(R^{5G})$, wherein $R^{4G}$ and $R^{5G}$ are the same or different alkyl groups having 1 to 8 carbon atoms, or $R^{4G}$ and $R^{5G}$ bind together to represent, together with the nitrogen atom to which $R^{4G}$ and $R^{5G}$ bind, a morpholine ring, pyrrole ring, or pyrrolidine ring.

(G-1-12) The compound according to (G-1), a tautomer or stereoisomer of the compound, or a pharmaceutically acceptable salt thereof, or a solvate thereof, wherein $R^{1G}$, $R^{2G}$, and $R^{3G}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, or hydroxyl group, $X^G$ is C,
$Y^G$ is N,
the double line consisting of the solid line and the broken line is a double bond,
$n^G$ is an integer of 0 to 3,
$Z^G$ is an atomic bond, and
$A^G$ is a benzene ring or pyridine ring which may have 1 to 3 of the same or different substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, amino group, an alkylamino group having 1 to 8 carbon atoms, and $N(R^{4G})(R^{5G})$, wherein $R^{4G}$ and $R^{5G}$ represent the same or different alkyl groups having 1 to 8 carbon atoms, or $R^{4G}$ and $R^{5G}$ bind together to represent, together with the nitrogen atom to which $R^{4G}$ and $R^{5G}$ bind, a morpholine ring, pyrrole ring, or pyrrolidine ring.

(G-1-13) The compound according to (G-1), or the compound according to any one of (G-1-1) to (G-1-12), a tautomer or stereoisomer of the compound, or a pharmaceutically acceptable salt thereof, or a solvate thereof, wherein $X^G$ and NHC(=O) are at para-positions on the phenyl group.

Examples of the pharmacologically acceptable salts of the compound of (G-1) include hydrochlorides, mesylates, and alkali metal salts such as those of sodium, potassium, and lithium. Further, there may be stereoisomers of the compounds of the present invention such as cis- and trans-isomers, optically active substances, and racemates, and these all fall within the scope of the present invention.

<Typical Compound IG-1>

[Formula 91]

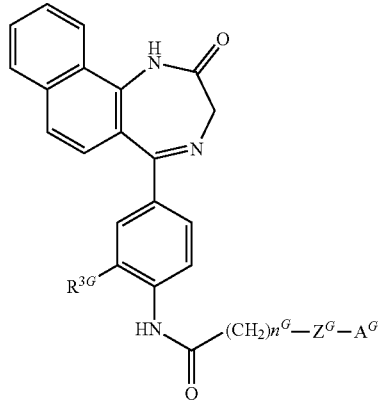

(In the formula, $R^{3G}$, $A^G$, $Z^G$, and $n^G$ are as shown in Tables 102 and 103.)

TABLE 102

| $R^{3G}$ | $n^G$ | $Z^G$ | $A^G$ |
|---|---|---|---|
| H | 2 | Bond | Pyridin-2-yl |
| H | 0 | Bond | (2-Et, 3-OH)Phenyl |
| H | 0 | Bond | (2-Et)Pyridin-3-yl |
| H | 0 | Bond | (2-Et, 6-OH)Phenyl |
| H | 0 | Bond | (3-Et)Pyridin-2-yl |
| H | 1 | O | Pyridin-2-yl |
| H | 1 | Bond | (2-OMe)Phenyl |
| H | 2 | Bond | Pyridin-3-yl |
| H | 2 | Bond | Phenyl |
| H | 2 | Bond | Cyclohexyl |
| H | 1 | Bond | Pyridin-2-yl |

TABLE 103

| $R^{3G}$ | $n^G$ | $Z^G$ | $A^G$ |
|---|---|---|---|
| H | 1 | Bond | Pyridin-3-yl |
| H | 1 | Bond | Pyridin-4-yl |
| H | 3 | Bond | Pyridin-2-yl |
| H | 1 | Bond | (2-NMe$_2$)Phenyl |
| OH | 1 | O | Pyridin-2-yl |
| OMe | 2 | O | Pyridin-2-yl |
| CN | 2 | Bond | Pyridin-2-yl |
| Me | 2 | Bond | Pyridin-2-yl |
| CF$_3$ | 1 | Bond | Pyridin-2-yl |
| F | 2 | Bond | Pyridin-2-yl |
| H | 0 | Bond | (2-NMe$_2$)Pyridin-3-yl |
| F | 2 | Bond | Phenyl |

<Typical Compound IG-2>

[Formula 92]

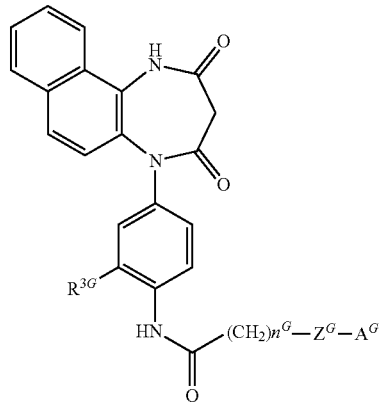

(In the formula, $R^{3G}$, $A^G$, $Z^G$, and $n^G$ are as shown in Tables 104 and 105.)

TABLE 104

| $R^{3G}$ | $n^G$ | $Z^G$ | $A^G$ |
|---|---|---|---|
| H | 2 | Bond | Pyridin-3-yl |
| H | 2 | Bond | Pyridin-4-yl |
| F | 0 | Bond | (2-tBu)Phenyl |
| H | 2 | Bond | Pyridin-2-yl |
| H | 0 | Bond | (2-NMe$_2$)Pyridin-3-yl |
| H | 2 | Bond | Cyclohexyl |
| H | 1 | Bond | Pyridin-2-yl |
| H | 1 | Bond | Pyridin-3-yl |

TABLE 105

| $R^{3G}$ | $n^G$ | $Z^G$ | $A^G$ |
|---|---|---|---|
| H | 1 | Bond | Pyridin-4-yl |
| H | 3 | Bond | Pyridin-2-yl |
| H | 1 | Bond | (2-NMe$_2$)Phenyl |
| OH | 1 | O | Pyridin-2-yl |
| OMe | 2 | O | Pyridin-2-yl |
| CN | 2 | Bond | Pyridin-2-yl |
| Me | 2 | Bond | Pyridin-2-yl |
| CF$_3$ | 1 | Bond | Pyridin-2-yl |
| F | 2 | Bond | Pyridin-2-yl |
| F | 2 | Bond | Phenyl |

<Typical Compound IG-3>

[Formula 93]

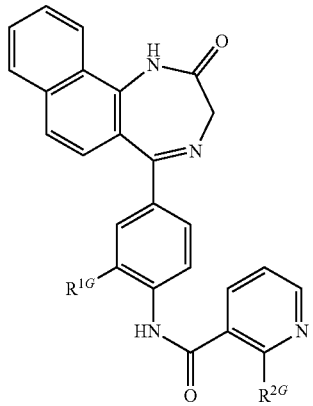

(In the formula, $R^{1G}$, $R^{2G}$, and type of salt are as shown in Tables 106 and 107.)

TABLE 106

| $R^{1G}$ | $R^{2G}$ | Salt |
|---|---|---|
| H | NMe$_2$ | 2HCl |
| H | NMe$_2$ | 2MsOH |
| H | 1H-Pyrrol-1-yl | 2HCl |
| H | Morpholin-4-yl | 2HCl |
| H | Pyrrolidin-1-yl | 2HCl |
| H | iPr | 2HCl |
| H | iPrNH | 2HCl |
| F | NMe$^2$ | |
| OH | NMe$^2$ | |
| F | 1H-Pyrrol-1-yl | |
| OH | Morpholin-4-yl | |

TABLE 107

| $R^{1G}$ | $R^{2G}$ | Salt |
|---|---|---|
| F | Pyrrolidin-1-yl | |
| OH | iPr | |
| F | iPrNH | |
| H | NEt$_2$ | |
| H | NHEt | |
| F | NHMe | |
| Me | 1H-Pyrrol-1-yl | |
| Me | Morpbolin-4-yl | |
| Me | Pyrrolidin-1-yl | |

Typical Compound IG-4

[Formula 94]

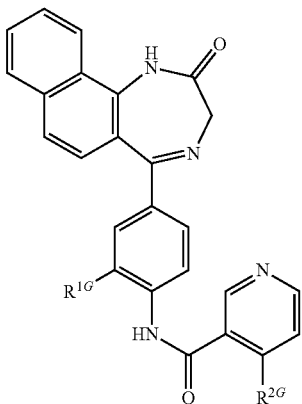

(In the formula, $R^{1G}$, $R^{2G}$, and type of salt are as shown in Table 108.)

TABLE 108

| $R^{1G}$ | $R^{2G}$ | Salt |
|---|---|---|
| H | NMe$_2$ | 2HCl |
| H | 1H-Pyrrol-1-yl | |
| H | Morpholin-4-yl | |
| H | Pyrrolidin-1-yl | |
| H | iPr | |
| H | iPrNH | |
| F | NMe$_2$ | |

Typical Compound IG-5

[Formula 95]

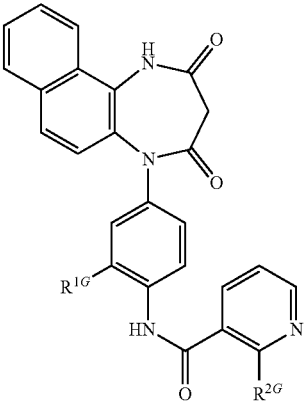

(In the formula, $R^{1G}$, $R^{2G}$, and type of salt are as shown in Table 109.)

TABLE 109

| $R^{1G}$ | $R^{2G}$ | Salt |
|---|---|---|
| H | NMe$_2$ | HCl |
| H | Morpholin-4-yl | HCl |
| H | Pyrrolidin-1-yl | |
| H | iPr | |
| H | iPrNH | |

TABLE 109-continued

| $R^{1G}$ | $R^{2G}$ | Salt |
|---|---|---|
| F | NMe$_2$ | |
| OH | NMe$_2$ | |
| F | 1H-Pyrrol-1-yl | |
| OH | Morpholin-4-yl | |
| F | Pyrrolidin-1-yl | |
| OH | iPr | |
| F | iPrNH | |
| H | NEt$_2$ | |
| H | NHEt | |
| F | NHMe | |
| Me | 1H-Pyrrol-1-yl | |
| Me | Morpholin-4-yl | |
| Me | Pyrrolidin-1-yl | |

As the active ingredient of the medicament of the present invention, there can be preferably used:

(H-1) a compound represented b the following the general formula (IH):

[Formula 96]

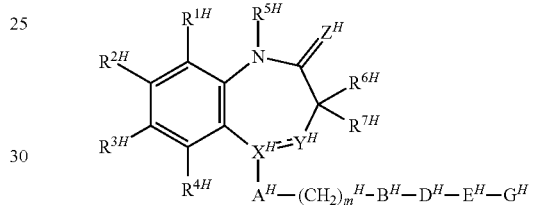

(IH)

wherein, in the formula, $R^{1H}$ and $R^{2H}$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), a phenyl group which may have a substituent, a pyridyl group which may have a substituent, or an aralkyl group (the aryl moiety thereof has 6 to 10 carbon atoms, and the alkylene moiety thereof has 1 to 8 carbon atoms), or $R^{1H}$ and $R^{2H}$ may bind together to form a condensed ring selected from naphthalene ring, quinoline ring, isoquinoline ring, tetrahydronaphthalene ring, indane ring, tetrahydroquinoline ring, and tetrahydroisoquinoline ring, together with the benzene ring to which they bind, and the ring constituted by $R^1$, $R^2$ binding together, and the carbon atoms to which $R^{1H}$ and $R^{2H}$ bind may be substituted with 1 to 4 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, sulfamoyl group, and an aralkyl group (the aryl moiety thereof has 6 to 10 carbon atoms, and the alkylene moiety thereof has 1 to 8 carbon atoms), $R^{3H}$ and $R^{4H}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety thereof has 1 to 8 carbon atoms), or an aralkyl group (the aryl moiety thereof has 6 to 10 carbon atoms, and the alkylene moiety thereof has 1 to 8 carbon atoms), $R^{5H}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, an aralkyl group (the aryl moiety thereof has 6 to 10 carbon atoms, and the alkylene moiety thereof has 1 to 8 carbon atoms), or an alkyl having 1 to 3 carbon atoms substituted with phenyl group, $R^{6H}$ and $R^{7H}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, amino group, or an alkyl group having 1 to 3 carbon atoms and substituted with phenyl group, $X^H$ represents C, CH, or N, $Y^H$ represents N, NH, or C(=O), provided that when $X^H$ is N, $Y^H$ is not N or NH, and when $X^H$ is C or CH, $Y^H$ is not C(=O), the double line consisting of the solid line and the broken line represents a single bond or a double bond, $Z^H$ represents oxygen atom or sulfur atom, $A^H$ represents benzene ring, pyridine ring, thiophene ring, pyrimidine ring, naphthalene ring, quinoline ring, or indole ring which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, an acylamino group having 2 to 8 carbon atoms and substituted with 1 to 3 halogen atoms, an alkylsulfonylamino group having 1 to 8 carbon atoms, carboxyl group, an acyl group having 2 to 8 carbon atoms, an alkoxycarbonyl group (the alkoxy moiety thereof has 1 to 8 carbon atoms), carbamoyl group, an alkylthio group having 1 to 8 carbon atoms, an alkylsulfinyl group having 1 to 8 carbon atoms, an alkylsulfonyl group having 1 to 8 carbon atoms, sulfamoyl group, an aralkyl group (the aryl moiety thereof has 6 to 10 carbon atoms, and the alkylene moiety thereof has 1 to 8 carbon atoms), phenyl group, and pyridyl group, or an atomic bond, $B^H$ represents $N(R^{8H})C(=O)$, NHCONH, $CON(R^{9H})$, NHC(=S)NH, $N(R^{10H})SO_2$, $SO_2N(R^{11H})$, $OSO_2$, or an atomic bond, wherein $R^{8H}$, $R^{9H}$, $R^{10H}$, and $R^{11H}$ represent hydrogen atom, an alkyl group having 1 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety thereof has 6 to 10 carbon atoms, and the alkylene moiety thereof has 1 to 8 carbon atoms), $D^H$ represents an alkylene chain having 1 to 6 carbon atoms which may have 1 to 4 of the same or different substituents selected from an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, and an aralkyl group (the aryl moiety thereof has 6 to 10 carbon atoms, and the alkylene moiety thereof has 1 to 8 carbon atoms), and may further contain a double bond, or an atomic bond, $E^H$ represents O, S, $NR^{12H}$, or an atomic bond, wherein $R^{12H}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety thereof has 6 to 10 carbon atoms, and the alkylene moiety thereof has 1 to 8 carbon atoms), $G^H$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, an alkylsulfonyl group having 1 to 6 carbon atoms, an aralkyl group (the aryl moiety thereof has 6 to 10 carbon atoms, and the alkylene moiety thereof has 1 to 8 carbon atoms), a phenyl group which may have a substituent, a pyridyl group which may have a substituent, an imidazolyl group which may have a substituent, an oxazolyl group which may have a substituent, and a thiazolyl group which may have a substituent, or a 5- or 6-membered heterocyclic ring which contains 1 to 4 nitrogen atoms as ring-constituting elements, and may have a substituent, and $m^H$ represents an integer of 0 to 5, provided that those compounds where $R^{1H}$ and $R^{2H}$ do not bind together to form a ring, $X^H$ is C, $Y^H$ is N, the double line consisting of the solid line and the broken line is a double bond, $Z^H$ is oxygen atom, $A^H$ is a benzene ring, $m^H$ is 0, $B^H$ is C(=O)NH, $E^H$ is an atomic bond, and $G^H$ is phenyl group are excluded.

In the aforementioned general formula OH), $R^1H$, $R^2H$, $R^3H$, $R^4H$, $R^5H$, $R^6H$, $R^7H$, $Z^H$, $X^H$, $Y^H$, $A^H$, $m^H$, $B^H$, $D^H$, $E^H$, and $G^H$ can be selected so that the compounds of the general formula (IH) include the compounds of the formula (IA) and the formula (IE) mentioned above.

As the compounds falling within the scope of the general formula (IH), the following compounds are preferred.

(H-2) The compound according to (H-1), wherein $X^H$ is N, $Y^H$ is C(=O), and the double line consisting of the solid line and the broken line is a single bond.

(H-3) The compound according to (H-1) or (H-2), wherein $X^H$ is C, $Y^H$ is N, and the double line consisting of the solid line and the broken line is a double bond.

(H-4) The compound according to any one of (H-1) to (H-3), wherein $Z^H$ is oxygen atom.

(H-5) The compound according to any one of (H-1) to (H-4), wherein $A^H$ is a phenyl group which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group (the aryl moiety thereof has 6 to 10 carbon atoms, and the alkylene moiety thereof has 1 to 8 carbon atoms), phenyl group, and pyridyl group.

(H-6) The compound according to any one of (H-1) to (H-5), wherein $B^H$ is NHC(=O).

(H-7) The compound according to any one of (H-1) to (H-6), wherein $D^H$ is an atomic bond.

(H-8) The compound according to any one of (H-1) to (H-7), wherein $E^H$ is an atomic bond.

(H-9) The compound according to any one of (H-1) to (H-8), wherein $G^H$ is piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine which may have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, and an alkylsulfonyl group having 1 to 6 carbon atoms.

(H-10) The compound according to any one of (H-1) to (H-9), wherein $m^H$ is 0.

(H-11) The compound according to any one of (H-1) to (H-10), wherein $R^{1H}$ and $R^{2H}$ bind together to form naphthalene ring together with the benzene ring to which they bind, and the benzene ring formed by $R^{1H}$, $R^{2H}$ binding together, and the carbon atoms to which $R^{1H}$ and $R^{2H}$ bind may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, and amino group.

(H-12) The compound according to any one of (H-1) to (H-11), wherein $R^{3H}$ and $R^{4H}$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, or an aralkyl group (the aryl moiety thereof has 6 to 10 carbon atoms, and the alkylene moiety thereof has 1 to 8 carbon atoms).

(H-13) The compound according to any one of (H-1) to (H-12), wherein $R^{5H}$ is hydrogen atom, an alkyl group having 1 to 8 carbon atoms, or an aralkyl group (the aryl moiety thereof has 6 to 10 carbon atoms, and the alkylene moiety thereof has 1 to 8 carbon atoms).

(H-14) The compound according to any one of (H-1) to (H-13), wherein $R^{6H}$ and $R^{7H}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, or an alkoxy group having 1 to 8 carbon atoms and substituted with 1 to 3 halogen atoms.

(H-15) The compound according to any one of (H-1) to (H-14), wherein $B^H$, $D^H$, and $E^H$ are atomic bonds, and $m^H$ is 0.

(H-16) The compound according to any one of (H-1) to (H-15), wherein $G^H$ is tetrazole, 1,2,4-triazole, 1,2,3-triazole, 1,2,4-oxadiazole, pyrazole, or imidazole which may have a substituent selected from an alkyl group having 1 to 8 carbon atoms, an alkyl group having 1 to 8 carbon atoms and substituted with 1 to 3 halogen atoms, a halogen atom, cyano group, oxo group, and thioxo group.

(H-17) The compound according to any one of (H-1) to (H-16), wherein $G^H$ is tetrazole.

(H-18) The compound according to any one of (H-1) to (H-17), wherein $R^{5H}$ is hydrogen atom, or an alkyl group having 1 to 8 carbon atoms.

(H-19) The compound according to any one of (H-1) to (H-18), wherein $R^{6H}$ is hydrogen atom, and $R^7H$ is hydrogen atom, or an alkyl group having 1 to 8 carbon atoms.

(H-20) The compound according to any one of (H-1) to (H-19), wherein $A^H$ is a benzene ring which may have an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, carboxyl group, an acyl group having 2 to 8 carbon atoms, or an alkoxycarbonyl group (the alkoxy moiety thereof has 1 to 8 carbon atoms), as a substituent.

(H-21) The compound according to any one of (H-1) to (H-20), wherein $R^{1H}$ and $R^{2H}$ bind together to form naphthalene ring together with the benzene ring to which they bind, and the benzene ring formed by $R^{1H}$, $R^{2H}$ binding together, and the carbon atoms to which $R^{1H}$ and $R^{2H}$ bind may be substituted with a substituent selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, carboxyl group, an acyl group having 2 to 8 carbon atoms, and an alkoxycarbonyl group (the alkoxy moiety thereof has 1 to 8 carbon atoms).

Specific examples of the preferred compounds of the general formula (IH), and salts thereof are shown below. However, the compounds and salts thereof usable as the active ingredient of the medicament of the present invention are not limited to these.

(Compound 1H) 5-(4-Benzoylaminophenyl)-1H-naphtho[1,2-b][1,4]diazepine-2,4(3H,5H)-dione
(Compound 2H) 5-[4-[(2-(Trifluoromethyl)benzoyl]aminophenyl]-1H-naphtho[1,2-b][1,4]diazepine-2,4(3H,5H)-dione
(Compound 3H) 5-[4-(3-Bromobenzoyl)aminophenyl]-1H-naphtho[1,2-b][1,4]diazepine-2,4(3H,5H)-dione
(Compound 4H) 5-[4-[4-(Trifluoromethyl)benzoyl]aminophenyl]-1H-naphtho[1,2-b][1,4]diazepine-2,4(3H,5H)-dione
(Compound 5H) 5-[4-(2-Methylbenzoyl)aminophenyl]-1H-naphtho[1,2-b][1,4]diazepine-2,4(3H,5H)-dione
(Compound 6H) 5-[4-(2,6-Dimethylbenzoylamino)phenyl]-1H-naphtho[1,2-b][1,4]diazepine-2,4(3H,5H)-dione
(Compound 7H) 5-[4-(2,6-Dichlorobenzoyl)aminophenyl]-1H-naphtho[1,2-b][1,4]diazepine-2,4(3H,5H)-dione
(Compound 8H) 5-[4-(3-Chlorobenzoyl)aminophenyl]-1H-naphtho[1,2-b][1,4]diazepine-2,4(3H,5H)-dione
(Compound 9H) 5-[4-(2-Phenylacetylamino)phenyl]-1H-naphtho[1,2-b][1,4]diazepine-2,4(3H,5H)-dione
(Compound 10H) 1-[4-(2,4-Dioxo-1,2,3,4-tetrahydronaphtho[1,2-b][1,4]diazepin-5-yl)phenyl]-3-phenylthiourea
(Compound 11H) 5-[4-(2,3-Dimethoxybenzoylamino)phenyl]-1H-naphtho[1,2-b][1,4]diazepine-2,4(3H,5H)-dione
(Compound 12H) 5-[4-(2-Methoxybenzoylamino)phenyl]-1H-naphtho[1,2-b][1,4]diazepine-2,4(3H,5H)-dione
(Compound 13H) 5-[4-[(2-Chlorophenylacetyl)amino]phenyl]-1H-naphtho[1,2-b][1,4]diazepine-2,4(3H,5H)-dione
(Compound 14H) 5-[4-(2,3-Dimethylbenzoylamino)phenyl]-1H-naphtho[1,2-b][1,4]diazepine-2,4(3H,5H)-dione
(Compound 15H) 5-[4-(2,5-Dimethylbenzoylamino)phenyl]-1H-naphtho[1,2-b][1,4]diazepine-2,4(3H,5H)-dione
(Compound 16H) 5-[4-(5-Bromo-2-chlorobenzoylamino)phenyl]-1H-naphtho[1,2-b][1,4]diazepine-2,4(3H,5H)-dione
(Compound 17H) 5-[4-(2,4-Dichlorobenzoylamino)phenyl]-1H-naphtho[1,2-b][1,4]diazepine-2,4(3H,5H)-dione
(Compound 18H) 5-[4-(2-Hydroxybenzoylamino)phenyl]-1H-naphtho[1,2-b][1,4]diazepine-2,4(3H,5H)-dione
(Compound 19H) 5-[4-(2,3-Dihydroxybenzoylamino)phenyl]-1H-naphtho[1,2-b][1,4]diazepine-2,4(3H,5H)-dione
(Compound 20H) 1-[4-(2,4-Dioxo-1,2,3,4-tetrahydronaphtho[1,2-b][1,4]diazepin-5-yl)phenyl]-3-phenylurea
(Compound 21H) 5-[4-[(2,6-Dichlorophenylacetyl)amino]phenyl]-1H-naphtho[1,2-b][1,4]diazepine-2,4(3H,5H)-dione
(Compound 22H) 5-[4-[(2-Methoxyphenylacetyl)amino]phenyl]-1H-naphtho[1,2-b][1,4]diazepine-2,4(3H,5H)-dione
(Compound 23H) 5-[4-[(2-Hydroxyphenylacetyl)amino]phenyl]-1H-naphtho[1,2-b][1,4]diazepine-2,4(3H,5H)-dione
(Compound 24H) 1-(2-Chlorophenyl)-3-[4-(2,4-dioxo-1,2,3,4-tetrahydronaphtho[1,2-b][1,4]diazepin-5-yl)phenyl]thiourea
(Compound 25H) 5-[4-[3-(Trifluoromethyl)benzoylamino]phenyl]-1H-naphtho[1,2-b][1,4]diazepine-2,4(3H,5H)-dione
(Compound 26H) 5-[4-[2-[(2-Trifluoromethyl)phenyl]acetylamino]phenyl]-1H-naphtho[1,2-b][1,4]diazepine-2,4(3H,5H)-dione
(Compound 27H) 1-(2-Chlorophenyl)-3-[4-(2,4-dioxo-1,2,3,4-tetrahydronaphtho[1,2-b][1,4]diazepin-5-yl)phenyl]urea
(Compound 28H) 5-[4-[(2-Phenylpropionyl)amino]phenyl]-1H-naphtho[1,2-b][1,4]diazepine-2,4(3H,5H)-dione
(Compound 29H) 5-[4-(2-Chloro-3-methoxybenzoylamino)phenyl]-1H-naphtho[1,2-b][1,4]diazepine-2,4(3H,5H)-dione
(Compound 30H) 5-[4-(3-Phenylpropionylamino)phenyl]-1H-naphtho[1,2-b][1,4]diazepine-2,4(3H,5H)-dione
(Compound 31H) 5-[4-[(1H-Indole-3-carbonyl)amino]phenyl]-1H-naphtho[1,2-b][1,4]diazepine-2,4(3H,5H)-dione
(Compound 32H) 5-[4-(2-Chloro-3-hydroxybenzoylamino)phenyl]-1H-naphtho[1,2-b][1,4]diazepine-2,4(3H,5H)-dione
(Compound 33H) 5-[4-[(2-Methyl-2-phenylpropionyl)amino]phenyl]-1H-naphtho[1,2-b][1,4]diazepine-2,4(3H,5H)-dione
(Compound 34H) 5-[4-(2-Phenoxyacetylamino)phenyl]-1H-naphtho[1,2-b][1,4]diazepine-2,4(3H,5H)-dione
(Compound 35H) 5-[4-[2-(2-Chloro-4-methoxyphenyl)acetylamino]phenyl]-1H-naphtho[1,2-b][1,4]diazepine-2,4(3H,5H)-dione
(Compound 36H) 5-[4-[(1-Methyl-1H-imidazole-2-carbonyl)amino]phenyl]-1H-naphtho[1,2-b][1,4]diazepine-2,4(3H,5H)-dione
(Compound 37H) 5-[4-[2-(2,4-Dichlorophenyl)acetylamino]phenyl]-1H-naphtho[1,2-b][1,4]diazepine-2,4(3H,5H)-dione
(Compound 38H) 5-[4-[2-(2-Chloro-4-hydroxyphenyl)acetylamino]phenyl]-1H-naphtho[1,2-b][1,4]diazepine-2,4(3H,5H)-dione
(Compound 39H) 5-[4-(3-Phenylpropenylamino)phenyl]-1H-naphtho[1,2-b][1,4]diazepine-2,4(3H,5H)-dione
(Compound 40H) 5-[4-[(3-Pyridylacetyl)amino]phenyl]-1H-naphtho[1,2-b][1,4]diazepine-2,4(3H,5H)-dione hydrochloride
(Compound 41H) 5-[4-(1H-Benzimidazole-2-carbonylamino)phenyl]-1H-naphtho[1,2-b][1,4]diazepine-2,4(3H,5H)-dione
(Compound 42H) 1-[4-(2,3-Dimethylbenzoylamino)phenyl]-7-methoxy-1H-1,5-benzodiazepine-2,4(3H,5H)-dione
(Compound 43H) 5-[4-[(Benzoylamino)methyl]phenyl]-1H-naphtho[1,2-b][1,4]diazepine-2,4(3H,5H)-dione
(Compound 44H) 5-[4-[(2-Chlorobenzoylamino)methyl]phenyl]-1H-naphtho[1,2-b][1,4]diazepine-2,4(3H,5H)-dione
(Compound 45H) 1-[4-(2,3-Dimethylbenzoylamino)phenyl]-7-hydroxy-1H-1,5-benzodiazepine-2,4(3H,5H)-dione
(Compound 46H) 5-[4-(2-Chlorobenzoylamino)phenyl]-1H-naphtho[1,2-b][1,4]diazepine-2,4(3H,5H)-dione (Compound 47H) 5-[4-(2-Bromobenzoylamino)phenyl]-1H-naphtho[1,2-b][1,4]diazepine-2,4(3H,5H)-dione
(Compound 48H) 5-[4-(2-Iodobenzoylamino)phenyl]-1H-naphtho[1,2-b][1,4]diazepine-2,4(3H,5H)-dione
(Compound 49H) 5-[4-(2,3-Dimethylbenzoylamino)-3-fluorophenyl]-1H-naphtho[1,2-b][1,4]diazepine-2,4(3H,5H)-dione
(Compound 50H) 5-[4-[2-(2-Methylphenyl)acetylamino]phenyl]-1H-naphtho[1,2-b][1,4]diazepine-2,4(3H,5H)-dione
(Compound 51H) 5-[4-[(Quinoxalin-2-yl)carbonylamino]phenyl]-1H-naphtho[1,2-b][1,4]diazepine-2,4(3H,5H)-dione
(Compound 52H) 5-[4-[(5-Methylthiophen-2-yl)carbonylamino]phenyl]-1H-naphtho[1,2-b][1,4]diazepine-2,4(3H,5H)-dione
(Compound 53H) 5-[3-[(2-Chlorophenylacetyl)amino]phenyl]-1H-naphtho[1,2-b][1,4]diazepine-2,4(3H,5H)-dione
(Compound 54H) 5-[4-[(2,4,6-Trimethylbenzoyl)amino]phenyl]-1H-naphtho[1,2-b][1,4]diazepine-2,4(3H,5H)-dione
(Compound 55H) 5-[4-(Cyclohexylcarbonylamino)phenyl]-1,2,3,4,8,9,10,11-octahydronaphtho[1,2-b][1,4]diazepine-2,4(3H,5H)-dione
(Compound 56H) 1-[4-(2,3-Dimethylbenzoyl)aminophenyl]-6-methyl-1H-1,5-benzodiazepine-2,4(3H,5H)-dione
(Compound 57H) 5-[4-[(2-Ethylbenzoyl)amino]phenyl]-1H-naphtho[1,2-b][1,4]diazepine-2,4(3H,5H)-dione
(Compound 58H) 5-[4-[(6-Methylpyridin-2-yl)carbonylamino]phenyl]-1,2,3,4,8,9,10,11-octahydronaphtho[1,2-b][1,4]diazepine-2,4(3H,5H)-dione
(Compound 59H) 5-[4-[(2-Methylpyridin-3-yl)carbonylamino]phenyl]-1,2,3,4,8,9,10,11-octahydronaphtho[1,2-b][1,4]diazepine-2,4(3H,5H)-dione
(Compound 60H) 1-[4-(2,4-Dioxo-1,2,3,4-tetrahydronaphtho[1,2-b][1,4]diazepin-5-yl)phenyl]-3-(2-methylphenyl)thiourea
(Compound 61H) 5-[4-(2-Methoxy-3-methylbenzoyl)aminophenyl]-1,2,3,4,8,9,10,11-octahydronaphtho[1,2-b][1,4]diazepine-2,4(3H,5H)-dione
(Compound 62H) 5-[4-(2,3-Dichlorobenzoyl)aminophenyl]-1,2,3,4,8,9,10,11-octahydronaphtho[1,2-b][1,4]diazepine-2,4(3H,5H)-dione
(Compound 63H) 5-[4-(2,3-Dimethylbenzoylamino)-3-hydroxyphenyl]-1H-naphtho[1,2-b][1,4]diazepine-2,4(3H,5H)-dione
(Compound 64H) 5-[4-(2-Chloro-3-methoxybenzoylamino)phenyl]-1,3-dihydronaphtho[1,2-e]-1,4-diazepin-2-one
(Compound 65H) 5-[4-[(4-Dimethylaminobenzoyl)amino]phenyl]-1H-naphtho[1,2-b][1,4]diazepine-2,4(3H,5H)-dione
(Compound 66H) 5-[4-[2-(2,4-Dichlorophenoxy)acetylamino]phenyl]-1H-naphtho[1,2-b][1,4]diazepine-2,4(3H,5H)-dione
(Compound 67H) 5-[4-[2-(2-Methylphenoxy)acetylamino]phenyl]-1H-naphtho[1,2-b][1,4]diazepine-2,4(3H,5H)-dione
(Compound 68H) N-[4-(2,4-Dioxo-1,2,3,4-tetrahydronaphtho[1,2-b][1,4]diazepin-5-yl)butyl]-2-chloro-3-methoxybenzamide
(Compound 69H) 5-[4-(2-Chloro-3-hydroxybenzoylamino)phenyl]-1,3-dihydronaphtho[1,2-e]-1,4-diazepin-2-one
(Compound 70H) 5-[4-(2-Acetylbenzoylamino)phenyl]-1H-naphtho[1,2-b][1,4]diazepine-2,4(3H,5H)-dione
(Compound 71H) 5-[4-(2-tert-Butylbenzoylamino)phenyl]-1H-naphtho[1,2-b][1,4]diazepine-2,4(3H,5H)-dione
(Compound 72H) 5-[2-(2-Iodobenzoyl)aminoethyl]-1H-naphtho[1,2-b][1,4]diazepine-2,4(3H,5H)-dione
(Compound 73H) 5-[3-[(2-Iodobenzoyl)amino]phenyl]-1H-naphtho[1,2-b][1,4]diazepine-2,4(3H,5H)-dione
(Compound 74H) 6,7-Dimethyl-1-[4-(2-iodobenzoyl)aminophenyl]-1H-1,5-benzodiazepine-2,4(3H,5H)-dione
(Compound 75H) 5-[4-[(1-Methylpiperidin-4-yl)carbonylamino]phenyl]-1H-naphtho[1,2-b][1,4]diazepine-2,4(3H,5H)-dione hydrochloride
(Compound 76H) 5-[4-[(Benzofuran-2-yl)carbonylamino]phenyl]-1H-naphtho[1,2-b][1,4]diazepine-2,4(3H,5H)-dione
(Compound 77H) 5-[4-[(1-Methyl-1H-indol-3-yl)carbonylamino]phenyl]-1H-naphtho[1,2-b][1,4]diazepine-2,4(3H,5H)-dione
(Compound 78H) 5-[4-(2-Propenylbenzoylamino)phenyl]-1H-naphtho[1,2-b][1,4]diazepine-2,4(3H,5H)-dione
(Compound 79H) 5-[4-(2-Propylbenzoylamino)phenyl]-1H-naphtho[1,2-b][1,4]diazepine-2,4(3H,5H)-dione
(Compound 80H) 5-[3-Fluoro-4-(2-iodobenzoylamino)phenyl]-1H-naphtho[1,2-b][1,4]diazepine-2,4(3H,5H)-dione
(Compound 81H) 5-[4-(2-Hydroxy-3-methylbenzoyl)aminophenyl]-1,2,3,4,8,9,10,11-octahydronaphtho[1,2-b][1,4]diazepine-2,4(3H,5H)-dione
(Compound 82H) 5-[4-[(2-Isopropoxybenzoyl)amino]phenyl]-1H-naphtho[1,2-b][1,4]diazepine-2,4(3H,5H)-dione
(Compound 83H) 5-[4-[(3-Methylthiophen-2-yl)carbonylamino]phenyl]-1H-naphtho[1,2-b][1,4]diazepine-2,4(3H,5H)-dione
(Compound 84H) 5-[4-(2-Phenoxypropionylamino)phenyl]-1H-naphtho[1,2-b][1,4]diazepine-2,4(3H,5H)-dione
(Compound 85H) 5-[4-[2-(4-Chloro-2-methylphenoxy)acetylamino]phenyl]-1H-naphtho[1,2-b][1,4]diazepine-2,4(3H,5H)-dione
(Compound 86H) 5-[4-(4-Fluoro-2-Trifluoromethylbenzoyl)aminophenyl]-1H-naphtho[1,2-b][1,4]diazepine-2,4(3H,5H)-dione
(Compound 87H) 5-[4-(4-Fluoro-2-methoxybenzoyl)aminophenyl]-1H-naphtho[1,2-b][1,4]diazepine-2,4(3H,5H)-dione
(Compound 88H) 5-[4-(4-Fluoro-2-hydroxybenzoyl)aminophenyl]-1H-naphtho[1,2-b][1,4]diazepine-2,4(3H,5H)-dione
(Compound 89H) 5-[3-[(2-Iodophenylacetyl)amino]phenyl]-1H-naphtho[1,2-b][1,4]diazepine-2,4(3H,5H)-dione
(Compound 90H) 5-[4-(2-Methyl-2-phenoxypropionylamino)phenyl]-1H-naphtho[1,2-b][1,4]diazepine-2,4(3H,5H)-dione
(Compound 91H) 5-[4-(2-tert-Butylbenzoylamino)phenyl]-1,3-dihydronaphtho[1,2-e]-1,4-diazepin-2-one
(Compound 92H) 5-[4-[(3-Dimethylaminobenzoyl)amino]phenyl]-1H-naphtho[1,2-b][1,4]diazepine-2,4(3H,5H)-dione
(Compound 93H) 5-[4-(4-Iodo-2-methoxybenzoylamino)phenyl]-1H-naphtho[1,2-b][1,4]diazepine-2,4(3H,5H)-dione
(Compound 94H) 5-[4-(6-Fluoro-2-methoxybenzoylamino)phenyl]-1H-naphtho[1,2-b][1,4]diazepine-2,4(3H,5H)-dione
(Compound 95H) 5-[4-(2-Hydroxy-4-iodobenzoylamino)phenyl]-1H-naphtho[1,2-b][1,4]diazepine-2,4(3H,5H)-dione
(Compound 96H) 5-[4-(6-Fluoro-2-hydroxyamino)phenyl]-1H-naphtho[1,2-b][1,4]diazepine-2,4(3H,5H)-dione
(Compound 97H) 5-[4-(2-Fluorobenzoyl)aminophenyl]-1H-naphtho[1,2-b][1,4]diazepine-2,4(3H,5H)-dione (Compound 98H) 5-[4-[(2-Dimethylaminobenzoyl)amino]phenyl]-1H-naphtho[1,2-b][1,4]diazepine-2,4(3H,5H)-dione (Compound 99H) 5-[4-(2-Methoxy-6-methylbenzoylamino)phenyl]-1H-naphtho[1,2-b][1,4]diazepine-2,4(3H,5H)-dione (Compound 100H) 5-[4-(2-Hydroxy-6-methylbenzoylamino)phenyl]-1H-naphtho[1,2-b][1,4]diazepine-2,4(3H,5H)-dione (Compound 101H) 5-[4-[3-(2-Methylphenyl)propionylamino]phenyl]-1H-naphtho[1,2-b][1,4]diazepine-2,4(3H,5H)-dione (Compound 102H) 5-(4-Phenylcarbamoylphenyl)-1H-naphtho[1,2-b][1,4]diazepine-2,4(3H,5H)-dione (Compound 103H) 5-(4-Benzylcarbamoylphenyl)-1H-naphtho[1,2-b][1,4]diazepine-2,4(3H,5H)-dione (Compound 104H) 5-[4-[3-(2-Methylphenyl)propenoylamino]phenyl]-1H-naphtho[1,2-b][1,4]diazepine-2,4(3H,5H)-dione (Compound 105H) 5-[4-[3-(2-Chlorophenyl)propionylamino]phenyl]-1H-naphtho[1,2-b][1,4]diazepine-2,4(3H,5H)-dione (Compound 106H) 5-[4-(2-Iodobenzoyl)aminophenyl]-1,2,3,4,8,9,10,11-octahydronaphtho[1,2-b][1,4]diazepine-2,4(3H,5H)-dione (Compound 107H) 5-[4-[(1-Methyl-1H-pyrrol-2-ylacetyl)amino]phenyl]-1,2,3,4,8,9,10,11-octahydronaphtho[1,2-b][1,4]diazepine-2,4(3H,5H)-dione (Compound 108H) 5-[4-(2-Chlorobenzyl)carbamoylphenyl]-1H-naphtho[1,2-b][1,4]diazepine-2,4(3H,5H)-dione (Compound 109H) 5-[4-[3-(2-Chlorophenyl)propenoylamino]phenyl]-1H-naphtho[1,2-b][1,4]diazepine-2,4(3H,5H)-dione (Compound 110H) 5-[4-(2-Chlorophenyl)carbamoylphenyl]-1H-naphtho[1,2-b][1,4]diazepine-2,4(3H,5H)-dione (Compound 111H) 5-[4-(6-Bromo-2,3-methylenedioxybenzoylamino)phenyl]-1H-naphtho[1,2-b][1,4]diazepine-2,4(3H,5H)-dione (Compound 112H) 5-[4-(6-Bromo-2-methoxybenzoylamino)phenyl]-1H-naphtho[1,2-b][1,4]diazepine-2,4(3H,5H)-dione (Compound 113H) 5-[4-[(2-tert-Butylbenzoyl)amino]phenyl]-1,2,3,4,8,9,10,11-octahydronaphtho[1,2-b][1,4]diazepine-2,4(3H,5H)-dione (Compound 114H) 5-[2-(2-Iodobenzoyl)aminopyridin-5-yl]-1H-naphtho[1,2-b][1,4]diazepine-2,4(3H,5H)-dione (Compound 115H) 5-[4-(6-Bromo-2-hydroxybenzoylamino)phenyl]-1H-naphtho[1,2-b][1,4]diazepine-2,4(3H,5H)-dione (Compound 116H) 5-[4-(6-Chloro-2-methoxybenzoylamino)phenyl]-1H-naphtho[1,2-b][1,4]diazepine-2,4(3H,5H)-dione (Compound 117H) 5-[4-(2-Iodobenzoylamino)phenyl]-1H-[1,4]diazepino[2,3-h]quinoline-2,4(3H,5H)-dione (Compound 118H) 5-[4-(6-Chloro-2-hydroxybenzoylamino)phenyl]-1H-naphtho[1,2-b][1,4]diazepine-2,4(3H,5H)-dione (Compound 119H) 5-[4-(2-Hydroxy-6-methoxybenzoylamino)phenyl]-1H-naphtho[1,2-b][1,4]diazepine-2,4(3H,5H)-dione (Compound 120H) 5-[4-[2-Methoxy-6-(trifluoromethyl)benzoylamino]phenyl]-1H-naphtho[1,2-b][1,4]diazepine-2,4(3H,5H)-dione (Compound 121H) 5-[4-[2-Hydroxy-6-(trifluoromethyl)benzoylamino]phenyl]-1H-naphtho[1,2-b][1,4]diazepine-2,4(3H,5H)-dione (Compound 122H) 5-[4-[(2-Isopropenylbenzoyl)amino]phenyl]-1,2,3,4,8,9,10,11-octahydronaphtho[1,2-b][1,4]diazepine-2,4(3H,5H)-dione (Compound 123H) 5-[4-[(2-Isopropylbenzoyl)amino]phenyl]-1,2,3,4,8,9,10,11-octahydronaphtho[1,2-b][1,4]diazepine-2,4(3H,5H)-dione (Compound 124H) 5-[4-[2-Chloro-5-(methylthio)benzoylamino]phenyl]-1H-naphtho[1,2-b][1,4]diazepine-2,4(3H,5H)-dione (Compound 125H) 5-[4-[2-(Methylthio)benzoylamino]phenyl]-1H-naphtho[1,2-b][1,4]diazepine-2,4(3H,5H)-dione (Compound 126H) 5-[4-[3-(Methylthio)benzoylamino]phenyl]-1H-naphtho[1,2-b][1,4]diazepine-2,4(3H,5H)-dione (Compound 127H) 5-[4-[2-Ethyl-6-methoxybenzoylamino]phenyl]-1H-naphtho[1,2-b][1,4]diazepine-2,4(3H,5H)-dione (Compound 128H) 5-[4-(3-Methanesulfonylbenzoylamino)phenyl]-1H-naphtho[1,2-b][1,4]diazepine-2,4(3H,5H)-dione (Compound 129H) 6-Ethyl-1-[4-(2-iodobenzoyl)aminophenyl]-1H-1,5-benzodiazepine-2,4(3H,5H)-dione (Compound 130H) 5-[4-[2-Ethyl-6-hydroxybenzoylamino]phenyl]-1H-naphtho[1,2-b][1,4]diazepine-2,4(3H,5H)-dione (Compound 131H) 5-[4-(3-Methanesulfinylbenzoylamino)phenyl]-1H-naphtho[1,2-b][1,4]diazepine-2,4(3H,5H)-dione (Compound 132H) 5-[4-(2-Chloro-5-methanesulfinylbenzoylamino)phenyl]-1H-naphtho[1,2-b][1,4]diazepine-2,4(3H,5H)-dione (Compound 133H) 5-[4-(2-Methanesulfinylbenzoylamino)phenyl]-1H-naphtho[1,2-b][1,4]diazepine-2,4(3H,5H)-dione (Compound 134H) 5-[4-[[2-(4-Morpholinyl)acetyl]amino]phenyl]-1,2,3,4,8,9,10,11-octahydronaphtho[1,2-b][1,4]diazepine-2,4(3H,5H)-dione hydrochloride (Compound 135H) 5-[4-(2-Chloro-6-methoxybenzoylamino)phenyl]-1,3-dihydronaphtho[1,2-e]-1,4-diazepin-2-one (Compound 136H) 5-[4-[[(3-Chloropyridin-2-yl)carbonyl]amino]phenyl]-1H-naphtho[1,2-b][1,4]diazepine-2,4(3H,5H)-dione (Compound 137H) 5-[4-(2-Chloro-6-hydroxybenzoylamino)phenyl]-1,3-dihydronaphtho[1,2-e]-1,4-diazepin-2-one (Compound 138H) 5-[4-(3-Chloro-2-methoxybenzoylamino)phenyl]-1H-naphtho[1,2-b][1,4]diazepine-2,4(3H,5H)-dione (Compound 139H) 5-[4-[(3-Methylpyridin-2-yl)carbonylamino]phenyl]-1H-naphtho[1,2-b][1,4]diazepine-2,4(3H,5H)-dione (Compound 140H) 5-[4-[[(3-Chloropyridin-2-yl)carbonyl]amino]phenyl]-1,2,3,4,8,9,10,11-octahydronaphtho[1,2-b][1,4]diazepine-2,4(3H,5H)-dione (Compound 141H) 5-[4-(3-Chloro-2-hydroxybenzoylamino)phenyl]-1H-naphtho[1,2-b][1,4]diazepine-2,4(3H,5H)-dione (Compound 142H) 5-[4-[[(3-Hydroxypyridin-2-yl)carbonyl]amino]phenyl]-1H-naphtho[1,2-b][1,4]diazepine-2,4(3H,5H)-dione (Compound 143H) 5-[4-[(3-Vinylpyridin-2-yl)carbonylamino]phenyl]-1H-naphtho[1,2-b][1,4]diazepine-2,4(3H,5H)-dione (Compound 144H) 5-[4-[(3-Ethylpyridin-2-yl)carbonylamino]phenyl]-1H-naphtho[1,2-b][1,4]diazepine-2,4(3H,5H)-dione (Compound 145H) N-[4-(2,4-Dioxo-1,2,3,4-tetrahydronaphtho[1,2-b][1,4]diazepin-5-yl)phenyl]-2-nitrobenzenesulfonamide
(Compound 146H) N-[4-(2,4-Dioxo-1,2,3,4-tetrahydronaphtho[1,2-b][1,4]diazepin-5-yl)phenyl]benzenesulfonamide
(Compound 147H) 3-Bromo-N-[4-(2,4-dioxo-1,2,3,4-tetrahydronaphtho[1,2-b][1,4]diazepin-5-yl)phenyl]benzenesulfonamide
(Compound 148H) N-[4-(2,4-Dioxo-1,2,3,4-tetrahydronaphtho[1,2-b][1,4]diazepin-5-yl)phenyl]-3-methoxybenzenesulfonamide
(Compound 149H) N-[3-(2-Oxo-2,3-dihydro-1H-naphtho[1,2-e][1,4]diazepin-5-yl)phenyl]benzenesulfonamide
(Compound 150H) N-[3-(2,4-Dioxo-1,2,3,4-tetrahydronaphtho[1,2-b][1,4]diazepin-5-yl)phenyl]-2-nitrobenzenesulfonamide
(Compound 151H) N-[4-(2,4-Dioxo-1,2,3,4,8,9,10,11-octahydro-naphtho[1,2-b][1,4]-diazepin-5-yl)phenyl]-2-nitrobenzenesulfonamide
(Compound 152H) N-[4-(2,4-Dioxo-1,2,3,4,8,9,10,11-octahydro-naphtho[1,2-b][1,4]-diazepin-5-yl)phenyl]-N-methyl-2-nitrobenzenesulfonamide
(Compound 153H) N-[3-(2,4-Dioxo-1,2,3,4-tetrahydronaphtho[1,2-b][1,4]diazepin-5-yl)phenyl]-N-methyl-2-nitrobenzenesulfonamide
(Compound 154H) 4-(2,4-Dioxo-1,2,3,4,8,9,10,11-octahydronaphtho[1,2-b][1,4]diazepin-5-yl)-N-phenylbenzenesulfonamide
(Compound 155H) N-[3-(2,4-Dioxo-1,2,3,4-tetrahydronaphtho[1,2-b][1,4]diazepin-5-yl)phenyl]-2-naphthalenesulfonamide
(Compound 156H) N-[3-(2,4-Dioxo-1,2,3,4-tetrahydronaphtho[1,2-b][1,4]diazepin-5-yl)phenyl]-1-naphthalenesulfonamide
(Compound 157H) N-[4-(2,4-Dioxo-1,2,3,4-tetrahydronaphtho[1,2-b][1,4]diazepin-5-yl)phenyl]cyclohexanesulfonamide
(Compound 158H) N-[4-(2,4-Dioxo-1,2,3,4-tetrahydronaphtho[1,2-b][1,4]diazepin-5-yl)phenyl]-3-pyridinesulfonamide hydrochloride
(Compound 159H) N-[4-(2,4-Dioxo-1,2,3,4-tetrahydronaphtho[1,2-b][1,4]diazepin-5-yl)phenyl]-4-isopropylbenzenesulfonamide
(Compound 160H) N-[4-(2,4-Dioxo-1,2,3,4-tetrahydronaphtho[1,2-b][1,4]diazepin-5-yl)phenyl]phenylmethanesulfonamide
(Compound 161H) N-[4-(2,4-Dioxo-1,2,3,4-tetrahydronaphtho[1,2-b][1,4]diazepin-5-yl)phenyl]-3-pyridinesulfonamide
(Compound 162H) N-[4-(2,4-Dioxo-1,2,3,4-tetrahydronaphtho[1,2-b][1,4]diazepin-5-yl)phenyl]-2-naphthalenesulfonamide
(Compound 163H) 4-(2,4-Dioxo-1,2,3,4,8,9,10,11-octahydronaphtho[1,2-b][1,4]diazepin-5-yl)phenyl 3-bromobenzenesulfonate
(Compound 164H) N-Benzyl-N-[4-(1-benzyl-2,4-dioxo-1,2,3,4-tetrahydronaphtho[1,2-b][1,4]diazepin-5-yl)phenyl]-2-nitrobenzenesulfonamide
(Compound 165H) N-Benzyl-N-[4-(2,4-dioxo-1,2,3,4-tetrahydronaphtho[1,2-b][1,4]diazepin-5-yl)phenyl]-2-nitrobenzenesulfonamide
(Compound 166H) 3-Bromo-N-[4-(2,4-dioxo-1,2,3,4-tetrahydronaphtho[1,2-b][1,4]diazepin-5-yl)phenyl]-N-methylbenzenesulfonamide
(Compound 167H) N-[4-(2,4-Dioxo-1,2,3,4-tetrahydronaphtho[1,2-b][1,4]diazepin-5-yl)phenyl]-N-methyl-2-nitrobenzenesulfonamide
(Compound 168H) N-[4-(2,4-Dioxo-1,2,3,4-tetrahydronaphtho[1,2-b][1,4]diazepin-5-yl)phenyl]-N-(2-hydroxyethyl)-2-nitrobenzenesulfonamide
(Compound 169H) N-[4-(7-Chloro-2,4-dioxo-2,3,4,5-tetrahydro-1H-benzo[b][1,4]diazepin-1-yl)phenyl]benzenesulfonamide
(Compound 170H) N-[4-(7-Bromo-2,4-dioxo-2,3,4,5-tetrahydro-1H-benzo[b][1,4]diazepin-1-yl)phenyl]benzenesulfonamide
(Compound 171H) N-[4-[(2,4-Dioxo-7-(trifluoromethyl)-2,3,4,5-tetrahydro-1H-benzo[b][1,4]diazepin-1-yl)]phenyl]benzenesulfonamide
(Compound 172H) N-[4-(2,4-Dioxo-2,3,4,5-tetrahydro-1H-benzo[b][1,4]diazepin-1-yl)phenyl]benzenesulfonamide
(Compound 173H) 1-(2-Chlorophenyl)-N-[4-(2,4-dioxo-1,2,3,4-tetrahydronaphtho[1,2-b][1,4]diazepin-5-yl)phenyl]methanesulfonamide
(Compound 174H) 1-(3-Bromophenyl)-N-[4-(2,4-dioxo-1,2,3,4-tetrahydronaphtho[1,2-b][1,4]diazepin-5-yl)phenyl]methanesulfonamide
(Compound 175H) N-[4-(2,4-Dioxo-1,2,3,4-tetrahydronaphtho[1,2-b][1,4]diazepin-5-yl)phenyl]-2-trifluoromethylbenzenesulfonamide
(Compound 176H) N-[4-(7-Bromo-6-methyl-2,4-dioxo-2,3,4,5-tetrahydro-1H-benzo[b][1,4]diazepin-1-yl)phenyl]benzenesulfonamide
(Compound 177H) 1-(2-Chlorophenyl)-N-[4-(2,4-dioxo-1,2,3,4,8,9,10,11-octahydronaphtho[1,2-b][1,4]diazepin-5-yl)phenyl]methanesulfonamide
(Compound 178H) 3-Bromo-N-[4-(2,4-dioxo-1,2,3,4,8,9,10,11-octahydronaphtho[1,2-b][1,4]diazepin-5-yl)phenyl]benzenesulfonamide
(Compound 179H) N-[4-(2,4-Dioxo-1,2,3,4,8,9,10,11-octahydronaphtho[1,2-b][1,4]diazepin-5-yl)phenyl]-3-methoxybenzenesulfonamide
(Compound 180H) 1-(2-Bromophenyl)-N-[4-(2,4-dioxo-1,2,3,4-tetrahydronaphtho[1,2-b][1,4]diazepin-5-yl)phenyl]methanesulfonamide
(Compound 181H) N-[4-(2,4-Dioxo-1,2,3,4-tetrahydronaphtho[1,2-b][1,4]diazepin-5-yl)phenyl]-1-(2-methylphenyl)methanesulfonamide
(Compound 182H) N-[4-(2,4-Dioxo-1,2,3,4-tetrahydronaphtho[1,2-b][1,4]diazepin-5-yl)phenyl]-1-(2-nitrophenyl)methanesulfonamide
(Compound 183H) N-[4-(2,4-Dioxo-1,2,3,4-tetrahydronaphtho[1,2-b][1,4]diazepin-5-yl)phenyl]-2-phenylethanesulfonamide
(Compound 184H) 1-(2,3-Dichlorophenyl)-N-[4-(2,4-dioxo-1,2,3,4,8,9,10,11-octahydronaphtho[1,2-b][1,4]diazepin-5-yl)phenyl]methanesulfonamide
(Compound 185H) 1-(2-Chlorophenyl)-N-[4-(2,4-dioxo-7-methoxy-1H-benzo[1,2-b][1,4]diazepin-1-yl)phenyl]methanesulfonamide
(Compound 186H) 1-(2-Chlorophenyl)-N-[4-(2,4-dioxo-7-hydroxy-1H-benzo[1,2-b][1,4]diazepin-1-yl)phenyl]methanesulfonamide
(Compound 187H) 1-(4-Chlorophenyl)-N-[4-(2,4-dioxo-1,2,3,4-tetrahydronaphtho[1,2-b][1,4]diazepin-5-yl)phenyl]methanesulfonamide
(Compound 188H) 1-(2-Chlorophenyl)-N-[4-(2,4-dioxo-1,2,3,4-tetrahydronaphtho[1,2-b][1,4]diazepin-5-yl)benzyl]methanesulfonamide (Compound 189H) 1-(2-Chlorophenyl)-N-[4-(2,4-dioxo-1,2,3,4-tetrahydronaphtho[1,2-b][1,4]diazepin-5-yl)-2-methoxyphenyl]methanesulfonamide (Compound 190H) 1-(2-Chlorophenyl)-N-[4-(2,4-dioxo-1,2,3,4-tetrahydronaphtho[1,2-b][1,4]diazepin-5-yl)-2-hydroxyphenyl]methanesulfonamide (Compound 191H) 1-(2,6-Dichlorophenyl)-N-[4-(2,4-dioxo-1,2,3,4,8,9,10,11-octahydronaphtho[1,2-b][1,4]diazepin-5-yl)phenyl]methanesulfonamide (Compound 192H) 1-(2-Chlorophenyl)-N-[4-(2,4-dioxo-6-methyl-1H-benzo[1,2-b][1,4]diazepin-1-yl)phenyl]methanesulfonamide (Compound 193H) 1-(2-Chlorophenyl)-N-[4-(2,4-dioxy-1,2,3,4-tetrahydronaphtho[1,2-b][1,4]diazepin-5-yl)propyl]methanesulfonamide (Compound 194H) 1-(2-Chlorophenyl)-N-[2-(2,4-dioxo-1,2,3,4-tetrahydronaphtho[1,2-b][1,4]diazepin-5-yl)ethyl]methanesulfonamide (Compound 195H) N-[4-(2,4-Dioxo-1,2,3,4,8,9,10,11-octahydronaphtho[1,2-b][1,4]diazepin-5-yl)phenyl]-1-(2-iodophenyl)methanesulfonamide (Compound 196H) 1-(2-Chlorophenyl)-N-[4-(2,4-dioxo-1,2,3,4,8,9,10,11-octahydronaphtho[1,2-b][1,4]diazepin-5-yl)phenyl]-N-methylmethanesulfonamide (Compound 197H) 1-(2-Chlorophenyl)-N-[4-(2-oxo-2,3-dihydro-1H-naphtho[1,2-e][1,4]diazepin-5-yl)phenyl]methanesulfonamide (Compound 198H) 1-[(2-Trifluoromethyl)phenyl]-N-[4-(2,4-dioxo-1,2,3,4-tetrahydronaphtho[1,2-b][1,4]diazepin-5-yl)phenyl]phenyl-N-methylmethanesulfonamide (Compound 199H) 1-(2-Ethylphenyl)-N-[4-(2,4-dioxo-1,2,3,4-tetrahydronaphtho[1,2-b][1,4]diazepin-5-yl)phenyl]phenyl-N-methylmethanesulfonamide (Compound 200H) 1-(2,3-Dimethylphenyl)-N-[4-(2,4-dioxo-1,2,3,4-tetrahydronaphtho[1,2-b][1,4]diazepin-5-yl)phenyl]phenyl-N-methylmethanesulfonamide (Compound 201H) 2-(2-Chlorophenyl)-N-[4-(2,4-dioxo-1,2,3,4-tetrahydronaphtho[1,2-b][1,4]diazepin-5-yl)phenyl]phenyl-N-methylethanesulfonamide (Compound 202H) 1-(2-Nitrophenyl)-N-[4-(2,4-dioxo-1,2,3,4-tetrahydronaphtho[1,2-b][1,4]diazepin-5-yl)phenyl]phenyl-N-methylmethanesulfonamide (Compound 203H) 1-(2-Aminophenyl)-N-[4-(2,4-dioxo-1,2,3,4-tetrahydronaphtho[1,2-b][1,4]diazepin-5-yl)phenyl]phenyl-N-methylmethanesulfonamide (Compound 204H) 1-(2-Dimethylaminophenyl)-N-[4-(2,4-dioxo-1,2,3,4-tetrahydronaphtho[1,2-b][1,4]diazepin-5-yl)phenyl]phenyl-N-methylmethanesulfonamide (Compound 205H) 5-[4-[(Pyridin-4-yl)carbonylamino]phenyl]-1H-naphtho[1,2-b][1,4]diazepine-2,4(3H,5H)-dione hydrochloride (Compound 206H) 5-[4-[2-[(Pyridin-3-yl)oxy]acetylamino]phenyl]-1H-naphtho[1,2-b][1,4]diazepine-2,4(3H,5H)-dione hydrochloride (Compound 207H) 5-[4-[(Pyridin-3-yl)carbonylamino]phenyl]-1H-naphtho[1,2-b][1,4]diazepine-2,4(3H,5H)-dione hydrochloride (Compound 208H) 5-[4-[(2-Methylpyridin-3-yl)carbonylamino]phenyl]-1H-naphtho[1,2-b][1,4]diazepine-2,4(3H,5H)-dione hydrochloride (Compound 209H) 5-[4-[(2-Chloropyridin-3-yl)carbonylamino]phenyl]-1H-naphtho[1,2-b][1,4]diazepine-2,4(3H,5H)-dione (Compound 210H) 5-[4-[2-[(Pyridin-2-yl)oxy]acetylamino]phenyl]-1H-naphtho[1,2-b][1,4]diazepine-2,4(3H,5H)-dione (Compound 211H) 5-[4-[[4-(Trifluoromethyl)pyridin-3-yl]carbonylamino]phenyl]-1H-naphtho[1,2-b][1,4]diazepine-2,4(3H,5H)-dione (Compound 212H) 5-[4-[(2-Chloropyridin-3-yl)carbonylamino]phenyl]-1H-[1,4]diazepino[2,3-f]isoquinoline-2,4(3H,5H)-dione (Compound 213H) 5-[4-[(2-Chloropyridin-3-yl)carbonylamino]phenyl]-8,9,10,11-tetrahydro-1H-[1,4]diazepino[2,3-f]isoquinoline-2,4(3H,5H)-dione (Compound 214H) 5-[4-[(2-Isopropylbenzoyl)amino]phenyl]-1H-naphtho[1,2-b][1,4]diazepine-2,4(3H,5H)-dione (Compound 215H) 5-[3-(1H-Tetrazol-5-yl)phenyl]-1H-naphtho[1,2-b][1,4]diazepine-2,4(3H,5H)-dione (Compound 216H) 5-[3-(1H-Tetrazol-5-yl)phenyl]-1H-naphtho[1,2-b][1,4]diazepine-2,4(3H,5H)-dione potassium salt (Compound 217H) 5-[4-(1H-Tetrazol-5-yl)phenyl]-1H-naphtho[1,2-b][1,4]diazepine-2,4(3H,5H)-dione (Compound 218H) 5-[4-(1H-Tetrazol-5-yl)phenyl]-1H-naphtho[1,2-b][1,4]diazepine-2,4(3H,5H)-dione sodium salt (Compound 219H) 1-Methyl-5-[3-(1H-tetrazol-5-yl)phenyl]-1H-naphtho[1,2-b][1,4]diazepine-2,4(3H,5H)-dione (Compound 220H) 1,3-Dimethyl-5-[3-(1H-tetrazol-5-yl)phenyl]-1H-naphtho[1,2-b][1,4]diazepine-2,4(3H,5H)-dione (Compound 221H) 5-[2-Chloro-5-(1H-tetrazol-5-yl)phenyl]-1H-naphtho[1,2-b][1,4]diazepine-2,4(3H,5H)-dione (Compound 222H) 5-[2-Chloro-5-(1H-tetrazol-5-yl)phenyl]-1H-naphtho[1,2-b][1,4]diazepine-2,4(3H,5H)-dione sodium salt (Compound 223H) 5-[2-Methyl-5-(1H-tetrazol-5-yl)phenyl]-1H-naphtho[1,2-b][1,4]diazepine-2,4(3H,5H)-dione (Compound 224H) 5-[2-Methyl-5-(1H-tetrazol-5-yl)phenyl]-1H-naphtho[1,2-b][1,4]diazepine-2,4(3H,5H)-dione sodium salt (Compound 225H) 5-[2-Bromo-5-(1H-tetrazol-5-yl)phenyl]-1H-naphtho[1,2-b][1,4]diazepine-2,4(3H,5H)-dione (Compound 226H) 5-[3-(2-Methyl-2H-tetrazol-5-yl)phenyl]-1H-naphtho[1,2-b][1,4]diazepine-2,4(3H,5H)-dione (Compound 227H) 5-[3-(1-Methyl-1H-tetrazol-5-yl)phenyl]-1H-naphtho[1,2-b][1,4]diazepine-2,4(3H,5H)-dione (Compound 228H) 5-[3-(5-Oxo-4H-[1,2,4]oxadiazol-3-yl)phenyl]-1H-naphtho[1,2-b][1,4]diazepine-2,4(3H,5H)-dione (Compound 229H) 5-[3-(5-Thioxo-4H-[1,2,4]oxadiazol-3-yl)phenyl]-1H-naphtho[1,2-b][1,4]diazepine-2,4(3H,5H)-dione (Compound 230H) 5-[3-(5-Thioxo-4H-[1,2,4]oxadiazol-3-yl)phenyl]-1H-naphtho[1,2-b][1,4]diazepine-2,4(3H,5H)-dione sodium salt (Compound 231H) 5-[3-(Oxazol-2-yl)phenyl]-1H-naphtho[1,2-b][1,4]diazepine-2,4(3H,5H)-dione (Compound 232H) 5-[3-(1H-Pyrazol-4-yl)phenyl]-1H-naphtho[1,2-b][1,4]diazepine-2,4(3H,5H)-dione (Compound 233H) N-[4-(2-Oxo-2,3-dihydro-1H-naphtho[1,2-e][1,4]-diazepin-5-yl)phenyl]-3-(pyridin-2-yl)propionic acid amide (Compound 234H) 2-Ethyl-3-hydroxy-N-[4-(2-oxo-2,3-dihydro-1H-naphtho[1,2-e][1,4]-diazepin-5-yl)phenyl]benzamide (Compound 235H) 2-Ethyl-N-[4-(2-oxo-2,3-dihydro-1H-naphtho[1,2-e][1,4]-diazepin-5-yl)phenyl]nicotinamide dihydrochloride (Compound 236H) 2-Ethyl-6-hydroxy-N-[4-(2-oxo-2,3-dihydro-1H-naphtho[1,2-e]1,4]-diazepin-5-yl)phenyl]benzamide (Compound 237H) 3-Ethyl-N-[4-(2-oxo-2,3-dihydro-1H-naphtho[1,2-e][1,4]-diazepin-5-yl)phenyl]picolinamide hydrochloride (Compound 238H) N-[4-(2-Oxo-2,3-dihydro-1H-naphtho[1,2-e][1,4]-diazepin-5-yl)phenyl]-2-(pyridin-2-yloxy)acetamide hydrochloride (Compound 239H) 2-(2-Methoxyphenyl)-N-[4-(2-oxo-2,3-dihydro-1H-naphtho[1,2-e][1,4]diazepin-5-yl)phenyl]acetamide (Compound 240H) N-[4-(2-Oxo-2,3-dihydro-1H-naphtho[1,2-e][1,4]diazepin-5-yl)-phenyl]-3-(pyridin-3-yl)propionamide dihydrochloride (Compound 241H) N-[4-(2-Oxo-2,3-dihydro-1H-naphtho[1,2-e][1,4]diazepin-5-yl)phenyl]-3-phenylpropanamide (Compound 242H) N-[4-(2,4-Dioxo-3,4-dihydro-1H-naphtho[1,2-b][1,4]diazepin-5(2H)-yl)-phenyl]-3-(pyridin-3-yl)propionamide hydrochloride (Compound 243H) N-[4-(2,4-Dioxo-3,4-dihydro-1H-naphtho[1,2-b][1,4]diazepin-5(2H)-yl)-phenyl]-3-(pyridin-4-yl)propionamide hydrochloride (Compound 244H) 2-tert-Butyl-N-[4-(2,4-dioxo-3,4-dihydro-1H-naphtho[1,2-b][1,4]diazepin-5(2H)-yl)2-fluorophenyl]benzamide (Compound 245H) N-[4-(2,4-Dioxo-3,4-dihydro-1H-naphtho[1,2-b][1,4]diazepin-5(2H)-yl)-phenyl]-3-(pyridin-2-yl)propionamide hydrochloride (Compound 246H) 2-Isopropyl-N-[4-(2-oxo-2,3-dihydro-1H-naphtho[1,2-e][1,4]diazepin-5yl)phenyl]nicotinamide dihydrochloride (Compound 247H) 2-(Isopropylamino)-N-[4-(2-oxo-2,3-dihydro-1H-naphtho[1,2-e][1,4]diazepin-5yl)phenyl]nicotinamide dihydrochloride The compounds represented by the general formula (IA) mentioned above are disclosed in WO2010/093061, the compounds represented by the general formula (IB) are disclosed in WO2012/008478, the compounds represented by the general formula (IC) are disclosed in WO2012/014910, the compounds represented by the general formula (ID) are disclosed in WO2012/017876, the compounds represented by the general formula (IE) are disclosed in WO2013/105608, the compounds represented by the general formula (IF) are disclosed in WO2015/005468, the compounds represented by the general formula (IG) are disclosed in WO2015/005467, and therefore any of these compounds can be easily obtained by referring to these international patent publications. The entire disclosures of these international patent publications are incorporated into the disclosure of the present specification by reference.

Specific examples of the preferred compounds falling within the scopes of the aforementioned general formulas IA) to (IG), and salts thereof are shown below. However, the compounds and salts thereof usable as the active ingredient of the medicament of the present invention are not limited to these.

(Compound 1A) 5-[3-(1H-Tetrazol-5-yl)phenyl]-1H-naphtho[1,2-b][1,4]diazepine-2,4(3H,5H)-dione (Compound 2A) 5-[3-(1H-Tetrazol-5-yl)phenyl]-1H-naphtho[1,2-b][1,4]diazepine-2,4(3H,5H)-dione potassium salt (Compound 3A) 5-[4-(1H-Tetrazol-5-yl)phenyl]-1H-naphtho[1,2-b][1,4]diazepine-2,4(3H,5H)-dione (Compound 4A) 5-[4-(1H-Tetrazol-5-yl)phenyl]-1H-naphtho[1,2-b][1,4]diazepine-2,4(3H,5H)-dione sodium salt (Compound 6A) 1-Methyl-5-[3-(1H-tetrazol-5-yl)phenyl]-1H-naphtho[1,2-b][1,4]diazepine-2,4(3H,5H)-dione (Compound 6A) 1,3-Dimethyl-5-[3-(1H-tetrazol-5-yl)phenyl]-1H-naphtho[1,2-b][1,4]diazepine-2,4(3H,5H)-dione (Compound 7A) 5-[2-Chloro-5-(1H-tetrazol-5-yl)phenyl]-1H-naphtho[1,2-b][1,4]diazepine-2,4(3H,5H)-dione (Compound 8A) 5-[2-Chloro-5-(1H-tetrazol-5-yl)phenyl]-1H-naphtho[1,2-b][1,4]diazepine-2,4(3H,5H)-dione sodium salt (Compound 9A) 5-[2-Methyl-5-(1H-tetrazol-5-yl)phenyl]-1H-naphtho[1,2-b][1,4]diazepine-2,4(3H,5H)-dione (Compound 10A) 5-[2-Methyl-5-(1H-tetrazol-5-yl)phenyl]-1H-naphtho[1,2-b][1,4]diazepine-2,4(3H,5H)-dione sodium salt (Compound 11A) 5-[2-Bromo-5-(1H-tetrazol-5-yl)phenyl]-1H-naphtho[1,2-b][1,4]diazepine-2,4(3H,5H)-dione (Compound 12A) 5-[3-(2-Methyl-2H-tetrazol-5-yl)phenyl]-1H-naphtho[1,2-b][1,4]diazepine-2,4(3H,5H)-dione (Compound 13A) 5-[3-(1-Methyl-1H-tetrazol-5-yl)phenyl]-1H-naphtho[1,2-b][1,4]diazepine-2,4(3H,5H)-dione (Compound 14A) 5-[3-(5-Oxo-4H-[1,2,4]oxadiazol-3-yl)phenyl]-1H-naphtho[1,2-b][1,4]diazepine-2,4(3H,5H)-dione (Compound 15A) 5-[3-(5-Thioxo-4H-[1,2,4]oxadiazol-3-yl)phenyl]-1H-naphtho[1,2-b][1,4]diazepine-2,4(3H,5H)-dione (Compound 16A) 5-[3-(5-Thioxo-4H-[1,2,4]oxadiazol-3-yl)phenyl]-1H-naphtho[1,2-b][1,4]diazepine-2,4(3H,5H)-dione sodium salt (Compound 17A) 5-[3-(Oxazol-2-yl)phenyl]-1H-naphtho[1,2-b][1,4]diazepine-2,4(3H,5H)-dione (Compound 18A) 5-[3-(1H-Pyrazol-4-yl)phenyl]-1H-naphtho[1,2-b][1,4]diazepine-2,4(3H,5H)-dione (Compound 1B) 5-(3-Cyanophenyl)-8,9,10,11-tetrahydronaphtho[2,1-b][1,4]diazepine-2,4(3H,5H)-dione (Compound 2B) 5-[3-(1H-Tetrazol-5-yl)phenyl]-8,9,10,11-tetrahydronaphtho[2,1-b][1,4]diazepine-2,4(3H,5H)-dione sodium salt (Compound 3B) 5-(3-Hydroxyphenyl)-8,9,10,11-tetrahydronaphtho[2,1-b][1,4]diazepine-2,4(3H,5H)-dione (Compound 4B) 5-(3-Cyanophenyl)-5,8,9,10-tetrahydroindeno[5,4-b][1,4]diazepine-2,4(1H,3H)-dione (Compound 5B) 5-[3-(1H-Tetrazol-5-yl)phenyl)-5,8,9,10-tetrahydroindeno[5,4-b][1,4]diazepine-2,4(1H,3H)-dione sodium salt (Compound 6B) 5-[3-(2-Methyl-2H-tetrazol-5-yl)phenyl)-5,8,9,10-tetrahydroindeno[5,4-b][1,4]diazepine-2,4(1H,3H)-dione (Compound 7B) 5-[3-(1-Methyl-1H-tetrazol-5-yl)phenyl)-5,8,9,10-tetrahydroindeno[5,4-b][1,4]diazepine-2,4(1H,3H)-dione (Compound 8B) 5-(3-tert-Butoxycarbonylaminophenyl)-1,5,8,9,10,11-hexahydronaphtho[1,2-b][1,4]diazepine-2,4-dione (Compound 9B) 5-(3-Aminophenyl)-1,5,8,9,10,11-hexahydronaphtho[1,2-b][1,4]diazepine-2,4-dione hydrochloride (Compound 10B) 5-[3-(2-Methyl-2H-tetrazol-5-yl)phenyl)-1,5,8,9,10,11-hexahydronaphtho[1,2-b][1,4]diazepine-2,4-dione (Compound 11B) 5-[3-(1-Methyl-1H-tetrazol-5-yl)phenyl)-1,5,8,9,10,11-hexahydronaphtho[1,2-b][1,4]diazepine-2,4-dione (Compound 12B) 5-(4-Aminophenyl)-1,5,8,9,10,11-hexahydronaphtho[1,2-b][1,4]diazepine-2,4-dione (Compound 13B) 5-(4-Methylaminophenyl)-1,5,8,9,10,11-hexahydronaphtho[1,2-b][1,4]diazepine-2,4-dione hydrochloride (Compound 14B) 5-(2,3-Dihydrobenzo[1,4]dioxin-6-yl)-1,5,8,9,10,11-hexahydronaphtho[1,2-b][1,4]diazepine-2,4-dione (Compound 15B) 5-(4-Methoxyphenyl)-1,5,8,9,10,11-hexahydronaphtho[1,2-b][1,4]diazepine-2,4-dione
(Compound 16B) 5-(4-Hydroxyphenyl)-1,5,8,9,10,11-hexahydronaphtho[1,2-b][1,4]diazepine-2,4-dione
(Compound 17B) 5-[4-(Isopropylcarbonylamino)phenyl]-1,5,8,9,10,11-hexahydronaphtho[1,2-b][1,4]diazepine-2,4-dione
(Compound 18B) 5-(3-Carbamoylphenyl)-1,5,8,10-tetrahydro-1H-indeno[6,7-b][1,4]diazepine-2,4-dione
(Compound 19B) 1-Acetyl-5-[3-(5-methyl-[1,3,4]oxadiazol-2-yl)phenyl]-1,5,8,10-tetrahydro-1H-indeno[6,7-b][1,4]diazepine-2,4-dione
(Compound 20B) 5-[3-(5-Methyl-[1,3,4]oxadiazol-2-yl)phenyl]-1,5,8,10-tetrahydro-1H-indeno[6,7-b][1,4]diazepine-2,4-dione
(Compound 21B) 5-[3-(5-Phenyl-[1,3,4]oxadiazol-2-yl)phenyl]-1,5,8,10-tetrahydro-1H-indeno[6,7-b][1,4]diazepine-2,4-dione
(Compound 1C) 4-(3-Cyanophenyl)-1,4-dihydrobenzo[f]quinoxaline-2,3-dione
(Compound 2C) 4-[3-(1H-Tetrazol-5-yl)phenyl]-1,4-dihydrobenzo[f]quinoxaline-2,3-dione sodium salt
(Compound 3C) 4-(3-Methoxyphenyl)-1,4-dihydrobenzo[f]quinoxaline-2,3-dione
(Compound 4C) 4-(3-Hydroxyphenyl)-1,4-dihydrobenzo[f]quinoxaline-2,3-dione sodium salt
(Compound 5C) 5-(3-Methoxyphenyl)-1,4,7,8,9,10-hexahydrobenzo[f]quinoxaline-2,3-dione
(Compound 6C) 5-(3-Hydroxyphenyl)-1,4,7,8,9,10-hexahydrobenzo[f]quinoxaline-2,3-dione
(Compound 7C) 4-(3-Aminophenyl)-1,4,7,8,9,10-hexahydrobenzo[f]quinoxaline-2,3-dione hydrochloride
(Compound 8C) 4-(1H-Indol-4-yl)-1,4,7,8,9,10-hexahydrobenzo[f]quinoxaline-2,3-dione
(Compound 9C) N-[3-(2,3-Dioxo-2,3,7,8,9,10-hexahydrobenzo[f]quinoxaline-4(1H)-yl)phenyl]-2-nitrobenzenesulfonamide
(Compound 10C) 4-(3-Methylaminophenyl)-1,4,7,8,9,10-hexahydrobenzo[f]quinoxaline-2,3-dione hydrochloride
(Compound 11C) 1-Methyl-4-(3-methylaminophenyl)-1,4,7,8,9,10-hexahydrobenzo[f]quinoxaline-2,3-dione hydrochloride
(Compound 12C) 4-(3-Fluorophenyl)-1,4-dihydrobenzo[f]quinoxaline-2,3-dione
(Compound 13C) 4-(3-Aminophenyl)-1,4-dihydrobenzo[f]quinoxaline-2,3-dione hydrochloride
(Compound 14C) 4-[3-[(2-Iodophenylacetyl)amino]phenyl)-1,4-dihydrobenzo[f]quinoxaline-2,3-dione
(Compound 15C) 4-[3-(5-Methyl-[1,3,4]oxadiazol-2-yl)phenyl]-1,4-dihydrobenzo[f]quinoxaline-2,3-dione
(Compound 16C) 4-[3-(3-Methyl-[1,2,4]oxadiazol-5-yl)phenyl]-1,4-dihydrobenzo[f]quinoxaline-2,3-dione
(Compound 17C) 4-(4-Hydroxyphenyl)-1,4-dihydrobenzo[f]quinoxaline-2,3-dione sodium salt
(Compound 18C) 4-(4-Aminophenyl)-1,4-dihydrobenzo[f]quinoxaline-2,3-dione hydrochloride
(Compound 19C) N-[4-(2,3-Dioxo-2,3-dihydrobenzo[f]quinoxaline-4(1H)-yl)phenyl]-2-nitrobenzenesulfonamide
(Compound 20C) 4-[4-(5-Methyl-[1,3,4]oxadiazol-2-yl)phenyl]-1,4-dihydrobenzo[f]quinoxaline-2,3-dione
(Compound 21C) 4-[3-[(2-Trifluoromethylbenzoyl)amino]phenyl)-2,3,7,8,9,10-hexahydro-1H-benzo[f]quinoxaline-2,3-dione
(Compound 22C) N-[3-(2,3-Dioxo-2,3,7,8,9,10-hexahydro-1H-benzo[f]quinoxalin-4-yl)phenyl]benzenesulfonamide
(Compound 23C) 3-Bromo-N-[3-(2,3-dioxo-2,3,7,8,9,10-hexahydro-1H-benzo[f]quinoxalin-4-yl)phenyl]benzenesulfonamide
(Compound 24C) N-[3-(2,3-Dioxo-2,3,7,8,9,10-hexahydro-1H-benzo[f]quinoxalin-4-yl)phenyl]-1-naphthalenesulfonamide
(Compound 25C) N-[3-(2,3-Dioxo-2,3,7,8,9,10-hexahydro-1H-benzo[f]quinoxalin-4-yl)phenyl]-2-naphthalenesulfonamide
(Compound 26C) N-[3-(2,3-Dioxo-2,3,7,8,9,10-hexahydro-1H-benzo[f]quinoxalin-4-yl)phenyl]-2-thiophenesulfonamide
(Compound 27C) N-[3-(2,3-Dioxo-2,3,7,8,9,10-hexahydro-1H-benzo[f]quinoxalin-4-yl)phenyl]-3-pyridinesulfonamide hydrochloride
(Compound 28C) N-[3-(2,3-Dioxo-2,3,7,8,9,10-hexahydro-1H-benzo[f]quinoxalin-4-yl)phenyl]-8-quinolinesulfonamide hydrochloride
(Compound 29C) 4-[3-(1H-Tetrazol-1-yl)phenyl]-2,3,7,8,9,10-tetrahydro-1H-benzo[f]quinoxaline-2,3-dione
(Compound 1D) 4-(3-Cyanophenyl)-1H-benzo[h]quinazolin-2-one
(Compound 2D) 4-[3-(1H-Tetrazol-5-yl)phenyl]-1H-benzo[h]quinazolin-2-one sodium salt
(Compound 3D) 4-(3-Methoxyphenyl)-1H-benzo[h]quinazolin-2-one
(Compound 4D) 4-(3-Hydroxyphenyl)-1H-benzo[h]quinazolin-2-one sodium salt
(Compound 5D) 4-(4-Methoxyphenyl)-1H-benzo[h]quinazolin-2-one
(Compound 6D) 4-(4-Hydroxyphenyl)-1H-benzo[h]quinazolin-2-one sodium salt
(Compound 7D) 4-(3-Aminophenyl)-1H-benzo[h]quinazolin-2-one hydrochloride
(Compound 8D) N-[3-(2-Oxo-1,2-dihydrobenzo[h]quinazolin-4-yl)phenyl]benzenesulfonamide
(Compound 1E) 5-(4-Benzoylaminophenyl)-1H-naphtho[1,2-b][1,4]diazepine-2,4(3H,5H)-dione
(Compound 2E) 5-[4-[(2-(Trifluoromethyl)benzoyl]aminophenyl]-1H-naphtho[1,2-b][1,4]diazepine-2,4(3H,5H)-dione
(Compound 3E) 5-[4-(3-Bromobenzoyl)aminophenyl]-1H-naphtho[1,2-b][1,4]diazepine-2,4(3H,5H)-dione
(Compound 4E) 5-[4-[4-(Trifluoromethyl)benzoyl]aminophenyl]-1H-naphtho[1,2-b][1,4]diazepine-2,4(3H,5H)-dione
(Compound 6E) 5-[4-(2-Methylbenzoyl)aminophenyl]-1H-naphtho[1,2-b][1,4]diazepine-2,4(3H,5H)-dione
(Compound 6E) 5-[4-(2,6-Dimethylbenzoylamino)phenyl]-1H-naphtho[1,2-b][1,4]diazepine-2,4(3H,5H)-dione
(Compound 7E) 5-[4-(2,6-Dichlorobenzoyl)aminophenyl]-1H-naphtho[1,2-b][1,4]diazepine-2,4(3H,5H)-dione
(Compound 8E) 5-[4-(3-Chlorobenzoyl)aminophenyl]-1H-naphtho[1,2-b][1,4]diazepine-2,4(3H,5H)-dione
(Compound 9E) 5-[4-(2-Phenylacetylamino)phenyl]-1H-naphtho[1,2-b][1,4]diazepine-2,4(3H,5H)-dione
(Compound 10E) 1-[4-(2,4-Dioxo-1,2,3,4-tetrahydronaphtho[1,2-b][1,4]diazepin-5-yl)phenyl]-3-phenylthiourea
(Compound 11E) 5-[4-(2,3-Dimethoxybenzoylamino)phenyl]-1H-naphtho[1,2-b][1,4]diazepine-2,4(3H,5H)-dione
(Compound 12E) 5-[4-(2-Methoxybenzoylamino)phenyl]-1H-naphtho[1,2-b][1,4]diazepine-2,4(3H,5H)-dione
(Compound 13E) 5-[4-[(2-Chlorophenylacetyl)amino]phenyl]-1H-naphtho[1,2-b][1,4]diazepine-2,4(3H,5H)-dione
(Compound 14E) 5-[4-(2,3-Dimethylbenzoylamino)phenyl]-1H-naphtho[1,2-b][1,4]diazepine-2,4(3H,5H)-dione (Compound 15E) 5-[4-(2,5-Dimethylbenzoylamino)phenyl]-1H-naphtho[1,2-b][1,4]diazepine-2,4(3H,5H)-dione
(Compound 16E) 5-[4-(5-Bromo-2-chlorobenzoylamino)phenyl]-1H-naphtho[1,2-b][1,4]diazepine-2,4(3H,5H)-dione
(Compound 17E) 5-[4-(2,4-Dichlorobenzoylamino)phenyl]-1H-naphtho[1,2-b][1,4]diazepine-2,4(3H,5H)-dione
(Compound 18E) 5-[4-(2-Hydroxybenzoylamino)phenyl]-1H-naphtho[1,2-b][1,4]diazepine-2,4(3H,5H)-dione
(Compound 19E) 5-[4-(2,3-Dihydroxybenzoylamino)phenyl]-1H-naphtho[1,2-b][1,4]diazepine-2,4(3H,5H)-dione
(Compound 20E) 1-[4-(2,4-Dioxo-1,2,3,4-tetrahydronaphtho[1,2-b][1,4]diazepin-5-yl)phenyl]-3-phenylurea
(Compound 21E) 5-[4-[(2,6-Dichlorophenylacetyl)amino]phenyl]-1H-naphtho[1,2-b][1,4]diazepine-2,4(3H,5H)-dione
(Compound 22E) 5-[4-[(2-Methoxyphenylacetyl)amino]phenyl]-1H-naphtho[1,2-b][1,4]diazepine-2,4(3H,5H)-dione
(Compound 23E) 5-[4-[(2-Hydroxyphenylacetyl)amino]phenyl]-1H-naphtho[1,2-b][1,4]diazepine-2,4(3H,5H)-dione
(Compound 24E) 1-(2-Chlorophenyl)-3-[4-(2,4-dioxo-1,2,3,4-tetrahydronaphtho[1,2-b][1,4]diazepin-5-yl)phenyl]thiourea
(Compound 25E) 5-[4-[3-(Trifluoromethyl)benzoylamino]phenyl]-1H-naphtho[1,2-b][1,4]diazepine-2,4(3H,5H)-dione
(Compound 26E) 5-[4-[2-[(2-Trifluoromethyl)phenyl]acetylamino]phenyl]-1H-naphtho[1,2-b][1,4]diazepine-2,4(3H,5H)-dione
(Compound 27E) 1-(2-Chlorophenyl)-3-[4-(2,4-dioxo-1,2,3,4-tetrahydronaphtho[1,2-b][1,4]diazepin-5-yl)phenyl]urea
(Compound 28E) 5-[4-[(2-Phenylpropionyl)amino]phenyl]-1H-naphtho[1,2-b][1,4]diazepine-2,4(3H,5H)-dione
(Compound 29E) 5-[4-(2-Chloro-3-methoxybenzoylamino)phenyl]-1H-naphtho[1,2-b][1,4]diazepine-2,4(3H,5H)-dione
(Compound 30E) 5-[4-(3-Phenylpropionylamino)phenyl]-1H-naphtho[1,2-b][1,4]diazepine-2,4(3H,5H)-dione
(Compound 31E) 5-[4-[(1H-Indole-3-carbonyl)amino]phenyl]-1H-naphtho[1,2-b][1,4]diazepine-2,4(3H,5H)-dione
(Compound 32E) 5-[4-(2-Chloro-3-hydroxybenzoylamino)phenyl]-1H-naphtho[1,2-b][1,4]diazepine-2,4(3H,5H)-dione
(Compound 33E) 5-[4-[(2-Methyl-2-phenylpropionyl)amino]phenyl]-1H-naphtho[1,2-b][1,4]diazepine-2,4(3H,5H)-dione
(Compound 34E) 5-[4-(2-Phenoxyacetylamino)phenyl]-1H-naphtho[1,2-b][1,4]diazepine-2,4(3H,5H)-dione
(Compound 35E) 5-[4-[2-(2-Chloro-4-methoxyphenyl)acetylamino]phenyl]-1H-naphtho[1,2-b][1,4]diazepine-2,4(3H,5H)-dione
(Compound 36E) 5-[4-[(1-Methyl-1H-imidazole-2-carbonyl)amino]phenyl]-1H-naphtho[1,2-b][1,4]diazepine-2,4(3H,5H)-dione
(Compound 37E) 5-[4-[2-(2,4-Dichlorophenyl)acetylamino]phenyl]-1H-naphtho[1,2-b][1,4]diazepine-2,4(3H,5H)-dione
(Compound 38E) 5-[4-[2-(2-Chloro-4-hydroxyphenyl)acetylamino]phenyl]-1H-naphtho[1,2-b][1,4]diazepine-2,4(3H,5H)-dione
(Compound 39E) 5-[4-(3-Phenylpropenylamino)phenyl]-1H-naphtho[1,2-b][1,4]diazepine-2,4(3H,5H)-dione
(Compound 40E) 5-[4-[(3-Pyridylacetyl)amino]phenyl]-1H-naphtho[1,2-b][1,4]diazepine-2,4(3H,5H)-dione hydrochloride
(Compound 41E) 5-[4-(1H-Benzimidazole-2-carbonylamino)phenyl]-1H-naphtho[1,2-b][1,4]diazepine-2,4(3H,5H)-dione
(Compound 42E) 1-[4-(2,3-Dimethylbenzoylamino)phenyl]-7-methoxy-1H-1,5-benzodiazepine-2,4(3H,5H)-dione
(Compound 43E) 5-[4-[(Benzoylamino)methyl]phenyl]-1H-naphtho[1,2-b][1,4]diazepine-2,4(3H,5H)-dione
(Compound 44E) 5-[4-[(2-Chlorobenzoylamino)methyl]phenyl]-1H-naphtho[1,2-b][1,4]diazepine-2,4(3H,5H)-dione
(Compound 45E) 1-[4-(2,3-Dimethylbenzoylamino)phenyl]-7-hydroxy-1H-1,5-benzodiazepine-2,4(3H,5H)-dione
(Compound 46E) 5-[4-(2-Chlorobenzoylamino)phenyl]-1H-naphtho[1,2-b][1,4]diazepine-2,4(3H,5H)-dione
(Compound 47E) 5-[4-(2-Bromobenzoylamino)phenyl]-1H-naphtho[1,2-b][1,4]diazepine-2,4(3H,5H)-dione
(Compound 48E) 5-[4-(2-Iodobenzoylamino)phenyl]-1H-naphtho[1,2-b][1,4]diazepine-2,4(3H,5H)-dione
(Compound 49E) 5-[4-(2,3-Dimethylbenzoylamino)-3-fluorophenyl]-1H-naphtho[1,2-b][1,4]diazepine-2,4(3H,5H)-dione
(Compound 50E) 5-[4-[2-(2-Methylphenyl)acetylamino]phenyl]-1H-naphtho[1,2-b][1,4]diazepine-2,4(3H,5H)-dione
(Compound 51E) 5-[4-[(Quinoxalin-2-yl)carbonylamino]phenyl]-1H-naphtho[1,2-b][1,4]diazepine-2,4(3H,5H)-dione
(Compound 52E) 5-[4-[(5-Methylthiophen-2-yl)carbonylamino]phenyl]-1H-naphtho[1,2-b][1,4]diazepine-2,4(3H,5H)-dione
(Compound 53E) 5-[3-[(2-Chlorophenylacetyl)amino]phenyl]-1H-naphtho[1,2-b][1,4]diazepine-2,4(3H,5H)-dione
(Compound 54E) 5-[4-[(2,4,6-Trimethylbenzoyl)amino]phenyl]-1H-naphtho[1,2-b][1,4]diazepine-2,4(3H,5H)-dione
(Compound 55E) 5-[4-(Cyclohexylcarbonylamino)phenyl]-1,2,3,4,8,9,10,11-octahydronaphtho[1,2-b][1,4]diazepine-2,4(3H,5H)-dione
(Compound 56E) 1-[4-(2,3-Dimethylbenzoyl)aminophenyl]-6-methyl-1H-1,5-benzodiazepine-2,4(3H,5H)-dione
(Compound 57E) 5-[4-[(2-Ethylbenzoyl)amino]phenyl]-1H-naphtho[1,2-b][1,4]diazepine-2,4(3H,5H)-dione
(Compound 58E) 5-[4-[(6-Methylpyridin-2-yl)carbonylamino]phenyl]-1,2,3,4,8,9,10,11-octahydronaphtho[1,2-b][1,4]diazepine-2,4(3H,5H)-dione
(Compound 59E) 5-[4-[(2-Methylpyridin-3-yl)carbonylamino]phenyl]-1,2,3,4,8,9,10,11-octahydronaphtho[1,2-b][1,4]diazepine-2,4(3H,5H)-dione
(Compound 60E) 1-[4-(2,4-Dioxo-1,2,3,4-tetrahydronaphtho[1,2-b][1,4]diazepin-5-yl)phenyl]-3-(2-methylphenyl)thiourea
(Compound 61E) 5-[4-(2-Methoxy-3-methylbenzoyl)aminophenyl]-1,2,3,4,8,9,10,11-octahydronaphtho[1,2-b][1,4]diazepine-2,4(3H,5H)-dione
(Compound 62E) 5-[4-(2,3-Dichlorobenzoyl)aminophenyl]-1,2,3,4,8,9,10,11-octahydronaphtho[1,2-b][1,4]diazepine-2,4(3H,5H)-dione
(Compound 63E) 5-[4-(2,3-Dimethylbenzoylamino)-3-hydroxyphenyl]-1H-naphtho[1,2-b][1,4]diazepine-2,4(3H,5H)-dione
(Compound 64E) 5-[4-(2-Chloro-3-methoxybenzoylamino)phenyl]-1,3-dihydronaphtho[1,2-e]-1,4-diazepin-2-one (Compound 65E) 5-[4-[(4-Dimethylaminobenzoyl)amino]phenyl]-1H-naphtho[1,2-b][1,4]diazepine-2,4(3H,5H)-dione
(Compound 66E) 5-[4-[2-(2,4-Dichlorophenoxy)acetylamino]phenyl]-1H-naphtho[1,2-b][1,4]diazepine-2,4(3H,5H)-dione
(Compound 67E) 5-[4-[2-(2-Methylphenoxy)acetylamino]phenyl]-1H-naphtho[1,2-b][1,4]diazepine-2,4(3H,5H)-dione
(Compound 68E) N-[4-(2,4-Dioxo-1,2,3,4-tetrahydronaphtho[1,2-b][1,4]diazepin-5-yl)butyl]-2-chloro-3-methoxybenzamide
(Compound 69E) 5-[4-(2-Chloro-3-hydroxybenzoylamino)phenyl]-1,3-dihydronaphtho[1,2-e]-1,4-diazepin-2-one
(Compound 70E) 5-[4-(2-Acetylbenzoylamino)phenyl]-1H-naphtho[1,2-b][1,4]diazepine-2,4(3H,5H)-dione
(Compound 71E) 5-[4-(2-tert-Butylbenzoylamino)phenyl]-1H-naphtho[1,2-b][1,4]diazepine-2,4(3H,5H)-dione
(Compound 72E) 5-[2-(2-Iodobenzoyl)aminoethyl]-1H-naphtho[1,2-b][1,4]diazepine-2,4(3H,5H)-dione
(Compound 73E) 5-[3-[(2-Iodobenzoyl)amino]phenyl]-1H-naphtho[1,2-b][1,4]diazepine-2,4(3H,5H)-dione
(Compound 74E) 6,7-Dimethyl-1-[4-(2-iodobenzoyl)aminophenyl]-1H-1,5-benzodiazepine-2,4(3H,5H)-dione
(Compound 75E) 5-[4-[(1-Methylpiperidin-4-yl)carbonylamino]phenyl]-1H-naphtho[1,2-b][1,4]diazepine-2,4(3H,5H)-dione hydrochloride
(Compound 76E) 5-[4-[(Benzofuran-2-yl)carbonylamino]phenyl]-1H-naphtho[1,2-b][1,4]diazepine-2,4(3H,5H)-dione
(Compound 77E) 5-[4-[(1-Methyl-1H-indol-3-yl)carbonylamino]phenyl]-1H-naphtho[1,2-b][1,4]diazepine-2,4(3H,5H)-dione
(Compound 78E) 5-[4-(2-Propenylbenzoylamino)phenyl]-1H-naphtho[1,2-b][1,4]diazepine-2,4(3H,5H)-dione
(Compound 79E) 5-[4-(2-Propylbenzoylamino)phenyl]-1H-naphtho[1,2-b][1,4]diazepine-2,4(3H,5H)-dione
(Compound 80E) 5-[3-Fluoro-4-(2-iodobenzoylamino)phenyl]-1H-naphtho[1,2-b][1,4]diazepine-2,4(3H,5H)-dione
(Compound 81E) 5-[4-(2-Hydroxy-3-methylbenzoyl)aminophenyl]-1,2,3,4,8,9,10,11-octahydronaphtho[1,2-b][1,4]diazepine-2,4(3H,5H)-dione
(Compound 82E) 5-[4-[(2-Isopropoxybenzoyl)amino]phenyl]-1H-naphtho[1,2-b][1,4]diazepine-2,4(3H,5H)-dione
(Compound 83E) 5-[4-[(3-Methylthiophen-2-yl)carbonylamino]phenyl]-1H-naphtho[1,2-b][1,4]diazepine-2,4(3H,5H)-dione
(Compound 84E) 5-[4-(2-Phenoxypropionylamino)phenyl]-1H-naphtho[1,2-b][1,4]diazepine-2,4(3H,5H)-dione
(Compound 85E) 5-[4-[2-(4-Chloro-2-methylphenoxy)acetylamino]phenyl]-1H-naphtho[1,2-b][1,4]diazepine-2,4(3H,5H)-dione
(Compound 86E) 5-[4-(4-Fluoro-2-trifluoromethylbenzoyl)aminophenyl]-1H-naphtho[1,2-b][1,4]diazepine-2,4(3H,5H)-dione
(Compound 87E) 5-[4-(4-Fluoro-2-methoxybenzoyl)aminophenyl]-1H-naphtho[1,2-b][1,4]diazepine-2,4(3H,5H)-dione
(Compound 88E) 5-[4-(4-Fluoro-2-hydrooxybenzoyl)aminophenyl]-1H-naphtho[1,2-b][1,4]diazepine-2,4(3H,5H)-dione
(Compound 89E) 5-[3-[(2-Iodophenylacetyl)amino]phenyl]-1H-naphtho[1,2-b][1,4]diazepine-2,4(3H,5H)-dione
(Compound 90E) 5-[4-(2-Methyl-2-phenoxypropionylamino)phenyl]-1H-naphtho[1,2-b][1,4]diazepine-2,4(3H,5H)-dione
(Compound 91E) 5-[4-(2-tert-Butylbenzoylamino)phenyl]-1,3-dihydronaphtho[1,2-e]-1,4-diazepin-2-one
(Compound 92E) 5-[4-[(3-Dimethylaminobenzoyl)amino]phenyl]-1H-naphtho[1,2-b][1,4]diazepine-2,4(3H,5H)-dione
(Compound 93E) 5-[4-(4-Iodo-2-methoxybenzoylamino)phenyl]-1H-naphtho[1,2-b][1,4]diazepine-2,4(3H,5H)-dione
(Compound 94E) 5-[4-(6-Fluoro-2-methoxybenzoylamino)phenyl]-1H-naphtho[1,2-b][1,4]diazepine-2,4(3H,5H)-dione
(Compound 95E) 5-[4-(2-Hydroxy-4-iodobenzoylamino)phenyl]-1H-naphtho[1,2-b][1,4]diazepine-2,4(3H,5H)-dione
(Compound 96E) 5-[4-(6-Fluoro-2-hydroxyamino)phenyl]-1H-naphtho[1,2-b][1,4]diazepine-2,4(3H,5H)-dione
(Compound 97E) 5-[4-(2-Fluorobenzoyl)aminophenyl]-1H-naphtho[1,2-b][1,4]diazepine-2,4(3H,5H)-dione
(Compound 98E) 5-[4-[(2-Dimethylaminobenzoyl)amino]phenyl]-1H-naphtho[1,2-b][1,4]diazepine-2,4(3H,5H)-dione
(Compound 99E) 5-[4-(2-Methoxy-6-methylbenzoylamino)phenyl]-1H-naphtho[1,2-b][1,4]diazepine-2,4(3H,5H)-dione
(Compound 100E) 5-[4-(2-Hydroxy-6-methylbenzoylamino)phenyl]-1H-naphtho[1,2-b][1,4]diazepine-2,4(3H,5H)-dione
(Compound 101E) 5-[4-[3-(2-Methylphenyl)propionylamino]phenyl]-1H-naphtho[1,2-b][1,4]diazepine-2,4(3H,5H)-dione
(Compound 102E) 5-(4-Phenylcarbamoylphenyl)-1H-naphtho[1,2-b][1,4]diazepine-2,4(3H,5H)-dione
(Compound 103E) 5-(4-Benzylcarbamoylphenyl)-1H-naphtho[1,2-b][1,4]diazepine-2,4(3H,5H)-dione
(Compound 104E) 5-[4-[3-(2-Methylphenyl)propenoylamino]phenyl]-1H-naphtho[1,2-b][1,4]diazepine-2,4(3H,5H)-dione
(Compound 105E) 5-[4-[3-(2-Chlorophenyl)propionylamino]phenyl]-1H-naphtho[1,2-b][1,4]diazepine-2,4(3H,5H)-dione
(Compound 106E) 5-[4-(2-Iodobenzoyl)aminophenyl]-1,2,3,4,8,9,10,11-octahydronaphtho[1,2-b][1,4]diazepine-2,4(3H,5H)-dione
(Compound 107E) 5-[4-[(1-Methyl-1H-pyrrol-2-ylacetyl)amino]phenyl]-1,2,3,4,8,9,10,11-octahydronaphtho[1,2-b][1,4]diazepine-2,4(3H,5H)-dione
(Compound 108E) 5-[4-(2-Chlorobenzyl)carbamoylphenyl]-1H-naphtho[1,2-b][1,4]diazepine-2,4(3H,5H)-dione
(Compound 109E) 5-[4-[3-(2-Chlorophenyl)propenoylamino]phenyl]-1H-naphtho[1,2-b][1,4]diazepine-2,4(3H,5H)-dione
(Compound 110E) 5-[4-(2-Chlorophenyl)carbamoylphenyl]-1H-naphtho[1,2-b][1,4]diazepine-2,4(3H,5H)-dione
(Compound 111E) 5-[4-(6-Bromo-2,3-methylenedioxybenzoylamino)phenyl]-1H-naphtho[1,2-b][1,4]diazepine-2,4(3H,5H)-dione
(Compound 112E) 5-[4-(6-Bromo-2-methoxybenzoylamino)phenyl]-1H-naphtho[1,2-b][1,4]diazepine-2,4(3H,5H)-dione
(Compound 113E) 5-[4-[(2-tert-Butylbenzoyl)amino]phenyl]-1,2,3,4,8,9,10,11-octahydronaphtho[1,2-b][1,4]diazepine-2,4(3H,5H)-dione
(Compound 114E) 5-[2-(2-Iodobenzoyl)aminopyridin-5-yl]-1H-naphtho[1,2-b][1,4]diazepine-2,4(3H,5H)-dione
(Compound 115E) 5-[4-(6-Bromo-2-hydroxybenzoylamino)phenyl]-1H-naphtho[1,2-b][1,4]diazepine-2,4(3H,5H)-dione (Compound 116E) 5-[4-(6-Chloro-2-methoxybenzoylamino)phenyl]-1H-naphtho[1,2-b][1,4]diazepine-2,4(3H,5H)-dione
(Compound 117E) 5-[4-(2-Iodobenzoylamino)phenyl]-1H-[1,4]diazepino[2,3-h]quinoline-2,4(3H,5H)-dione
(Compound 118E) 5-[4-(6-Chloro-2-hydroxybenzoylamino)phenyl]-1H-naphtho[1,2-b][1,4]diazepine-2,4(3H,5H)-dione
(Compound 119E) 5-[4-(2-Hydroxy-6-methoxybenzoylamino)phenyl]-1H-naphtho[1,2-b][1,4]diazepine-2,4(3H,5H)-dione
(Compound 120E) 5-[4-[2-Methoxy-6-(trifluoromethyl)benzoylamino]phenyl]-1H-naphtho[1,2-b][1,4]diazepine-2,4(3H,5H)-dione
(Compound 121E) 5-[4-[2-Hydroxy-6-(trifluoromethyl)benzoylamino]phenyl]-1H-naphtho[1,2-b][1,4]diazepine-2,4(3H,5H)-dione
(Compound 122E) 5-[4-[(2-Isopropenylbenzoyl)amino]phenyl]-1,2,3,4,8,9,10,11-octahydronaphtho[1,2-b][1,4]diazepine-2,4(3H,5H)-dione
(Compound 123E) 5-[4-[(2-Isopropylbenzoyl)amino]phenyl]-1,2,3,4,8,9,10,11-octahydronaphtho[1,2-b][1,4]diazepine-2,4(3H,5H)-dione
(Compound 124E) 5-[4-[2-Chloro-5-(methylthio)benzoylamino]phenyl]-1H-naphtho[1,2-b][1,4]diazepine-2,4(3H,5H)-dione
(Compound 125E) 5-[4-[2-(Methylthio)benzoylamino]phenyl]-1H-naphtho[1,2-b][1,4]diazepine-2,4(3H,5H)-dione
(Compound 126E) 5-[4-[3-(Methylthio)benzoylamino]phenyl]-1H-naphtho[1,2-b][1,4]diazepine-2,4(3H,5H)-dione
(Compound 127E) 5-[4-[2-Ethyl-6-methoxybenzoylamino]phenyl]-1H-naphtho[1,2-b][1,4]diazepine-2,4(3H,5H)-dione
(Compound 128E) 5-[4-(3-Methanesulfonylbenzoylamino)phenyl]-1H-naphtho[1,2-b][1,4]diazepine-2,4(3H,5H)-dione
(Compound 129E) 6-Ethyl-1-[4-(2-iodobenzoyl)aminophenyl]-1H-1,5-benzodiazepine-2,4(3H,5H)-dione
(Compound 130E) 5-[4-[2-Ethyl-6-hydroxybenzoylamino]phenyl]-1H-naphtho[1,2-b][1,4]diazepine-2,4(3H,5H)-dione
(Compound 131E) 5-[4-(3-Methanesulfinylbenzoylamino)phenyl]-1H-naphtho[1,2-b][1,4]diazepine-2,4(3H,5H)-dione
(Compound 132E) 5-[4-(2-Chloro-5-methanesulfinylbenzoylamino)phenyl]-1H-naphtho[1,2-b][1,4]diazepine-2,4(3H,5H)-dione
(Compound 133E) 5-[4-(2-Methanesulfinylbenzoylamino)phenyl]-1H-naphtho[1,2-b][1,4]diazepine-2,4(3H,5H)-dione
(Compound 134E) 5-[4-[[2-(4-Morpholinyl)acetyl]amino]phenyl]-1,2,3,4,8,9,10,11-octahydronaphtho[1,2-b][1,4]diazepine-2,4(3H,5H)-dione hydrochloride
(Compound 135E) 5-[4-(2-Chloro-6-methoxybenzoylamino)phenyl]-1,3-dihydronaphtho[1,2-e]-1,4-diazepin-2-one
(Compound 136E) 5-[4-[[(3-Chloropyridin-2-yl)carbonyl]amino]phenyl]-1H-naphtho[1,2-b][1,4]diazepine-2,4(3H,5H)-dione
(Compound 137E) 5-[4-(2-Chloro-6-hydroxybenzoylamino)phenyl]-1,3-dihydronaphtho[1,2-e]-1,4-diazepin-2-one
(Compound 138E) 5-[4-(3-Chloro-2-methoxybenzoylamino)phenyl]-1H-naphtho[1,2-b][1,4]diazepine-2,4(3H,5H)-dione
(Compound 139E) 5-[4-[(3-Methylpyridin-2-yl)carbonylamino]phenyl]-1H-naphtho[1,2-b][1,4]diazepine-2,4(3H,5H)-dione
(Compound 140E) 5-[4-[[(3-Chloropyridin-2-yl)carbonyl]amino]phenyl]-1,2,3,4,8,9,10,11-octahydronaphtho[1,2-b][1,4]diazepine-2,4(3H,5H)-dione
(Compound 141E) 5-[4-(3-Chloro-2-hydroxybenzoylamino)phenyl]-1H-naphtho[1,2-b][1,4]diazepine-2,4(3H,5H)-dione
(Compound 142E) 5-[4-[[(3-Hydroxypyridin-2-yl)carbonyl]amino]phenyl]-1H-naphtho[1,2-b][1,4]diazepine-2,4(3H,5H)-dione
(Compound 143E) 5-[4-[(3-Vinylpyridin-2-yl)carbonylamino]phenyl]-1H-naphtho[1,2-b][1,4]diazepine-2,4(3H,5H)-dione
(Compound 144E) 5-[4-[(3-Ethylpyridin-2-yl)carbonylamino]phenyl]-1H-naphtho[1,2-b][1,4]diazepine-2,4(3H,5H)-dione
(Compound 145E) N-[4-(2,4-Dioxo-1,2,3,4-tetrahydronaphtho[1,2-b][1,4]diazepin-5-yl)phenyl]-2-nitrobenzenesulfonamide
(Compound 146E) N-[4-(2,4-Dioxo-1,2,3,4-tetrahydronaphtho[1,2-b][1,4]diazepin-5-yl)phenyl]benzenesulfonamide
(Compound 147E) 3-Bromo-N-[4-(2,4-dioxo-1,2,3,4-tetrahydronaphtho[1,2-b][1,4]diazepin-5-yl)phenyl]benzenesulfonamide
(Compound 148E) N-[4-(2,4-Dioxo-1,2,3,4-tetrahydronaphtho[1,2-b][1,4]diazepin-5-yl)phenyl]-3-methoxybenzenesulfonamide
(Compound 149E) N-[3-(2-Oxo-2,3-dihydro-1H-naphtho[1,2-e][1,4]diazepin-5-yl)phenyl]benzenesulfonamide
(Compound 150E) N-[3-(2,4-Dioxo-1,2,3,4-tetrahydronaphtho[1,2-b][1,4]diazepin-5-yl)phenyl]-2-nitrobenzenesulfonamide
(Compound 151E) N-[4-(2,4-Dioxo-1,2,3,4,8,9,10,11-octahydronaphtho[1,2-b][1,4]-diazepin-5-yl)phenyl]-2-nitrobenzenesulfonamide
(Compound 152E) N-[4-(2,4-Dioxo-1,2,3,4,8,9,10,11-octahydro-naphtho[1,2-b][1,4]-diazepin-5-yl)phenyl]-N-methyl-2-nitrobenzenesulfonamide
(Compound 153E) N-[3-(2,4-Dioxo-1,2,3,4-tetrahydronaphtho[1,2-b][1,4]diazepin-5-yl)phenyl]-N-methyl-2-nitrobenzenesulfonamide
(Compound 154E) 4-(2,4-Dioxo-1,2,3,4,8,9,10,11-octahydronaphtho[1,2-b][1,4]diazepin-5-yl)-N-phenylbenzenesulfonamide
(Compound 155E) N-[3-(2,4-Dioxo-1,2,3,4-tetrahydronaphtho[1,2-b][1,4]diazepin-5-yl)phenyl]-2-naphthalenesulfonamide
(Compound 156E) N-[3-(2,4-Dioxo-1,2,3,4-tetrahydronaphtho[1,2-b][1,4]diazepin-5-yl)phenyl]-1-naphthalenesulfonamide
(Compound 157E) N-[4-(2,4-Dioxo-1,2,3,4-tetrahydronaphtho[1,2-b][1,4]diazepin-5-yl)phenyl]cyclohexanesulfonamide
(Compound 158E) N-[4-(2,4-Dioxo-1,2,3,4-tetrahydronaphtho[1,2-b][1,4]diazepin-5-yl)phenyl]-3-pyridinesulfonamide hydrochloride
(Compound 159E) N-[4-(2,4-Dioxo-1,2,3,4-tetrahydronaphtho[1,2-b][1,4]diazepin-5-yl)phenyl]-4-isopropylbenzenesulfonamide
(Compound 160E) N-[4-(2,4-Dioxo-1,2,3,4-tetrahydronaphtho[1,2-b][1,4]diazepin-5-yl)phenyl]phenylmethanesulfonamide (Compound 161E) N-[4-(2,4-Dioxo-1,2,3,4-tetrahydronaphtho[1,2-b][1,4]diazepin-5-yl)phenyl]-3-pyridinesulfonamide (Compound 162E) N-[4-(2,4-Dioxo-1,2,3,4-tetrahydronaphtho[1,2-b][1,4]diazepin-5-yl)phenyl]-2-naphthalenesulfonamide (Compound 163E) 4-(2,4-Dioxo-1,2,3,4,8,9,10,11-octahydronaphtho[1,2-b][1,4]diazepin-5-yl)phenyl 3-bromobenzenesulfonate (Compound 164E) N-Benzyl-N-[4-(1-benzyl-2,4-dioxo-1,2,3,4-tetrahydronaphtho[1,2-b][1,4]diazepin-5-yl)phenyl]-2-nitrobenzenesulfonamide (Compound 165E) N-Benzyl-N-[4-(2,4-dioxo-1,2,3,4-tetrahydronaphtho[1,2-b][1,4]diazepin-5-yl)phenyl]-2-nitrobenzenesulfonamide (Compound 166E) 3-Bromo-N-[4-(2,4-dioxo-1,2,3,4-tetrahydronaphtho[1,2-b][1,4]diazepin-5-yl)phenyl]-N-methylbenzenesulfonamide (Compound 167E) N-[4-(2,4-Dioxo-1,2,3,4-tetrahydronaphtho[1,2-b][1,4]diazepin-5-yl)phenyl]-N-methyl-2-nitrobenzenesulfonamide (Compound 168E) N-[4-(2,4-Dioxo-1,2,3,4-tetrahydronaphtho[1,2-b][1,4]diazepin-5-yl)phenyl]-N-(2-Hydroxyethyl)-2-nitrobenzenesulfonamide (Compound 169E) N-[4-(7-Chloro-2,4-dioxo-2,3,4,5-tetrahydro-1H-benzo[b][1,4]diazepin-1-yl)phenyl]benzenesulfonamide (Compound 170E) N-[4-(7-Bromo-2,4-dioxo-2,3,4,5-tetrahydro-1H-benzo[b][1,4]diazepin-1-yl)phenyl]benzenesulfonamide (Compound 171E) N-[4-[(2,4-Dioxo-7-(trifluoromethyl)-2,3,4,5-tetrahydro-1H-benzo[b][1,4]diazepin-1-yl)]phenyl]benzenesulfonamide (Compound 172E) N-[4-(2,4-Dioxo-2,3,4,5-tetrahydro-1H-benzo[b][1,4]diazepin-1-yl)phenyl]benzenesulfonamide (Compound 173E) 1-(2-Chlorophenyl)-N-[4-(2,4-dioxo-1,2,3,4-tetrahydronaphtho[1,2-b][1,4]diazepin-5-yl)phenyl]methanesulfonamide (Compound 174E) 1-(3-Bromophenyl)-N-[4-(2,4-dioxo-1,2,3,4-tetrahydronaphtho[1,2-b][1,4]diazepin-5-yl)phenyl]methanesulfonamide (Compound 175E) N-[4-(2,4-Dioxo-1,2,3,4-tetrahydronaphtho[1,2-b][1,4]diazepin-5-yl)phenyl]-2-trifluoromethylbenzenesulfonamide (Compound 176E) N-[4-(7-Bromo-6-methyl-2,4-dioxo-2,3,4,5-tetrahydro-1H-benzo[b][1,4]diazepin-1-yl)phenyl]benzenesulfonamide (Compound 177E) 1-(2-Chlorophenyl)-N-[4-(2,4-dioxo-1,2,3,4,8,9,10,11-octahydronaphtho[1,2-b][1,4]diazepin-5-yl)phenyl]methanesulfonamide (Compound 178E) 3-Bromo-N-[4-(2,4-dioxo-1,2,3,4,8,9,10,11-octahydronaphtho[1,2-b][1,4]diazepin-5-yl)phenyl]benzenesulfonamide (Compound 179E) N-[4-(2,4-Dioxo-1,2,3,4,8,9,10,11-octahydronaphtho[1,2-b][1,4]diazepin-5-yl)phenyl]-3-methoxybenzenesulfonamide (Compound 180E) 1-(2-Bromophenyl)-N-[4-(2,4-dioxo-1,2,3,4-tetrahydronaphtho[1,2-b][1,4]diazepin-5-yl)phenyl]methanesulfonamide (Compound 181E) N-[4-(2,4-Dioxo-1,2,3,4-tetrahydronaphtho[1,2-b][1,4]diazepin-5-yl)phenyl]-1-(2-methylphenyl)methanesulfonamide (Compound 182E) N-[4-(2,4-Dioxo-1,2,3,4-tetrahydronaphtho[1,2-b][1,4]diazepin-5-yl)phenyl]-1-(2-nitrophenyl)methanesulfonamide (Compound 183E) N-[4-(2,4-Dioxo-1,2,3,4-tetrahydronaphtho[1,2-b][1,4]diazepin-5-yl)phenyl]-2-phenylethanesulfonamide (Compound 184E) 1-(2,3-Dichlorophenyl)-N-[4-(2,4-dioxo-1,2,3,4,8,9,10,11-octahydronaphtho[1,2-b][1,4]diazepin-5-yl)phenyl]methanesulfonamide (Compound 185E) 1-(2-Chlorophenyl)-N-[4-(2,4-dioxo-7-methoxy-1H-benzo[1,2-b][1,4]diazepin-1-yl)phenyl]methanesulfonamide (Compound 186E) 1-(2-Chlorophenyl)-N-[4-(2,4-dioxo-7-hydroxy-1H-benzo[1,2-b][1,4]diazepin-1-yl)phenyl]methanesulfonamide (Compound 187E) 1-(4-Chlorophenyl)-N-[4-(2,4-dioxo-1,2,3,4-tetrahydronaphtho[1,2-b][1,4]diazepin-5-yl)phenyl]methanesulfonamide (Compound 188E) 1-(2-Chlorophenyl)-N-[4-(2,4-dioxo-1,2,3,4-tetrahydronaphtho[1,2-b][1,4]diazepin-5-yl)benzyl]methanesulfonamide (Compound 189E) 1-(2-Chlorophenyl)-N-[4-(2,4-dioxo-1,2,3,4-tetrahydronaphtho[1,2-b][1,4]diazepin-5-yl)-2-methoxyphenyl]methanesulfonamide (Compound 190E) 1-(2-Chlorophenyl)-N-[4-(2,4-dioxo-1,2,3,4-tetrahydronaphtho[1,2-b][1,4]diazepin-5-yl)-2-hydroxyphenyl]methanesulfonamide (Compound 191E) 1-(2,6-Dichlorophenyl)-N-[4-(2,4-dioxo-1,2,3,4,8,9,10,11-octahydronaphtho[1,2-b][1,4]diazepin-5-yl)phenyl]methanesulfonamide (Compound 192E) 1-(2-Chlorophenyl)-N-[4-(2,4-dioxo-6-methyl-1H-benzo[1,2-b][1,4]diazepin-1-yl)phenyl]methanesulfonamide (Compound 193E) 1-(2-Chlorophenyl)-N-[4-(2,4-dioxy-1,2,3,4-tetrahydronaphtho[1,2-b][1,4]diazepin-5-yl)propyl]methanesulfonamide (Compound 194E) 1-(2-Chlorophenyl)-N-[2-(2,4-dioxo-1,2,3,4-tetrahydronaphtho[1,2-b][1,4]diazepin-5-yl)ethyl]methanesulfonamide (Compound 195E) N-[4-(2,4-Dioxo-1,2,3,4,8,9,10,11-octahydronaphtho[1,2-b][1,4]diazepin-5-yl)phenyl]-1-(2-iodophenyl)methanesulfonamide (Compound 196E) 1-(2-Chlorophenyl)-N-[4-(2,4-dioxo-1,2,3,4,8,9,10,11-octahydronaphtho[1,2-b][1,4]diazepin-5-yl)phenyl]-N-methylmethanesulfonamide (Compound 197E) 1-(2-Chlorophenyl)-N-[4-(2-oxo-2,3-dihydro-1H-naphtho[1,2-e][1,4]diazepin-5-yl)phenyl]methanesulfonamide (Compound 198E) 1-[(2-Trifluoromethyl)phenyl]-N-[4-(2,4-dioxo-1,2,3,4-tetrahydronaphtho[1,2-b][1,4]diazepin-5-yl)phenyl]phenyl-N-methylmethanesulfonamide (Compound 199E) 1-(2-Ethylphenyl)-N-[4-(2,4-dioxo-1,2,3,4-tetrahydronaphtho[1,2-b][1,4]diazepin-5-yl)phenyl]phenyl-N-methylmethanesulfonamide (Compound 200E) 1-(2,3-Dimethylphenyl)-N-[4-(2,4-dioxo-1,2,3,4-tetrahydronaphtho[1,2-b][1,4]diazepin-5-yl)phenyl]phenyl-N-methylmethanesulfonamide (Compound 201E) 2-(2-Chlorophenyl)-N-[4-(2,4-dioxo-1,2,3,4-tetrahydronaphtho[1,2-b][1,4]diazepin-5-yl)phenyl]phenyl-N-methylethanesulfonamide (Compound 202E) 1-(2-Nitrophenyl)-N-[4-(2,4-dioxo-1,2,3,4-tetrahydronaphtho[1,2-b][1,4]diazepin-5-yl)phenyl]phenyl-N-methylmethanesulfonamide (Compound 203E) 1-(2-Aminophenyl)-N-[4-(2,4-dioxo-1,2,3,4-tetrahydronaphtho[1,2-b][1,4]diazepin-5-yl)phenyl]phenyl-N-methylmethanesulfonamide (Compound 204E) 1-(2-Dimethylaminophenyl)-N-[4-(2,4-dioxo-1,2,3,4-tetrahydronaphtho[1,2-b][1,4]diazepin-5-yl)phenyl]phenyl-N-methylmethanesulfonamide (Compound 205E) 5-[4-[(Pyridin-4-yl)carbonylamino]phenyl]-1H-naphtho[1,2-b][1,4]diazepine-2,4(3H,5H)-dione hydrochloride
(Compound 206E) 5-[4-[2-[(Pyridin-3-yl)oxy]acetylamino]phenyl]-1H-naphtho[1,2-b][1,4]diazepine-2,4(3H,5H)-dione hydrochloride
(Compound 207E) 5-[4-[(Pyridin-3-yl)carbonylamino]phenyl]-1H-naphtho[1,2-b][1,4]diazepine-2,4(3H,5H)-dione hydrochloride
(Compound 208E) 5-[4-[(2-Methylpyridin-3-yl)carbonylamino]phenyl]-1H-naphtho[1,2-b][1,4]diazepine-2,4(3H,5H)-dione hydrochloride
(Compound 209E) 5-[4-[(2-Chloropyridin-3-yl)carbonylamino]phenyl]-1H-naphtho[1,2-b][1,4]diazepine-2,4(3H,5H)-dione
(Compound 210E) 5-[4-[2-[(Pyridin-2-yl)oxy]acetylamino]phenyl]-1H-naphtho[1,2-b][1,4]diazepine-2,4(3H,5H)-dione
(Compound 211E) 5-[4-[[4-(Trifluoromethyl)pyridin-3-yl]carbonylamino]phenyl]-1H-naphtho[1,2-b][1,4]diazepine-2,4(3H,5H)-dione
(Compound 212E) 5-[4-[(2-Chloropyridin-3-yl)carbonylamino]phenyl]-1H-[1,4]diazepino[2,3-f]isoquinoline-2,4(3H,5H)-dione
(Compound 213E) 5-[4-[(2-Chloropyridin-3-yl)carbonylamino]phenyl]-8,9,10,11-tetrahydro-1H-[1,4]diazepino[2,3-f]isoquinoline-2,4(3H,5H)-dione
(Compound 214E) 5-[4-[(2-Isopropylbenzoyl)amino]phenyl]-1H-naphtho[1,2-b][1,4]diazepine-2,4(3H,5H)-dione
(Compound 1F) 5-[4-[5-(2-Methoxybenzyl)-1H-tetrazol-1-yl]phenyl]-1H-naphtho[1,2-b][1,4]diazepine-2,4(3H,5H)-dione
(Compound 2F) 5-[4-[5-(2-Hydroxybenzyl)-1H-tetrazol-1-yl]phenyl]-1H-naphtho[1,2-b][1,4]diazepine-2,4(3H,5H)-dione
(Compound 3F) 5-[4-[5-[2-(Pyridin-3-yl)ethyl]-1H-tetrazol-1-yl]phenyl]-1H-naphtho[1,2-b][1,4]diazepine-2,4(3H,5H)-dione hydrochloride
(Compound 4F) 5-[4-(5-Phenethyl-1H-tetrazol-1-yl)phenyl]-1H-naphtho[1,2-b][1,4]diazepine-2,4(3H,5H)-dione
(Compound 5F) 5-[4-[5-(Pyridin-4-ylmethyl)-1H-tetrazol-1-yl]phenyl]-1H-naphtho[1,2-b][1,4]diazepine-2,4(3H,5H)-dione
(Compound 6F) 5-[4-(5-Benzyl-1H-tetrazol-1-yl)phenyl]-1H-naphtho[1,2-b][1,4]diazepine-2,4(3H,5H)-dione
(Compound 7F) 5-[4-[5-(Pyridin-3-ylmethyl)-1H-tetrazol-1-yl]phenyl]-1H-naphtho[1,2-b][1,4]diazepine-2,4(3H,5H)-dione
(Compound 8F) 7-Methoxy-1-[4-[5-(2-methoxybenzyl)-1H-tetrazol-1-yl]phenyl]-1H-benzo[b][1,4]diazepine-2,4(3H,5H)-dione
(Compound 9F) 5-[6-[5-(2-Methoxybenzyl)-1H-tetrazol-1-yl]pyridin-3-yl]-1H-naphtho[1,2-b][1,4]diazepine-2,4(3H,5H)-dione
(Compound 10F) 5-[4-[5-(2-Cyclohexylethyl)-1H-tetrazol-1-yl]phenyl]-1H-naphtho[1,2-b][1,4]diazepine-2,4(3H,5H)-dione
(Compound 11F) 5-[6-[5-(2-Hydroxybenzyl)]-1H-tetrazol-1-yl]pyridin-3-yl]-1H-naphtho[1,2-b][1,4]diazepine-2,4(3H,5H)-dione
(Compound 12F) 5-[4-[5-[2-(Pyridin-4-yl)ethyl]-1H-tetrazol-1-yl]phenyl]-1H-naphtho[1,2-b][1,4]diazepine-2,4(3H,5H)-dione hydrochloride
(Compound 13F) 5-[4-[5-(Pyridin-2-ylmethyl)-1H-tetrazol-1-yl]phenyl]-1H-naphtho[1,2-b][1,4]diazepine-2,4(3H,5H)-dione
(Compound 14F) 5-[4-[5-[2-(Pyridin-2-yl)ethyl]-1H-tetrazol-1-yl]phenyl]-1H-naphtho[1,2-b][1,4]diazepine-2,4(3H,5H)-dione hydrochloride
(Compound 15F) 5-[4-[5-[(1H-Imidazol-1-yl)methyl]-1H-tetrazol-1-yl]phenyl]-1H-naphtho[1,2-b][1,4]diazepine-2,4(3H,5H)-dione
(Compound 16F) 5-[4-[5-[2-(1H-Imidazol-1-yl)ethyl]-1H-tetrazol-1-yl]phenyl]-1H-naphtho[1,2-b][1,4]diazepine-2,4(3H,5H)-dione
(Compound 17F) 5-[4-[5-[2-(Pyridin-2-yl)ethyl]-1H-tetrazol-1-yl]phenyl]-1H-naphtho[1,2-e][1,4]diazepin-2(3H)-one dihydrochloride
(Compound 18F) 5-[4-[5-(2-Methoxyphenethyl)-1H-tetrazol-1-yl]phenyl]-1H-naphtho[1,2-b][1,4]diazepine-2,4(3H,5H)-dione
(Compound 19F) 5-[4-[5-(2-Methoxybenzyl)-1H-tetrazol-1-yl]phenyl]-1H-naphtho[1,2-e][1,4]diazepin-2(3H)-one
(Compound 20F) 5-[4-[5-(3-Phenylpropyl)-1H-tetrazol-1-yl]phenyl]-1H-naphtho[1,2-b][1,4]diazepine-2,4(3H,5H)-dione
(Compound 21F) 5-[4-(2-Phenethyl-1H-imidazol-1-yl)phenyl]-1H-naphtho[1,2-b][1,4]diazepine-2,4(3H,5H)-dione hydrochloride
(Compound 22F) 5-[4-(1-Phenethyl-1H-imidazol-2-yl)phenyl]-1H-naphtho[1,2-b][1,4]diazepine-2,4(3H,5H)-dione hydrochloride
(Compound 23F) 5-[4-[1-(4-Chlorobenzyl)-1H-imidazol-2-yl]phenyl]-1H-naphtho[1,2-b][1,4]diazepine-2,4(3H,5H)-dione hydrochloride
(Compound 24F) 5-[4-[1-(2-Methoxybenzyl)-1H-imidazol-2-yl]phenyl]-1H-naphtho[1,2-b][1,4]diazepine-2,4(3H,5H)-dione
(Compound 25F) 5-[4-[1-(3-Methoxyphenethyl)-1H-imidazol-2-yl]phenyl]-1H-naphtho[1,2-b][1,4]diazepine-2,4(3H,5H)-dione
(Compound 26F) 5-[4-[1-(3-Methoxyphenethyl)-1H-imidazol-2-yl]phenyl]-1H-naphtho[1,2-b][1,4]diazepine-2,4(3H,5H)-dione hydrochloride
(Compound 27F) 5-[4-[1-(3-Hydroxyphenethyl)-1H-imidazol-2-yl]phenyl]-1H-naphtho[1,2-b][1,4]diazepine-2,4(3H,5H)-dione
(Compound 28F) 5-[4-[1-(2,4,6-Trimethylbenzyl)-1H-imidazol-2-yl]phenyl]-1H-naphtho[1,2-b][1,4]diazepine-2,4(3H,5H)-dione hydrochloride
(Compound 29F) 4-[3-[5-[2-(Pyridin-2-yl)ethyl]-1H-tetrazol-1-yl]phenyl]-benzo[f]quinoxaline-2,3(1H,4H)-dione hydrochloride
(Compound 30F) 5-[4-[5-[2-(6-Methylpyridin-2-ylethyl)-1H-tetrazol-1-yl]-phenyl]-1H-naphtho[1,2-b][1,4]diazepine-2,4(3H,5H)-dione hydrochloride
(Compound 31F) 5-[4-[(2-(3-Fluorophenyl)ethyl)-1H-imidazol-1-yl]phenyl]-1H-naphtho[1,2-b][1,4]diazepine-2,4(3H,5H)-dione hydrochloride
(Compound 32F) 5-[4-[(2-(2-Methoxyphenyl)ethyl)-1H-imidazol-1-yl]phenyl]-1H-naphtho[1,2-b][1,4]diazepine-2,4(3H,5H)-dione hydrochloride
(Compound 33F) 5-[4-[(2-(4-Fluorophenyl)ethyl)-1H-imidazol-1-yl]phenyl]-1H-naphtho[1,2-b][1,4]diazepine-2,4(3H,5H)-dione hydrochloride
(Compound 34F) 5-[4-[(2-(2-Fluorophenyl)ethyl)-1H-imidazol-1-yl]phenyl]-1H-naphtho[1,2-b][1,4]diazepine-2,4(3H,5H)-dione hydrochloride
(Compound 35F) 5-[4-[1-[2-(Trifluoromethyl)benzyl]-1H-imidazol-2-yl]phenyl]-1H-naphtho[1,2-b][1,4]diazepine-2,4(3H,5H)-dione hydrochloride (Compound 36F) 5-[4-[2-[4-(Trifluoromethyl)phenylethyl]-1H-imidazol-1-yl]phenyl]-1H-naphtho[1,2-b][1,4]diazepine-2,4(3H,5H)-dione hydrochloride
(Compound 37F) 5-[4-[2-(2,6-Dimethylphenylethyl)-1H-imidazol-1-yl]phenyl]-1H-naphtho[1,2-b][1,4]diazepine-2,4(3H,5H)-dione hydrochloride
(Compound 38F) 5-[4-[2-[3-(Trifluoromethyl)phenylethyl]-1H-imidazol-1-yl]phenyl]-1H-naphtho[1,2-b][1,4]diazepine-2,4(3H,5H)-dione hydrochloride
(Compound 39F) 5-[4-[5-[2-(Pyridin-2-yl)ethyl]-1H-tetrazol-1-yl]phenyl]-1H-naphtho[1,2-e][1,4]diazepin-2(3H)-one dihydrochloride
(Compound 40F) 5-[4-(5-Phenethyl-1H-tetrazol-1-yl)phenyl]-1H-naphtho[1,2-e][1,4]diazepin-2(3H)-one
(Compound 41F) 5-[4-(2-Phenethyl-1H-imidazol-1-yl)phenyl]-1H-naphtho[1,2-e][1,4]diazepin-2(3H)-one dihydrochloride
(Compound 42F) 5-[4-[2-(3-Methoxyphenethyl)-1H-imidazol-1-yl]phenyl]-1H-naphtho[1,2-b][1,4]diazepine-2,4(3H,5H)-dione hydrochloride
(Compound 43F) 5-[4-[2-(3-Hydroxyphenethyl)-1H-imidazol-1-yl]phenyl]-1H-naphtho[1,2-b][1,4]diazepine-2,4(3H,5H)-dione hydrochloride
(Compound 44F) 3-[2-[1-[4-(2,4-Dioxo-3,4-dihydro-1H-naphtho[1,2-b][1,4]diazepin-5(2H)-yl)phenyl]-1H-tetrazol-5-yl]ethyl]benzonitrile
(Compound 45F) 3-[2-[1-[4-(2,4-Dioxo-3,4-dihydro-1H-naphtho[1,2-b][1,4]diazepin-5(2H)-yl)phenyl]-1H-tetrazol-5-yl]ethyl]benzamide
(Compound 46F) 5-[4-[5-[2-(2-Methoxypyridin-3-yl)ethyl]-1H-tetrazol-1-yl]phenyl]-1H-naphtho[1,2-b][1,4]diazepine-2,4(3H,5H)-dione
(Compound 47F) 5-[4-[5-[2-(Dimethylamino)benzyl]-1H-tetrazol-1-yl]phenyl]-1H-naphtho[1,2-b][1,4]diazepine-2,4(3H,5H)-dione mesylate
(Compound 48F) 4-[2-[1-[4-(2,4-Dioxo-3,4-dihydro-1H-naphtho[1,2-b][1,4]diazepin-5(2H)-yl)phenyl]-1H-imidazol-2-yl]ethyl]benzonitrile
(Compound 49F) 4-[2-[1-[4-(2,4-Dioxo-3,4-dihydro-1H-naphtho[1,2-b][1,4]diazepin-5(2H)-yl)phenyl]-1H-imidazol-2-yl]ethyl]benzamide
(Compound 50F) 5-[4-(2-Phenyl-1H-imidazol-1-yl)phenyl]-1H-naphtho[1,2-b][1,4]diazepine-2,4(3H,5H)-dione
(Compound 51F) 5-[4-[2-(2-Methoxyphenyl)-1H-imidazol-1-yl]phenyl]-1H-naphtho[1,2-b][1,4]diazepine-2,4(3H,5H)-dione
(Compound 52F) 2-[[2-[4-(2,4-Dioxo-3,4-dihydro-1H-naphtho[1,2-b][1,4]diazepin-5(2H)-yl)phenyl]-1H-imidazol-1-yl]methyl]benzonitrile
(Compound 53F) 2-[[2-[4-(2,4-Dioxo-3,4-dihydro-1H-naphtho[1,2-b][1,4]diazepin-5(2H)-yl)phenyl]-1H-imidazol-1-yl]methyl]benzamide
(Compound 54F) 2-[2-[1-[4-(2,4-Dioxo-3,4-dihydro-1H-naphtho[1,2-b][1,4]diazepin-5(2H)-yl)phenyl]-1H-imidazol-2-yl]ethyl]benzonitrile
(Compound 55F) 2-[2-[1-[4-(2,4-Dioxo-3,4-dihydro-1H-naphtho[1,2-b][1,4]diazepin-5(2H)-yl)phenyl]-1H-imidazol-2-yl]ethyl]benzamide
(Compound 56F) 3-[2-[1-[4-(2,4-Dioxo-3,4-dihydro-1H-naphtho[1,2-b][1,4]diazepin-5(2H)-yl)phenyl]-1H-imidazol-2-yl]ethyl]benzonitrile
(Compound 57F) 3-[2-[1-[4-(2,4-Dioxo-3,4-dihydro-1H-naphtho[1,2-b][1,4]diazepin-5(2H)-yl)phenyl]-1H-imidazol-2-yl]ethyl]benzamide
(Compound 58F) 3-[2-[1-[4-(2,4-Dioxo-3,4-dihydro-1H-naphtho[1,2-b][1,4]diazepin-5(2H)-yl)phenyl]-1H-imidazol-2-yl]ethyl]benzamide hydrochloride
(Compound 59F) 5-[4-[2-[4-(Methylsulfonyl)phenethyl]-1H-imidazol-1-yl]phenyl]-1H-naphtho[1,2-b][1,4]diazepine-2,4(3H,5H)-dione hydrochloride
(Compound 60F) 5-[4-[2-(2-Fluoro-3-methoxyphenethyl)-1H-imidazol-1-yl]phenyl]-1H-naphtho[1,2-b][1,4]diazepine-2,4(3H,5H)-dione hydrochloride
(Compound 61F) 5-[4-[2-(3-Methoxyphenethyl)-1H-imidazol-1-yl]phenyl]-5,8,9,10-tetrahydroindeno[4,5-b][1,4]diazepine-2,4(1H,3H)-dione hydrochloride
(Compound 62F) 5-[4-[2-[2-(Thiophen-3-yl)ethyl]-1H-imidazol-1-yl]phenyl]-1H-naphtho[1,2-b][1,4]diazepine-2,4(3H,5H)-dione hydrochloride
(Compound 63F) 5-[4-[1-(2-Aminobenzyl)-1H-imidazol-2-yl]phenyl]-1H-naphtho[1,2-b][1,4]diazepine-2,4(3H,5H)-dione
(Compound 64F) 5-[3-Methoxy-4-(1-phenethyl-1H-imidazol-2-yl)-phenyl]-1H-naphtho[1,2-b][1,4]diazepine-2,4(3H,5H)-dione
(Compound 65F) 5-[3-Hydroxy-4-(1-phenethyl-1H-imidazol-2-yl)-phenyl]-1H-naphtho[1,2-b][1,4]diazepine-2,4(3H,5H)-dione
(Compound 66F) 5-[4-[2-[2-(Furan-2-yl)ethyl]-1H-imidazol-1-yl]-phenyl]-1H-naphtho[1,2-b][1,4]diazepine-2,4(3H,5H)-dione hydrochloride
(Compound 67F) 5-[4-[2-(2-Fluorophenethyl)-1H-imidazol-1-yl]phenyl]-5,8,9,10-tetrahydroindeno[4,5-b][1,4]diazepine-2,4(1H,3H)-dione
(Compound 68F) 5-[4-[2-(Phenoxymethyl)-1H-imidazol-1-yl]phenyl]-1H-naphtho[1,2-b][1,4]diazepine-2,4(3H,5H)-dione
(Compound 69F) 5-[4-[5-[2-Methyl-2-(pyridin-2-yl)propyl]-1H-tetrazol-1-yl]phenyl]-1H-naphtho[1,2-b][1,4]diazepine-2,4(3H,5H)-dione hydrochloride
(Compound 70F) 5-[4-[5-[2-(3-Methoxypyridin-2-yl)ethyl]-1H-tetrazol-1-yl]phenyl]-1H-naphtho[1,2-b][1,4]diazepine-2,4(3H,5H)-dione hydrochloride
(Compound 71F) 5-[4-[[2-(Pyridin-2-yl)ethyl]-1H-imidazol-1-yl]phenyl]-1H-naphtho[1,2-b][1,4]diazepine-2,4(3H,5H)-dione dihydrochloride
(Compound 72F) 5-[4-(5-Phenyl-1H-imidazol-4-yl)phenyl]-1H-naphtho[1,2-b][1,4]diazepine-2,4(3H,5H)-dione hydrochloride
(Compound 73F) 5-[4-[(5-Phenylethyl)-1H-imidazol-4-yl]phenyl]-1H-naphtho[1,2-b][1,4]diazepine-2,4(3H,5H)-dione hydrochloride
(Compound 74F) 5-[4-(4,4-Dimethyl-2-phenethyl-4,5-dihydro-1H-imidazol-1-yl)phenyl]-1H-naphtho[1,2-b][1,4]diazepine-2,4(3H,5H)-dione hydrochloride
(Compound 75F) 5-[4-[2-[(2-Methoxyphenyl)amino]-1H-imidazol-1-yl]phenyl]-1H-naphtho[1,2-b][1,4]diazepine-2,4(3H,5H)-dione
(Compound 76F) 5-[4-[2-(Phenylamino)-1H-imidazol-1-yl]phenyl]-1H-naphtho[1,2-b][1,4]diazepine-2,4(3H,5H)-dione
(Compound 77F) 5-[4-[1-[(6-Methoxypyridin-2-yl)methyl]-1H-imidazol-2-yl]phenyl]-1H-naphtho[1,2-b][1,4]diazepine-2,4(3H,5H)-dione hydrochloride
(Compound 78F) 5-[4-[1-[(6-Hydroxypyridin-2-yl)methyl]-1H-imidazol-2-yl]phenyl]-1H-naphtho[1,2-b][1,4]diazepine-2,4(3H,5H)-dione hydrochloride
(Compound 79F) 5-[4-[2-(3-Fluorophenethyl)-1H-imidazol-1-yl]phenyl]-5,8,9,10-tetrahydroindeno[4,5-b][1,4]diazepine-2,4(1H,3H)-dione hydrochloride
(Compound 80F) 5-[4-[2-[(Phenylamino)methyl]-1H-imidazol-1-yl]phenyl]-1H-naphtho[1,2-b][1,4]diazepine-2,4(3H,5H)-dione (Compound 81F) 3-[[2-[4-[2,4-Dioxo-3,4-dihydro-1H-naphtho[2,1-b][1,4]diazepine-5-(2H)-yl]phenyl]-1H-imidazol-1-yl]methyl]benzonitrile (Compound 82F) 3-[[2-[4-[2,4-Dioxo-3,4-dihydro-1H-naphtho[2,1-b][1,4]diazepine-5-(2H)-yl]phenyl]-1H-imidazol-1-yl]methyl]benzamide (Compound 83F) 5-[4-[(2-(3-Fluoro-2-methoxyphenyl)ethyl)-1H-imidazol-1-yl]phenyl]-1H-naphtho[1,2-b][1,4]diazepine-2,4(3H,5H)-dione hydrochloride (Compound 1G) N-[4-(2-Oxo-2,3-dihydro-1H-naphtho[1,2-e][1,4]-diazepin-5-yl)phenyl]-3-(pyridin-2-yl)propionic acid amide (Compound 2G) 2-Ethyl-3-hydroxy-N-[4-(2-oxo-2,3-dihydro-1H-naphtho[1,2-e][1,4]-diazepin-5-yl)phenyl]benzamide (Compound 3G) 2-Ethyl-N-[4-(2-oxo-2,3-dihydro-1H-naphtho[1,2-e][1,4]-diazepin-5-yl)phenyl]nicotinamide dihydrochloride (Compound 4G) 2-Ethyl-6-hydroxy-N-[4-(2-oxo-2,3-dihydro-1H-naphtho[1,2-e][1,4]-diazepin-5-yl)phenyl]benzamide (Compound 5G) 3-Ethyl-N-[4-(2-oxo-2,3-dihydro-1H-naphtho[1,2-e][1,4]-diazepin-5-yl)phenyl]picolinamide hydrochloride (Compound 6G) N-[4-(2-Oxo-2,3-dihydro-1H-naphtho[1,2-e][1,4]-diazepin-5-yl)phenyl]-2-(pyridin-2-yloxy)acetamide hydrochloride (Compound 7G) 2-(2-Methoxyphenyl)-N-[4-(2-oxo-2,3-dihydro-1H-naphtho[1,2-e][1,4]diazepin-5-yl)phenyl]acetamide (Compound 8G) N-[4-(2-Oxo-2,3-dihydro-1H-naphtho[1,2-e][1,4]diazepin-5-yl)-phenyl]-3-(pyridin-3-yl)propionamide dihydrochloride (Compound 9G) N-[4-(2-Oxo-2,3-dihydro-1H-naphtho[1,2-e][1,4]diazepin-5-yl)phenyl]-3-phenylpropanamide (Compound 10G) N-[4-(2,4-Dioxo-3,4-dihydro-1H-naphtho[1,2-b][1,4]diazepin-5(2H)-yl)-phenyl]-3-(pyridin-3-yl)propionamide hydrochloride (Compound 11G) N-[4-(2,4-Dioxo-3,4-dihydro-1H-naphtho[1,2-b][1,4]diazepin-5(2H)-yl)-phenyl]-3-(pyridin-4-yl)propionamide hydrochloride (Compound 12G) 2-tert-Butyl-N-[4-(2,4-dioxo-3,4-dihydro-1H-naphtho[1,2-b][1,4]diazepin-5(2H)-yl)2-fluorophenyl]benzamide (Compound 13G) N-[4-(2,4-Dioxo-3,4-dihydro-1H-naphtho[1,2-b][1,4]diazepin-5(2H)-yl)-phenyl]-3-(pyridin-2-yl)propionamide hydrochloride (Compound 14G) 2-(Dimethylamino)-N-[4-(2,4-dioxo-2,3-dihydro-1H-naphtho[1,2-b][1,4]diazepin-5(2H)-yl)phenyl]nicotinamide hydrochloride (Compound 15G) 2-(Dimethylamino)-N-[4-(2-oxo-2,3-dihydro-1H-naphtho[1,2-e][1,4]diazepin-5-yl)phenyl]nicotinamide dihydrochloride (Compound 16G) 2-(Dimethylamino)-N-[4-(2-oxo-2,3-dihydro-1H-naphtho[1,2-e][1,4]diazepin-5-yl)phenyl]nicotinamide dihydrochloride (Compound 17G) 2-(Dimethylamino)-N-[4-(2-oxo-2,3-dihydro-1H-naphtho[1,2-e][1,4]diazepin-5-yl)phenyl]nicotinamide dimethanesulfonate (Compound 18G) N-[4-(2,4-Dioxo-3,4-dihydro-1H-naphtho[1,2-b][1,4]diazepin-5(2H)-yl)phenyl]-2-(morpholin-4-yl)nicotinamide hydrochloride (Compound 19G) N-[4-(2-Oxo-2,3-dihydro-1H-naphtho[1,2-e][1,4]-diazepin-5-yl)phenyl]-2-(1H-pyrrol-1-yl)nicotinamide dihydrochloride (Compound 20G) 2-(Morpholin-4-yl)-N-[4-(2-oxo-2,3-dihydro-1H-naphtho[1,2-e][1,4]-diazepin-5-yl)phenyl]nicotinamide dihydrochloride (Compound 21G) N-[4-(2-Oxo-2,3-dihydro-1H-naphtho[1,2-e][1,4]-diazepin-5-yl)phenyl]-2-(pyrrolidin-1-yl)nicotinamide dihydrochloride (Compound 22G) 4-(Dimethylamino)-N-[4-(2-oxo-2,3-dihydro-1H-naphtho[1,2-e][1,4]diazepin-5yl)phenyl]nicotinamide dihydrochloride (Compound 23G) 2-Isopropyl-N-[4-(2-oxo-2,3-dihydro-1H-naphtho[1,2-e][1,4]diazepin-5yl)phenyl]nicotinamide dihydrochloride (Compound 24G) 2-(Isopropylamino)-N-[4-(2-oxo-2,3-dihydro-1H-naphtho[1,2-e][1,4]diazepin-5yl)phenyl]nicotinamide dihydrochloride Compounds preferred as the active ingredient of the medicament of the present invention are 5-[4-[(2-chlorophenylacetyl)amino]phenyl]-1H-naphtho[1,2-b][1,4]diazepine-2,4(3H,5H)-dione; 1-[4-(2,4-dioxo-1,2,3,4-tetrahydronaphtho[1,2-b][1,4]diazepin-5-yl)phenyl]-3-phenylurea; 5-[4-(2-iodobenzoylamino)phenyl]-1H-naphtho[1,2-b][1,4]diazepine-2,4(3H,5H)-dione; 5-[4-(2-iodobenzoyl)aminophenyl]-1,2,3,4,8,9,10,11-octahydronaphtho[1,2-b][1,4]diazepine-2,4(3H,5H)-dione; 5-[4-(6-chloro-2-hydroxybenzoylamino)phenyl]-1H-naphtho[1,2-b][1,4]diazepine-2,4(3H,5H)-dione; 1-(2-chlorophenyl)-N-[4-(2,4-dioxo-1,2,3,4-tetrahydronaphtho[1,2-b][1,4]diazepin-5-yl)phenyl]methanesulfonamide; 1-(2-chlorophenyl)-N-[4-(2,4-dioxo-1,2,3,4,8,9,10,11-octahydronaphtho[1,2-b][1,4]diazepin-5-yl)phenyl]-N-methylmethanesulfonamide; 1-(2-chlorophenyl)-N-[4-(2-oxo-2,3-dihydro-1H-naphtho[1,2-e][1,4]diazepin-5-yl)phenyl]methanesulfonamide; 5-[4-[(2-methylpyridin-3-yl)carbonylamino]phenyl]-1H-naphtho[1,2-b][1,4]diazepine-2,4(3H,5H)-dione hydrochloride; 5-[4-[(2-chloropyridin-3-yl)carbonylamino]phenyl]-1H-naphtho[1,2-b][1,4]diazepine-2,4(3H,5H)-dione; 5-[4-[2-[(pyridin-2-yl)oxy]acetylamino]phenyl]-1H-naphtho[1,2-b][1,4]diazepine-2,4(3H,5H)-dione, which all fall within the scope of the general formula (IE), 5-[3-(1H-tetrazol-5-yl)phenyl]-1H-naphtho[1,2-b][1,4]diazepine-2,4(3H,5H)-dione; 5-[4-(1H-tetrazol-5-yl)phenyl]-1H-naphtho[1,2-b][1,4]diazepine-2,4(3H,5H)-dione; 5-[3-(oxazol-2-yl)phenyl]-1H-naphtho[1,2-b][1,4]diazepine-2,4(3H,5H)-dione; and 5-[3-(1H-pyrazol-4-yl)phenyl]-1H-naphtho[1,2-b][1,4]diazepine-2,4(3H,5H)-dione, which all fall within the scope of the general formula (IA), and particularly preferred compounds are 5-[4-(2-iodobenzoyl)aminophenyl]-1H-naphtho[1,2-b][1,4]diazepine-2,4(3H,5H)-dione, which falls within the scope of the general formula (IE), and 5-[3-(1H-tetrazol-5-yl)phenyl]-1H-naphtho[1,2-b][1,4]diazepine-2,4(3H,5H)-dione, which falls within the scope of the general formula (IA). However, the active ingredient of the medicament of the present invention is not limited to the specific compounds mentioned above.

The compounds represented by the aforementioned general formulas (IA) to (IH) may have one or two or more asymmetric carbons depending on type of substituent. Arbitrary optical isomers occurring due to the presence of such asymmetric carbons, arbitrary mixtures of optical isomers, racemates, diastereoisomers occurring due to the presence of two or more asymmetric carbons, arbitrary mixtures of diastereoisomers, and the like may also be used as the active ingredient of the medicament of the present invention. When the compounds represented by the aforementioned general formulas IA) to (IH) contain a double bond or a cyclic structure, such compounds may exist as geometrical isomers, and pure geometrical isomers as well as mixtures thereof at arbitrary ratios can be used as the active ingredient of the medicament of the present invention.

As the active ingredient of the medicament of the present invention, besides the compounds represented by the aforementioned general formulas (IA) to (IH), an acid addition salt or a base addition salt of these compounds may also be used. As the acid addition salt, for example, mineral acid salts such as hydrochloride, sulfate, and nitrate, organic acid salts such as p-toluenesulfonate, oxalate, and malate, and the like can be used, but it is not limited to these. As the base addition salt, for example, metal salts such as sodium salt, potassium salt, magnesium salt, and calcium salt, ammonium salts, organic amine salts such as triethylamine salt and ethanolamine salt, and the like can be mentioned, but it is not limited to these. It is preferable to use a physiologically acceptable salt among these salts as the active ingredient of the medicament of the present invention. An arbitrary hydrate or solvate of the compounds in free form and the compounds in the form of a salt may also be used as the active ingredient of the medicament of the present invention.

The compounds preferred as the active ingredient of the medicament of the present invention can exhibit superior central migration in an EAE model animal (for example, EAE model rat) than in a healthy animal. For example, when a compound preferred as the active ingredient of the medicament of the present invention was orally administered to an EAE model rat or a healthy rat once (10 mg/kg) or repeatedly (10 mg/kg, twice a day for 7 days), and concentration of the compound in the cerebrospinal fluid was measured by using LC/MS/MS, the concentration of the compound in the cerebrospinal fluid of the EAE model rat was higher than the concentration of the compound in the cerebrospinal fluid of the healthy rat, and the ratio of the compound concentration in the cerebrospinal fluid to the compound concentration in the plasma (cerebrospinal fluid concentration/plasma concentration) was higher in the EAE model rat than in the healthy rat.

Therefore, as one embodiment of the present invention, the compounds preferred as the active ingredient of the medicament of the present invention show superior central migration in a human suffering from multiple sclerosis than in a healthy person.

The medicament of the present invention can be used for preventive and/or therapeutic treatment of multiple sclerosis. The medicament of the present invention can exhibit high effectiveness on a pain in multiple sclerosis, especially a neuropathic pain accompanying multiple sclerosis. A convalescent neuropathic pain accompanying multiple sclerosis is an especially suitable target for application of the medicament of the present invention.

Examples of the pain in multiple sclerosis include, for example, pain of muscle or bone structure, paroxysmal pain, chronic pain, and the like. Examples of the pain of muscle or bone structure include arthralgia accompanying reduction of muscular power and spasm, muscular pain (muscle contracture etc.), pain of tendon or ligament, and the like, and it may be produced as pain of hip joint, leg, arm, or back. The paroxysmal pain is a sharply stabbing pain, and frequently occurs in the face (trigeminal neuralgia etc.), and it may occur as an electric shock-like pain from the back of the head to the spine (L'hermitte's sign), when the head is inclined forward. The chronic pain is a pain that frequently occurs in multiple sclerosis, and includes abnormal sensation (numbness, prick pain feeling, stabbing pain, tremor, sensation of pressure, hyperesthesia of the skin, etc.), dysesthesia (burning sensation, ache, sensation of pressure, etc.), and the like. All of these pains may be a target of the application of the medicament of the present invention. However, the target of the application of the medicament of the present invention is not limited to these.

Although the medicament of the present invention can be orally or parenterally administered, oral administration is preferred. The medicament of the present invention can be produced by a usual method used in the field of drug manufacturing as a medicament in a proper dosage form such as tablet, granule, powder, capsule, suspension, injection, and suppository. For example, in the case of tablet, usual excipients, disintegrating agents, binders, lubricants, dyes, and the like can be used. Examples of excipient include lactose, D-mannitol, crystalline cellulose, glucose, and the like, examples of disintegrating agent include starch, carboxymethylcellulose calcium (CMC-Ca), and the like, examples of lubricant include magnesium stearate, talc, and the like, and examples of binder include hydroxypropylcellulose (HPC), gelatin, polyvinylpyrrolidone (PVP), and the like. For manufacturing injection, solvents, stabilizers, dissolving aids, suspending agents, emulsifiers, soothing agents, buffering agents, preservatives, and the like are used. These pharmaceutical additives and methods for preparing the medicament can be appropriately chosen by those skilled in the art.

Although dose of the medicament of the present invention is not particularly limited, it is generally administered to an adult at a daily dose of about 0.01 to 100 mg as an injection, or at a daily dose of about 1 to 2000 mg by oral administration in terms of the amount of the active ingredient. However, the dose is not limited to the aforementioned dose, and can be increased or decreased depending on age, symptoms, and the like.

EXAMPLES

Hereafter, the present invention will be more specifically explained with reference to examples. However, the scope of the present invention is not limited by the following examples.

In the following examples, as P2X4 antagonists, 5-[4-(2-iodobenzoyl)aminophenyl]-1H-naphtho[1,2-b][1,4]diazepine-2,4(3H,5H)-dione (the compound of WO2013/105608, Example 48, henceforth referred to as "compound A") and 5-[3-(1H-tetrazol-5-yl)phenyl]-1H-naphtho[1,2-b][1,4]diazepine-2,4(3H,5H)-dione sodium salt (sodium salt of the compound of WO2010/93061, Example 1, henceforth referred to as "compound B") were used.

Example 1

The P2X4 receptor antagonist activities of the compound A and compound B were measured by the following method.

The ATP receptor (human P2X4) was introduced into the 1321N1 cells, and the cells were used as a P2X4 receptor-stably expressing system. The P2X4 receptor-expressing cells were inoculated on a 96-well plate, cultured for 24 hours under the conditions of 37° C. and 5% $CO_2$, and used for calcium measurement. Fura-2AM, which is a fluorescent calcium indicator, was dissolved in an extracellular fluid for calcium imaging, and the inoculated cells were treated with the solution, and left standing at room temperature for 45 minutes so that Fura-2AM was taken into the cells. For the measurement, a microplate reader, EnVision (PerkinElmer), was used. Light emitted from a xenon lamp was passed through each of filters for 340 nm and 380 nm, and irradiated on the cells, fluorescences $F_{340}$ and Faso at 510 nm emitted from the cells were measured, and change of value of the ratio $F_{340}/F_{380}$ was used as an index of change of intracellular calcium. The measurement was performed by adding ATP to each well at a final concentration of 1 µM, and observing ATP-induced intracellular calcium response over time. Inhibitory activity of a test substance was calculated by performing the measurement after a pretreatment with the test substance with addition of ATP for 15 minutes, and comparing the result with the result obtained in the absence of the test substance. The results are shown in Table 110 mentioned below.

TABLE 110

| Test substance | $IC_{50}$ (µM) |
|---|---|
| Compound A | 0.30 |
| Compound B | 0.53 |

Example 2

By mRNA expression analysis and immunohistological analysis using experimental autoimmune encephalomyelitis (EAE) model rats, increase of the expression of P2X4 receptor in the spine of autoimmune neuritis was examined.

For the expression analysis of mRNA, the spines of the EAE model group and the control group were used. On Days 7, 14, 21, and 28, phosphate buffered saline (PBS) was transcardially perfused in the anesthetized rats, and then the fifth lumbar cord (L5) regions of the spines were extracted. After homogenization of the extracted spine, the total RNAs were extracted from it by using RNeasy Lipid Tissue Mini Kit, and cDNAs were synthesized by using the mRNAs as the templates and Transcriptor First Strand cDNA Synthesis Kit (04897030001, Roche Diagnostics Japan Co., Ltd.). The expression amounts of the P2X4 receptor and GAPDH were quantitatively analyzed from the synthesized cDNAs by using LightCycler TaqMan Master and a real-time PCR system (LightCycler ST300). As the primers for rat P2X4 receptor, gtgacaaccaaagccaaagg (forward) (SEQ ID NO: 2) and catgatgaagagggagtttcc (reverse) (SEQ ID NO: 3) were used, and as the probe, Universal Probe #76 (04688996001, Roche Diagnostics Japan Co., Ltd.) was used. As the primers for GAPDH, agcttgtcatcaacgggaag (forward) (SEQ ID NO: 4) and tttgatgttagtggggtctcg (reverse) (SEQ ID NO: 5) were used, and as the probe, Universal Probe #9 (04685075001, Roche Diagnostics Japan Co., Ltd.) was used.

The obtained measurement data were analyzed by the second derivative maximum method using Lightcycler Software Version 3.5, and copy numbers of the P2X4 receptor and GAPDH (housekeeping gene) were calculated. In order to compare the expression amounts of the P2X4 receptor among the samples, P2X4/GAPDH ratios were further calculated, and daily basis change of the expression was observed on the basis of ratio of the ratios (EAE model group/control group).

The change of the P2X4 receptor expression is shown in FIG. 1. It was observed that the expression of the mRNA for the P2X4 receptor markedly increased in the spine L5 region on Day 14 and thereafter compared with the control group in which only the adjuvant was administered.

Example 3

EAE model rats were prepared by the same method as that of Example 2. On Days 7, 14, 21, and 28, PBS was transcardially perfused in the rats anesthetized with pentobarbital, and then perfusion fixation was performed with 4% neutrally buffered paraformaldehyde. Then, the fifth lumbar cord (L5) region of the spine was extracted from each EAR rat, and a frozen section was prepared. Immunohistological staining was performed by using the P2X4 receptor antibody (Alomone Labs) and Iba1 antibody (Abcam).

The obtained immunohistological staining images are shown in FIG. 2. The P2X4 receptor-positive cells markedly increased in the EAE model rats on Day 14 and thereafter. The P2X4 receptor signal was observed on the cells positive to Iba1 (ionized calcium binding adapter molecule 1), which is a gene marker specifically expressed in macrophage/microglia cells. For the control animals, P2X4 receptor-positive cells were hardly observed throughout the observation period.

Example 4

EAE model rats were prepared by the same method as that of Example 2. Daily basis changes of symptoms, weight, and pain threshold were observed at a frequency of 3 times a week. The compound A was repetitively orally administered twice a day at a dose of 10 mg/kg over 22 days from Day 0. For symptom observation, behaviors of the animals allowed to freely act were scored in accordance with the criteria shown in Table 111. The pain threshold was measured after the animals were put into a cage for measurement of which floor is made of a wire gauze, and acclimatized in the environment for 20 minutes or longer. The measurement of the pain threshold was performed according to the method of Chaplan et al. using 7 of von Frey filaments giving different stimulation intensities, and the 50% pain threshold was calculated by the up-down method of Dixon.

TABLE 111

| EAE score for symptom observation | |
|---|---|
| Score 0 | No abnormality |
| Score 1 | Reduction of tail strain |
| Score 2 | Dragging of tail |
| Score 3 | Abnormal walk |
| Score 4 | Hemiplegia of hind limbs |
| Score 5 | Paraplegia of hind limbs |
| Score 6 | Tetraplegia |
| Score 7 | Near death |
| Score 8 | Death |

The influence of the preventive administration of the compound A to the EAE model rats on the pain threshold is shown in FIG. 3. The repetitive preventive oral administration of the compound A continuously suppressed mechanical allodynia induced by EAE.

Example 5

EAE model rats were prepared by the same method as that of Example 2. Daily basis changes of symptoms, weight, and pain threshold were observed at a frequency of 3 times a week. The compound A was repetitively orally administered twice a day at a dose of 10 mg/kg over 21 days from the day on which average of the EAR scores became 2 or larger (Day 10).

The influence of the therapeutic administration of the compound A to the EAE model rats on the pain threshold is shown in FIG. 4. The repetitive therapeutic oral administration of the compound A suppressed mechanical allodynia induced by EAE.

Example 6

A polystyrene catheter having an external diameter of 0.30 mm was detained in the subarachnoid cavity in each of 10 weeks old LEW/CrlCrlj female rats. After about one week from the detainment of the catheter for administration in the subarachnoid cavity, EAE model rats were prepared by the same method as that of Example 2. Immediately after the preparation of the EAE model rats, an osmotic pressure pump (2ML2, ALZET) filled with the compound B and a medium was detained in each anesthetized rat, and connected with the previously detained catheter. The compound B was continuously administered into the subarachnoid cavity at a dose of 10 nmol/5 µL/hr for about 14 days. Daily basis changes of symptoms, weight, and pain threshold were observed at a frequency of 3 times a week.

The influence of the preventive continuous administration of the compound B to the EAE model rats on the pain threshold is shown in FIG. 5. The preventive continuous administration of the compound B suppressed mechanical allodynia induced by EAE.

What is claimed is:

1. A method of therapeutic treatment of multiple sclerosis, the method comprising administering a medicament which contains a compound having a P2X4 receptor antagonist activity, or a salt thereof, or a hydrate or solvate thereof as an active ingredient, wherein the compound or a salt thereof is a compound selected from the following compounds:

5-(4-benzoylaminophenyl)-1H-naphtho[1,2-b][1,4]diazepine-2,4(3H,5H)-dione;
5-[4-[(2-(trifluoromethyl)benzoyl]aminophenyl]-1H-naphtho[1,2-b][1,4]diazepine-2,4(3H,5H)-dione;
5-[4-(3-bromobenzoyl)aminophenyl]-1H-naphtho[1,2-b][1,4]diazepine-2,4(3H,5H)-dione;
5-[4-[4-(trifluoromethyl)benzoyl]aminophenyl]-1H-naphtho[1,2-b][1,4]diazepine-2,4(3H,5H)-dione;
5-[4-(2-methylbenzoyl)aminophenyl]-1H-naphtho[1,2-b][1,4]diazepine-2,4(3H,5H)-dione;
5-[4-(2,6-dimethylbenzoylamino)phenyl]-1H-naphtho[1,2-b][1,4]diazepine-2,4(3H,5H)-dione;
5-[4-(2,6-dichlorobenzoyl)aminophenyl]-1H-naphtho[1,2-b][1,4]diazepine-2,4(3H,5H)-dione;
5-[4-(3-chlorobenzoyl)aminophenyl]-1H-naphtho[1,2-b][1,4]diazepine-2,4(3H,5H)-dione;
5-[4-(2-phenylacetylamino)phenyl]-1H-naphtho[1,2-b][1,4]diazepine-2,4(3H,5H)-dione;
1-[4-(2,4-dioxo-1,2,3,4-tetrahydronaphtho[1,2-b][1,4]diazepin-5-yl)phenyl]-3-phenylthiourea;
5-[4-(2,3-dimethoxybenzoylamino)phenyl]-1H-naphtho[1,2-b][1,4]diazepine-2,4(3H,5H)-dione;
5-[4-(2-methoxybenzoylamino)phenyl]-1H-naphtho[1,2-b][1,4]diazepine-2,4(3H,5H)-dione;
5-[4-[(2-chlorophenylacetyl)amino]phenyl]-1H-naphtho[1,2-b][1,4]diazepine-2,4(3H,5H)-dione;
5-[4-(2,3-dimethylbenzoylamino)phenyl]-1H-naphtho[1,2-b][1,4]diazepine-2,4(3H,5H)-dione;
5-[4-(2,5-dimethylbenzoylamino)phenyl]-1H-naphtho[1,2-b][1,4]diazepine-2,4(3H,5H)-dione;
5-[4-(5-bromo-2-chlorobenzoylamino)phenyl]-1H-naphtho[1,2-b][1,4]diazepine-2,4(3H,5H)-dione;
5-[4-(2,4-dichlorobenzoylamino)phenyl]-1H-naphtho[1,2-b][1,4]diazepine-2,4(3H,5H)-dione;
5-[4-(2-hydroxybenzoylamino)phenyl]-1H-naphtho[1,2-b][1,4]diazepine-2,4(3H,5H)-dione;
5-[4-(2,3-dihydroxybenzoylamino)phenyl]-1H-naphtho[1,2-b][1,4]diazepine-2,4(3H,5H)-dione;
1-[4-(2,4-dioxo-1,2,3,4-tetrahydronaphtho[1,2-b][1,4]diazepin-5-yl)phenyl]-3-phenylurea;
5-[4-[(2,6-dichlorophenylacetyl)amino]phenyl]-1H-naphtho[1,2-b][1,4]diazepine-2,4(3H,5H)-dione;
5-[4-[(2-methoxyphenylacetyl)amino]phenyl]-1H-naphtho[1,2-b][1,4]diazepine-2,4(3H,5H)-dione;
5-[4-[(2-hydroxyphenylacetyl)amino]phenyl]-1H-naphtho[1,2-b][1,4]diazepine-2,4(3H,5H)-dione;
1-(2-chlorophenyl)-3-[4-(2,4-dioxo-1,2,3,4-tetrahydronaphtho[1,2-b][1,4]diazepin-5-yl)phenyl]thiourea;
5-[4-[3-(trifluoromethyl)benzoylamino]phenyl]-1H-naphtho[1,2-b][1,4]diazepine-2,4(3H,5H)-dione;
5-[4-[2-[(2-trifluoromethyl)phenyl]acetylamino]phenyl]-1H-naphtho[1,2-b][1,4]diazepine-2,4(3H,5H)-dione;
1-(2-chlorophenyl)-3-[4-(2,4-dioxo-1,2,3,4-tetrahydronaphtho[1,2-b][1,4]diazepin-5-yl)phenyl]urea;
5-[4-[(2-phenylpropionyl)amino]phenyl]-1H-naphtho[1,2-b][1,4]diazepine-2,4(3H,5H)-dione;
5-[4-(2-chloro-3-methoxybenzoylamino)phenyl]-1H-naphtho[1,2-b][1,4]diazepine-2,4(3H,5H)-dione;
5-[4-(3-phenylpropionylamino)phenyl]-1H-naphtho[1,2-b][1,4]diazepine-2,4(3H,5H)-dione;
5-[4-[(1H-indole-3-carbonyl)amino]phenyl]-1H-naphtho[1,2-b][1,4]diazepine-2,4(3H,5H)-dione;
5-[4-(2-chloro-3-hydroxybenzoylamino)phenyl]-1H-naphtho[1,2-b][1,4]diazepine-2,4(3H,5H)-dione;
5-[4-[(2-methyl-2-phenylpropionyl)amino]phenyl]-1H-naphtho[1,2-b][1,4]diazepine-2,4(3H,5H)-dione;
5-[4-(2-phenoxyacetylamino)phenyl]-1H-naphtho[1,2-b][1,4]diazepine-2,4(3H,5H)-dione;
5-[4-[2-(2-chloro-4-methoxyphenyl)acetylamino]phenyl]-1H-naphtho[1,2-b][1,4]diazepine-2,4(3H,5H)-dione;
5-[4-[(1-methyl-1H-imidazole-2-carbonyl)amino]phenyl]-1H-naphtho[1,2-b][1,4]diazepine-2,4(3H,5H)-dione;
5-[4-[2-(2,4-dichlorophenyl)acetylamino]phenyl]-1H-naphtho[1,2-b][1,4]diazepine-2,4(3H,5H)-dione;
5-[4-[2-(2-chloro-4-hydroxyphenyl)acetylamino]phenyl]-1H-naphtho[1,2-b][1,4]diazepine-2,4(3H,5H)-dione;
5-[4-(3-phenylpropenylamino)phenyl]-1H-naphtho[1,2-b][1,4]diazepine-2,4(3H,5H)-dione;
5-[4-[(3-pyridylacetyl)amino]phenyl]-1H-naphtho[1,2-b][1,4]diazepine-2,4(3H,5H)-dione hydrochloride;
5-[4-(1H-benzimidazole-2-carbonylamino)phenyl]-1H-naphtho[1,2-b][1,4]diazepine-2,4(3H,5H)-dione;
1-[4-(2,3-dimethylbenzoylamino)phenyl]-7-methoxy-1H-1,5-benzodiazepine-2,4(3H,5H)-dione;
5-[4-[(benzoylamino)methyl]phenyl]-1H-naphtho[1,2-b][1,4]diazepine-2,4(3H,5H)-dione;
5-[4-[(2-chlorobenzoylamino)methyl]phenyl]-1H-naphtho[1,2-b][1,4]diazepine-2,4(3H,5H)-dione;
1-[4-(2,3-dimethylbenzoylamino)phenyl]-7-hydroxy-1H-1,5-benzodiazepine-2,4(3H,5H)-dione;
5-[4-(2-chlorobenzoylamino)phenyl]-1H-naphtho[1,2-b][1,4]diazepine-2,4(3H,5H)-dione;
5-[4-(2-bromobenzoylamino)phenyl]-1H-naphtho[1,2-b][1,4]diazepine-2,4(3H,5H)-dione;
5-[4-(2-iodobenzoylamino)phenyl]-1H-naphtho[1,2-b][1,4]diazepine-2,4(3H,5H)-dione;
5-[4-(2,3-dimethylbenzoylamino)-3-fluorophenyl]-1H-naphtho[1,2-b][1,4]diazepine-2,4(3H,5H)-dione;
5-[4-[2-(2-methylphenyl)acetylamino]phenyl]-1H-naphtho[1,2-b][1,4]diazepine-2,4(3H,5H)-dione;

5-[4-[(quinoxalin-2-yl)carbonylamino]phenyl]-1H-naphtho[1,2-b][1,4]diazepine-2,4(3H,5H)-dione;
5-[4-[(5-methylthiophen-2-yl)carbonylamino]phenyl]-1H-naphtho[1,2-b][1,4]diazepine-2,4(3H,5H)-dione;
5-[3-[(2-chlorophenylacetyl)amino]phenyl]-1H-naphtho[1,2-b][1,4]diazepine-2,4(3H,5H)-dione;
5-[4-[(2,4,6-trimethylbenzoyl)amino]phenyl]-1H-naphtho[1,2-b][1,4]diazepine-2,4(3H,5H)-dione;
5-[4-(cyclohexylcarbonylamino)phenyl]-1,2,3,4,8,9,10,11-octahydronaphtho[1,2-b][1,4]diazepine-2,4(3H,5H)-dione;
1-[4-(2,3-dimethylbenzoyl)aminophenyl]-6-methyl-1H-1,5-benzodiazepine-2,4(3H,5H)-dione;
5-[4-[(2-ethylbenzoyl)amino]phenyl]-1H-naphtho[1,2-b][1,4]diazepine-2,4(3H,5H)-dione;
5-[4-[(6-methylpyridin-2-yl)carbonylamino]phenyl]-1,2,3,4,8,9,10,11-octahydronaphtho[1,2-b][1,4]diazepine-2,4(3H,5H)-dione;
5-[4-[(2-methylpyridin-3-yl)carbonylamino]phenyl]-1,2,3,4,8,9,10,11-octahydronaphtho[1,2-b][1,4]diazepine-2,4(3H,5H)-dione;
1-[4-(2,4-dioxo-1,2,3,4-tetrahydronaphtho[1,2-b][1,4]diazepin-5-yl)phenyl]-3-(2-methylphenyl)thiourea;
5-[4-(2-methoxy-3-methylbenzoyl)aminophenyl]-1,2,3,4,8,9,10,11-octahydronaphtho[1,2-b][1,4]diazepine-2,4(3H,5H)-dione;
5-[4-(2,3-dichlorobenzoyl)aminophenyl]-1,2,3,4,8,9,10,11-octahydronaphtho[1,2-b][1,4]diazepine-2,4(3H,5H)-dione;
5-[4-(2,3-dimethylbenzoylamino)-3-hydroxyphenyl]-1H-naphtho[1,2-b][1,4]diazepine-2,4(3H,5H)-dione;
5-[4-(2-chloro-3-methoxybenzoylamino)phenyl]-1,3-dihydronaphtho[1,2-e]-1,4-diazepin-2-one;
5-[4-[(4-dimethylaminobenzoyl)amino]phenyl]-1H-naphtho[1,2-b][1,4]diazepine-2,4(3H,5H)-dione;
5-[4-[2-(2,4-dichlorophenoxy)acetylamino]phenyl]-1H-naphtho[1,2-b][1,4]diazepine-2,4(3H,5H)-dione;
5-[4-[2-(2-methylphenoxy)acetylamino]phenyl]-1H-naphtho[1,2-b][1,4]diazepine-2,4(3H,5H)-dione;
N-[4-(2,4-dioxo-1,2,3,4-tetrahydronaphtho[1,2-b][1,4]diazepin-5-yl)butyl]-2-chloro-3-methoxybenzamide;
5-[4-(2-chloro-3-hydroxybenzoylamino)phenyl]-1,3-dihydronaphtho[1,2-e]-1,4-diazepin-2-one;
5-[4-(2-acetylbenzoylamino)phenyl]-1H-naphtho[1,2-b][1,4]diazepine-2,4(3H,5H)-dione;
5-[4-(2-tert-butylbenzoylamino)phenyl]-1H-naphtho[1,2-b][1,4]diazepine-2,4(3H,5H)-dione;
5-[2-(2-iodobenzoyl)aminoethyl]-1H-naphtho[1,2-b][1,4]diazepine-2,4(3H,5H)-dione;
5-[3-[(2-iodobenzoyl)amino]phenyl]-1H-naphtho[1,2-b][1,4]diazepine-2,4(3H,5H)-dione;
6,7-dimethyl-1-[4-(2-iodobenzoyl)aminophenyl]-1H-1,5-benzodiazepine-2,4(3H,5H)-dione;
5-[4-[(1-methylpiperidin-4-yl)carbonylamino]phenyl]-1H-naphtho[1,2-b][1,4]diazepine-2,4(3H,5H)-dione hydrochloride;
5-[4-[(benzofuran-2-yl)carbonylamino]phenyl]-1H-naphtho[1,2-b][1,4]diazepine-2,4(3H,5H)-dione;
5-[4-[(1-methyl-1H-indol-3-yl)carbonylamino]phenyl]-1H-naphtho[1,2-b][1,4]diazepine-2,4(3H,5H)-dione;
5-[4-(2-propenylbenzoylamino)phenyl]-1H-naphtho[1,2-b][1,4]diazepine-2,4(3H,5H)-dione;
5-[4-(2-propylbenzoylamino)phenyl]-1H-naphtho[1,2-b][1,4]diazepine-2,4(3H,5H)-dione;
5-[3-fluoro-4-(2-iodobenzoylamino)phenyl]-1H-naphtho[1,2-b][1,4]diazepine-2,4(3H,5H)-dione;
5-[4-(2-hydroxy-3-methylbenzoyl)aminophenyl]-1,2,3,4,8,9,10,11-octahydronaphtho[1,2-b][1,4]diazepine-2,4(3H,5H)-dione;
5-[4-[(2-isopropoxybenzoyl)amino]phenyl]-1H-naphtho[1,2-b][1,4]diazepine-2,4(3H,5H)-dione;
5-[4-[(3-methylthiophen-2-yl)carbonylamino]phenyl]-1H-naphtho[1,2-b][1,4]diazepine-2,4(3H,5H)-dione;
5-[4-(2-phenoxypropionylamino)phenyl]-1H-naphtho[1,2-b][1,4]diazepine-2,4(3H,5H)-dione;
5-[4-[2-(4-chloro-2-methylphenoxy)acetylamino]phenyl]-1H-naphtho[1,2-b][1,4]diazepine-2,4(3H,5H)-dione;
5-[4-(4-fluoro-2-trifluoromethylbenzoyl)aminophenyl]-1H-naphtho[1,2-b][1,4]diazepine-2,4(3H,5H)-dione;
5-[4-(4-fluoro-2-methoxybenzoyl)aminophenyl]-1H-naphtho[1,2-b][1,4]diazepine-2,4(3H,5H)-dione;
5-[4-(4-fluoro-2-hydroxybenzoyl)aminophenyl]-1H-naphtho[1,2-b][1,4]diazepine-2,4(3H,5H)-dione;
5-[3-[(2-iodophenylacetyl)amino]phenyl]-1H-naphtho[1,2-b][1,4]diazepine-2,4(3H,5H)-dione;
5-[4-(2-methyl-2-phenoxypropionylamino)phenyl]-1H-naphtho[1,2-b][1,4]diazepine-2,4(3H,5H)-dione;
5-[4-(2-tert-butylbenzoylamino)phenyl]-1,3-dihydronaphtho[1,2-e]-1,4-diazepin-2-one;
5-[4-[(3-dimethylaminobenzoyl)amino]phenyl]-1H-naphtho[1,2-b][1,4]diazepine-2,4(3H,5H)-dione;
5-[4-(4-iodo-2-methoxybenzoylamino)phenyl]-1H-naphtho[1,2-b][1,4]diazepine-2,4(3H,5H)-dione;
5-[4-(6-fluoro-2-methoxybenzoylamino)phenyl]-1H-naphtho[1,2-b][1,4]diazepine-2,4(3H,5H)-dione;
5-[4-(2-hydroxy-4-iodobenzoylamino)phenyl]-1H-naphtho[1,2-b][1,4]diazepine-2,4(3H,5H)-dione;
5-[4-(6-fluoro-2-hydroxyamino)phenyl]-1H-naphtho[1,2-b][1,4]diazepine-2,4(3H,5H)-dione;
5-[4-(2-fluorobenzoyl)aminophenyl]-1H-naphtho[1,2-b][1,4]diazepine-2,4(3H,5H)-dione;
5-[4-[(2-dimethylaminobenzoyl)amino]phenyl]-1H-naphtho[1,2-b][1,4]diazepine-2,4(3H,5H)-dione;
5-[4-(2-methoxy-6-methylbenzoylamino)phenyl]-1H-naphtho[1,2-b][1,4]diazepine-2,4(3H,5H)-dione;
5-[4-(2-hydroxy-6-methylbenzoylamino)phenyl]-1H-naphtho[1,2-b][1,4]diazepine-2,4(3H,5H)-dione;
5-[4-[3-(2-methylphenyl)propionylamino]phenyl]-1H-naphtho[1,2-b][1,4]diazepine-2,4(3H,5H)-dione;
5-(4-phenylcarbamoylphenyl)-1H-naphtho[1,2-b][1,4]diazepine-2,4(3H,5H)-dione;
5-(4-benzylcarbamoylphenyl)-1H-naphtho[1,2-b][1,4]diazepine-2,4(3H,5H)-dione;
5-[4-[3-(2-methylphenyl)propenoylamino]phenyl]-1H-naphtho[1,2-b][1,4]diazepine-2,4(3H,5H)-dione;
5-[4-[3-(2-chlorophenyl)propionylamino]phenyl]-1H-naphtho[1,2-b][1,4]diazepine-2,4(3H,5H)-dione;
5-[4-(2-iodobenzoyl)aminophenyl]-1,2,3,4,8,9,10,11-octahydronaphtho[1,2-b][1,4]diazepine-2,4(3H,5H)-dione;
5-[4-[(1-methyl-1H-pyrrol-2-yl)acetyl)amino]phenyl]-1,2,3,4,8,9,10,11-octahydronaphtho[1,2-b][1,4]diazepine-2,4(3H,5H)-dione;
5-[4-(2-chlorobenzyl)carbamoylphenyl]-1H-naphtho[1,2-b][1,4]diazepine-2,4(3H,5H)-dione;
5-[4-[3-(2-chlorophenyl)propenoylamino]phenyl]-1H-naphtho[1,2-b][1,4]diazepine-2,4(3H,5H)-dione;
5-[4-(2-chlorophenyl)carbamoylphenyl]-1H-naphtho[1,2-b][1,4]diazepine-2,4(3H,5H)-dione;
5-[4-(6-bromo-2,3-methylenedioxybenzoylamino)phenyl]-1H-naphtho[1,2-b][1,4]diazepine-2,4(3H,5H)-dione;

5-[4-(6-bromo-2-methoxybenzoylamino)phenyl]-1H-naphtho[1,2-b][1,4]diazepine-2,4(3H,5H)-dione;
5-[4-[(2-tert-butylbenzoyl)amino]phenyl]-1,2,3,4,8,9,10,11-octahydronaphtho[1,2-b][1,4]diazepine-2,4(3H,5H)-dione;
5-[2-(2-iodobenzoyl)aminopyridin-5-yl]-1H-naphtho[1,2-b][1,4]diazepine-2,4(3H,5H)-dione;
5-[4-(6-bromo-2-hydroxybenzoylamino)phenyl]-1H-naphtho[1,2-b][1,4]diazepine-2,4(3H,5H)-dione;
5-[4-(6-chloro-2-methoxybenzoylamino)phenyl]-1H-naphtho[1,2-b][1,4]diazepine-2,4(3H,5H)-dione;
5-[4-(2-iodobenzoylamino)phenyl]-1H-[1,4]diazepino[2,3-h]quinoline-2,4(3H,5H)-dione;
5-[4-(6-chloro-2-hydroxybenzoylamino)phenyl]-1H-naphtho[1,2-b][1,4]diazepine-2,4(3H,5H)-dione;
5-[4-(2-hydroxy-6-methoxybenzoylamino)phenyl]-1H-naphtho[1,2-b][1,4]diazepine-2,4(3H,5H)-dione;
5-[4-[2-methoxy-6-(trifluoromethyl)benzoylamino]phenyl]-1H-naphtho[1,2-b][1,4]diazepine-2,4(3H,5H)-dione;
5-[4-[2-hydroxy-6-(trifluoromethyl)benzoylamino]phenyl]-1H-naphtho[1,2-b][1,4]diazepine-2,4(3H,5H)-dione;
5-[4-[(2-isopropenylbenzoyl)amino]phenyl]-1,2,3,4,8,9,10,11-octahydronaphtho[1,2-b][1,4]diazepine-2,4(3H,5H)-dione;
5-[4-[(2-isopropylbenzoyl)amino]phenyl]-1,2,3,4,8,9,10,11-octahydronaphtho[1,2-b][1,4]diazepine-2,4(3H,5H)-dione;
5-[4-[2-chloro-5-(methylthio)benzoylamino]phenyl]-1H-naphtho[1,2-b][1,4]diazepine-2,4(3H,5H)-dione;
5-[4-[2-(methylthio)benzoylamino]phenyl]-1H-naphtho[1,2-b][1,4]diazepine-2,4(3H,5H)-dione;
5-[4-[3-(methylthio)benzoylamino]phenyl]-1H-naphtho[1,2-b][1,4]diazepine-2,4(3H,5H)-dione;
5-[4-[2-ethyl-6-methoxybenzoylamino]phenyl]-1H-naphtho[1,2-b][1,4]diazepine-2,4(3H,5H)-dione;
5-[4-(3-methanesulfonylbenzoylamino)phenyl]-1H-naphtho[1,2-b][1,4]diazepine-2,4(3H,5H)-dione;
6-ethyl-1-[4-(2-iodobenzoyl)aminophenyl]-1H-1,5-benzodiazepine-2,4(3H,5H)-dione;
5-[4-[2-ethyl-6-hydroxybenzoylamino]phenyl]-1H-naphtho[1,2-b][1,4]diazepine-2,4(3H,5H)-dione;
5-[4-(3-methanesulfinylbenzoylamino)phenyl]-1H-naphtho[1,2-b][1,4]diazepine-2,4(3H,5H)-dione;
5-[4-(2-chloro-5-methanesulfinylbenzoylamino)phenyl]-1H-naphtho[1,2-b][1,4]diazepine-2,4(3H,5H)-dione;
5-[4-(2-methanesulfinylbenzoylamino)phenyl]-1H-naphtho[1,2-b][1,4]diazepine-2,4(3H,5H)-dione;
5-[4-[[2-(4-morpholinyl)acetyl]amino]phenyl]-1,2,3,4,8,9,10,11-octahydronaphtho[1,2-b][1,4]diazepine-2,4(3H,5H)-dione hydrochloride;
5-[4-(2-chloro-6-methoxybenzoylamino)phenyl]-1,3-dihydronaphtho[1,2-e]-1,4-diazepin-2-one;
5-[4-[[(3-chloropyridin-2-yl)carbonyl]amino]phenyl]-1H-naphtho[1,2-b][1,4]diazepine-2,4(3H,5H)-dione;
5-[4-(2-chloro-6-hydroxybenzoylamino)phenyl]-1,3-dihydronaphtho[1,2-e]-1,4-diazepin-2-one;
5-[4-(3-chloro-2-methoxybenzoylamino)phenyl]-1H-naphtho[1,2-b][1,4]diazepine-2,4(3H,5H)-dione;
5-[4-[(3-methylpyridin-2-yl)carbonylamino]phenyl]-1H-naphtho[1,2-b][1,4]diazepine-2,4(3H,5H)-dione;
5-[4-[[(3-chloropyridin-2-yl)carbonyl]amino]phenyl]-1,2,3,4,8,9,10,11-octahydronaphtho[1,2-b][1,4]diazepine-2,4(3H,5H)-dione;
5-[4-(3-chloro-2-hydroxybenzoylamino)phenyl]-1H-naphtho[1,2-b][1,4]diazepine-2,4(3H,5H)-dione;
5-[4-[[(3-hydroxypyridin-2-yl)carbonyl]amino]phenyl]-1H-naphtho[1,2-b][1,4]diazepine-2,4(3H,5H)-dione;
5-[4-[(3-vinylpyridin-2-yl)carbonylamino]phenyl]-1H-naphtho[1,2-b][1,4]diazepine-2,4(3H,5H)-dione;
5-[4-[(3-ethylpyridin-2-yl)carbonylamino]phenyl]-1H-naphtho[1,2-b][1,4]diazepine-2,4(3H,5H)-dione;
N-[4-(2,4-dioxo-1,2,3,4-tetrahydronaphtho[1,2-b][1,4]diazepin-5-yl)phenyl]-2-nitrobenzenesulfonamide;
N-[4-(2,4-dioxo-1,2,3,4-tetrahydronaphtho[1,2-b][1,4]diazepin-5-yl)phenyl]benzenesulfonamide;
3-bromo-N-[4-(2,4-dioxo-1,2,3,4-tetrahydronaphtho[1,2-b][1,4]diazepin-5-yl)phenyl]benzenesulfonamide;
N-[4-(2,4-dioxo-1,2,3,4-tetrahydronaphtho[1,2-b][1,4]diazepin-5-yl)phenyl]-3-methoxybenzenesulfonamide;
N-[3-(2-oxo-2,3-dihydro-1H-naphtho[1,2-e][1,4]diazepin-5-yl)phenyl]benzenesulfonamide;
N-[3-(2,4-dioxo-1,2,3,4-tetrahydronaphtho[1,2-b][1,4]diazepin-5-yl)phenyl]-2-nitrobenzenesulfonamide;
N-[4-(2,4-dioxo-1,2,3,4,8,9,10,11-octahydronaphtho[1,2-b][1,4]diazepin-5-yl)phenyl]-2-nitrobenzenesulfonamide;
N-[4-(2,4-dioxo-1,2,3,4,8,9,10,11-octahydronaphtho[1,2-b][1,4]-diazepin-5-yl)phenyl]-N-methyl-2-nitrobenzenesulfonamide;
N-[3-(2,4-dioxo-1,2,3,4-tetrahydronaphtho[1,2-b][1,4]diazepin-5-yl)phenyl]-N-methyl-2-nitrobenzenesulfonamide;
4-(2,4-dioxo-1,2,3,4,8,9,10,11-octahydronaphtho[1,2-b][1,4]diazepin-5-yl)-N-phenylbenzenesulfonamide;
N-[3-(2,4-dioxo-1,2,3,4-tetrahydronaphtho[1,2-b][1,4]diazepin-5-yl)phenyl]-2-naphthalenesulfonamide;
N-[3-(2,4-dioxo-1,2,3,4-tetrahydronaphtho[1,2-b][1,4]diazepin-5-yl)phenyl]-1-naphthalenesulfonamide;
N-[4-(2,4-dioxo-1,2,3,4-tetrahydronaphtho[1,2-b][1,4]diazepin-5-yl)phenyl]cyclohexanesulfonamide;
N-[4-(2,4-dioxo-1,2,3,4-tetrahydronaphtho[1,2-b][1,4]diazepin-5-yl)phenyl]-3-pyridinesulfonamide hydrochloride;
N-[4-(2,4-dioxo-1,2,3,4-tetrahydronaphtho[1,2-b][1,4]diazepin-5-yl)phenyl]-4-isopropylbenzenesulfonamide;
N-[4-(2,4-dioxo-1,2,3,4-tetrahydronaphtho[1,2-b][1,4]diazepin-5-yl)phenyl]phenylmethanesulfonamide;
N-[4-(2,4-dioxo-1,2,3,4-tetrahydronaphtho[1,2-b][1,4]diazepin-5-yl)phenyl]-3-pyridinesulfonamide;
N-[4-(2,4-dioxo-1,2,3,4-tetrahydronaphtho[1,2-b][1,4]diazepin-5-yl)phenyl]-2-naphthalenesulfonamide;
4-(2,4-dioxo-1,2,3,4,8,9,10,11-octahydronaphtho[1,2-b][1,4]diazepin-5-yl)phenyl 3-bromobenzenesulfonate;
N-benzyl-N-[4-(1-benzyl-2,4-dioxo-1,2,3,4-tetrahydronaphtho[1,2-b][1,4]diazepin-5-yl)phenyl]-2-nitrobenzenesulfonamide;
N-benzyl-N-[4-(2,4-dioxo-1,2,3,4-tetrahydronaphtho[1,2-b][1,4]diazepin-5-yl)phenyl]-2-nitrobenzenesulfonamide;
3-bromo-N-[4-(2,4-dioxo-1,2,3,4-tetrahydronaphtho[1,2-b][1,4]diazepin-5-yl)phenyl]-N-methylbenzenesulfonamide;
N-[4-(2,4-dioxo-1,2,3,4-tetrahydronaphtho[1,2-b][1,4]diazepin-5-yl)phenyl]-N-methyl-2-nitrobenzenesulfonamide;
N-[4-(2,4-dioxo-1,2,3,4-tetrahydronaphtho[1,2-b][1,4]diazepin-5-yl)phenyl]-N-(2-hydroxyethyl)-2-nitrobenzenesulfonamide;
N-[4-(7-chloro-2,4-dioxo-2,3,4,5-tetrahydro-1H-benzo[b][1,4]diazepin-1-yl)phenyl]benzenesulfonamide;
N-[4-(7-bromo-2,4-dioxo-2,3,4,5-tetrahydro-1H-benzo[b][1,4]diazepin-1-yl)phenyl]benzenesulfonamide;

N-[4-[(2,4-dioxo-7-(trifluoromethyl)-2,3,4,5-tetrahydro-1H-benzo[b][1,4]diazepin-1-yl)]phenyl]benzenesulfonamide;

N-[4-(2,4-dioxo-2,3,4,5-tetrahydro-1H-benzo[b][1,4]diazepin-1-yl)phenyl]benzenesulfonamide;

1-(2-chlorophenyl)-N-[4-(2,4-dioxo-1,2,3,4-tetrahydronaphtho[1,2-b][1,4]diazepin-5-yl)phenyl]methanesulfonamide;

1-(3-bromophenyl)-N-[4-(2,4-dioxo-1,2,3,4-tetrahydronaphtho[1,2-b][1,4]diazepin-5-yl)phenyl]methanesulfonamide;

N-[4-(2,4-dioxo-1,2,3,4-tetrahydronaphtho[1,2-b][1,4]diazepin-5-yl)phenyl]-2-trifluoromethylbenzenesulfonamide;

N-[4-(7-bromo-6-methyl-2,4-dioxo-2,3,4,5-tetrahydro-1H-benzo[b][1,4]diazepin-1-yl)phenyl]benzenesulfonamide;

1-(2-chlorophenyl)-N-[4-(2,4-dioxo-1,2,3,4,8,9,10,11-octahydronaphtho[1,2-b][1,4]diazepin-5-yl)phenyl]methanesulfonamide;

3-bromo-N-[4-(2,4-dioxo-1,2,3,4,8,9,10,11-octahydronaphtho[1,2-b][1,4]diazepin-5-yl)phenyl]benzenesulfonamide;

N-[4-(2,4-dioxo-1,2,3,4,8,9,10,11-octahydronaphtho[1,2-b][1,4]diazepin-5-yl)phenyl]-3-methoxybenzenesulfonamide;

1-(2-bromophenyl)-N-[4-(2,4-dioxo-1,2,3,4-tetrahydronaphtho[1,2-b][1,4]diazepin-5-yl)phenyl]methanesulfonamide;

N-[4-(2,4-dioxo-1,2,3,4-tetrahydronaphtho[1,2-b][1,4]diazepin-5-yl)phenyl]-1-(2-methylphenyl)methanesulfonamide;

N-[4-(2,4-dioxo-1,2,3,4-tetrahydronaphtho[1,2-b][1,4]diazepin-5-yl)phenyl]-1-(2-nitrophenyl)methanesulfonamide;

N-[4-(2,4-dioxo-1,2,3,4-tetrahydronaphtho[1,2-b][1,4]diazepin-5-yl)phenyl]-2-phenylethanesulfonamide;

1-(2,3-dichlorophenyl)-N-[4-(2,4-dioxo-1,2,3,4,8,9,10,11-octahydronaphtho[1,2-b][1,4]diazepin-5-yl)phenyl]methanesulfonamide;

1-(2-chlorophenyl)-N-[4-(2,4-dioxo-7-methoxy-1H-benzo[1,2-b][1,4]diazepin-1-yl)phenyl]methanesulfonamide;

1-(2-chlorophenyl)-N-[4-(2,4-dioxo-7-hydroxy-1H-benzo[1,2-b][1,4]diazepin-1-yl)phenyl]methanesulfonamide;

1-(4-chlorophenyl)-N-[4-(2,4-dioxo-1,2,3,4-tetrahydronaphtho[1,2-b][1,4]diazepin-5-yl)phenyl]methanesulfonamide;

1-(2-chlorophenyl)-N-[4-(2,4-dioxo-1,2,3,4-tetrahydronaphtho[1,2-b][1,4]diazepin-5-yl)benzyl]methanesulfonamide;

1-(2-chlorophenyl)-N-[4-(2,4-dioxo-1,2,3,4-tetrahydronaphtho[1,2-b][1,4]diazepin-5-yl)-2-methoxyphenyl]methanesulfonamide;

1-(2-chlorophenyl)-N-[4-(2,4-dioxo-1,2,3,4-tetrahydronaphtho[1,2-b][1,4]diazepin-5-yl)-2-hydroxyphenyl]methanesulfonamide;

1-(2,6-dichlorophenyl)-N-[4-(2,4-dioxo-1,2,3,4,8,9,10,11-octahydronaphtho[1,2-b][1,4]diazepin-5-yl)phenyl]methanesulfonamide;

1-(2-chlorophenyl)-N-[4-(2,4-dioxo-6-methyl-1H-benzo[1,2-b][1,4]diazepin-1-yl)phenyl]methanesulfonamide;

1-(2-chlorophenyl)-N-[4-(2,4-dioxy-1,2,3,4-tetrahydronaphtho[1,2-b][1,4]diazepin-5-yl)propyl]methanesulfonamide;

1-(2-chlorophenyl)-N-[2-(2,4-dioxo-1,2,3,4-tetrahydronaphtho[1,2-b][1,4]diazepin-5-yl)ethyl]methanesulfonamide;

N-[4-(2,4-dioxo-1,2,3,4,8,9,10,11-octahydronaphtho[1,2-b][1,4]diazepin-5-yl)phenyl]-1-(2-iodophenyl)methanesulfonamide;

1-(2-chlorophenyl)-N-[4-(2,4-dioxo-1,2,3,4,8,9,10,11-octahydronaphtho[1,2-b][1,4]diazepin-5-yl)phenyl]-N-methylmethanesulfonamide;

1-(2-chlorophenyl)-N-[4-(2-oxo-2,3-dihydro-1H-naphtho[1,2-e][1,4]diazepin-5-yl)phenyl]methanesulfonamide;

1-[(2-trifluoromethyl)phenyl]-N-[4-(2,4-dioxo-1,2,3,4-tetrahydronaphtho[1,2-b][1,4]diazepin-5-yl)phenyl]phenyl-N-methylmethanesulfonamide;

1-(2-ethylphenyl)-N-[4-(2,4-dioxo-1,2,3,4-tetrahydronaphtho[1,2-b][1,4]diazepin-5-yl)phenyl]phenyl-N-methylmethanesulfonamide;

1-(2,3-dimethylphenyl)-N-[4-(2,4-dioxo-1,2,3,4-tetrahydronaphtho[1,2-b][1,4]diazepin-5-yl)phenyl]phenyl-N-methylmethanesulfonamide;

2-(2-chlorophenyl)-N-[4-(2,4-dioxo-1,2,3,4-tetrahydronaphtho[1,2-b][1,4]diazepin-5-yl)phenyl]phenyl-N-methylethanesulfonamide;

1-(2-nitrophenyl)-N-[4-(2,4-dioxo-1,2,3,4-tetrahydronaphtho[1,2-b][1,4]diazepin-5-yl)phenyl]phenyl-N-methylmethanesulfonamide;

1-(2-aminophenyl)-N-[4-(2,4-dioxo-1,2,3,4-tetrahydronaphtho[1,2-b][1,4]diazepin-5-yl)phenyl]phenyl-N-methylmethanesulfonamide;

1-(2-dimethylaminophenyl)-N-[4-(2,4-dioxo-1,2,3,4-tetrahydronaphtho[1,2-b][1,4]diazepin-5-yl)phenyl]phenyl-N-methylmethanesulfonamide;

5-[4-[(pyridin-4-yl)carbonylamino]phenyl]-1H-naphtho[1,2-b][1,4]diazepine-2,4(3H,5H)-dione hydrochloride;

5-[4-[2-[(pyridin-3-yl)oxy]acetylamino]phenyl]-1H-naphtho[1,2-b][1,4]diazepine-2,4(3H,5H)-dione hydrochloride;

5-[4-[(pyridin-3-yl)carbonylamino]phenyl]-1H-naphtho[1,2-b][1,4]diazepine-2,4(3H,5H)-dione hydrochloride;

5-[4-[(2-methylpyridin-3-yl)carbonylamino]phenyl]-1H-naphtho[1,2-b][1,4]diazepine-2,4(3H,5H)-dione hydrochloride;

5-[4-[(2-chloropyridin-3-yl)carbonylamino]phenyl]-1H-naphtho[1,2-b][1,4]diazepine-2,4(3H,5H)-dione;

5-[4-[2-[(pyridin-2-yl)oxy]acetylamino]phenyl]-1H-naphtho[1,2-b][1,4]diazepine-2,4(3H,5H)-dione;

5-[4-[[4-(trifluoromethyl)pyridin-3-yl]carbonylamino]phenyl]-1H-naphtho[1,2-b][1,4]diazepine-2,4(3H,5H)-dione;

5-[4-[(2-chloropyridin-3-yl)carbonylamino]phenyl]-1H-[1,4]diazepino[2,3-f]isoquinoline-2,4(3H,5H)-dione;

5-[4-[(2-chloropyridin-3-yl)carbonylamino]phenyl]-8,9,10,11-tetrahydro-1H-[1,4]diazepino[2,3-f]isoquinoline-2,4(3H,5H)-dione;

5-[4-[(2-isopropylbenzoyl)amino]phenyl]-1H-naphtho[1,2-b][1,4]diazepine-2,4(3H,5H)-dione;

N-[4-(2-oxo-2,3-dihydro-1H-naphtho[1,2-e][1,4]-diazepin-5-yl)phenyl]-3-(pyridin-2-yl)propionic acid amide;

2-ethyl-3-hydroxy-N-[4-(2-oxo-2,3-dihydro-1H-naphtho[1,2-e][1,4]-diazepin-5-yl)phenyl]benzamide;

2-ethyl-N-[4-(2-oxo-2,3-dihydro-1H-naphtho[1,2-e][1,4]-diazepin-5-yl)phenyl]nicotinamide dihydrochloride;

2-ethyl-6-hydroxy-N-[4-(2-oxo-2,3-dihydro-1H-naphtho[1,2-e][1,4]-diazepin-5-yl)phenyl]benzamide;

3-ethyl-N-[4-(2-oxo-2,3-dihydro-1H-naphtho[1,2-e][1,4]-diazepin-5-yl)phenyl]picolinamide hydrochloride;
N-[4-(2-oxo-2,3-dihydro-1H-naphtho[1,2-e][1,4]-diazepin-5-yl)phenyl]-2-(pyridin-2-yloxy)acetamide hydrochloride;
2-(2-methoxyphenyl)-N-[4-(2-oxo-2,3-dihydro-1H-naphtho[1,2-e][1,4]diazepin-5-yl)phenyl]acetamide;
N-[4-(2-oxo-2,3-dihydro-1H-naphtho[1,2-e][1,4]diazepin-5-yl)-phenyl]-3-(pyridin-3-yl)propionamide dihydrochloride;
N-[4-(2-oxo-2,3-dihydro-1H-naphtho[1,2-e][1,4]diazepin-5-yl)phenyl]-3-phenylpropanamide;
N-[4-(2,4-dioxo-3,4-dihydro-1H-naphtho[1,2-b][1,4]diazepin-5(2H)-yl)-phenyl]-3-(pyridin-3-yl)propionamide hydrochloride;
N-[4-(2,4-dioxo-3,4-dihydro-1H-naphtho[1,2-b][1,4]diazepin-5(2H)-yl)-phenyl]-3-(pyridin-4-yl)propionamide hydrochloride;
2-tert-butyl-N-[4-(2,4-dioxo-3,4-dihydro-1H-naphtho[1,2-b][1,4]diazepin-5(2H)-yl)-2-fluorophenyl]benzamide;
N-[4-(2,4-dioxo-3,4-dihydro-1H-naphtho[1,2-b][1,4]diazepin-5(2H)-yl)-phenyl]-3-(pyridin-2-yl)propionamide hydrochloride;
2-(dimethylamino)-N-[4-(2,4-dioxo-2,3-dihydro-1H-naphtho[1,2-b][1,4]diazepin-5(2H)-yl)phenyl]nicotinamide hydrochloride;
2-(dimethylamino)-N-[4-(2-oxo-2,3-dihydro-1H-naphtho[1,2-e][1,4]diazepin-5-yl)phenyl]nicotinamide dihydrochloride;
2-(dimethylamino)-N-[4-(2-oxo-2,3-dihydro-1H-naphtho[1,2-e][1,4]diazepin-5-yl)phenyl]nicotinamide dihydrochloride;
2-(dimethylamino)-N-[4-(2-oxo-2,3-dihydro-1H-naphtho[1,2-e][1,4]diazepin-5-yl)phenyl]nicotinamide dimethanesulfonate;
N-[4-(2,4-dioxo-3,4-dihydro-1H-naphtho[1,2-b][1,4]-diazepin-5(2H)-yl)phenyl]-2-(morpholin-4-yl)nicotinamide hydrochloride;
N-[4-(2-oxo-2,3-dihydro-1H-naphtho[1,2-e][1,4]-diazepin-5-yl)phenyl]-2-(1H-pyrrol-1-yl)nicotinamide dihydrochloride;
2-(morpholin-4-yl)-N-[4-(2-oxo-2,3-dihydro-1H-naphtho[1,2-e][1,4]-diazepin-5-yl)phenyl]nicotinamide dihydrochloride;
N-[4-(2-oxo-2,3-dihydro-1H-naphtho[1,2-e][1,4]-diazepin-5-yl)phenyl]-2-(pyrrolidin-1-yl)nicotinamide dihydrochloride;
4-(dimethylamino)-N-[4-(2-oxo-2,3-dihydro-1H-naphtho[1,2-e][1,4]diazepin-5-yl)phenyl]nicotinamide dihydrochloride;
2-isopropyl-N-[4-(2-oxo-2,3-dihydro-1H-naphtho[1,2-e][1,4]diazepin-5-yl)phenyl]nicotinamide dihydrochloride; and
2-(isopropylamino)-N-[4-(2-oxo-2,3-dihydro-1H-naphtho[1,2-e][1,4]diazepin-5-yl)phenyl]nicotinamide dihydrochloride.

2. A method of therapeutic treatment of multiple sclerosis, the method comprising administering a medicament which contains a compound having P2X4 receptor antagonist activity, or a salt thereof, or a hydrate or solvate thereof as an active ingredient, wherein the cpmpound is a compound represented by the following the general formula (IE):

[Formula 16]

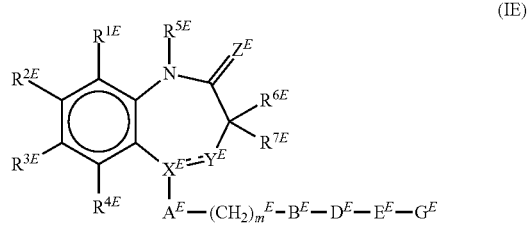

(IE)

wherein, in the formula, $R^{1E}$ and $R^{2E}$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group wherein the alkoxy group contains has 1 to 8 carbon atoms, a phenyl group which can have a substituent, a pyridyl group which can have a substituent, or an aralkyl group wherein the aryl group contains 6 to 10 carbon atoms and the alkylene group contains 1 to 8 carbon atoms, or $R^{1E}$ and $R^{2E}$ can bind together to form a condensed ring selected from naphthalene ring, quinoline ring, isoquinoline ring, tetrahydronaphthalene ring, indane ring, tetrahydroquinoline ring, and tetrahydroisoquinoline ring together with the benzene ring to which they bind, and the ring formed by $R^{1E}$, $R^{2E}$ binding together, and the carbon atoms to which $R^{1E}$ and $R^{2E}$ bind may be substituted with 1 to 4 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group wherein the alkoxy group contains 1 to 8 carbon atoms, and an aralkyl group wherein the aryl group contains 6 to 10 carbon atoms and the alkylene group contains 1 to 8 carbon atoms, $R^{3E}$ and $R^{4E}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group wherein the alkoxy group contains 1 to 8 carbon atoms, or an aralkyl group wherein the aryl group contains 6 to 10 carbon atoms and the alkylene group contains 1 to 8 carbon atoms, $R^{5E}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group wherein the aryl group contains 6 to 10 carbon atoms and the alkylene group contains 1 to 8 carbon atoms, $R^{6E}$ and $R^{7E}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, or amino group, $X^E$ represents C, CH, or N, $Y^E$ represents N, NH, or C(=O), provided that when $X^E$ is N, $Y^E$ is not N or NH, and when $X^E$ is C or CH, $Y^E$ is not C(=O), the double line consisting of the solid line and the broken line represents a single bond or a double bond, $Z^E$ represents oxygen atom or sulfur atom, $A^E$ represents benzene ring, pyridine ring, thiophene ring, pyrimidine ring, naphthalene ring, quinoline ring, or indole ring which can have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group wherein the aryl group contains 6 to 10 carbon atoms and the alkylene group contains 1 to 8 carbon atoms, phenyl group, and pyridyl group, or an atomic bond, $B^E$ represents $N(R^{8E})C(=O)$, NHCONH, $CON(R^{9E})$, NHC(=S)NH, $N(R^{10E})SO_2$, $SO_2N(R^{11E})$, or $OSO_2$, wherein $R^{8E}$, $R^{9E}$, $R^{10E}$, and $R^{11E}$ represent hydrogen atom, an alkyl group having 1 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group wherein the aryl group contains 6 to 10 carbon atoms and the alkylene group contains 1 to 8 carbon atoms, $D^E$ represents an alkylene chain having 1 to 6 carbon atoms which can have 1 to 4 of the same or different substituents selected from an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group wherein the aryl group contains 6 to 10 carbon atoms and the alkylene group contains 1 to 8 carbon atoms, and may further contain a double bond, or an atomic bond, $E^E$ represents O, S, $NR^{12E}$, or an atomic bond, wherein $R^{12E}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group wherein the aryl group contains has 6 to 10 carbon atoms and the alkylene group contains 1 to 8 carbon atoms, $G^E$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine which can have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, an alkylsulfonyl group having 1 to 6 carbon atoms, an aralkyl group wherein the aryl group contains 6 to 10 carbon atoms and the alkylene group contains 1 to 8 carbon atoms, a phenyl group which can have a substituent, a pyridyl group which can have a substituent, an imidazolyl group which can have a substituent, an oxazolyl group can have a substituent, and a thiazolyl group which can have a substituent, and $m^E$ represents an integer of 0 to 5, provided that compounds where $R^{1E}$ and $R^{2E}$ do not bind together to form a ring, $X^E$ is C, $Y^E$ is N, the double line consisting of the solid line and the broken line is a double bond, $Z^E$ is oxygen atom, $A^E$ is a benzene ring, $m^E$ is 0, $B^E$ is C(=O)NH, $E^E$ is an atomic bond, and $G^E$ is phenyl group are excluded.

3. The method according to claim 1, wherein the compound is a compound represented by the following the general formula (IIE):

[Formula 17]

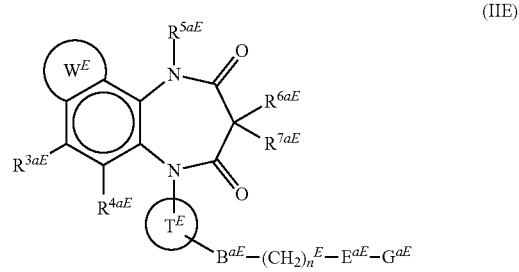

(IIE)

wherein, in the formula,

[Formula 18]

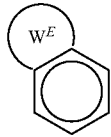

represents naphthalene ring, quinoline ring, isoquinoline ring, tetrahydronaphthalene ring, indane ring, tetrahydroquinoline ring, or tetrahydroisoquinoline ring, and these rings may be substituted with 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group wherein the alkoxy group contains 1 to 8 carbon atoms, and an aralkyl group wherein the aryl group contains 6 to 10 carbon atoms and the alkylene group contains has 1 to 8 carbon atoms, $R^{3aE}$ and $R^{4aE}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group wherein the alkoxy group contains 1 to 8 carbon atoms, or an aralkyl group wherein the aryl group contains 6 to 10 carbon atoms and the alkylene group contains 1 to 8 carbon atoms, $R^{5aE}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group wherein the aryl group contains 6 to 10 carbon atoms and the alkylene group contains 1 to 8 carbon atoms, $R^{6aE}$ and $R^{7aE}$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, or amino group,

[Formula 19]

represents benzene ring, pyridine ring, thiophene ring, pyrimidine ring, naphthalene ring, quinoline ring, or indole ring which can have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an aralkyl group wherein the aryl group contains 6 to 10 carbon atoms and the alkylene group contains 1 to 8 carbon atoms, phenyl group, and pyridyl group, $B^{aE}$ represents $N(R^{8aE})C(=O)$, NHCONH, $CON(R^{9aE})$, $NHC(=S)NH$, $N(R^{10aE})SO_2$, $SO_2N(R^{11aE})$, or $OSO_2$, wherein $R^{8aE}$, $R^{9aE}$, $R^{10aE}$, and $R^{11aE}$ represent hydrogen atom, an alkyl group having 1 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group wherein the aryl group contains 6 to 10 carbon atoms and the alkylene group contains 1 to 8 carbon atoms, $E^{aE}$ represents O, S, $NR^{12aE}$, or an atomic bond, wherein $R^{12aE}$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group wherein the aryl group contains has 6 to 10 carbon atoms and the alkylene group contains has 1 to 8 carbon atoms, $G^{aE}$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine which can have 1 to 4 of the same or different substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acyl group having 2 to 8 carbon atoms, methylenedioxy group, carboxyl group, an alkylsulfinyl group having 1 to 6 carbon atoms, an alkylthio group having 1 to 6 carbon atoms, an alkylsulfonyl group having 1 to 6 carbon atoms, an aralkyl group wherein the aryl group contains 6 to 10 carbon atoms and the alkylene group contains 1 to 8 carbon atoms, a phenyl group which may can have a substituent, a pyridyl group which can have a substituent, an imidazolyl group which can have a substituent, an oxazolyl group which can have a substituent, and a thiazolyl group which can have a substituent, and $n^E$ represents an integer of 0 to 5.

4. A method of therapeutic treatment of multiple sclerosis, the method comprising administering a medicament which contains a compound having P2X4 receptor antagonist activity, or a shift thereof, or a hydrate or solvate thereof as an active ingredient, wherein the compound is a compound represented by the following general formula (IG):

[Formula 21]

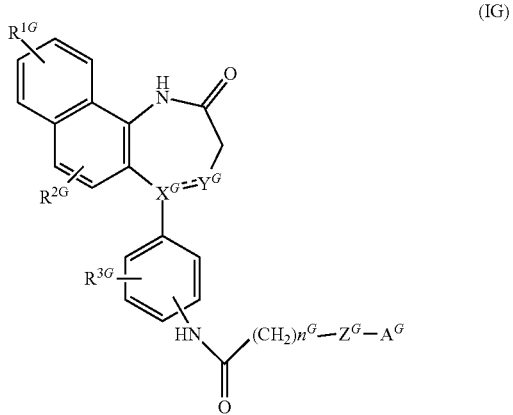

(IG)

wherein, in the formula, $R^{1G}$, $R^{2G}$, and $R^{3G}$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, or a dialkylamino group having 2 to 8 carbon atoms, $X^G$ represents C or N, $Y^G$ represents N or C(=O), provided that when $X^G$ is C, $Y^G$ represents N, and when $X^G$ is N, $Y^G$ represents C(=O), the double line consisting of the solid line and the broken line represents a single bond or a double bond, $n^G$ represents an integer of 0 to 6, $Z^G$ represents O, S, or an atomic bond, and $A^G$ represents benzene ring, pyridine ring, piperazine ring, piperidine ring, or morpholine ring which can have 1 to 5 of the same or different substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and $N(R^{4G})(R^{5G})$, wherein $R^{4G}$ and $R^{5G}$ represent the same or different alkyl groups having 1 to 8 carbon atoms, or $R^{4G}$, $R^{5G}$ and the nitrogen atom to which $R^{4G}$ and $R^{5G}$ bind together to represent a 5- to 7-membered ring which may further contain oxygen atom or sulfur atom as a ring-forming heteroatom.

5. The method according to claim 1, wherein the compound is 5-[4-[2-(trifluoromethyl)benzoyl]aminophenyl]-1H-naphtho[1,2-b][1,4]diazepine-2,4(3H,5H)-dione.

6. The method according to claim 1, wherein the compound is 5-[4-(2-iodobenzoylamino)phenyl]-1H-naphtho[1,2-b][1,4]diazepine-2,4(3H,5H)-dione.

7. The method according to claim 1, wherein the compound is 5-[4-[(2-ethylbenzoyl)amino]phenyl]-1H-naphtho[1,2-b][1,4]diazepine-2,4(3H,5H)-dione.

8. The method according to claim 1, wherein the compound is 5-[4-(2-tert-butylbenzoylamino)phenyl]-1H-naphtho[1,2-b][1,4]diazepine-2,4(3H,5H)-dione.

9. The method according to claim 1, wherein the compound is 5-[4-(6-chloro-2-hydroxybenzoylamino)phenyl]-1H-naphtho[1,2-b][1,4]diazepine-2,4(3H,5H)-dione.

10. The method according to claim 1, wherein the compound is 1-(2-chlorophenyl)-N-[4-(2,4-dioxo-1,2,3,4-tetrahydronaphtho[1,2-b][1,4]diazepin-5-yl) phenyl]methanesulfonamide.

11. The method according to claim 1, wherein the compound is 5-[4-[(2-isopropylbenzoyl)amino]phenyl]-1H-naphtho[1,2-b][1,4]diazepine-2,4(3H,5H)-dione.

12. The method according to claim 1, wherein the compound salt is 2-(dimethylamino)-N-[4-(2-oxo-2,3-dihydro-1H-naphtho[1,2-e][1,4]diazepin-5-yl) phenyl]nicotinamide dihydrochloride.

13. The method according to claim 1, wherein the compound salt is 2-(dimethylamino)-N-[4-(2-oxo-2,3-dihydro-1H-naphtho[1,2-e][1,4]diazepin-5-yl) phenyl]nicotinamide dimethanesulfonate.

14. The method according to claim 1 wherein the medicament is a medicament for therapeutic treatment of a pain accompanying multiple sclerosis.

15. The method according to claim 14, wherein the pain is a neuropathic pain.

16. The method according to claim 15, which is a medicament for use in therapeutic treatment of a neuropathic pain accompanying multiple sclerosis in a convalescent stage.

17. The method according to claim 2, wherein the medicament is a medicament for therapeutic treatment of a pain accompanying multiple sclerosis.

18. The method according to claim 17, wherein the pain is a neuropathic pain.

19. The method according to claim 18, which is a medicament for use in therapeutic treatment of a neuropathic pain accompanying multiple sclerosis in a convalescent stage.

20. The method according to claim 4, wherein the medicament is a medicament for therapeutic treatment of a pain accompanying multiple sclerosis.

21. The method according to claim 20, wherein the pain is a neuropathic pain.

22. The method according to claim 21, which is a medicament for use in therapeutic treatment of a neuropathic pain accompanying multiple sclerosis in a convalescent stage.

* * * * *

```
                       SEQUENCE LISTING

<160> NUMBER OF SEQ ID NOS: 5

<210> SEQ ID NO 1
<211> LENGTH: 17
<212> TYPE: PRT
<213> ORGANISM: Cavia porcellus

<400> SEQUENCE: 1

Tyr Gly Ser Leu Pro Gln Lys Ser Gln Arg Ser Gln Asp Glu Asn Pro
1               5                   10                  15

Val

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtgacaacca aagccaaagg                                                 20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
catgatgaag agggagtttt cc                                              22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agcttgtcat caacgggaag                                                 20

<210> SEQ ID NO 5
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 5
tttgatgtta gtggggtctc g                                             21
```